(12) United States Patent
Milgram et al.

(10) Patent No.: US 11,807,634 B2
(45) Date of Patent: Nov. 7, 2023

(54) CYCLOPROPYL DIHYDROQUINOLINE SULFONAMIDE COMPOUNDS

(71) Applicant: AMGEN INC., Thousand Oaks, CA (US)

(72) Inventors: Benjamin C Milgram, Cambridge, MA (US); Isaac E Marx, Arlington, MA (US); John Stellwagen, Beverly, MA (US); Wei Zhao, Westford, MA (US); Alan H. Cherney, Somerville, MA (US)

(73) Assignee: AMGEN INC., Thousand Oaks, CA (US)

( * ) Notice: Subject to any disclaimer, the term of this patent is extended or adjusted under 35 U.S.C. 154(b) by 33 days.

(21) Appl. No.: 17/344,939

(22) Filed: Jun. 10, 2021

(65) Prior Publication Data

US 2021/0387977 A1 Dec. 16, 2021

Related U.S. Application Data

(60) Provisional application No. 63/036,999, filed on Jun. 10, 2020.

(51) Int. Cl.
*C07D 413/12* (2006.01)

(52) U.S. Cl.
CPC .................. *C07D 413/12* (2013.01)

(58) Field of Classification Search
CPC .................................................. C07D 413/12
See application file for complete search history.

(56) References Cited

U.S. PATENT DOCUMENTS

| | | | |
|---|---|---|---|
| 4,412,994 A | 11/1983 | Sloan et al. | |
| 8,101,647 B2 | 1/2012 | Chafeev et al. | |
| 8,314,097 B2 | 11/2012 | Ksander et al. | |
| 10,383,866 B2 * | 8/2019 | Weiss | A61P 29/02 |
| 10,472,356 B2 * | 11/2019 | Weiss | A61P 29/00 |
| 10,729,684 B2 * | 8/2020 | Weiss | C07D 413/14 |

FOREIGN PATENT DOCUMENTS

| | | |
|---|---|---|
| EP | 0039051 A2 | 7/1985 |
| EP | 0039051 B1 | 7/1985 |
| WO | 2013134518 A1 | 9/2013 |
| WO | 2014201206 A1 | 12/2014 |
| WO | 2017106871 A1 | 6/2017 |

OTHER PUBLICATIONS

Berge, S.M., et al., "Pharmaceutical Salts," J. Pharma Sciences. 66:1-19 (1977).
Bundgaard, H., et al., "A Novel Solution-Stable, Water-Soluble Prodrug Type for Drugs Containing a Hydroxyl or an NH-Acidic Group," J. Med Chem. 32:2503-2507 (1989).
Cox, J.J., et al., "An SCN9A channelopathy causes congenital inability to experience pain," Nature. 444:894-898 (2006).
Dib-Hajj, S.D., et al., "NaN, a novel voltage-gated Na channel, is expressed preferentially in peripheral sensory neurons and down-regulated after axotomy," Proc. Natl. Acad. Sci. 95:8963-8968 (1998).
Dib-Hajj, S.D., et al., "The NaV1.7 sodium channel: from molecule to man," Nat. Review. 14:49-62 (2013).
Do, M.T., et al., "Subthreshold Sodium Currents and Pacemaking of Subthalamic Neurons: Modulation by Slow Inactivation," Neuron. 39:109-120 (2003).
Drenth, J.P.H., et al., "SCN9A Mutations Define Primary Erythermalgia as a Neuropathic Disorder of Voltage Gated Sodium Channels," J. Invest Dermatol 124:1333-1338 (2005).
Ettinger, A., et al., "Use of Antiepileptic Drugs for Nonepileptic Conditions: Psychiatric Disorders and Chronic Pain," Neurotherapeutics. 4:75-83 (2007).
Fertleman, C.R., et al., "SCN9A Mutations in Paroxysmal Extreme Pain Disorder: Allelic Variants Underlie Distinct Channel Defects and Phenotypes," Neuron. 52:767-774 (2006).
Gillet, L, et al., "Voltage-gated Sodium Channel Activity Promotes Cysteine Cathepsin-dependent Invasiveness and Colony Growth of Human Cancer Cells," J. Biological Chemistry 284:8680-8691 (2009).
Goldberg, Y.P., et al., "Loss-of-function mutations in the NaV1.7 gene underlie congenital indifference to pain in multiple human populations," Clin. Genet. 71:311-319 (2007).
Goldin, A.L., "Resurgence of Sodium Channel Research," Annu. Rev. Physiol. 63:871-894 (2001).

(Continued)

*Primary Examiner* — Kamal A Saeed
(74) *Attorney, Agent, or Firm* — Elsa D. Lemoine

(57) ABSTRACT

The present invention provides a compound of Formula (I):

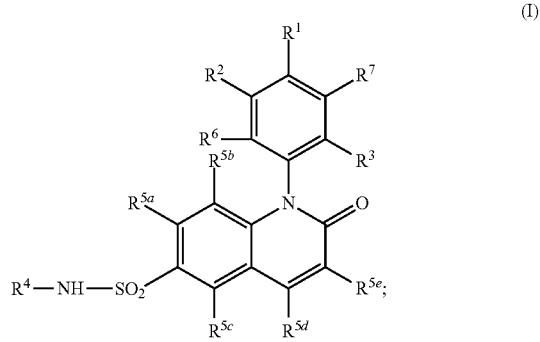

an enantiomer, diastereoisomer, atropisomer thereof, a mixture thereof, or a pharmaceutically acceptable salt thereof, that inhibits voltage-gated sodium channels, in particular NaV1.7. The compounds are useful for the treatment of diseases associated with the activity of sodium channels such as pain disorders, cough, and itch. Also provided are pharmaceutical compositions containing the compounds of the present invention. Also further provided is an atropi-selective preparation of said compounds of Formula (I), and intermediate thereof.

27 Claims, No Drawings

(56) References Cited

OTHER PUBLICATIONS

Gonzalez, J.E., et al., "Small Molecule Blockers of Voltage-gated Sodium Channels," Methods Principles in Med. Chem. 29:168-192 (2006).
Hains, B., et al., "Upregulation of Sodium Channel NaV1.3 and Functional Involvement in Neuronal Hyperexcitability Associated with Central Neuropathic Pain after Spinal Cord Injury," J. Neuroscience. 23(26):8881-8892 (2003).
Halford, B., "Changing the Channel," CE. News. pp. 10-14 (2014).
Halladay, J., et al., "An 'all-inclusive' 96-well cytochrome P450 induction method: Measuring enzyme activity, mRNA levels, protein levels, and cytotoxicity from one well using cryopreserved human hepatocytes," J. Pharmacol. Toxicol. Methods. 66:270-275 (2012).
Hamann, M., et al., "Motor disturbances in mice with deficiency of the sodium channel gene Scn8a show features of human dystonia," Exp. Neurol. 184(2):830-838 (2003).
Haufe, V., et al., "The promiscuous nature of the cardiac sodium current," J Mol. Cell Cardiol. 42(3):469-477 (2007).
Hille, B., "Ion Channels of Excitable Membranes," Sinauer Associates. 3rd Ed. (2001).
Johannessen, L.C., "Antiepileptic Drugs in Non-Epilepsy Disorders Relations between Mechanisms of Action and Clinical Efficacy," CNS Drugs 22(1):27-47 (2008).
Kim, D.Y., et al., "BACE1 regulates voltage-gated sodium channels and neuronal activity," Nat. Cell Biol. 9(7):755-764 (2007).
Kornecook, T.J., et al., "Pharmacologic Characterization of AMG8379, a Potent and Selective Small Molecule Sulfonamide Antagonist of the Voltage-Gated Sodium Channel NaV1.7," J. Pharmacol. Ex Ther. 362:146-160 (2017).
Liu, H., et al., "Mutations in Cardiac Sodium Channels," Am. J. Pharmacogenomics. 3(3):173-179 (2003).
McKinney, B.C. et al., "Exaggerated emotional behavior in mice heterozygous null for the sodium channel Scn8a (NaV1.6)," Genes Brain Behav. 7(6)629-638 (2008).
Morinville, A., et al., "Distribution of the Voltage-Gated Sodium Channel NaV1.7 in the Rat: Expression in the Autonomic and Endocrine Systems," J. Comp. Neurol. 504:680-689 (2007).
Puopolo, M., et al., "Roles of Subthreshold Calcium Current and Sodium Current in Spontaneous Firing of Mouse Midbrain Dopamine Neurons," J. of Neuro. 27(3):645-656 (2007).
Raymond, C.K., et al., "Expression of Alternatively Spliced Sodium Channel Subunit Genes," J. Bio. Chem. 279(44):46234-46241 (2004).
Svensson, L., et al., "The Design and Bioactivation of Presystemically Stable Prodrugs," Drug Metabolism Rev. 19(2):165-194 (1988).
Tamaoka, A., "Paramyotonia Congenita and Skeletal Sodium Channelopathy," Internal Med. 42(9):769-770 (2003).
Waxman, S.G., "Axonal conduction and injury in multiple sclerosis: the role of sodium channels," Nature Neurosci. 7:932-941 (2006).
Wood, J.N., et al., "Voltage-Gated Sodium Channel Blockers; Target Validation and Therapeutic Potential," Curr. Top Med. Chem. 5:529-537 (2005).
Woodruff-Pak, D.S., et al., "Inactivation of Sodium Channel Scn8A (Nav1.6) in Purkinje Neurons Impairs Learning in Morris Water Maze and Delay but Not Trace Eyeblink Classical Conditioning," Behav. Neurosci. 120(2):229-240 (2006).
Yang, Y., et al., "Mutations in SCN9A, encoding a sodium channel alpha subunit, in patients with primary erythermalgia," J. Med. Genet. 41:171-174 (2004).
Yu, F.H., et al., "Reduced sodium current in GABAergic interneurons in a mouse model of severe myoclonic epilepsy in infancy," Nat. Neuroscience, 9(9)1142-1149 (2006).
T. Higuchi and W. Stella, "Pro-drugs as Novel Delivery Systems," vol. 14 of the A.C.S. Symposium Series, and in Bioreversible Carriers in Drug Design, ed. Robert Gould, American Pharmaceutical Association and Pergamon Press (1975).
Federal Register/vol. 71(176) Notices, Department of Health and Human Services, Food and Drug Admin., Draft Guidance for Industry on Drug Interaction Studies-Study Design, Data Analysis, and Implications for Dosing and Labelling; Availability, pp. 53696-53697, Sep. 12, 2006.
Bundgaard, H., Design of Prodrugs, Publisher: Elsevier (1985) (Table of Contents Only).

\* cited by examiner

CYCLOPROPYL DIHYDROQUINOLINE SULFONAMIDE COMPOUNDS

CROSS REFERENCES TO RELATED APPLICATIONS

This application claims priority from U.S. Provisional Application No. 63/036,999, filed Jun. 10, 2020.

FIELD OF THE INVENTION

The present invention provides compounds that are inhibitors of voltage-gated sodium channels (NaV), in particular NaV 1.7, and are useful for the treatment of diseases treatable by inhibition of sodium channels such as pain disorders. Also provided are pharmaceutical compositions containing compounds of the present invention.

BACKGROUND OF THE INVENTION

A 2011 report of the institute of medicine estimates that 100 million adults in the US, roughly 30% of the population, suffer from chronic pain (C & E News, Bethany Halford, "Changing the Channel", published 3-24). Chronic pain by definition involves abnormal electrical spiking of neurons in the pain pathways: peripheral sensory neurons, spinal cord neurons, neurons in the pain matrix of the brain (e.g., somatosensory cortex, insular cortex, anterior cingular cortex), and/or neurons in brainstem. Although firing of these neurons is modulated and governed by many different receptors, enzymes, and growth factors, in most neurons the fast upstroke of the electrical spike is produced by entry of sodium ions through voltage-gated sodium channels (Hille B, Ion Channels of Excitable Membranes. Sinauer Associates, Inc.: Sunderland Mass., 3$^{rd}$ Ed. 2001). There are nine different isoforms of voltage-gated sodium channel (NaV 1.1-NaV 1.9), and they have distinct expression patterns in tissues including neurons and cardiac and skeletal muscle (Goldin, A. L, "Resurgence of sodium channel research," *Ann Rev Physiol* 63:871-894, 2001; Wood, J. N. and, Boorman, J. "Voltage-gated sodium channel blockers; target validation and therapeutic potential" *Curr. Top Med. Chem.* 5:529-537, 2005).

NaV1.1 and NaV1.2 are highly expressed in the brain (Raymond, C. K., et al., J. Biol. Chem. (2004) 279 (44): 46234-41) and are vital to normal brain function. Some loss of function due to NaV 1.1 mutations in humans, have resulted in epilepsy, presumably as these channels are expressed in inhibitory neurons (Yu, F. H., et al., Nat. Neuroscience (2006), 9 (9) 1142-1149). NaV1.1 is also expressed in the peripheral nervous system and inhibition of NaV1.1 in the periphery may provide relief of pain. Hence, while inhibiting NaV1.1 may provide use fro treating pain, it may also be undesirable possibly leading to anxiety and over excitability. NaV1.3 is expressed primarily in the fetal central nervous system, and expression was found to be upregulated after nerve injury in rats (Hains, B. D., et al., J. Neuroscience (2030) 23(26):8881-8892). NaV1.4 is expressed primarily in skeletal muscle. Mutations of the gene and its' product have significant impact on muscle function, including paralysis (Tamaoka A., Internal Medicine (2003), (9):769-770). NaV1.5 is expressed mainly in cardiac myocytes, including atria, ventricles, the sino-atrial node, atrioventricular node and cardiac Purkinje fibers. The rapid upstroke of the cardiac action potential and the rapid impulse conduction through cardiac tissue is due to the opening of the NaV1.5 channel. Mutations of the NaV1.5 channel have resulted in arrhythmic syndromes, including QTc prolongation, Brugada syndrome (BS), sudden unexpected nocturnal death syndrome (SUNDS) and sudden infant death syndrome (SIDS) (Liu, H., et al., Am. J. Pharmacogenomics (2003), 3(3):173-179). NaV1.6 is widely distributed voltage-gated sodium channel expressed throughout the central and peripheral nervous system. NaV1.8 is expressed primarily in sensory ganglia of the peripheral nervous system, such as the dorsal root ganglia. There are no identified NaV1.8 mutations that produce varied pain responses in humans. NaV1.8 differs from most neuronal NaV isotypes in that it is insensitive to inhibition by tetrodotoxin. NaV1.9, similar to NaV1.8, is also a tetrodotoxin insensitive sodium channels expressed primarily in dorsal root ganglia neurons (Dib-Hajj, S. D., et al., Proc. Natl. Acad. Sci. USA (1998), 95(15):8963-8968).

Recent evidence from several independent genetic studies has shown that the tetrodotoxin-sensitive voltage-gated sodium ion channel NaV 1.7 (SCN9A) is required to sense pain. Rare genetic forms of severe chronic pain, Primary Erythromelalgia and Paroxysmal Extreme Pain Disorder, result from mutations that increase the activity of NaV 1.7 (Fertleman C. R., Baker M. D., Parker K. A., Moffatt S., et al., "SCN9A mutations in paroxysmal extreme pain disorder: allelic variants underlie distinct channel defects and phenotypes," Neuron 52:767-774, 2006; Yang Y., Wang Y., Li S, et al., "Mutations in SCN9A, encoding a sodium channel alpha subunit, in patients with primary erythermalgia," J. Med. Genet. 41:171-174, 2004; Drenth J. P. H., te Morsche R. H. M., Guillet G., Taieb A., et al., "SCN9A mutations define primary erythermalgia as a neuropathic disorder of voltage gated sodium channels," *J Invest Dermatol* 124:1333-1338). Conversely, two separate clinical studies have determined that the root cause of the genetic disorder Congenital Indifference to Pain (CIP) is a loss of function of NaV 1.7 via mutations that truncate the protein and destroy function (Cox J. J., Reimann F, Nicholas A. K., et al. "An SCN9A channelopathy causes congenital inability to experience pain," *Nature* 444:894-898, 2006; Goldberg Y. P., MacFarlane J., MacDonald M. L., Thompson J., et al. "Loss-of-function mutations in the NaV1.7 gene underlie congenital indifference to pain in multiple human populations," *Clin Genet* 71:311-319, 2007). The disorder is inherited in Mendelian recessive manner with 100% penetrance. The phenotype associated with CIP is extreme: affected individuals are reported to have experienced painless burns, childbirth, appendicitis, and bone fractures, as well as to have insensitivity to clinical measures of pain such as pinprick ortendon pressure. Yet sensory, motor, autonomic, and other measured functions are normal, with the only reported abnormality being anosmia (inability to smell). These studies indicate that among the many possible targets in the pain pathway, NaV 1.7 governs one or more control points critical for pain perception.

Nonselective sodium channel inhibitors such as lidocaine, mexiletine, and carbamazepine show clinical efficacy in chronic pain, including neuropathic pain, but they are limited in dose and in use, likely due to effects on sodium channels outside the pain pathway. Lidocaine is a local anesthetic that doctors use for minor surgery. Dentists use novocaine. However, these compounds do not distinguish between the various sodium channel subtypes, making them unsuitable for use as systemic pain killers. "If you give a drug that blocks NaV1.7 but also blocks NaV1.5, the patient will die of heart failure," says Glenn F. King, a professor at Australia's University of Queensland who studies venoms that block ion channels. "It will be a completely painless death, but the patient will die nonetheless." Thus, selectivity for NaV1.7 is desired, particularly over NaV1.5. Researchers have tailored their efforts to find a molecule that inhibitors or block the activity of only NaV1.7. To compound this problem, the identity, every location, every function and/or the tertiary structures of each subtype of voltage gated sodium channel proteins are not known or completely understood.

Consequently, a number of researchers are attempting to identify small molecule inhibitors of NaV1.7. For example, Chafeev et. al. disclose spiro-oxindole compound for the treatment and/or prevention of sodium channel-mediated diseases, such as pain, in U.S. Pat. No. 8,101,647. International Publications WO 2013/134518 and WO 2014/201206 disclose sulfonamide derivatives which are different from the sulfonamide derivatives of the present invention. Thus, there is a need to identify NaV1.7 inhibitors selective over at least NaV1.5 to treat pain. The present invention provides compounds that are selective inhibitors of NaV 1.7. over at least NaV1.5.

SUMMARY OF THE INVENTION

In embodiment 1, the present invention provides a compound of Formula (I), an enantiomer, diastereoisomer, atropisomer thereof, or a mixture thereof, or a pharmaceutically acceptable salt thereof,

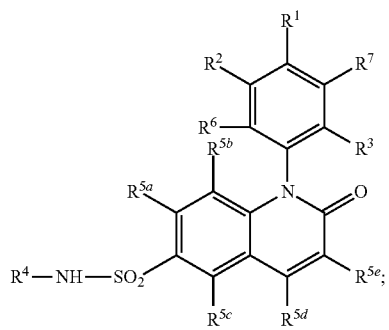

(I)

wherein:

$R^1$ is a cyclopropyl ring; or a 4-, 5-, 6-, 7-, or 8-membered bicyclic ring containing 0, 1, 2 or 3 N atoms and 0, 1, or 2 atoms selected from O and S; and wherein said cyclopropyl ring or bicyclic ring is substituted by 0, 1, 2 or 3 $R^{1a}$ groups selected from hydroxy, halo, $C_{1-8}$alk, $C_{1-8}$haloalk, —O—$C_{1-4}$alk, —O—$C_{1-8}$haloalk, —C(=O)$C_{1-4}$alk, —O—C(=O)$C_{1-4}$alk, —NH$_2$, —NHC$_{1-4}$alk, —N(C$_{1-4}$alk)C$_{1-4}$alk, 3-, 4-, or 5-membered cycloalkyl, or 6-membered aryl;

$R^2$ is H, halo, CN, $C_{1-6}$alk, or $C_{1-6}$haloalk:

$R^3$ is $C_{1-6}$alk, $C_{1-6}$haloalk. —O—$C_{1-6}$alk, —O-cyclopropyl, or —O-cyclobutyl;

$R^4$ is a 5- to 6-membered heteroaryl;

Each of $R^6$ and $R^7$ is hydrogen; and

Each of $R^{5a}$; $R^{5b}$; $R^{5c}$; $R^{5d}$; and $R^{5e}$ is independently hydrogen or halo.

In sub-embodiment 1a of embodiment 1, the compound of Formula (I) has a sub-formula of (Ia):

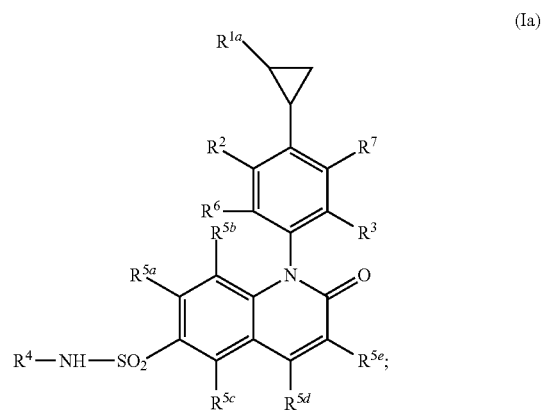

(Ia)

wherein $R^{1a}$ is fluoro, methyl, —O—CF$_3$, —CH$_2$—O—CF$_3$, CF$_3$, cyclopropyl, or phenyl.

In a more preferred sub embodiment 1a of embodiment 1, $R^{1a}$ is methyl, CF$_3$, or phenyl; and $R^4$ is isoxazolyl or pyridazinyl.

In a most preferred sub embodiment 1a of embodiment 1, $R^{1a}$ is CF$_3$; $R^2$ is F; and $R^4$ is isoxazolyl.

In sub-embodiment 1b of embodiment 1, the compound of formula (I) has a sub-formula of (Ib):

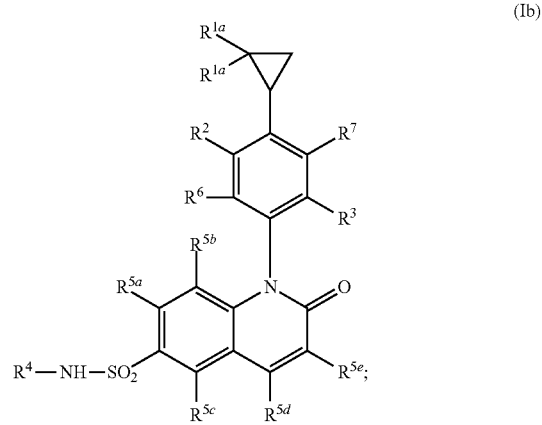

(Ib)

wherein $R^{1a}$ is fluoro, methyl, or CF$_3$.

In a further sub embodiment 1b of embodiment 1, $R^{1a}$ is fluoro or methyl.

In sub-embodiment 1c of embodiment 1, the compound of Formula (I) has a sub-formula of (Ic):

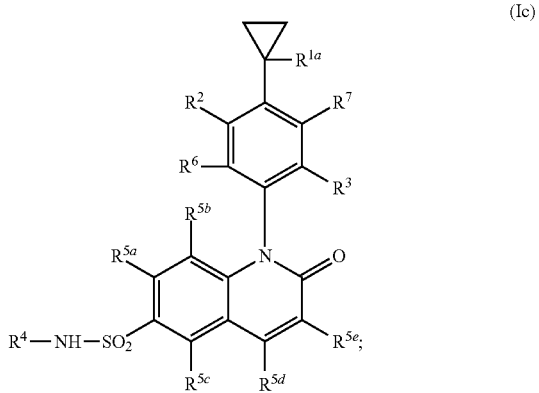

(Ic)

wherein $R^{1a}$ is fluoro, methyl, or $CF_3$. In a further sub embodiment 1c of embodiment 1, $R^{1a}$ is $CF_3$.

In sub-embodiment Id of embodiment 1, the compound of formula (I) has a sub-formula of (Id):

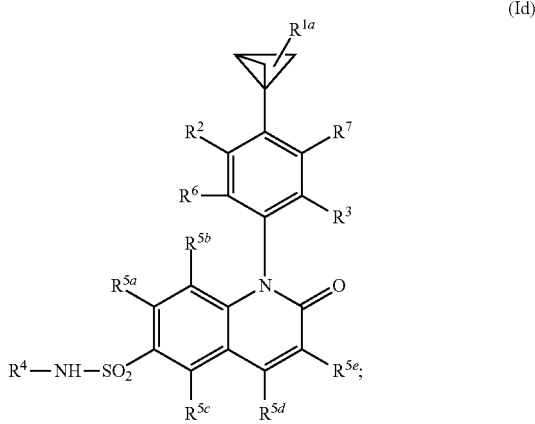

(Id)

wherein $R^{1a}$ is fluoro, methyl, or $CF_3$. In a further sub embodiment Id of embodiment 1, $R^{1a}$ is $CF_3$.

In embodiment 2, the present invention provides compounds of Formula (I), an enantiomer, diastereoisomer, atropisomer thereof, or a mixture thereof, or a pharmaceutically acceptable salt thereof, wherein $R^{1a}$ group is selected from halo, $C_{1-8}$alk, —O—$C_{1-4}$alk, $C_{1-8}$haloalk, cyclopropyl, or phenyl; wherein said $C_{1-8}$haloalk is $C_{1-8}$fluoroalkyl.

In embodiment 3, the present invention provides compounds of Formula (I), an enantiomer, diastereoisomer, atropisomer thereof, or a mixture thereof, or a pharmaceutically acceptable salt thereof, wherein $R^1$ is a cyclopropyl ring; or a 4-, 5-, or 6-membered bicyclic ring; wherein said bicyclic ring contains 0 N, O, and S atoms; and wherein said cyclopropyl ring or bicyclic ring is substituted by 1, 2 or 3 $R^{1a}$ groups selected from F, —$CF_3$, —O—$CF_3$, —$C(CH_3)_3$, cyclopropyl, or phenyl.

In embodiment 4, the present invention provides compounds of Formula (I), an enantiomer, diastereoisomer, atropisomer thereof, or a mixture thereof, or a pharmaceutically acceptable salt thereof, wherein $R^1$ is a cyclopropyl ring or bicyclo[1.1.0]butan-1-yl ring; wherein each ring is substituted by 1 or 2 F or —$CF_3$.

In embodiment 5, the present invention provides compounds of Formula (I), an enantiomer, diastereoisomer, atropisomer thereof, or a mixture thereof, or a pharmaceutically acceptable salt thereof, wherein $R^1$ is a cyclopropyl ring substituted by 1 or 2 F or —$CF_3$; wherein said cyclopropyl ring is a tram isomer.

In embodiment 6, the present invention provides compounds of Formula (I), an enantiomer, diastereoisomer, atropisomer thereof, or a mixture thereof, or a pharmaceutically acceptable salt thereof, wherein $R^1$ is a bicyclo[1.1.0]butan-1-yl ring substituted by 1 or 2 F or —$CF_3$.

In embodiment 7, the present invention provides compounds of Formula (I), an enantiomer, diastereoisomer, atropisomer thereof, or a mixture thereof, or a pharmaceutically acceptable salt thereof, wherein $R^2$ is H, fluoro, chloro, CN, methyl, $CF_3$, $CHF_2$, or $CH_2F$. In sub embodiment 7a of embodiment 7, $R^2$ is fluoro.

In embodiment 8, the present invention provides compounds of Formula (I), an enantiomer, diastereoisomer, atropisomer thereof, or a mixture thereof, or a pharmaceutically acceptable salt thereof, wherein $R^2$ is H, fluoro, chloro, CN, or methyl.

In embodiment 9, the present invention provides compounds of Formula (I), an enantiomer, diastereoisomer, atropisomer thereof, or a mixture thereof, or a pharmaceutically acceptable salt thereof, wherein $R^2$ is H or fluoro.

In embodiment 10, the present invention provides compounds of Formula (I), an enantiomer, diastereoisomer, atropisomer thereof, or a mixture thereof, or a pharmaceutically acceptable salt thereof, wherein $R^3$ is methoxy.

In embodiment 11, the present invention provides compounds of Formula (I), an enantiomer, diastereoisomer, atropisomer thereof, or a mixture thereof, or a pharmaceutically acceptable salt thereof, wherein $R^4$ is a 5-membered heteroaryl.

In embodiment 12, the present invention provides compounds of Formula (I), an enantiomer, diastereoisomer, atropisomer thereof, or a mixture thereof, or a pharmaceutically acceptable salt thereof, wherein $R^4$ is a 6-membered heteroaryl.

In embodiment 13, the present invention provides compounds of Formula (I), an enantiomer, diastereoisomer, atropisomer thereof, or a mixture thereof, or a pharmaceutically acceptable salt thereof, wherein $R^4$ is isoxazolyl, pyridazinyl, thiazolyl, thiadiazolyl, oxazolyl, or pyrimidinyl. In a sub embodiment of embodiment 13a of embodiment 13, $R^4$ is isoxazolyl, pyridazinyl, or pyrimidyl. In another sub embodiment 13b of embodiment 13, $R^4$ is isoxazolyl.

In embodiment 14, the present invention provides compounds of Formula (I), an enantiomer, diastereoisomer, atropisomer thereof, or a mixture thereof, or a pharmaceutically acceptable salt thereof, wherein a) each of $R^{5a}$; $R^{5b}$; $R^{5c}$; $R^{5d}$; and $R^{5e}$ is hydrogen; b) $R^{5a}$ is F; and each of $R^{5b}$; $R^{5c}$; $R^{5d}$; and $R^{5e}$ is hydrogen; or c) $R^{5d}$ is F; and each of $R^{5a}$; $R^{5b}$; $R^{5c}$; and $R^{5e}$ is hydrogen.

In embodiment 14a, the present invention provides compounds of Formula (I), an enantiomer, diastereoisomer, atropisomer thereof, or a mixture thereof, or a pharmaceutically acceptable salt thereof, wherein each of $R^{5a}$; $R^{5b}$; $R^{5c}$; $R^{5d}$; and $R^{5e}$ is hydrogen.

In embodiment 14b, the present invention provides compounds of Formula (I), an enantiomer, diastereoisomer, atropisomer thereof, or a mixture thereof, or a pharmaceutically acceptable salt thereof, wherein $R^{5a}$ is F; and each of $R^{5b}$; $R^{5c}$; $R^{5d}$; and $R^{5e}$ is hydrogen.

In embodiment 14c, the present invention provides compounds of Formula (I), an enantiomer, diastereoisomer, atropisomer thereof, or a mixture thereof, or a pharmaceutically acceptable salt thereof, wherein $R^{5d}$ is F; and each of $R^{5a}$; $R^{5b}$; $R^{5c}$; and $R^{5e}$ is hydrogen.

In embodiment 15, the present invention provides compounds of Formula (I), an enantiomer, diastereoisomer, atropisomer thereof, or a mixture thereof, or a pharmaceutically acceptable salt thereof, wherein said compound of Formula (I) is of formula (Ia):

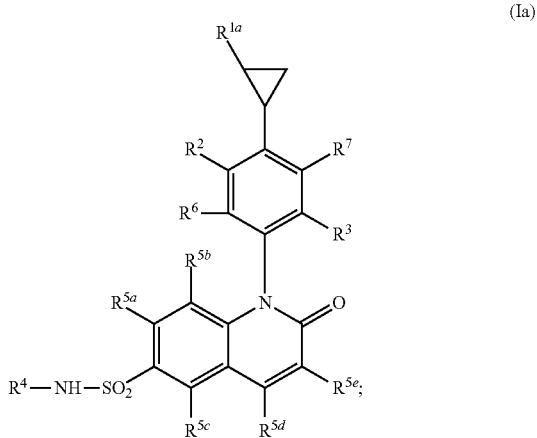

(Ia)

wherein each $R^{1a}$ is independently fluoro, methyl, —O—CF$_3$, CF$_3$, cyclopropyl, or phenyl.

In embodiment 15a, the present invention provides compounds of Formula (I), an enantiomer, diastereoisomer, atropisomer thereof, or a mixture thereof, or a pharmaceutically acceptable salt thereof, wherein $R^{1a}$ is CF$_3$ or methyl; the cyclopropyl ring is a trans isomer; $R^2$ is H or F; $R^4$ is isoxazolyl, pyridazinyl, thiazolyl, or thiadiazolyl; and $R^{5a}$ is H or F.

In embodiment 15b, the present invention provides compounds of Formula (I), an enantiomer, diastereoisomer, atropisomer thereof, or a mixture thereof, or a pharmaceutically acceptable salt thereof, wherein $R^{1a}$ is CF$_3$ or methyl; the cyclopropyl ring is a cis isomer; $R^2$ is H or F; $R^4$ is isoxazolyl, pyridazinyl, thiazolyl, or thiadiazolyl; and $R^{5a}$ is H or F.

In embodiment 15c, the present invention provides compounds of Formula (I), an enantiomer, diastereoisomer, atropisomer thereof, or a mixture thereof, or a pharmaceutically acceptable salt thereof, wherein $R^{1a}$ is CF$_3$; the cyclopropyl ring is a trans isomer; $R^2$ is H; $R^4$ is isoxazolyl, pyridazinyl, thiazolyl, or thiadiazolyl; and $R^{5a}$ is F. In sub embodiment of embodiment 15c, preferably, $R^4$ is isoxazolyl.

In embodiment 15d, the present invention provides compounds of Formula (I), an enantiomer, diastereoisomer, atropisomer thereof, or a mixture thereof, or a pharmaceutically acceptable salt thereof, wherein $R^{1a}$ is CF$_3$; the cyclopropyl ring is a trans isomer; $R^2$ is F; $R^4$ is isoxazolyl, pyridazinyl, thiazolyl, or thiadiazolyl; and $R^{5a}$ is H. In sub embodiment of embodiment 15d, preferably, $R^4$ is isoxazolyl.

In embodiment 16, the present invention provides compounds of Formula (I), an enantiomer, diastereoisomer, atropisomer thereof, or a mixture thereof, or a pharmaceutically acceptable salt thereof, wherein said compound is an atropisomer and is a P atropisomer.

In embodiment 17, the present invention provides compounds of Formula (I), an enantiomer, diastereoisomer, atropisomer thereof, or a mixture thereof, or a pharmaceutically acceptable salt thereof, wherein the compound is selected from:

| EX # | CHEMICAL NAME |
|---|---|
| 1 | (P)-1-(4-(2,2-dimethylcyclopropyl)-5-fluoro-2-methoxyphenyl)-N-(isoxazol-3-yl)-2-oxo-1,2-dihydroquinoline-6-sulfonamide |
| 2 | (P)-1-(4-(2,2-dimethylcyclopropyl)-2-methoxyphenyl)-N-(isoxazol-3-yl)-2-oxo-1,2-dihydroquinoline-6-sulfonamide |
| 3 | trans-1-(5-fluoro-2-methoxy-4-(2-(trifluoromethyl)cyclopropyl)phenyl)-N-(isoxazol-3-yl)-2-oxo-1,2-dihydroquinoline-6-sulfonamide |
| 4 | (P)-1-(5-fluoro-2-methoxy-4-((1S,2S)-2-(trifluoromethyl)cyclopropyl)phenyl)-N-(isoxazol-3-yl)-2-oxo-1,2-dihydroquinoline-6-sulfonamide |
| 5 | (P)-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide |
| 6 | (P)-1-(5-fluoro-2-methoxy-4-((1R,2R)-2-methylcyclopropyl)phenyl)-N-(isoxazol-3-yl)-2-oxo-1,2-dihydroquinoline-6-sulfonamide |
| 7 | (P)-1-(5-fluoro-2-methoxy-4-((1S,2S)-2-methylcyclopropyl)phenyl)-N-(isoxazol-3-yl)-2-oxo-1,2-dihydroquinoline-6-sulfonamide |
| 8 | (P)-1-(5-fluoro-2-methoxy-4-((1R,2R)-2-phenylcyclopropyl)phenyl)-N-(isoxazol-3-yl)-2-oxo-1,2-dihydroquinoline-6-sulfonamide |
| 9 | (P)-1-(5-fluoro-2-methoxy-4-((1S,2S)-2-phenylcyclopropyl)phenyl)-N-(isoxazol-3-yl)-2-oxo-1,2-dihydroquinoline-6-sulfonamide |
| 10 | (P)-(R)-1-(4-(2,2-difluorocyclopropyl)-5-fluoro-2-methoxyphenyl)-N-(isoxazol-3-yl)-2-oxo-1,2-dihydroquinoline-6-sulfonamide |
| 11 | (P)-(S)-1-(4-(2,2-difluorocyclopropyl)-5-fluoro-2-methoxyphenyl)-N-(isoxazol-3-yl)-2-oxo-1,2-dihydroquinoline-6-sulfonamide |
| 12 | (P)-1-(5-chloro-2-methoxy-4-((1S,2S)-2-(trifluoromethyl)cyclopropyl)phenyl)-2-oxo-N-(pyrimidin-2-yl)-1,2-dihydroquinoline-6-sulfonamide |
| 13 | (P)-1-(5-chloro-2-methoxy-4-((1R,2R)-2-(trifluoromethyl)cyclopropyl)phenyl)-2-oxo-N-(pyrimidin-2-yl)-1,2-dihydroquinoline-6-sulfonamide |
| 14 | (P)-1-(5-chloro-2-methoxy-4-((1R,2R)-2-(trifluoromethyl)cyclopropyl)phenyl)-2-oxo-N-(pyridazin-3-yl)-1,2-dihydroquinoline-6-sulfonamide |
| 15 | (P)-1-(5-chloro-2-methoxy-4-((1S,2S)-2-(trifluoromethyl)cyclopropyl)phenyl)-2-oxo-N-(pyridazin-3-yl)-1,2-dihydroquinoline-6-sulfonamide |
| 16 | (P)-1-(5-fluoro-2-methoxy-4-((1R,2R)-2-(trifluoromethyl)cyclopropyl)phenyl)-2-oxo-N-(pyridazin-3-yl)-1,2-dihydroquinoline-6-sulfonamide |
| 17 | (P)-1-(5-fluoro-2-methoxy-4-((1S,2S)-2-(trifluoromethyl)cyclopropyl)phenyl)-2-oxo-N-(pyridazin-3-yl)-1,2-dihydroquinoline-6-sulfonamide |
| 18 | (P)-1-(5-chloro-2-methoxy-4-((1R,2R)-2-(trifluoromethyl)cyclopropyl)phenyl)-N-(isoxazol-3-yl)-2-oxo-1,2-dihydroquinoline-6-sulfonamide |
| 19 | (P)-1-(5-chloro-2-methoxy-4-((1S,2S)-2-(trifluoromethyl)cyclopropyl)phenyl)-N-(isoxazol-3-yl)-2-oxo-1,2-dihydroquinoline-6-sulfonamide |
| 20 | (P)-1-(5-fluoro-2-methoxy-4-((1R,2R)-2-(trifluoromethyl)cyclopropyl)phenyl)-2-oxo-N-(pyrimidin-2-yl)-1,2-dihydroquinoline-6-sulfonamide |
| 21 | (P)-1-(5-fluoro-2-methoxy-4-((1S,2S)-2-(trifluoromethyl)cyclopropyl)phenyl)-2-oxo-N-(pyrimidin-2-yl)-1,2-dihydroquinoline-6-sulfonamide |
| 22 | (P)-1-(5-fluoro-2-methoxy-4-(1-(trifluoromethyl)cyclopropyl)phenyl)-N-(isoxazol-3-yl)-2-oxo-1,2-dihydroquinoline-6-sulfonamide |
| 23 | (P)-1-(5-fluoro-2-methoxy-4-(1-(trifluoromethyl)cyclopropyl)phenyl)-2-oxo-N-(pyrimidin-2-yl)-1,2-dihydroquinoline-6-sulfonamide |
| 24 | (P)-1-(5-chloro-2-methoxy-4-(1-(trifluoromethyl)cyclopropyl)phenyl)-N-(isoxazol-3-yl)-2-oxo-1,2-dihydroquinoline-6-sulfonamide |
| 25 | (P)-1-(5-chloro-2-methoxy-4-(1-(trifluoromethyl)cyclopropyl)phenyl)-2-oxo-N-(pyrimidin-2-yl)-1,2-dihydroquinoline-6-sulfonamide |

-continued

| EX # | CHEMICAL NAME |
|---|---|
| 26 | (P)-N-(isoxazol-3-yl)-1-(2-methoxy-5-methyl-4-((1R,2R)-2-(trifluoromethyl)cyclopropyl)phenyl)-2-oxo-1,2-dihydroquinoline-6-sulfonamide |
| 27 | (P)-N-(isoxazol-3-yl)-1-(2-methoxy-5-methyl-4-((1S,2S)-2-(trifluoromethyl)cyclopropyl)phenyl)-2-oxo-1,2-dihydroquinoline-6-sulfonamide |
| 28 | (P)-1-(2-methoxy-5-methyl-4-((1R,2R)-2-(trifluoromethyl)cyclopropyl)phenyl)-2-oxo-N-(pyrimidin-2-yl)-1,2-dihydroquinoline-6-sulfonamide |
| 29 | (P)-1-(2-methoxy-5-methyl-4-((1S,2S)-2-(trifluoromethyl)cyclopropyl)phenyl)-2-oxo-N-(pyrimidin-2-yl)-1,2-dihydroquinoline-6-sulfonamide |
| 30 | (P)-1-(4-((1S,2S)-[1,1'-bi(cyclopropan)]-2-yl)-5-fluoro-2-methoxyphenyl)-N-(isoxazol-3-yl)-2-oxo-1,2-dihydroquinoline-6-sulfonamide |
| 31 | (P)-1-(4-((1R,2S)-[1,1'-bi(cyclopropan)]-2-yl)-5-fluoro-2-methoxyphenyl)-N-(isoxazol-3-yl)-2-oxo-1,2-dihydroquinoline-6-sulfonamide |
| 32 | (P)-1-(5-fluoro-2-methoxy-4-((1R,2R)-2-((trifluoromethoxy)methyl)cyclopropyl)phenyl)-N-(isoxazol-3-yl)-2-oxo-1,2-dihydroquinoline-6-sulfonamide |
| 33 | (P)-1-(5-fluoro-2-methoxy-4-((1S,2S)-2-((trifluoromethoxy)methyl)cyclopropyl)phenyl)-N-(isoxazol-3-yl)-2-oxo-1,2-dihydroquinoline-6-sulfonamide |
| 34 | (P)-1-(5-fluoro-2-methoxy-4-((1R,2R)-2-(trifluoromethyl)cyclopropyl)phenyl)-2-oxo-N-(1,2,4-thiadiazol-5-yl)-1,2-dihydroquinoline-6-sulfonamide |
| 35 | (P)-1-(5-fluoro-2-methoxy-4-((1R,2R)-2-(trifluoromethyl)cyclopropyl)phenyl)-N-(oxazol-2-yl)-2-oxo-1,2-dihydroquinoline-6-sulfonamide |
| 36 | (P)-1-(5-fluoro-2-methoxy-4-((1S,2S)-2-(trifluoromethyl)cyclopropyl)phenyl)-N-(oxazol-2-yl)-2-oxo-1,2-dihydroquinoline-6-sulfonamide |
| 37 | (P)-1-(5-cyano-2-methoxy-4-((1S,2S)-2-(trifluoromethyl)cyclopropyl)phenyl)-N-(isoxazol-3-yl)-2-oxo-1,2-dihydroquinoline-6-sulfonamide |
| 38 | (P)-N-(isoxazol-3-yl)-1-(2-methoxy-4-((1R,2R)-2-(trifluoromethyl) cyclopropyl)phenyl)-2-oxo-1,2-dihydroquinoline-6-sulfonamide |
| 39 | (P)-N-(isoxazol-3-yl)-1-(2-methoxy-4-((1S,2S)-2-(trifluoromethyl) cyclopropyl)phenyl)-2-oxo-1,2-dihydroquinoline-6-sulfonamide |
| 40 | (P)-1-(5-fluoro-2-methoxy-4-((1R,2R)-2-(trifluoromethyl)cyclopropyl)phenyl)-2-oxo-N-(1,3,4-thiadiazol-2-yl)-1,2-dihydroquinoline-6-sulfonamide |
| 41 | (P)-6-(benzylthio)-1-(5-fluoro-2-hydroxy-4-((1S,2S)-2-(trifluoromethyl)cyclopropyl)phenyl)quinolin-2(1H)-one |
| 42 | (P)-1-(5-fluoro-2-methoxy-4-(1-(trifluoromethyl)cyclopropyl)phenyl)-N-(isoxazol-3-yl)-2-oxo-1,2-dihydroquinoline-6-sulfonamide |
| 43 | (M)-1-(5-fluoro-2-methoxy-4-(1-(trifluoromethyl)cyclopropyl)phenyl)-N-(isoxazol-3-yl)-2-oxo-1,2-dihydroquinoline-6-sulfonamide |
| 44 | (P)-4-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide |
| 45 | (P)-7-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide |
| 46 | (P)-7-fluoro-1-(5-fluoro-2-methoxy-4-((1S,2S)-2-(trifluoromethyl)cyclopropyl)phenyl)-N-(isoxazol-3-yl)-2-oxo-1,2-dihydroquinoline-6-sulfonamide |
| 47 | (P)-7-fluoro-N-(isoxazol-3-yl)-1-(2-methoxy-4-((1R,2R)-2-(trifluoromethyl)cyclopropyl)phenyl)-2-oxo-1,2-dihydroquinoline-6-sulfonamide |
| 48 | (P)-7-fluoro-N-(isoxazol-3-yl)-1-(2-methoxy-4-((1S,2S)-2-(trifluoromethyl)cyclopropyl)phenyl)-2-oxo-1,2-dihydroquinoline-6-sulfonamide |

In embodiment 18, the present invention provides compounds of Formula (I), an enantiomer, diastereoisomer, atropisomer thereof, or a mixture thereof, or a pharmaceutically acceptable salt thereof, wherein the compound is selected from:

| Ex. # | CHEMICAL NAME |
|---|---|
| 4 | (P)-1-(5-fluoro-2-methoxy-4-((1S,2S)-2-(trifluoromethyl)cyclopropyl)phenyl)-N-(isoxazol-3-yl)-2-oxo-1,2-dihydroquinoline-6-sulfonamide |
| 5 | (P)-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide |
| 7 | (P)-1-(5-fluoro-2-methoxy-4-((1S,2S)-2-methylcyclopropyl)phenyl)-N-(isoxazol-3-yl)-2-oxo-1,2-dihydroquinoline-6-sulfonamide |
| 8 | (P)-1-(5-fluoro-2-methoxy-4-((1R,2R)-2-phenylcyclopropyl)phenyl)-N-(isoxazol-3-yl)-2-oxo-1,2-dihydroquinoline-6-sulfonamide |
| 9 | (P)-1-(5-fluoro-2-methoxy-4-((1S,2S)-2-phenylcyclopropyl)phenyl)-N-(isoxazol-3-yl)-2-oxo-1,2-dihydroquinoline-6-sulfonamide |
| 17 | (P)-1-(5-fluoro-2-methoxy-4-((1S,2S)-2-(trifluoromethyl)cyclopropyl)phenyl)-2-oxo-N-(pyridazin-3-yl)-1,2-dihydroquinoline-6-sulfonamide |
| 18 | (P)-1-(5-chloro-2-methoxy-4-((1R,2R)-2-(trifluoromethyl)cyclopropyl)phenyl)-N-(isoxazol-3-yl)-2-oxo-1,2-dihydroquinoline-6-sulfonamide |
| 34 | (P)-1-(5-fluoro-2-methoxy-4-((1R,2R)-2-(trifluoromethyl)cyclopropyl)phenyl)-2-oxo-N-(1,2,4-thiadiazol-5-yl)-1,2-dihydroquinoline-6-sulfonamide |
| 37 | (P)-1-(5-cyano-2-methoxy-4-((1S,2S)-2-(trifluoromethyl)cyclopropyl)phenyl)-N-(isoxazol-3-yl)-2-oxo-1,2-dihydroquinoline-6-sulfonamide |
| 38 | (P)-N-(isoxazol-3-yl)-1-(2-methoxy-4-((1R,2R)-2-(trifluoromethyl) cyclopropyl)phenyl)-2-oxo-1,2-dihydroquinoline-6-sulfonamide |
| 39 | (P)-N-(isoxazol-3-yl)-1-(2-methoxy-4-((1S,2S)-2-(trifluoromethyl) cyclopropyl)phenyl)-2-oxo-1,2-dihydroquinoline-6-sulfonamide |
| 40 | (P)-1-(5-fluoro-2-methoxy-4-((1R,2R)-2-(trifluoromethyl)cyclopropyl)phenyl)-2-oxo-N-(1,3,4-thiadiazol-2-yl)-1,2-dihydroquinoline-6-sulfonamide |
| 41 | (P)-6-(benzylthio)-1-(5-fluoro-2-hydroxy-4-((1S,2S)-2-(trifluoromethyl)cyclopropyl)phenyl)quinolin-2(1H)-one |
| 44 | (P)-4-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide |
| 45 | (P)-7-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide |
| 47 | (P)-7-fluoro-N-(isoxazol-3-yl)-1-(2-methoxy-4-((1R,2R)-2-(trifluoromethyl)cyclopropyl)phenyl)-2-oxo-1,2-dihydroquinoline-6-sulfonamide |

In embodiment 18a, the present invention provides compounds of Formula (I), an enantiomer, diastereoisomer, atropisomer thereof, or a mixture thereof, or a pharmaceutically acceptable salt thereof, wherein the compound is (P)-1-(5-fluoro-2-methoxy-4-((1S,2S)-2-(trifluoromethyl)cyclopropyl)phenyl)-N-(isoxazol-3-yl)-2-oxo-1,2-dihydroquinoline-6-sulfonamide.

In embodiment 18b, the present invention provides compounds of Formula (I), an enantiomer, diastereoisomer, atropisomer thereof, or a mixture thereof, or a pharmaceutically acceptable salt thereof, wherein the compound is (P)-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide.

In embodiment 18c, the present invention provides compounds of Formula (I), an enantiomer, diastereoisomer, atropisomer thereof, or a mixture thereof, or a pharmaceutically acceptable salt thereof, wherein the compound is (P)-1-(5-fluoro-2-methoxy-4-((1S,2S)-2-methylcyclopropyl)phenyl)-N-(isoxazol-3-yl)-2-oxo-1,2-dihydroquinoline-6-sulfonamide.

In embodiment 18d, the present invention provides compounds of Formula (I), an enantiomer, diastereoisomer, atropisomer thereof, or a mixture thereof, or a pharmaceutically acceptable salt thereof, wherein is (P)-1-(5-fluoro-2-methoxy-4-((1R,2R)-2-phenylcyclopropyl)phenyl)-N-(isoxazol-3-yl)-2-oxo-1,2-dihydroquinoline-6-sulfonamide.

In embodiment 18e, the present invention provides compounds of Formula (I), an enantiomer, diastereoisomer, atropisomer thereof, or a mixture thereof, or a pharmaceutically acceptable salt thereof, wherein the compound is (P)-1-(5-fluoro-2-methoxy-4-((1S,2S)-2-phenylcyclopropyl)phenyl)-N-(isoxazol-3-yl)-2-oxo-1,2-dihydroquinoline-6-sulfonamide.

In embodiment 18f, the present invention provides compounds of Formula (I), an enantiomer, diastereoisomer, atropisomer thereof, or a mixture thereof, or a pharmaceutically acceptable salt thereof, wherein the compound is (P)-1-(5-fluoro-2-methoxy-4-((1S,2S)-2-(trifluoromethyl)cyclopropyl)phenyl)-2-oxo-N-(pyridazin-3-yl)-1,2-dihydroquinoline-6-sulfonamide.

In embodiment 18 g, the present invention provides compounds of Formula (I), an enantiomer, diastereoisomer, atropisomer thereof, or a mixture thereof, or a pharmaceutically acceptable salt thereof, wherein the compound is (P)-1-(5-chloro-2-methoxy-4-((1R,2R)-2-(trifluoromethyl)cyclopropyl)phenyl)-N-(isoxazol-3-yl)-2-oxo-1,2-dihydroquinoline-6-sulfonamide.

In embodiment 18h, the present invention provides compounds of Formula (I), an enantiomer, diastereoisomer, atropisomer thereof, or a mixture thereof, or a pharmaceutically acceptable salt thereof, wherein the compound is (P)-1-(5-fluoro-2-methoxy-4-((1R,2R)-2-(trifluoromethyl)cyclopropyl)phenyl)-2-oxo-N-(1,2,4-thiadiazol-5-yl)-1,2-dihydroquinoline-6-sulfonamide.

In embodiment 18i, the present invention provides compounds of Formula (I), an enantiomer, diastereoisomer, atropisomer thereof, or a mixture thereof, or a pharmaceutically acceptable salt thereof, wherein the compound is (P)-1-(5-cyano-2-methoxy-4-((1S,2S)-2-(trifluoromethyl)cyclopropyl)phenyl)-N-(isoxazol-3-yl)-2-oxo-1,2-dihydroquinoline-6-sulfonamide.

In embodiment 18j, the present invention provides compounds of Formula (I), an enantiomer, diastereoisomer, atropisomer thereof, or a mixture thereof, or a pharmaceutically acceptable salt thereof, wherein the compound is (P)-N-(isoxazol-3-yl)-1-(2-methoxy-4-((1R,2R)-2-(trifluoromethyl)cyclopropyl)phenyl)-2-oxo-1,2-dihydroquinoline-6-sulfonamide.

In embodiment 18k, the present invention provides compounds of Formula (I), an enantiomer, diastereoisomer, atropisomer thereof, or a mixture thereof, or a pharmaceutically acceptable salt thereof, wherein the compound is (P)-N-(isoxazol-3-yl)-1-(2-methoxy-4-((1S,2S)-2-(trifluoromethyl) cyclopropyl)phenyl)-2-oxo-1,2-dihydroquinoline-6-sulfonamide.

In embodiment 18l, the present invention provides compounds of Formula (I), an enantiomer, diastereoisomer, atropisomer thereof, or a mixture thereof, or a pharmaceutically acceptable salt thereof, wherein the compound is (P)-1-(5-fluoro-2-methoxy-4-((1R,2R)-2-(trifluoromethyl)cyclopropyl)phenyl)-2-oxo-N-(1,3,4-thiadiazol-2-yl)-1,2-dihydroquinoline-6-sulfonamide.

In embodiment 18m, the present invention provides compounds of Formula (I), an enantiomer, diastereoisomer, atropisomer thereof, or a mixture thereof, or a pharmaceutically acceptable salt thereof, wherein the compound is (P)-6-(benzylthio)-1-(5-fluoro-2-hydroxy-4-((1S,2S)-2-(trifluoromethyl)cyclopropyl)phenyl)quinolin-2(1H)-one.

In embodiment 18n, the present invention provides compounds of Formula (I), an enantiomer, diastereoisomer, atropisomer thereof, or a mixture thereof, or a pharmaceutically acceptable salt thereof, wherein the compound is (P)-4-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide.

In embodiment 18o, the present invention provides compounds of Formula (I), an enantiomer, diastereoisomer, atropisomer thereof, or a mixture thereof, or a pharmaceutically acceptable salt thereof, wherein the compound is (P)-7-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide.

In embodiment 18p, the present invention provides compounds of Formula (I), an enantiomer, diastereoisomer, atropisomer thereof, or a mixture thereof, or a pharmaceutically acceptable salt thereof, wherein the compound is (P)-7-fluoro-N-(isoxazol-3-yl)-1-(2-methoxy-4-((1R,2R)-2-(trifluoromethyl)cyclopropyl)phenyl)-2-oxo-1,2-dihydroquinoline-6-sulfonamide.

In embodiment 19, the present invention provides a P atropisomer of each individual compound, independently, or a mixture thereof, or pharmaceutically acceptable salts thereof, recited in embodiment 18a to 18p.

In embodiment 20, the present invention provides an M atropisomer of each individual compound, independently, or a mixture thereof, or pharmaceutically acceptable salts thereof, recited in embodiments 18a to 18p.

In embodiment 21, the present invention provides compounds of Formula (I), an enantiomer, diastereoisomer, atropisomer thereof, or a mixture thereof, or a pharmaceutically acceptable salt thereof, wherein said compound of Formula (I) is of formula (Ia):

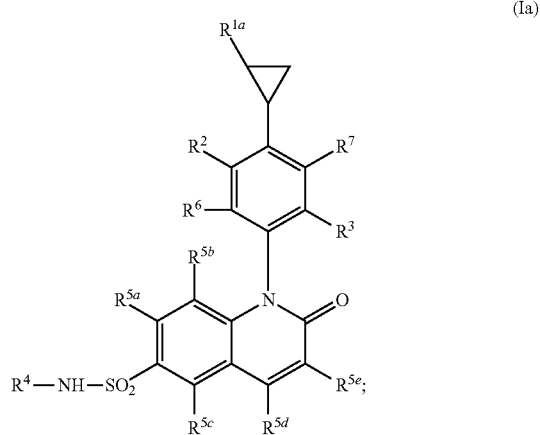

(Ia)

wherein said compound is selected from:

| EX # | CHEMICAL NAME |
|---|---|
| 3 | trans-1-(5-fluoro-2-methoxy-4-(2-(trifluoromethyl)cyclopropyl)phenyl)-N-(isoxazol-3-yl)-2-oxo-1,2-dihydroquinoline-6-sulfonamide |
| 4 | (P)-1-(5-fluoro-2-methoxy-4-((1S,2S)-2-(trifluoromethyl)cyclopropyl)phenyl)-N-(isoxazol-3-yl)-2-oxo-1,2-dihydroquinoline-6-sulfonamide |
| 5 | (P)-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide |

| EX # | CHEMICAL NAME |
|---|---|
| 6 | (P)-1-(5-fluoro-2-methoxy-4-((1R,2R)-2-methylcyclopropyl)phenyl)-N-(isoxazol-3-yl)-2-oxo-1,2-dihydroquinoline-6-sulfonamide |
| 7 | (P)-1-(5-fluoro-2-methoxy-4-((1S,2S)-2-methylcyclopropyl)phenyl)-N-(isoxazol-3-yl)-2-oxo-1,2-dihydroquinoline-6-sulfonamide |
| 8 | (P)-1-(5-fluoro-2-methoxy-4-((1R,2R)-2-phenylcyclopropyl)phenyl)-N-(isoxazol-3-yl)-2-oxo-1,2-dihydroquinoline-6-sulfonamide |
| 9 | (P)-1-(5-fluoro-2-methoxy-4-((1S,2S)-2-phenylcyclopropyl)phenyl)-N-(isoxazol-3-yl)-2-oxo-1,2-dihydroquinoline-6-sulfonamide |
| 12 | (P)-1-(5-chloro-2-methoxy-4-((1S,2S)-2-(trifluoromethyl)cyclopropyl)phenyl)-2-oxo-N-(pyrimidin-2-yl)-1,2-dihydroquinoline-6-sulfonamide |
| 14 | (P)-1-(5-chloro-2-methoxy-4-((1R,2R)-2-(trifluoromethyl)cyclopropyl)phenyl)-2-oxo-N-(pyridazin-3-yl)-1,2-dihydroquinoline-6-sulfonamide |
| 15 | (P)-1-(5-chloro-2-methoxy-4-((1S,2S)-2-(trifluoromethyl)cyclopropyl)phenyl)-2-oxo-N-(pyridazin-3-yl)-1,2-dihydroquinoline-6-sulfonamide |
| 16 | (P)-1-(5-fluoro-2-methoxy-4-((1R,2R)-2-(trifluoromethyl)cyclopropyl)phenyl)-2-oxo-N-(pyridazin-3-yl)-1,2-dihydroquinoline-6-sulfonamide |
| 17 | (P)-1-(5-fluoro-2-methoxy-4-((1S,2S)-2-(trifluoromethyl)cyclopropyl)phenyl)-2-oxo-N-(pyridazin-3-yl)-1,2-dihydroquinoline-6-sulfonamide |
| 18 | (P)-1-(5-chloro-2-methoxy-4-((1R,2R)-2-(trifluoromethyl)cyclopropyl)phenyl)-N-(isoxazol-3-yl)-2-oxo-1,2-dihydroquinoline-6-sulfonamide |
| 20 | (P)-1-(5-fluoro-2-methoxy-4-((1R,2R)-2-(trifluoromethyl)cyclopropyl)phenyl)-2-oxo-N-(pyrimidin-2-yl)-1,2-dihydroquinoline-6-sulfonamide |
| 21 | (P)-1-(5-fluoro-2-methoxy-4-((1S,2S)-2-(trifluoromethyl)cyclopropyl)phenyl)-2-oxo-N-(pyrimidin-2-yl)-1,2-dihydroquinoline-6-sulfonamide |
| 26 | (P)-N-(isoxazol-3-yl)-1-(2-methoxy-5-methyl-4-((1R,2R)-2-(trifluoromethyl)cyclopropyl)phenyl)-2-oxo-1,2-dihydroquinoline-6-sulfonamide |
| 27 | (P)-N-(isoxazol-3-yl)-1-(2-methoxy-5-methyl-4-((1S,2S)-2-(trifluoromethyl)cyclopropyl)phenyl)-2-oxo-1,2-dihydroquinoline-6-sulfonamide |
| 28 | (P)-1-(2-methoxy-5-methyl-4-((1R,2R)-2-(trifluoromethyl)cyclopropyl)phenyl)-2-oxo-N-(pyrimidin-2-yl)-1,2-dihydroquinoline-6-sulfonamide |
| 29 | (P)-1-(2-methoxy-5-methyl-4-((1S,2S)-2-(trifluoromethyl)cyclopropyl)phenyl)-2-oxo-N-(pyrimidin-2-yl)-1,2-dihydroquinoline-6-sulfonamide |
| 30 | (P)-1-(4-((1S,2S)-[1,1'-bi(cyclopropan)]-2-yl)-5-fluoro-2-methoxyphenyl)-N-(isoxazol-3-yl)-2-oxo-1,2-dihydroquinoline-6-sulfonamide |
| 32 | (P)-1-(5-fluoro-2-methoxy-4-((1R,2R)-2-((trifluoromethoxy)methyl)cyclopropyl)phenyl)-N-(isoxazol-3-yl)-2-oxo-1,2-dihydroquinoline-6-sulfonamide |
| 34 | (P)-1-(5-fluoro-2-methoxy-4-((1R,2R)-2-(trifluoromethyl)cyclopropyl)phenyl)-2-oxo-N-(1,2,4-thiadiazol-5-yl)-1,2-dihydroquinoline-6-sulfonamide |
| 35 | (P)-1-(5-fluoro-2-methoxy-4-((1R,2R)-2-(trifluoromethyl)cyclopropyl)phenyl)-N-(oxazol-2-yl)-2-oxo-1,2-dihydroquinoline-6-sulfonamide |
| 37 | (P)-1-(5-cyano-2-methoxy-4-((1S,2S)-2-(trifluoromethyl)cyclopropyl)phenyl)-N-(isoxazol-3-yl)-2-oxo-1,2-dihydroquinoline-6-sulfonamide |
| 38 | (P)-N-(isoxazol-3-yl)-1-(2-methoxy-4-((1R,2R)-2-(trifluoromethyl) cyclopropyl)phenyl)-2-oxo-1,2-dihydroquinoline-6-sulfonamide |
| 39 | (P)-N-(isoxazol-3-yl)-1-(2-methoxy-4-((1S,2S)-2-(trifluoromethyl) cyclopropyl)phenyl)-2-oxo-1,2-dihydroquinoline-6-sulfonamide |
| 40 | (P)-1-(5-fluoro-2-methoxy-4-((1R,2R)-2-(trifluoromethyl)cyclopropyl)phenyl)-2-oxo-N-(1,3,4-thiadiazol-2-yl)-1,2-dihydroquinoline-6-sulfonamide |
| 41 | (P)-6-(benzylthio)-1-(5-fluoro-2-hydroxy-4-((1S,2S)-2-(trifluoromethyl)cyclopropyl)phenyl)quinolin-2(1H)-one |
| 44 | (P)-4-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide |
| 45 | (P)-7-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide |
| 46 | (P)-7-fluoro-1-(5-fluoro-2-methoxy-4-((1S,2S)-2-(trifluoromethyl)cyclopropyl)phenyl)-N-(isoxazol-3-yl)-2-oxo-1,2-dihydroquinoline-6-sulfonamide |
| 47 | (P)-7-fluoro-N-(isoxazol-3-yl)-1-(2-methoxy-4-((1R,2R)-2-(trifluoromethyl)cyclopropyl)phenyl)-2-oxo-1,2-dihydroquinoline-6-sulfonamide |
| 48 | (P)-7-fluoro-N-(isoxazol-3-yl)-1-(2-methoxy-4-((1S,2S)-2-(trifluoromethyl)cyclopropyl)phenyl)-2-oxo-1,2-dihydroquinoline-6-sulfonamide |

In embodiment 22, the present invention provides pharmaceutical compositions comprising a compound, an enantiomer, diastereoisomer, atropisomer thereof, or a mixture thereof, or pharmaceutically acceptable salts thereof, in accordance with any one of embodiments 1, 2, 3, 4, 5, 6, 7, 8, 9, 10, 11, 12, 13, 14, 15, 16, 17, 18, 19, 20, 21, or any sub embodiments thereof, and a pharmaceutically acceptable excipient.

In embodiment 23, the present invention provides methods of treating pain, cough, or itch, the methods comprising administering to a patient in need thereof a therapeutically effective amount of a compound, an enantiomer, diastereoisomer, atropisomer thereof, or a mixture thereof, or pharmaceutically acceptable salts thereof, in accordance with any one of embodiments 1, 2, 3, 4, 5, 6, 7, 8, 9, 10, 11, 12, 13, 14, 15, 16, 17, 18, 19, 20, 21, or any sub embodiments thereof.

In embodiment 24, the present invention provides methods of embodiment 23 wherein the pain is selected from chronic pain, acute pain, neuropathic pain, pain associated with rheumatoid arthritis, pain associated with osteoarthritis, pain associated with cancer, peripheral diabetic neuropathy, and neuropathic low back pain.

In embodiment 25, the present invention provides methods of embodiment 23 wherein the cough is selected from post viral cough, viral cough, or acute viral cough. See Dib-Hajj. et. al., "The $Na_V1.7$ sodium channel: from molecule to man", *Nature Reviews Neuroscience* (2013), 14, 49-62.

In embodiment 26, the present invention provides a method of preparation of a compound of Formula (A):

(A)

wherein R is halo or the group

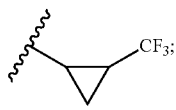

comprising:
1) reacting a trans olefin compound of Formula (B):

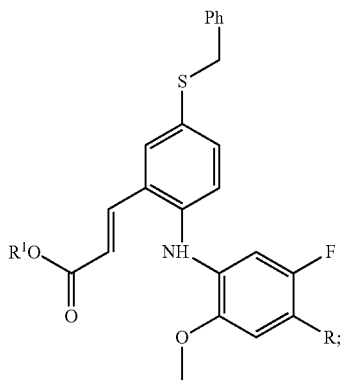

wherein R is halo or the group

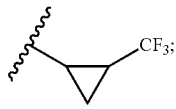 [SMILES: *C1CC1C(F)(F)F]

and $R^1$ is $C_1$-$C_6$alkyl;
with a UV light or near UV light; to form a cis olefin compound (C); and
2) reacting said compound (C) with a chiral acid in an organic solvent to form said compound of Formula (A).

In embodiment 27, the present invention provides a method of embodiment 26, wherein said chiral acid is a phosphorus chiral acid.

In embodiment 28, the present invention provides a method of embodiment 26, wherein said chiral acid is (S)-TRIP having the Formula:

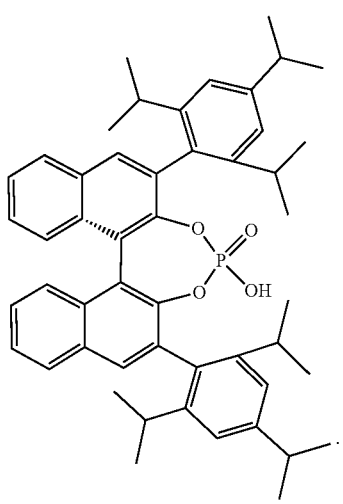

In embodiment 29, the present invention provides a method of embodiment 26, wherein said organic solvent is dichloromethane.

In embodiment 30, the present invention provides a method of embodiment 26, wherein said R is bromo.

In embodiment 31, the present invention provides a method of embodiment 26, wherein said R is the group

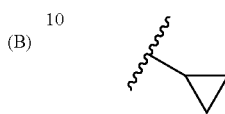

In embodiment 32, the present invention provides a method of embodiment 26, wherein said $R^1$ is ethyl; wherein the compound of Formula (B) has the formula:

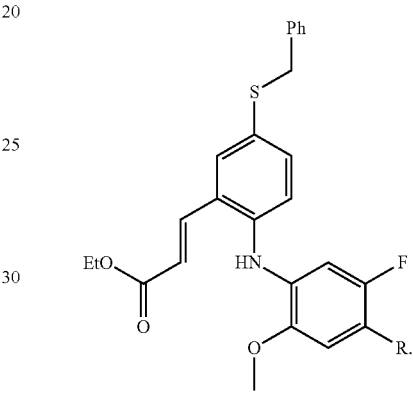

In embodiment 33, the present invention provides a method of embodiment 26, wherein in reaction (2), a P atropisomer of said compound of Formula (A) is selectively formed.

In embodiment 34, the present invention provides a method of embodiment 26, wherein said compound of Formula (A) is used as an intermediate compound in preparation of a compound of Formula (I):

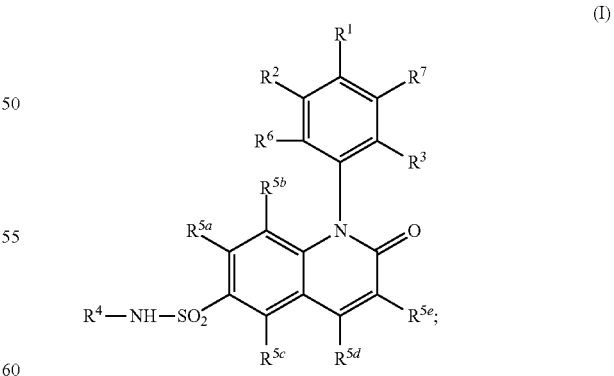

or a pharmaceutically acceptable salt thereof;
Wherein:
$R^1$ is a cyclopropyl ring; or a 4-, 5-, 6-, 7-, or 8-membered bicyclic ring containing 0, 1, 2 or 3 N atoms and 0, 1, or 2 atoms selected from O and S; and wherein said cyclopropyl ring or bicyclic ring is substituted by 0, 1, 2 or 3 $R^{1a}$ groups selected from hydroxy, halo, $C_{1-8}$alk, $C_{1-8}$haloalk, —O—$C_{1-4}$alk, —O—$C_{1-8}$haloalk, —C(=O)$C_{1-4}$alk, —O—C(=O)$C_{1-4}$alk, —NH$_2$, —NH$C_{1-4}$alk, —N($C_{1-4}$alk)$C_{1-4}$alk, 3-, 4-, or 5-membered cycloalkyl, or 6-membered aryl;

$R^2$ is H, halo, CN, $C_{1-6}$alk, or $C_{1-6}$haloalk;

$R^3$ is $C_{1-6}$alk, $C_{1-6}$haloalk, —O—$C_{1-6}$alk, —O-cyclopropyl, or —O-cyclobutyl;

$R^4$ is a 5- to 6-membered heteroaryl;

Each of $R^6$ and $R^7$ is hydrogen; and

Each of $R^{5a}$; $R^{5b}$; $R^{5c}$; $R^{5d}$; and $R^{5e}$ is independently hydrogen or halo; and Wherein a P atropisomer of said compound of Formula (I) is selectively formed.

DETAILED DESCRIPTION OF THE INVENTION

The present invention provides compounds of Formula (I), as defined above, an enantiomer, diastereoisomer, atropisomer thereof, or a mixture thereof, or pharmaceutically acceptable salts thereof. The present invention also provides pharmaceutical compositions comprising a compound of Formula (I), compound, an enantiomer, diastereoisomer, atropisomer thereof, or a mixture thereof, or pharmaceutically acceptable salts thereof, and methods of treating diseases and/or conditions, such as pain, using compounds of Formula (I), compound, an enantiomer, diastereoisomer, atropisomer thereof, or a mixture thereof, or pharmaceutically acceptable salts thereof.

The term "$C_{\alpha-\beta}$alk" as used herein means an alkyl group comprising a minimum of α and a maximum of β carbon atoms in a branched or linear relationship or any combination of the two, wherein α and β represent integers. A designation of $C_0$alk indicates a direct bond. Examples of $C_{1-6}$alk include, but are not limited to the following:

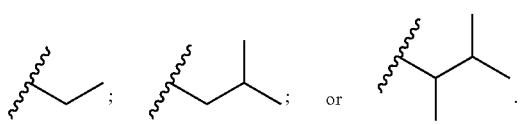

The term "halo" or "halogen" means a halogen atoms selected from F, Cl, Br or I.

The term "$C_{\alpha-\beta}$haloalk" as used herein means an alk group, as defined herein, in which at least one of the hydrogen atoms has been replaced with a halo atom, as defined herein. Common $C_{\alpha-\beta}$haloalk groups are $C_{1-3}$fluoroalk. An example of a common $C_{1-3}$fluoroalk group is C F$_3$.

The term "cycloalkyl" as used herein means a cyclic, nonaromatic hydrocarbon. Examples of cycloalkyl groups include cyclopropyl, cyclobutyl, cyclopentyl, cyclohexyl and cycloheptyl. A cycloalkyl group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "aryl" as used herein means a cyclic, aromatic hydrocarbon. Examples of aryl groups include phenyl and naphthyl. Common aryl groups are six to thirteen membered rings.

The term "embodiment" includes any and all sub-embodiments, including those labelled as 'a', 'b', 'c', etc. For example, embodiment 18 includes any and all sub-embodiments 18a to 18p.

The term "heteroaryl" as used herein means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heteroatoms are particularly common.

The term "heteroatom" as used herein means an oxygen, nitrogen or sulfur atom.

The term "monocyclic ring" as used herein means a group that features one single ring. A monocyclic ring can be carbocyclic (all of the ring atoms are carbons), or heterocyclic (the rings atoms include at least 1 heteroatom, for example, 1, 2 or 3 heteroatoms, such as N, O, or S, in addition to carbon atoms). Examples of monocyclic rings include, but are not limited to: cyclobutyl, cyclopentyl, or cyclohexyl.

The term "bicyclic ring" as used herein means a group that features two joined rings. A bicyclic ring can be carbocyclic (all of the ring atoms are carbons), or heterocyclic (the rings atoms include at least 1 heteroatom, for example, 1, 2 or 3 heteroatoms, such as N, O, or S, in addition to carbon atoms). The two rings can both be aliphatic (e.g. decalin and norbornane), or can be aromatic (e.g, naphthalene), or a combination of aliphatic and aromatic (e.g. tetralin). Bicyclic rings include:

(a) spirocyclic compounds, wherein the two rings share only one single atom, the spiro atom, winch is usually a quaternary carbon. Examples of spirocyclic compound include, but are not limited to:

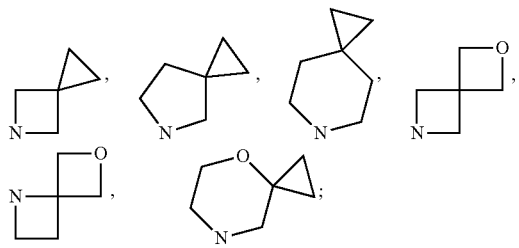

(b) fused bicyclic compounds, wherein two rings share two adjacent atoms. In other words, tire rings share one covalent bond, i.e. the bridgehead atoms are directly connected (e.g. α-thujene and decalin). Examples of fused bicyclic rings include, but are not limited to:

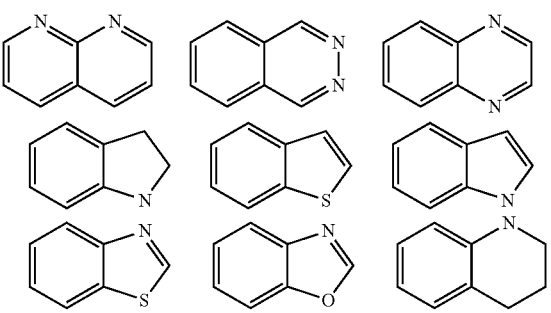

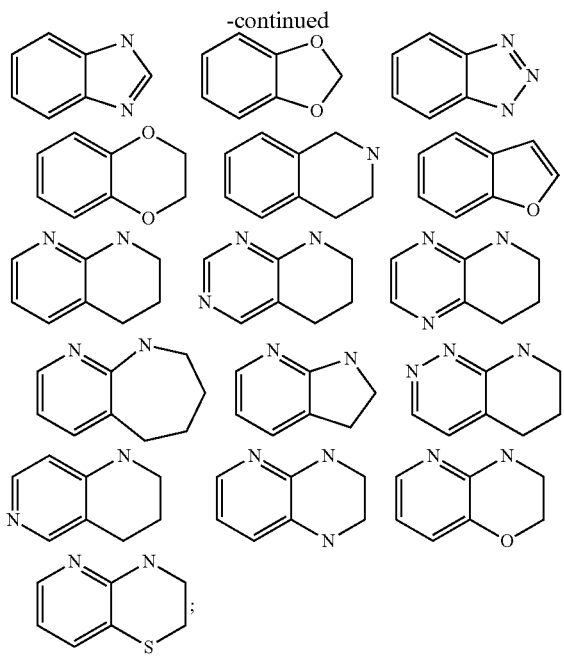

(c) bridged bicyclic compounds, wherein the two rings share three or more atoms, separating the two bridgehead atoms by a bridge containing at least one atom. For example, norbornane, also known as bicyclo[2.2.1]heptane, can be thought of as a pair of cyclopentane rings each sharing three of their five carbon atoms. Examples of bridged bicyclic rings include, but are not limited to:

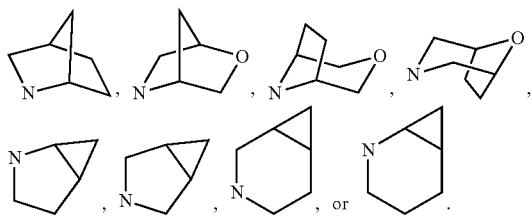

The term "saturated, partially-saturated or unsaturated" includes substituents saturated with hydrogens, substituents completely unsaturated with hydrogens and substituents partially saturated with hydrogens.

The term "pharmaceutically acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. For additional examples of "pharmacologically acceptable salts," and Berge et al., J. Pharm. Sci. 66:1 (1977).

The term "substituted" means that a hydrogen atom on a molecule or group is replaced with a group or atom other than hydrogen. Typical substituents include: halogen, $C_{1-8}$alkyl, hydroxyl, $C_{1-8}$alkoxy, —$NR^xR^x$, nitro, cyano, halo or perhalo$C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each $R^x$ is independently hydrogen or $C_1$-$C_8$ alkyl. It is noted that when the substituent is —$NR^xR^x$, the $R^x$ groups may be joined together with the nitrogen atom to form a ring. A group or atom that replaces a hydrogen atom is also called a substituent.

Any particular molecule or group can have one or more substituent depending on the number of hydrogen atoms that can be replaced.

The term "unsubstituted" means a hydrogen atom on a molecule or group.

The symbol represents a covalent bond and can also be used in a radical group to indicate the point of attachment to another group. In chemical structures, the symbol is commonly used to represent a methyl group in a molecule.

The term "leaving group" generally refers to groups readily displaceable by a nucleophile, such as an amine, a thiol or an alcohol nucleophile, or by metallic agent such as boronic acids or boronates under transition metal catalyzed coupling conditions. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

The term "protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxy carbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkyenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A tert-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, 4/11/81) discloses Mannich-base hydroxamic acid prodrugs, their preparation and use.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of Formula (I), or a salt of a compound of Formula (I), or a formulation containing a compound of Formula (I), or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied overtime.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered by a tablet, while another is administered by injection or orally as syrup. All combinations, delivery methods and administration sequences are contemplated.

The compounds of the present invention may be used in the manufacture of a medicament for the treatment of a disease and/or condition mediated by NaV 1.7, such as pain, chronic cough or itch.

Pain is typically divided into primary types: chronic and acute pain based on the duration of the pain. Typically, chronic pain lasts for longer than 3 months. Examples of chronic pain include pain associated with rheumatoid arthritis, osteoarthritis, lumbosacral radiculopathy or cancer. Chronic pain also includes idiopathic pain, which is pain that has no identified cause. An example of idiopathic pain is fibromyalgia.

Another type of pain is nociceptive pain. Nociceptive pain is caused by stimulation of peripheral nerve fibers that respond to highly noxious events such as thermal, mechanical or chemical stimuli.

Still another type of pain is neuropathic pain. Neuropathic pain is pain that is caused by damage or disease affecting a part of the nervous system. Phantom limb pain is a type of neuropathic pain. In phantom limb pain, the body detects pain from a part of a body that no longer exists. For example, a person who has had a leg amputated may feel leg pain even though the leg no longer exists.

In one embodiment of the methods of treatment provided by the present invention using the compounds of Formula (I), or pharmaceutically acceptable salts thereof, the disease is chronic pain. In another aspect, the chronic pain is associated with, but are not limited to, post-herpetic neuralgia (shingles), rheumatoid arthritis, osteoarthritis, diabetic neuropathy, complex regional pain syndrome (CRPS), cancer or chemotherapy-induced pain, chronic back pain, phantom limb pain, trigeminal neuralgia, HIV-induced neuropathy, cluster headache disorders, and migraine, primary erythromelalgia, and paroxysmal extreme pain disorder. Other indications for NaV 1.7 inhibitors include, but are not limited to, depression (Morinville et al., *J Comp Neurol.*, 504:680-689 (2007)), bipolar and other CNS disorders (Ettinger and Argoff, *Neurotherapeutics*, 4:75-83 (2007)), epilepsy: ibid., and Gonzalez, Termin, Wilson, *Methods and Principles in Medicinal Chemistry*, 29:168-192 (2006)), multiple sclerosis (Waxman, *Nature Neurosci.* 1:932-941 (2006)), Parkinson's (Do and Bean, *Neuron* 39:109-120 (2003); Puopolo et al., *J. Neurosci.* 27:645-656 (2007)), restless legs syndrome, ataxia, tremor, muscle weakness, dystonia, tetanus (Hamann M., et. al., *Exp. Neurol.* 184(2):

830-838, 2003), anxiety, depression: McKinney B. C, et. al., *Genes Brain Behav.* 7(6):629-638, 2008), learning and memory, cognition (Woodruff-Pak D. S., et. al., *Behav. Neurosci.* 120(2):229-240, 2006), cardiac arrhythmia and fibrillation, contractility, congestive heart failure, sick sinus syndrome (Haufe V., et. al., *J Mol. Cell Cardiol.* 42(3):469-477, 2007), schizophrenia, neuroprotection after stroke, drug and alcohol abuse (Johannessen L. C., *CNS Drugs* 22(1)27-47, 2008), Alzheimer's (Kim D. Y., et. al., *Nat. Cell. Biol.* 9(7):755-764, 2007), and cancer (Gillet L., et. al, *J. Biol Chem* 2009, January 28 (epub)).

Another aspect of the invention relates to a method of treating acute and/or chronic inflammatory and neuropathic pain, dental pain, general headache, migraine, cluster headache, mixed-vascular and non-vascular syndromes, tension headache, general inflammation, arthritis, rheumatic diseases, rheumatoid arthritis, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation pain syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to the present invention. A preferred type of pain to be treated is chronic neuropathic pain. Another preferred type of pain to be treated is chronic inflammatory pain.

In another aspect of the invention, the compounds of the present invention can be used in combination with other compounds that are used to treat pain. Examples of such other compounds include, but are not limited to aspirin, celecoxib, hydrocodone, oxycodone, codeine, fentanyl, ibuprofen, ketoprofen, naproxen, acetaminophen, gabapentin and pregabalin. Examples of classes of medicines that contain compounds that can be used in combination with the compounds of the present invention include non-steroidal anti-inflammatory compounds (NSAIDS), steroidal compounds, cyclooxygenase inhibitors and opiod analgesics.

The compounds of the present invention may also be used to treat diabetes, obesity and/or to facilitate weight loss.

The compounds of the present invention may be used in combination with other pharmaceutically active compounds. It is noted that the term "pharmaceutically active compounds" can include biologies, such as proteins, antibodies and peptibodies.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed by said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragées, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Ophthalmic formulations, eye ointments, powders, and solutions are also contemplated as being within the scope of this invention.

The compounds of the present invention can be administered to a patient at therapeutically effective dosage levels. The specific dosage and dosage range that can be used depends on a number of factors, including the requirements of the patient, the severity of the condition or disease being treated, and the pharmacological activity of the compound being administered.

The compounds of the present invention can be administered as pharmaceutically acceptable salts, co-crystals, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$—$C_{12}$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as (3-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

In addition, if a compound of the present invention comprises a sulfonamide moiety, a prodrug can be formed by replacement of the sulfonamide N(H) with a group such as —CH$_2$P(O)(O($C_1$-$C_6$)alkyl)$_2$ or —CH$_2$OC(O)($C_1$-$C_6$)alkyl.

The compounds of the present invention also include tautomeric forms of prodrugs.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond or disubstituted cycloalkyl group, both the cis and trans isomers, unless the specific isomer is specified, as well as mixtures, are contemplated. In disubstituted cycloalkyl containing compounds, the cis and trans isomers refer to the relative positions of the substitutions.

For example:

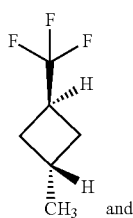

(A)

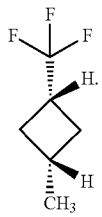

(B)

(A) represents trans cyclobutyl isomer because the —CF$_3$ group is pointing up while the —CH$_3$ group is pointing down, while (B) represents cis cyclobutyl isomer because both the —CF$_3$ group and the —CH$_3$ groups are pointing down.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers.

The compounds of general Formula (I) may also exist in the form of atropisomers. Atropisomers are compounds with identical structural formulae, but which have a particular spatial configuration resulting from a restricted rotation around a single bond, due to a major steric hindrance on either side of this single bond. Atropisomerism is independent of the presence of stereogenic elements, such as an asymmetric carbon. The terms "P atropisomer" or "M atropisomer" are used herein in order to be able to clearly name two atropisomers of the same pair. For example, the following compound of Intermediate B1, Step 1, having the structure below can be separated into the pair of atropisomers P and M via a chiral column:

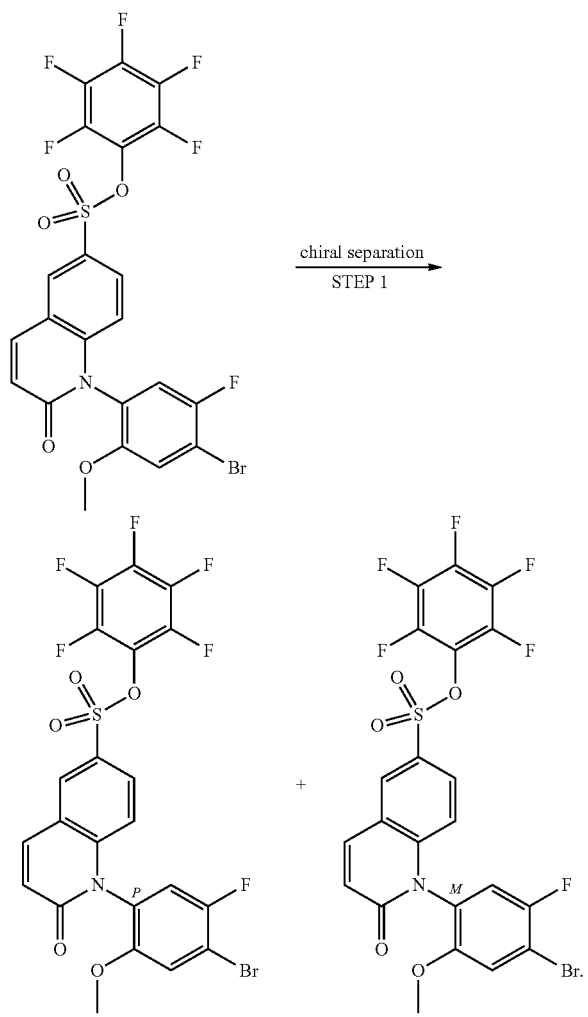

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention. Other examples of tautomerism are as follows:

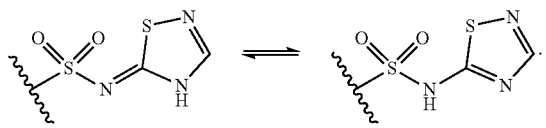 [SMILES: *S(=O)(=O)/N=c1/[nH]cns1 ; *S(=O)(=O)Nc1ncns1]

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$. In another aspect, the compounds of the present invention contain one or more deuterium atoms (2H) in place of one or more hydrogen atoms.

Compounds of the present invention that contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

All patents and other publications recited herein are hereby incorporated by reference in their entirety.

The examples presented below illustrate specific embodiments of the present invention. These examples are meant to be representative and are not intended to limit the scope of the claims in any manner.

It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity was measured using high performance liquid chromatography (HPLC) system with UV detection at 254 nm and 215 nm (System A: HALO C8, 3.0×50 mm, 2.7 μm, 5 to 95% $CH_3CN$ in $H_2O$ with 0.1% TFA for 2.0 min at 2.0 mL/min) (Agilent Technologies, Santa Clara, Calif.). Silica gel chromatography was generally performed with prepacked silica gel cartridges (Biotage, Uppsala, Sweden or Teledyne-Isco, Lincoln, Nebr.). $^{1}H$ NMR spectra were recorded on a Bruker AV-400 (400 MHz) spectrometer (Bruker Corporation, Madison, Wis.) or a Varian (Agilent Technologies, Santa Clara, Calif.) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series (Agilent Technologies, Santa Clara, Calif.) LC/MS with UV detection at 254 nm and 215 nm and a low resonance electrospray mode (ESI).

The following abbreviations may be used herein:
2-PrOH Isopropanol
AgOTf silver(I) trifluoromethanesulfonate
AIBN Azobisisobutyronitrile
aq. Aqueous
Bu Butyl
ca. Circa
Cm centimeter(s)
CPhos 2-dicyclohexylphosphino-2',6'-dimethylamino-1,1'-biphenyl
DAST diethylaminosulfur trifluoride
Dba Dibenzylideneacetone
DCM Dichloromethane
Deoxy-Fluor bis(2-methoxyethyl)aminosulfur trifluoride
DIPEA N,N-diisopropylethylamine
DMF N,N-dimethylformamide
DMSO Dimethylsulfoxide
ESI or ES electrospray ionization
Et Ethyl
$Et_2O$ diethyl ether
EtOAc ethyl acetate
EtOH Ethanol
G gram(s)
H hour(s)
HPLC high pressure liquid chromatography
IPA 2-propanol
Kg kilogram(s)
L liter(s)
LCMS liquid chromatography mass spectroscopy
LHMDS lithium hexamethyldisilazide
M Molar
m/z mass divided by charge
Me Methyl
MeOH Methanol
Me-THF Methyl tetrahydrofuran
Mg milligram(s)
MHz Megahertz
Min minute(s)
mL or ml milliliter(s)
Mmol millimole(s)
Mol mole(s)
MTBE methyl tert-butyl ether
N Normal
NaOMe sodium methoxide
n-Bu n-butyl
$NEt_3$ Triethylamine
NMR nuclear magnetic resonance
OAc Acetate
OTf Trifluoromethanesulfonate
PFP-OH Perfluorophenol
Ph Phenyl
PhMe Toluene
PMB 4-methoxybenzyl
Ppm parts per million
Pr Propyl
Rac racemic
Rt room temperature
sat. Saturated SFC supercritical fluid chromatography
TBAF tetra-n-butylammonium fluoride
TFA trifluoroacetic acid
THF Tetrahydrofuran
$Ti(OiPr)_4$ titanium(IV) isopropoxide
TLC thin-layer chromatography
$TMS-CF_3$ (trifluoromethyl)trimethylsilane
wt % percentage by weight
XantPhos 4,5-bis(diphenylphosphino)-9,9-dimethylxanthene
XtalFluor-M difluoro(morpholino)sulfonium tetrafluoroborate The following compounds presented herein, as examples of the present invention, and intermediates thereof as building blocks to prepare compounds provided by the invention, may be made by the various methods and synthetic strategies taught herein below. These compounds, and others provided by the invention, may also be prepared using methods described in International Publication No. WO2014/201206, filed Jun. 12, 2014, which specification is incorporated herein by reference in their entirety.

In addition, the present inventors have developed a photochemical atrop-selective ring-closure to form N-aryl quinolinones compounds. Specifically, the P atropisomer compound 3 is selectively formed in the photochemical reaction of the invention. A general representation of the photochemistry step of the present invention is described below:

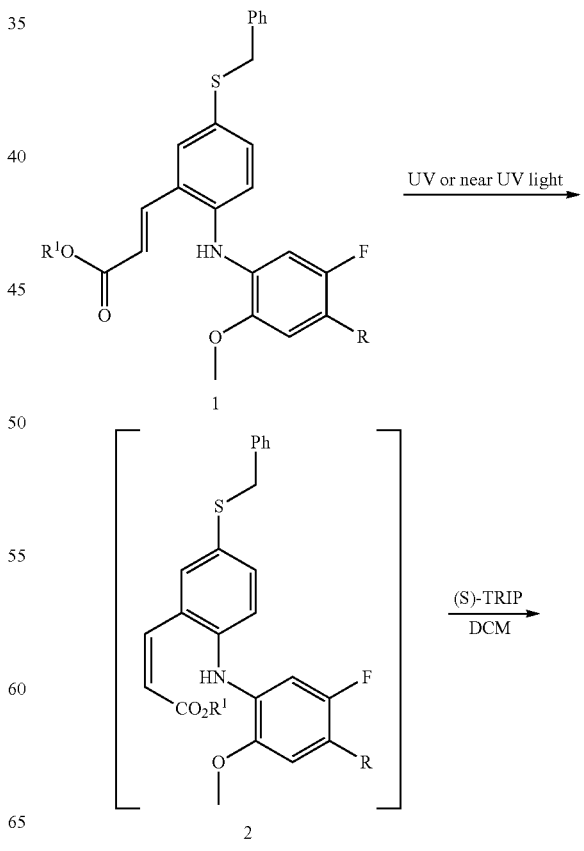

-continued

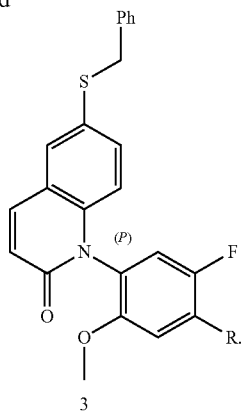

The reaction relies on UV or near-UV light to excite the olefin 1; wherein R is halo or the group

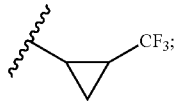

and $R^1$ is $C_1$-$C_6$alkyl; and induce a cis-trans isomerization to transiently form 2; wherein each R and $R^1$ is as defined above. Preferably, $R^1$ is ethyl. Cis olefin 2 can then be activated by chiral acid (S)-TRIP to asymmetrically form ring-closed quinolinone 3, wherein R is as defined above. Preferably, R is Br or A screen of chiral phosphoric acids revealed that (S)-TRIP was the preferred chiral acid. The preferred organic solvent is dichloromethane. The photochemical reaction has been scaled to 1 g in a batch reactor and has also been demonstrated in a small photochemical flow reactor.

The present photochemical step can operate well without the present of a bulky barrier substituent to rotation, such as tert-butyl group in the starting material. Rather, the present novel photochemical step has been demonstrated in the presence of a much smaller methoxy group in the starting material. The mild reaction conditions further allow for compounds with low barriers to rotation to be prepared in a stereoselective fashion.

The following compounds presented herein, as examples of the present invention, and intermediates thereof as building blocks to prepare compounds provided by the invention, may be made by the various methods and synthetic strategies taught herein below. These compounds, and others provided by the invention, may also be prepared using methods described in PCT/US2014/042055, filed Dec. 18, 2014 or PCT/US2016/067617; filed Dec. 19, 2016, which specification is incorporated herein by reference in its entirety.

Intermediate A: (P)-1-(4-BROMO-5-FLUORO-2-METHOXYPHENYL)-N-(ISOXAZOL-3-YL)-2-OXO-1,2-DIHYDROQUINOLINE-6-SULFONAMIDE

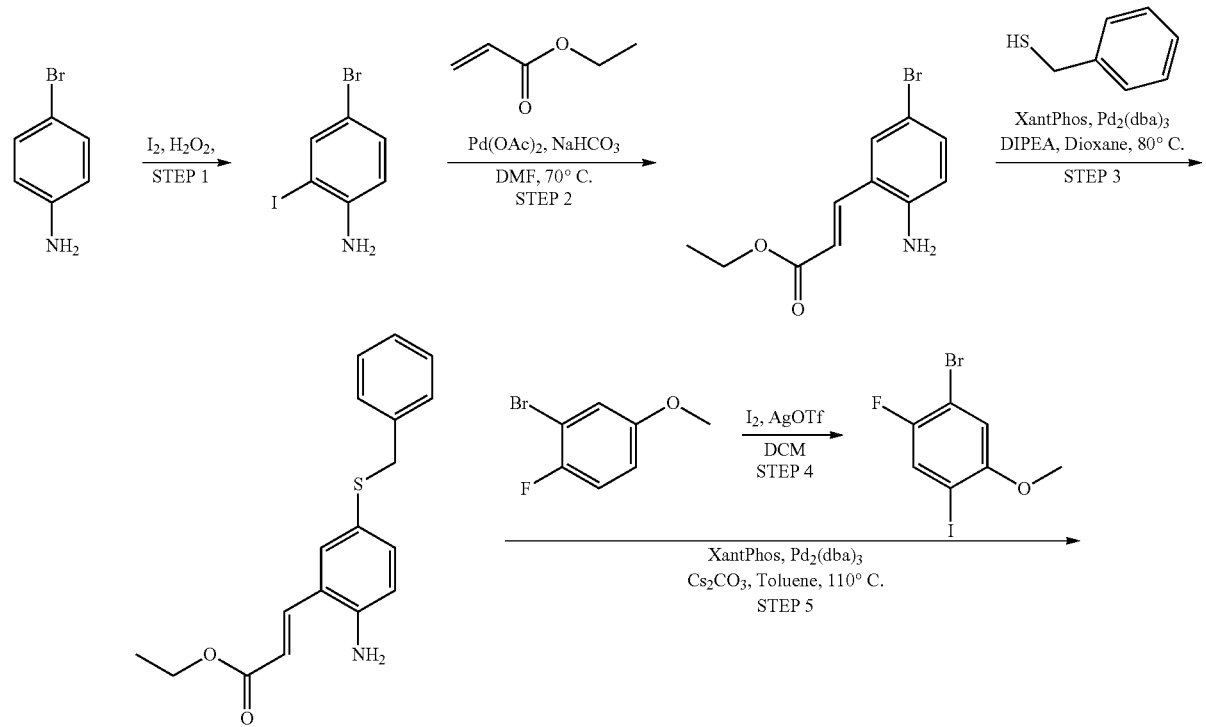

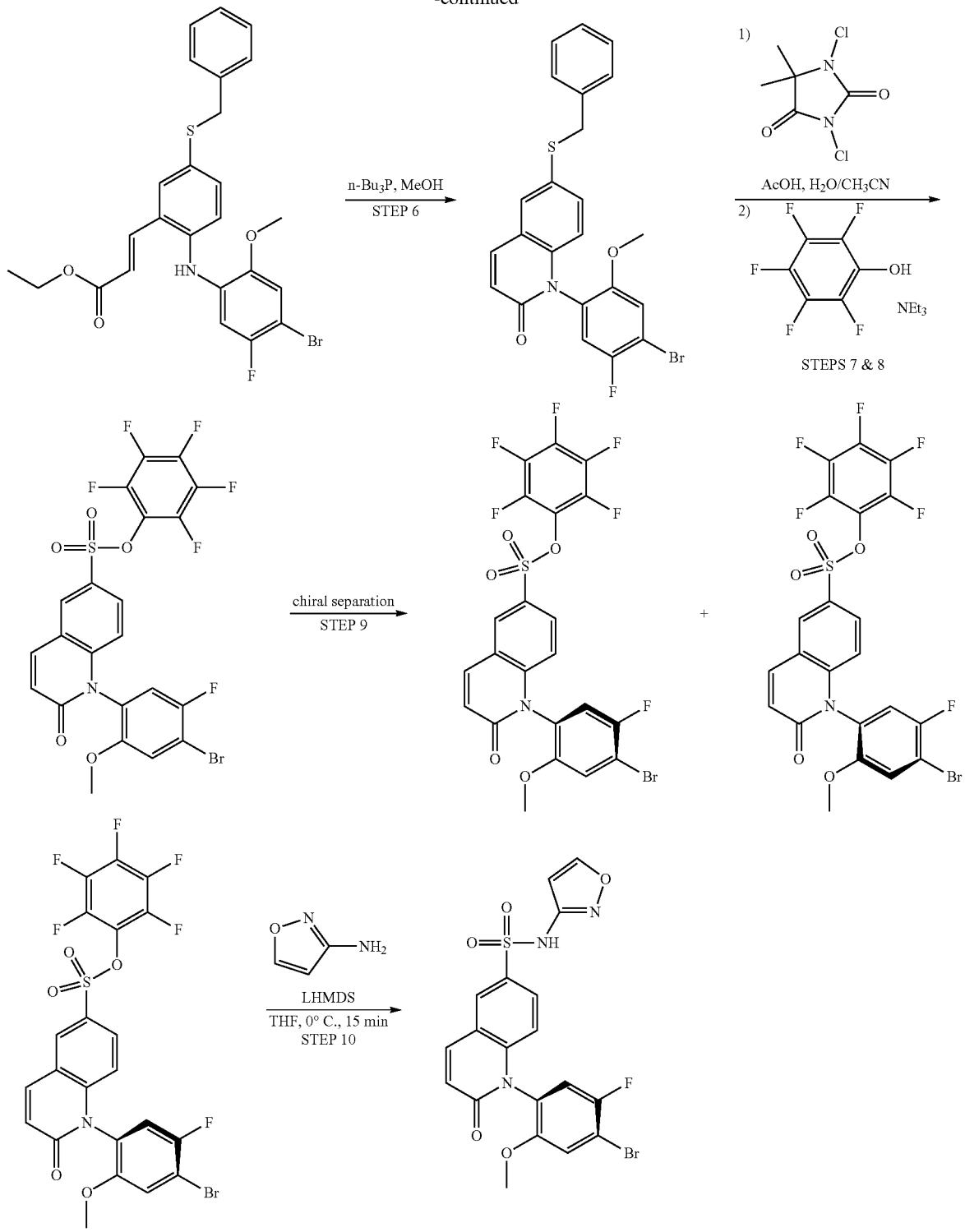

Step 1: 4-BROMO-2-IODOANILINE

To a solution of 4-bromo-aniline (500 g, 2.90 mol) in cyclohexane (2.5 L) was added iodine (368 g, 1.45 mol) and the mixture was heated at 50° C. After 30 min, the reaction mixture became homogenous, and 30% aqueous hydrogen peroxide solution (250 mL) was added to the reaction mixture. The reaction was heated for 4 h at 50° C. The reaction was cooled to room temperature, diluted with ethyl acetate (5.0 L) and washed with aqueous sodium sulphite (2.5 kg in 4.0 L) solution. The organic layer was washed with water (3.0 L) and brine (3.0 L) dried over magnesium sulfate, filtered and concentrated under reduced pressure to obtain the initial product which was purified by column chromatography (silica gel; mesh size 60-120, elution 0-20% ethyl acetate and hexanes) to get 4-bromo-2-iodoaniline (650 g, 75%), as an off white solid. TLC solvent system: 100% hexanes. Product's $R_f$: 0.6. MS (ESI, positive ion) m/z: 297.0 (M+1). $^1$H NMR (400 MHz, CDCl$_3$) δ 7.72 (d, J=2.5 Hz, 1H), 7.23 (dd, J=8.4, 2.1 Hz, 1H), 6.62 (d, J=8.3 Hz, 1H), 4.09 (s, 2H).

Step 2: ETHYL (E)-3-(2-AMINO-5-BROMOPHENYL)ACRYLATE

To a solution of 4-bromo-2-iodoaniline (750 g, 2.51 mol) in DMF (5.0 L) was added ethyl acrylate (277 g, 2.76 mol) and sodium bicarbonate (680 g, 6.29 mol). The reaction mixture was degassed with nitrogen for 20 min followed by the addition of palladium acetate (28.8 g, 128.27 mmol). The reaction mixture was heated at 70° C. for 3 h. The reaction was filtered through CELITE® and the CELITE bed was washed with ethyl acetate (2×500 mL). The filtrate was concentrated under reduced pressure to obtain a residue which was purified by column chromatography (silica gel; mesh size 60-120, elution 0-20% ethyl acetate in hexanes) to obtain (E)-ethyl 3-(2-amino-5-bromophenyl)acrylate (620 g, 77%), as yellow solid. TLC solvent system: 20% ethyl acetate in hexanes. Product's $R_f$: 0.4. MS (ESI, positive ion) m/z; 270.2 (M+1). $^1$H NMR (400 MHz, DMSO) δ 7.75 (d, J=16.1 Hz, 1H), 7.57 (d, J=2.0 Hz, 1H), 7.16 (dd, J=9.1, 2.4 Hz, 1H), 6.66 (d, J=8.6 Hz, 1H), 6.43 (d, J=8.6 Hz, 1H), 5.81 (s, 2H), 4.20 (q, J=7.2 Hz, 2H), 1.27 (t, J=7.2 Hz, 3H). Other acrylates can be used in place of ethyl acrylate to provide different esters. For example methyl acrylate, propyl acrylate, butyl acrylate, and others may be used instead of ethyl acrylate.

Step 3: ETHYL (E)-3-(2-AMINO-5-(BENZYLTHIO)PHENYL)ACRYLATE

To a solution of (E)-ethyl 3-(2-amino-5-bromophenyl) acrylate (620 g, 2.29 mol) in 1,4-dioxane (4.0 L) was added DIPEA (1.26 L, 8.88 mol, 3.9 equiv, GLR) and the mixture was degassed with nitrogen for 20 mins. XantPhos (92.9 g, 106 mmol), and tris(dibenzylideneacetone)dipalladium(0) (84 g, 91.0 mmol) were added to the reaction mixture. The mixture was purged with nitrogen and heated to 80° C. for 30 min. The reaction was cooled to RT, benzyl mercaptan (455.5 g, 3.67 mol) was added, and the reaction was heated at 80° C. for an additional 4 h. The reaction was cooled to room temperature and diluted with ethyl acetate (4.0 L). The mixture was filtered through CELITE and the CELITE bed was washed with ethyl acetate (2×1.0 L). The filtrate was concentrated under reduced pressure to obtain the initial product which was purified by chromatography (silica gel; mesh size 60-120, elution 0-40% ethyl acetate and petroleum ether) to obtain (E)-ethyl 3-(2-amino-5-(benzylthio) phenyl)acrylate (520 g, 72.0%), as yellow solid. TLC solvent system: 30% ethyl acetate in hexanes. Product's $R_f$: 0.4. MS (ESI, positive ion) m/z; 314.1 (M+1). $^1$H NMR (400 MHz, DMSO) δ 7.79 (d, J=16.1 Hz, 1H), 7.37 (d, J=2.0 Hz, 1H), 7.25-7.17 (m, 5H) 7.10 (dd, J=8.4, 2.1 Hz, 1H), 6.61 (d, J=8.3 Hz, 1H), 6.32 (d, J=15.2 Hz, 1H), 5.75 (s, 2H), 4.20 (q, J=7.2 Hz, 2H), 4.01 (s, 2H), 1.27 (t, J=7.2 Hz, 3H).

Step 4: 1-BROMO-2-FLUORO-4-IODO-5-METHOXYBENZENE

To a solution of 2-bromo-1-fluoro-4-methoxybenzene (500.0 g, 2.44 mol) in DCM (5.0 L) was added silver trifluoromethanesulfonate (686.0 g, 2.68 mol) and the reaction mixture was stirred for 20 min. Iodine (678.0 g, 2.68 mol) was added to the reaction and the mixture was stirred at room temperature for 16 h. The mixture was diluted with DCM (3.0 L) and filtered through CELITE. The CELITE bed was washed with DCM (2×1.0 L) and the filtrate was washed with 20% aqueous sodium thiosulfate (3.0 L) and saturated aqueous sodium bicarbonate solution (3.0 L). The organic layer was dried over sodium sulfate, filtered and concentrated under reduced pressure to obtain the Initial product which was purified by chromatography (silica gel; mesh size 60-120, elution 0-5% ethyl acetate and petroleum ether) to get 1-bromo-2-fluoro-4-iodo-5-methoxybenzene (720 g, 87%), as off-white solid. TLC solvent system: 100% hexanes. Product's $R_f$: 0.6. MS (ESI, positive ion) m/z: 331.0 (M+1). H NMR (400 MHz, CDCl$_3$) δ 7.55 (d, J=7.2 Hz, 1H), 6.95 (d, J=5.6 Hz, 1H), 3.89 (s, 3H).

Step 5: ETHYL (E)-3-(5-(BENZYLTHIO)-2-((4-BROMO-5-FLUORO-2-METHOXYPHENYL)AMINO)PHENYL) ACRYLATE To a solution of (E)-ethyl 3-(2-amino-5-(benzylthio)phenyl)acrylate (300 g, 958.1 mmol) and 1-bromo-2-fluoro-4-iodo-5-methoxybenzene (348.0 g, 1051.6 mmol) in toluene (2.5 L) was added Cs$_2$CO$_3$ (468 g, 1436.3 mmol) and the mixture was degassed with nitrogen for 20 mins. Pd$_2$(dba)$_3$ (35 g, 38.2 mmol) and XantPhos (44.6 g, 76.4 mmol) were added to the reaction mixture and the mixture was heated at 110° C. for 5 h. The reaction mixture was allowed to cool to room temperature, diluted with dichloromethane (2.0 L) and filtered through CELITE. The filtrate was concentrated under reduced pressure to obtain the Initial product which was purified by stirring with 5% ethyl acetate in hexanes (3.0 L) for 30 min and filtered to obtain (E)-ethyl 3-(5-(benzylthio)-2-((4-bromo-5-fluoro-2-methoxyphenyl) amino)phenyl)acrylate (350 g, 71%) as yellow solid. TLC solvent system: 30% ethyl acetate in hexanes. Product's $R_f$: 0.5. MS (ESI, positive ion) m/z; 516.2 (M+1). $^1$H NMR (400 MHz, DMSO) δ 7.73-7.61 (m, 3H), 7.34-7.15 (m, 6H), 7.02 (d, J=11.4 Hz, 1H), 6.60 (d, J=21.2 Hz, 1H), 6.33 (d, J=14.1 Hz, 1H), 4.26 (s, 2H), 4.16-4.09 (m, 2H), 3.81 (s, 3H), 1.22 (t, J=7.2 Hz, 3H). Note: NH proton not observed.

Step 6: 6-(BENZYLTHIO)-1-(4-BROMO-5-FLUORO-2-METHOXYPHENYL)QUINOLIN-2 (1H)-ONE To a solution of (E)-ethyl 3-(5-(benzylthio)-2-((4-bromo-5-fluoro-2-methoxyphenyl)amino)phenyl)acrylate (250.0 g, 484.0 mmol) in methanol (2.5 L) was added tri(n-butyl) phosphine (50% solution in ethyl acetate, 48.9 mL, 96.8 mmol) and the reaction mixture was heated at 70° C. for 5 h. The reaction mixture was allowed to cool to rt, concentrated under reduced pressure to obtain the Initial product which was purified by stirring with 5% ethyl acetate in hexanes (1.0 mL) and filtered to obtain 6-(benzylthio)-1-(4-bromo-5-fluoro-2-methoxyphenyl)quinolin-2(1H)-one (201.0 g, 88%) as an off white solid. TLC solvent system: 30% ethyl acetate in hexanes. Product's $R_f$: 0.3. MS (ESI, positive ion) m/z; 470.0 (M+1). $^1$H NMR (400 MHz, DMSO) δ 7.92 (d, J=9.1 Hz, 1H), 7.79 (d, J=1.7 Hz, 1H), 7.65 (d, J=6.1 Hz, 1H), 7.57 (d, J=8.8 Hz, 1H), 7.40-7.22 (m, 6H), 6.68 (d, J=9.6 Hz, 1H), 6.56 (d, J=8.8 Hz, 1H), 4.24 (s, 2H), 3.69 (s, 3H).

Steps 7 & 8: PERFLUOROPHENYL 1-(4-BROMO-5-FLUORO-2-METHOXYPHENYL)-2-OXO-1,2-DIHYDRO QUINOLINE-6-SULFONATE To a solution of 6-(benzylthio)-1-(4-bromo-5-fluoro-2-methoxyphenyl)quinolin-2(1H)-one (250.0 g, 531.5 mmol) in acetonitrile (2.5 L) were added acetic acid (200 mL) and water (130 mL). The resulting mixture was cooled to 0° C. and 1,3-dichloro-5,5-dimethylimidazolidine-2,4-dione (188.5 g, 956.7 mmol) was added portion-wise over 20 min keeping the internal temperature below 5° C. The resulting suspension was stirred at 0-5° C. under nitrogen for 45 min. Then a solution of pentafluorophenol (127.2 g, 690.95 mmol) in acetonitrile (200 mL) was added over 5 min followed by NEt$_3$ (307.7 mL, 2.12 mol) over 20 min keeping the internal temperature below 5° C. The mixture was continued to be stirred at 0-5° C. for 30 min. Water (4.0 L) was added and extracted with ethyl acetate (2×2.0 L). The organic layer was washed with brine (1.0 L), dried over sodium sulfate, filtered and concentrated under reduced pressure to obtain the crude which was purified by stirring with isopropyl alcohol:hexanes (1:1, 1.0 L) and filtered to obtain perfluorophenyl 1-(4-bromo-5-fluoro-2-methoxyphenyl)-2-oxo-1,2-dihydroquinoline-6-sulfonate (190 g, 60%) as white solid. TLC solvent system: 30% ethyl acetate in petroleum ether, Product's R$_f$: 0.4. MS (ESI, positive ion) m/z; 594.2 (M+1). $^1$H-NMR (400 MHz, DMSO) δ ppm 8.60 (d, J=2.0 Hz, 1H), 8.26 (d, J=9.8 Hz, 1H), 7.95 (dd, J=2.2, 9.1 Hz, 1H), 7.70 (t, J=8.6 Hz, 2H), 6.95-6.88 (m, 2H), 3.72 (s, 3H).

Step 9: (P)-PERFLUOROPHENYL 1-(4-BROMO-5-FLUORO-2-METHOXYPHENYL)-2-OXO-1,2-DIHYDROQUINOLINE-6-SULFONATE Racemic perfluorophenyl 1-(4-bromo-5-fluoro-2-methoxyphenyl)-2-oxo-1,2-dihydroquinoline-6-sulfonate (76.90 g) was separated via Chiralcel OJ column (40% MeOH/60% CO$_2$) to give (P)-perfluorophenyl 1-(4-bromo-5-fluoro-2-methoxyphenyl)-2-oxo-1,2-dihydroquinoline-6-sulfonate and (M)-perfluorophenyl 1-(4-bromo-5-fluoro-2-methoxyphenyl)-2-oxo-1,2-dihydroquinoline-6-sulfonate as pale yellow flocculent solids. Data for peak 1: m/z (ESI) 594.0 (M+H)+. Data for peak 2: m/z (ESI) 594.0 (M+H)+.

Step 10: (P)-1-(4-BROMO-5-FLUORO-2-METHOXYPHENYL)-N-(ISOXAZOL-3-YL)-2-OXO-1,2-DIHYDROQUINOLINE-6-SULFONAMIDE A THF (200 mL) solution of (P)-perfluorophenyl 1-(4-bromo-5-fluoro-2-methoxyphenyl)-2-oxo-1,2-dihydroquinoline-6-sulfonate (6.00 g, 10.10 mmol) and 3-aminoisoxazole (0.821 mL, 11.11 mmol) in a 250-mL round-bottom flask was cooled to 0° C., and lithium bis(trimethylsilyl)amide, (1.0 M solution in THF, 21.20 mL, 21.20 mmol) was added dropwise. After stirring the yellow solution at 0° C. for 15 min, it was quenched at 0° C. with 1 N HCl and extracted thrice with EtOAc. The organic extracts were combined, dried over MgSO$_4$, filtered, and concentrated to a light tan residue. Et$_2$O was added, and the slurry was titurated and sonicated. Filtration afforded an off-white solid, which was washed twice with Et$_2$O and dried in vacuo to afford 3.88 g of product as an off-white solid. The filtrate was concentrated in vacuo and purified via column chromatography (12 g silica gel, 35% to 100% EtOAc/hept gradient) to afford an additional 1.36 g of product as a pale yellow flocculent solid. A total of 5.24 g of (P)-1-(4-bromo-5-fluoro-2-methoxyphenyl)-N-(isoxazol-3-yl)-2-oxo-1,2-dihydroquinoline-6-sulfonamide was afforded. m/z (ESI) 494.1 (M+H)+.

Intermediate B: 1-(4-BROMO-5-FLUORO-2-METHOXYPHENYL)-N-(ISOXAZOL-3-YL)-2-OXO-1,2-DIHYDROQUINOLINE-6-SULFONAMIDE

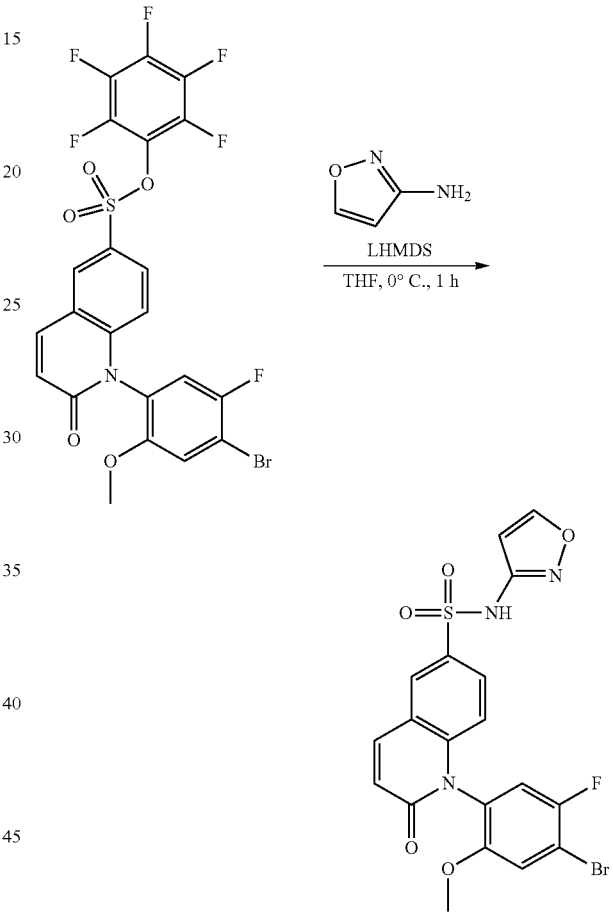

A THF (159 mL) solution of perfluorophenyl 1-(4-bromo-5-fluoro-2-methoxyphenyl)-2-oxo-1,2-dihydroquinoline-6-sulfonate (9.45 g, 15.90 mmol) and 3-aminoisoxazole (1.292 mL, 17.49 mmol) in a 500-mL round-bottom flask was cooled to 0° C., and lithium bis(trimethylsilyl)amide (1.0 M solution in THF, 33.4 mL, 33.4 mmol) was added dropwise. After stirring the solution at 0° C. for 1 h, it was quenched at 0° C. with 1 N HCl and extracted thrice with EtOAc. The organic extracts were combined, dried over MgSO$_4$, filtered, and concentrated to a light tan residue, affording 3.81 g of the product. The filtrate contained product by LCMS and was accordingly concentrated in vacuo and purified via column chromatography (120 g silica gel, 20% to 80% EtOAc/heptane gradient) afforded an additional 1.01 g of product. 1-(4-bromo-5-fluoro-2-methoxyphenyl)-N-(isoxazol-3-yl)-2-oxo-1,2-dihydroquinoline-6-sulfonamide (4.82 g, 9.75 mmol, 61.3% yield) was afforded as an off-white solid. m/z (ESI) 494.1 (M+H)$^+$.

Intermediate C: 1-(4-BROMO-2-METHOXYPHE-NYL)-N-(ISOXAZOL-3-YL)-2-OXO-1,2-DIHYD-ROQUINOLINE-6-SULFONAMIDE

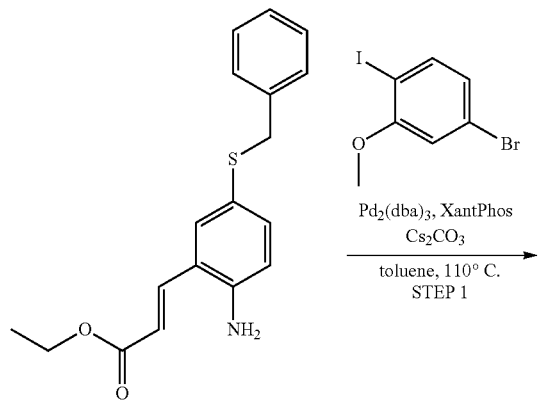

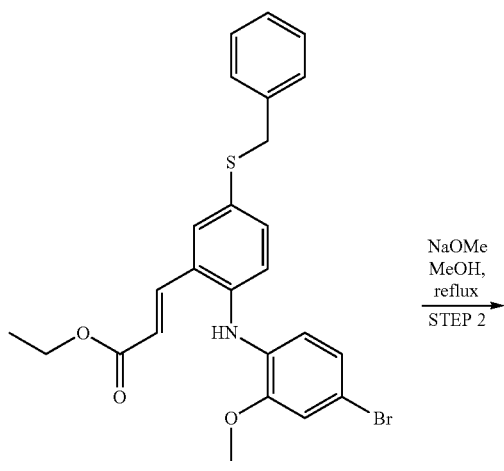

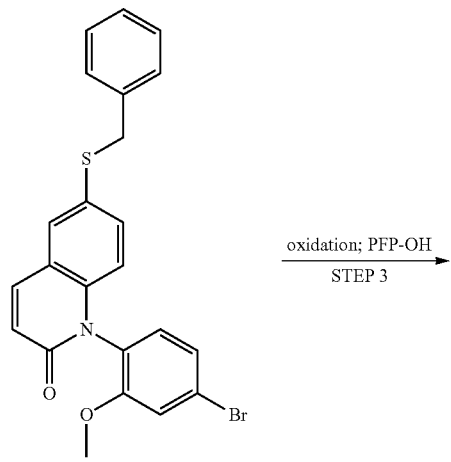

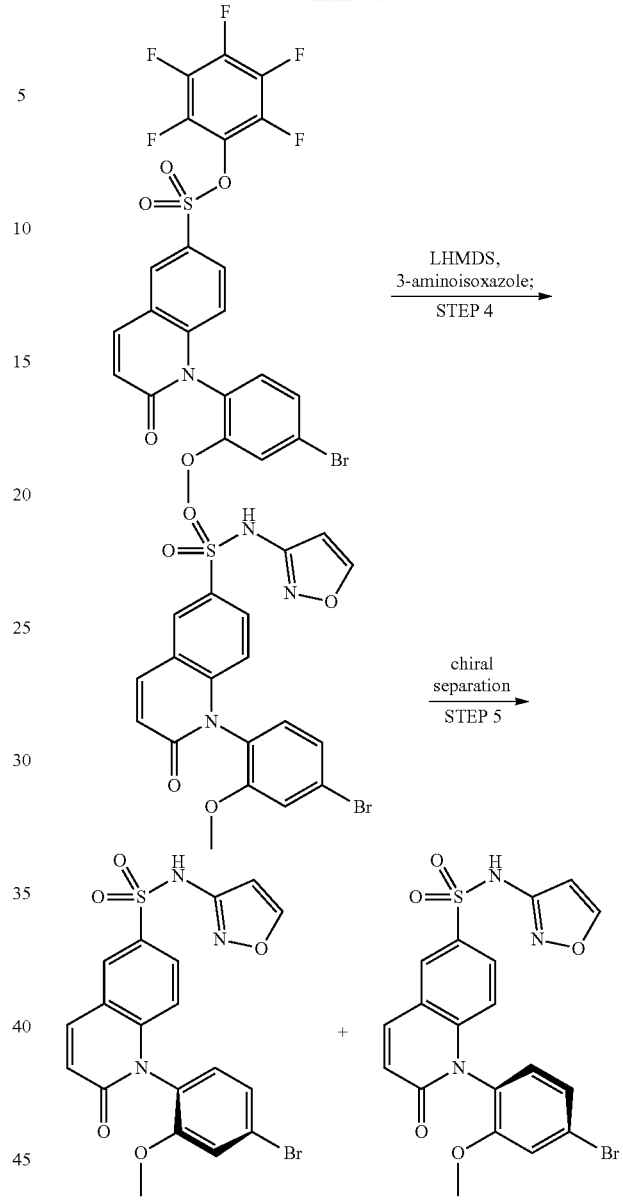

Step 1: (E)-ETHYL 3-(5-(BENZYLTHIO)-2-((4-BROMO-2-METHOXYPHENYL)AMINO)PHE-NYL)ACRYLATE A round-bottom flask was charged with (E)-ethyl 3-(2-amino-5-(benzylthio)phenyl)acrylate (2.39 g, 7.63 mmol), 4-bromo-1-iodo-2-methoxybenzene (2.86 g, 9.15 mmol), XantPhos (0.221 g, 0.381 mmol), tris(dibenzylideneacetone)dipalladium(0) (0.175 g, 0.191 mmol), and cesium carbonate (4.97 g, 15.25 mmol) were added. A reflux condenser was attached and the flask was lowered into a 110° C. heating bath. After 2 h, an additional portion of cesium carbonate (1.4 g) was added, and the bath temperature was raised to 120° C. The mixture was heated for another 2 h then cooled to room temperature, diluted with EtOAc, and filtered through CELITE with the aid of EtOAc. The filtrate was concentrated. The oily residue was taken up in 2-PrOH. The mixture was concentrated to give a yellow solid with some oily solid present. The mixture was taken up in 2-PrOH to give a suspension, and the suspension was stirred for 16 h. The mixture was filtered, and the filtered solid was washed with 2-PrOH (3×). The collected solid was dried on the filter under a flow of $N_2$ for 15 min to give (E)-ethyl 3-(5-(benzylthio)-2-((4-bromo-2-methoxyphenyl)amino)phenyl)acrylate (3.136 g, 6.29 mmol, 83% yield) as a bright-yellow solid. $^1$H NMR (400 MHz, DMSO-$d_6$) δ ppm 7.72 (d, J=16.0 Hz, 1H), 7.68 (d, J=2.2 Hz, 1H), 7.47 (s, 1H), 7.37-7.19 (m, 6H), 7.13 (d, J=2.2 Hz, 1H), 6.94 (dd, J=2.2, 8.4 Hz, 1H), 6.86 (d, J=8.5 Hz, 1H), 6.55 (s, 1H), 6.52 (d, J=7.7 Hz, 1H), 4.24 (s, 2H), 4.15 (q, J=7.1 Hz, 2H), 3.82 (s, 3H), 1.23 (t, J=7.1 Hz, 3H). m/z (ESI) 498.0 (M+H)$^+$.

Step 2: 6-(BENZYLTHIO)-1-(4-BROMO-2-METHOXYPHENYL)QUINOLIN-2(1H)-ONE

A round-bottom flask was charged with (E)-ethyl 3-(5-(benzylthio)-2-((4-bromo-2-methoxyphenyl)amino)phenyl)acrylate (3.13 g, 6.28 mmol) and MeOH (31.4 mL) to give a yellow suspension. Sodium methoxide (25 wt % in MeOH, 0.271 mL, 1.256 mmol) was added. A reflux condenser was attached, and the flask was lowered into a 75° C. heating bath. The bath quickly spiked to ca. 80-85° C., but returned to 70-75° C. after 30 min. The reaction was stirred for 16 h, and the mixture was diluted with DCM and concentrated. The residue was purified by chromatography on silica gel (50-g SNAP Ultra column, 25-g silica gel loading column, 10-60% EtOAc/Heptane) to give 6-(benzylthio)-1-(4-bromo-2-methoxyphenyl)quinolin-2(1H)-one (1.95 g, 4.31 mmol, 69% yield) as a yellow solid. $^1$H NMR (400 MHz, DMSO-$d_6$) δ ppm 7.94 (d, J=9.5 Hz, 1H), 7.78 (d, J=2.2 Hz, 1H), 7.50 (d, J=2.1 Hz, 1H), 7.43-7.16 (m, 8H), 6.66 (d, J=9.6 Hz, 1H), 6.47 (d, J=8.8 Hz, 1H), 4.23 (s, 2H), 3.69 (s, 3H). m/z (ESI) 452.0 (M+H)$^+$.

Step 3: PERFLUOROPHENYL 1-(4-BROMO-2-METHOXYPHENYL)-2-OXO-1,2-DIHYDROQUINOLINE-6-SULFONATE A round-bottom flask was charged with 6-(benzylthio)-1-(4-bromo-2-methoxyphenyl)quinolin-2(1H)-one (1.777 g, 3.93 mmol), acetonitrile (18.49 mL), acetic acid (0.693 mL), and water (0.462 mL) to give a solution. The flask was cooled in an ice-water bath for 10 min, then 1,3-dichloro-5,5-dimethylimidazolidine-2,4-dione (0.813 g, 4.12 mmol) was added in one portion. After 20 min, an additional portion of 1,3-dichloro-5,5-dimethylimidazolidine-2,4-dione (0.813 g, 4.12 mmol) was added in one portion. After another 20 min, 2,3,4,5,6-pentafluorophenol (1.085 g, 5.89 mmol) was added, and the mixture was stirred for 5 min. Triethylamine (2.190 mL, 15.71 mmol) was added dropwise over 30 s then the mixture was stirred for 20 min. The reaction mixture was diluted with water and extracted with DCM (3×). The combined organic extracts were dried over sodium sulfate, filtered, and concentrated. The residue was purified by chromatography on silica gel (50-g SNAP Ultra column, 25-g silica gel loading column, 10-60% EtOAc/Heptane). Perfluorophenyl 1-(4-bromo-2-methoxyphenyl)-2-oxo-1,2-dihydroquinoline-6-sulfonate (1.644 g, 2.85 mmol, 72.6% yield) was isolated as a white foam. $^1$H NMR (400 MHz, DMSO-$d_6$) δ ppm 8.59 (d, J=2.2 Hz, 1H), 8.24 (d, J=9.6 Hz, 1H), 7.95 (dd, J=2.3, 9.1 Hz, 1H), 7.56 (d, J=1.9 Hz, 1H), 7.44-7.26 (m, 2H), 6.86 (dd, J=9.4, 13.7 Hz, 2H), 3.72 (s, 3H). m/z (ESI) 575.9 (M+H)+.

Step 4: 1-(4-BROMO-2-METHOXYPHENYL)-N-(ISOXAZOL-3-YL)-2-OXO-1,2-DIHYDROQUINOLINE-6-SULFONAMIDE A round-bottom flask was charged with perfluorophenyl 1-(4-bromo-2-methoxyphenyl)-2-oxo-1,2-dihydroquinoline-6-sulfonate (1.070 g, 1.857 mmol), isoxazol-3-amine (0.158 mL, 2.135 mmol) and THF (12 mL) to give a clear solution. The flask was cooled in an ice-water bath for 10 min, then lithium bis(trimethylsilyl)amide (1 M in THF, 3.90 mL, 3.90 mmol) was added dropwise. After 10 min, the mixture was diluted with EtOAc and washed with 1 N aq. HCl. The aq. layer was washed with EtOAc. The combined organic extracts were dried over sodium sulfate, filtered, and concentrated. The residue was purified by chromatography (50-g SNAP Ultra column, 25-g silica gel loading column, 0-5% MeOH/DCM) to give 1-(4-bromo-2-methoxyphenyl)-N-(isoxazol-3-yl)-2-oxo-1,2-dihydroquinoline-6-sulfonamide (0.867 g) as a tan foam that was ca. 90% pure. m/z (ESI) 476.1 (M+H)$^+$.

Step 5: (P)-1-(4-BROMO-2-METHOXYPHENYL)-N-(ISOXAZOL-3-YL)-2-OXO-1,2-DIHYDROQUINOLINE-6-SULFONAMIDE Racemic 1-(4-bromo-2-methoxyphenyl)-N-(isoxazol-3-yl)-2-oxo-1,2-dihydroquinoline-6-sulfonamide (400 mg) was purified using a (S,S) Whelk-O, 2×15 cm column. The mobile phase was run under isocratic conditions; supercritical $CO_2$ with 60% isopropanol; flow rate: 80 mL/min. The first eluting peak was assigned (M)-1-(4-bromo-2-methoxyphenyl)-N-(isoxazol-3-yl)-2-oxo-1,2-dihydroquinoline-6-sulfonamide (150 mg). The second eluting peak was assigned (P)-1-(4-bromo-2-methoxyphenyl)-N-(isoxazol-3-yl)-2-oxo-1,2-dihydroquinoline-6-sulfonamide (154 mg). Data for peak 1: $^1$H NMR (400 MHz, ACETONITRILE-$d_3$) δ ppm 8.65-8.94 (m, 1H), 8.37 (d, J=1.9 Hz, 1H), 8.23 (d, J=2.3 Hz, 1H), 7.97 (d, J=9.3 Hz, 1H), 7.78 (dd, J=8.9, 2.3 Hz, 1H), 7.43 (d, J=2.1 Hz, 1H), 7.34 (dd, J=8.3, 2.1 Hz, 1H), 7.16 (d, J=8.3 Hz, 1H), 6.70-6.80 (m, 2H), 6.45 (d, J=1.9 Hz, 1H), 3.69 (s, 3H). m/z (ESI, positive ion) 476.0 (M+H)$^+$. Data for peak 2: $^1$H NMR (400 MHz, ACETONITRILE-$d_3$) δ ppm 8.72-8.87 (m, 1H), 8.37 (d, J=1.7 Hz, 1H), 8.23 (d, J=2.1 Hz, 1H), 7.97 (d, J=9.5 Hz, 1H), 7.78 (dd, J=9.0, 2.2 Hz, 1H), 7.43 (d, J=2.1 Hz, 1H), 7.34 (dd, J=8.3, 1.9 Hz, 1H), 7.16 (d, J=8.3 Hz, 1H), 6.69-6.80 (m, 2H), 6.45 (d, J=1.9 Hz, 1H), 3.69 (s, 3H). m/z (ESI, positive ion) 476.0 (M+H)$^+$.

Intermediate D: N-(4-METHOXYBENZYL)ISOXAZOL-3-AMINE

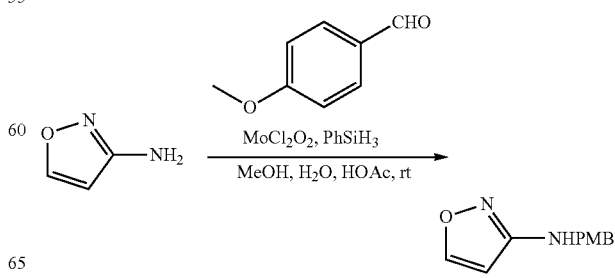

To a 20-L round-bottom flask was added isoxazol-3-amine (150 g, 1784 mmol) and 4-methoxybenzaldehyde (274 g, 2016 mmol) in methanol (9000 mL), water (150 mL), and acetic acid (101 mL) and stirred for 15 min at room temperature. Then molybdenum dichloride dioxide (17.74 g, 89 mmol) and phenylsilane (193 g, 1784 mmol) were added. The reaction mixture was stirred at room temperature for 16 h. After completion of the reaction, the reaction mass was concentrated, diluted with dichloromethane (5000 mL) and washed with sat. aq. NaHCO$_3$ (2000 mL). The organic layer was washed with water (2000 mL) and dried over Na$_2$SO$_4$. The solution was filtered and concentrated in vacuo to give the Initial product as an orange solid. The Initial product was absorbed onto a plug of silica gel and purified by column chromatography (Silica gel, 60-120 mesh) eluting with a gradient of 0% to 30% EtOAc in hexane, to provide N-(4-methoxybenzyl)isoxazol-3-amine (272 g, 1332 mmol, 75% yield) as an off-white solid. $^1$H NMR (400 MHz, DMSO-d$_6$) δ ppm 8.36 (d, J=1.8 Hz, 1H), 7.16-7.37 (m, 2H), 6.71-6.97 (m, 2H), 6.56 (t, J=6.0 Hz, 1H), 5.97 (d, J=1.8 Hz, 1H), 4.18 (d, J=6.0 Hz, 2H), 3.73 (s, 3H). m/z (ESI, positive ion) 205.1 (M+H)$^+$.

Intermediate E: (P)-1-(4-BROMO-5-FLUORO-2-METHOXYPHENYL)-N-(ISOXAZOL-3-YL)-N-(4-METHOXYBENZYL)-2-OXO-1,2-DIHYDROQUINOLINE-6-SULFONAMIDE A 250-mL round-bottom flask was charged with (P)-perfluorophenyl 1-(4-bromo-5-fluoro-2-methoxyphenyl)-2-oxo-1,2-dihydroquinoline-6-sulfonate (11.34 g, 19.08 mmol) and N-(4-methoxybenzyl)isoxazol-3-amine (4.09 g, 20.04 mmol), then purged with nitrogen. Tetrahydrofuran (191 mL) was introduced, and the resultant brown solution cooled to 0° C. A solution of lithium bis(trimethylsilyl)amide (1.0 M in THF, 21.0 mL, 21.0 mmol) was added dropwise via syringe to the stirred reaction mixture over 10 min. After 15 min, 1.0 N HCl (100 mL) was introduced and the resultant reaction mixture was allowed to warm to rt. The mixture was diluted with and EtOAc (100 mL) and the layers were separated, and the aqueous layer was further extracted with EtOAc (2×100 mL). The combined organic layers were then washed with brine (100 mL), dried over anhydrous sodium sulfate, filtered, and concentrated under reduced pressure. The residue was then purified by flash column chromatography (100 g Biotage column, eluent: gradient, 0 to 100% EtOAc in heptane with 10% CH$_2$Cl$_2$ as an additive) to afford (P)-1-(4-bromo-5-fluoro-2-methoxyphenyl)-N-(isoxazol-3-yl)-N-(4-methoxybenzyl)-2-oxo-1,2-dihydroquinoline-6-sulfonamide (9.54 g, 15.53 mmol, 81% yield) as a white amorphous solid. $^1$H NMR (400 MHz, DMSO-d$_6$) δ ppm 8.82 (d, J=2.0 Hz, 1H), 8.38 (d, J=2.3 Hz, 1H), 8.17 (d, J=9.4 Hz, 1H), 7.76 (t, J=5.1 Hz, 1H), 7.68 (d, J=6.1 Hz, 1H), 7.63 (d, J=8.5 Hz, 1H), 7.26 (d, J=7.9 Hz, 2H), 6.91-6.78 (m, 4H), 6.74 (d, J=2.0 Hz, 1H), 4.92 (s, 2H), 3.73-3.69 (m, 6H), 3.32 (s, 1H). m/z (ESI) 615.1 (M+H)$^+$.

Intermediate F: (P)-1-(5-FLUORO-2-METHOXY-4-VINYLPHENYL)-N-(ISOXAZOL-3-YL)-2-OXO-1,2-DIHYDROQUINOLINE-6-SULFONAMIDE

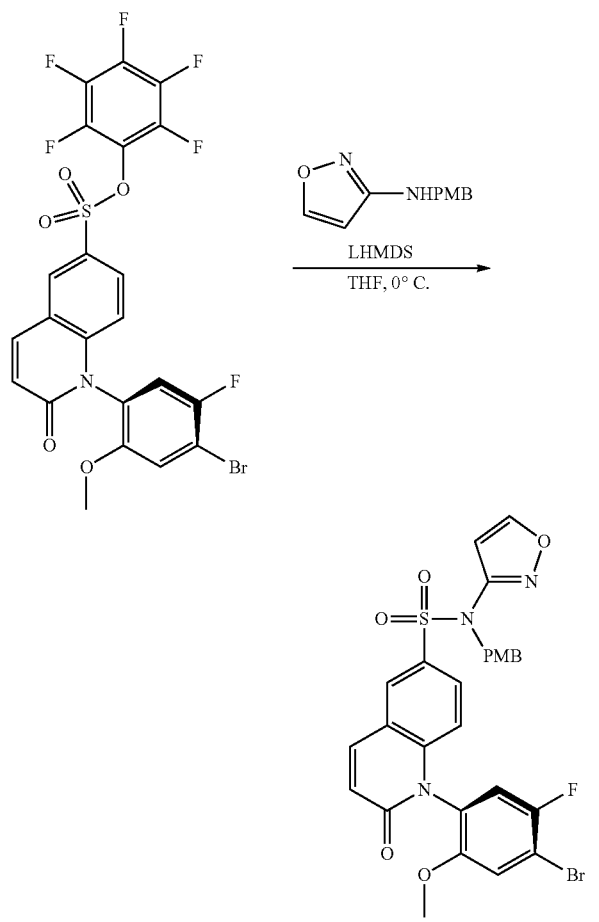

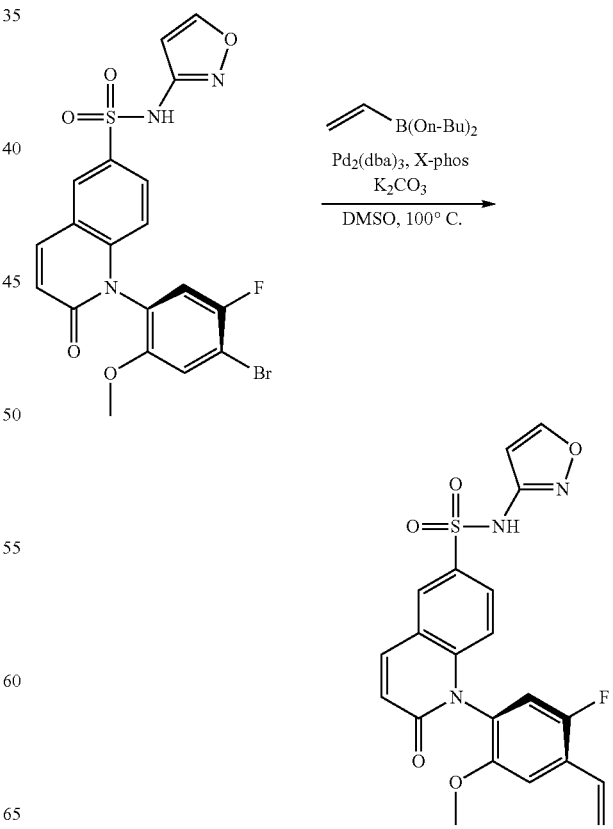

A vial was charged with (P)-1-(4-bromo-5-fluoro-2-methoxyphenyl)-N-(isoxazol-3-yl)-2-oxo-1,2-dihydroquinoline-6-sulfonamide (0.300 g, 0.607 mmol), tris(dibenzylideneacetone)dipalladium(0) (0.056 g, 0.061 mmol), 2-(dicyclohexylphosphino)-2',4',6'-tri-1-propyl-1,1'-biphenyl (0.058 g, 0.121 mmol), and potassium carbonate (0.419 g, 3.03 mmol). DMSO (3.0 mL) and vinylboronic acid dibutyl ester (0.40 mL, 1.8 mmol) were added. The reaction was heated to 100° C. and stirred for two hours. The reaction was diluted with ethyl acetate and washed with 1 N HCl solution. The aqueous layer was extracted with ethyl acetate, and the combined organic layers were washed with brine, dried with sodium sulfate, filtered, and concentrated. The material was purified via column chromatography (RediSep Gold 40 g column, gradient elution 0-50% [3:1 EtOAc/EtOH]:heptane) to afford (P)-1-(5-fluoro-2-methoxy-4-vinylphenyl)-N-(isoxazol-3-yl)-2-oxo-1,2-dihydroquinoline-6-sulfonamide (0.206 g, 0.467 mmol, 77% yield) as a light yellow solid. m/z (ESI, positive ion) 442.0 (M+H)$^+$.

Intermediate G:
1-BROMO-2-CHLORO-4-IODO-5-METHOXYBENZENE

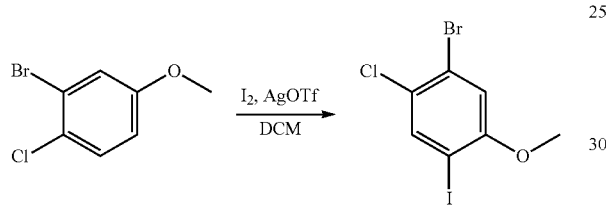

To a solution of 2-bromo-1-chloro-4-methoxybenzene (500 g, 2258 mmol) in dichloromethane (7500 mL) was added silver(I) trifluoromethanesulfonate (638 g, 2483 mmol) at ambient temperature under nitrogen environment. The reaction mixture was stirred for 20 mins at ambient temperature and iodine (630 g, 2483 mmol) was added. The reaction mixture was stirred at ambient temperature for 16 h. The mixture was then diluted with DCM (4500 mL) and filtered through CELITE. The CELITE bed was washed with DCM (2×1.0 L). The filtrate was washed with 20% aqueous sodium thiosulfate (5.0 L) and saturated aqueous sodium bicarbonate solution (5.0 L). The organic layer was dried over sodium sulfate, filtered and concentrated under reduced pressure to obtain the Initial product which was purified by column chromatography (silica gel; mesh size 60-120, elution 0-5% ethyl acetate and petroleum ether) to afford 1-bromo-2-chloro-4-iodo-5-methoxybenzene (610 g, 1756 mmol, 78% yield) as off-white solid. $^1$H NMR (400 MHz, CDCl$_3$) δ ppm 7.83 (s, 1H), 7.03 (s, 1H), 3.89 (s, 3H).

Intermediate H:
N-(4-METHOXYBENZYL)PYRIMIDIN-2-AMINE

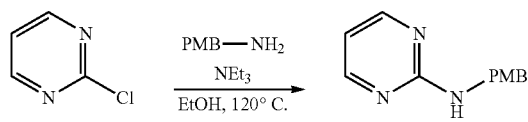

In a 50-mL microwave vial were successively dissolved in EtOH (20 mL), 2-chloropyrimidine (1.5 g, 13.10 mmol), (4-methoxyphenyl)methanamine (2.15 g, 15.72 mmol), and triethylamine (2.65 g, 26.2 mmol). The reaction tube was sealed, and irradiated in the cavity of a microwave reactor at a ceiling temperature of 120° C. at 80 W maximum power for 1 h. After the reaction mixture was cooled with an air flow for 15 min, it was diluted with water (100 mL), extracted with CH$_2$Cl$_2$ (2×150 mL) and dried over Na$_2$SO$_4$. The reaction mixture was diluted with water (50 mL) and extracted with ethyl acetate (2×50 mL). The organic extract was washed with sat. aq. NaCl (1×50 mL) and dried over Na$_2$SO$_4$. The solution was filtered and concentrated in vacuo to give the Initial product as a yellow oil. The Initial product was absorbed onto a plug of silica gel and purified by chromatography through a Redi-Sep pre-packed silica gel column (12 g), eluting with a gradient of 20% to 30% EtOAc in hexane, to provide N-(4-methoxybenzyl)pyrimidin-2-amine (1.5 g, 6.97 mmol, 53% yield) as an off white solid. m/z (ESI) 216.2 (M+H)$^+$.

Intermediate I: (P)-1-(4-BROMO-5-CHLORO-2-METHOXYPHENYL)-N-(4-METHOXYBENZYL)-2-OXO-N-(PYRIMIDIN-2-YL)-1,2-DIHYDROQUINOLINE-6-SULFONAMIDE

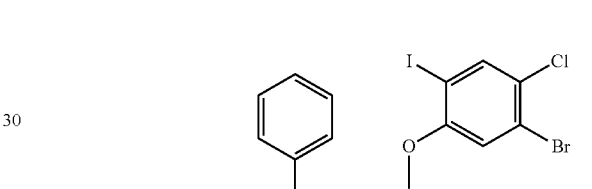

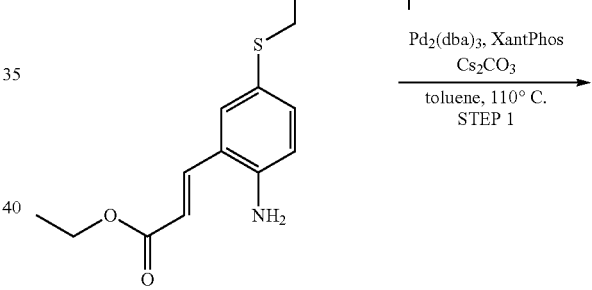

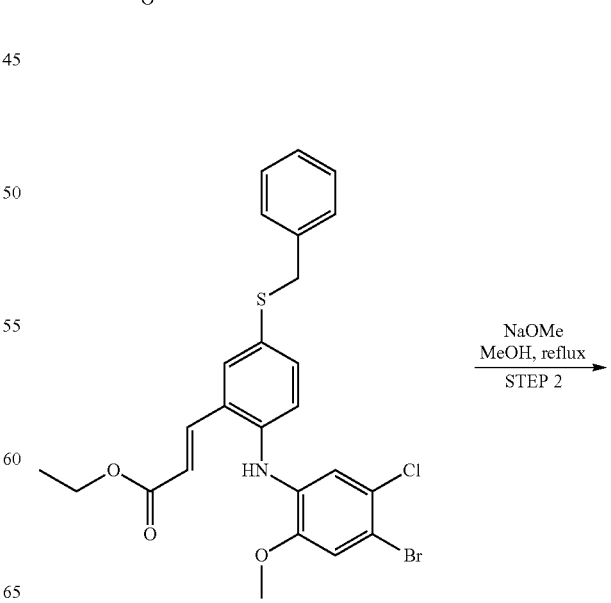

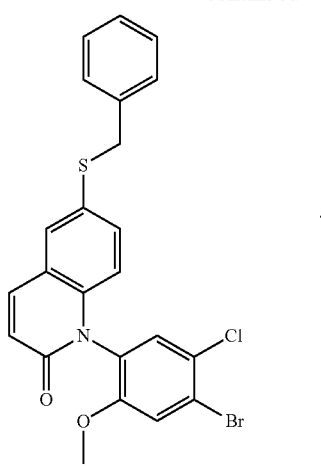
oxidation: PFP-OH
STEP 3
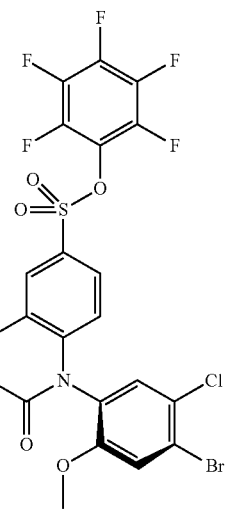
chiral separation
STEP 4
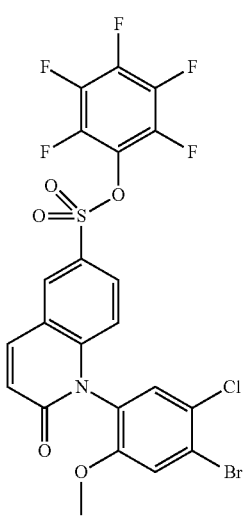
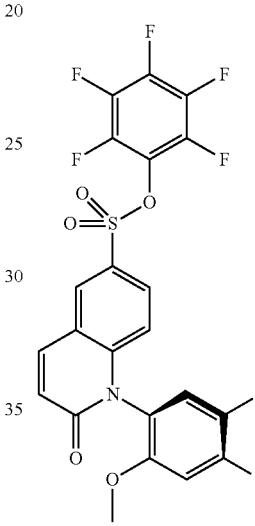
NaOt-pentoxide
THF, 0° C.
STEP 5
+
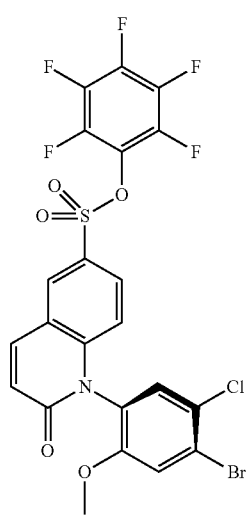
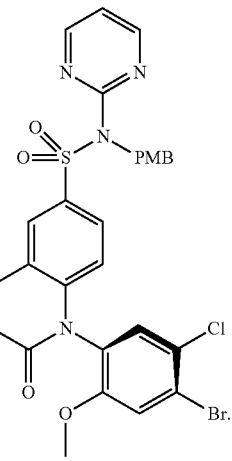
Step 1: (E)-3-(5-(BENZYLTHIO)-2-((4-BROMO-5-CHLORO-2-METHOXYPHENYL)AMINO)PHENYL)ACRYLATE
To a solution of ethyl (E)-3-(2-amino-5-(benzylthio)phenyl)acrylate (175 g, 555.0 mmol) and 1-bromo-2-chloro-4-iodo-5-methoxybenzene (231.3 g, 666.2, mmol) in toluene (1.5 L) was added cesium carbonate (357.5 g, 1100 mmol) and the mixture was degassed with nitrogen for 20 mins.

tris(dibenzylideneacetone)dipalladium(0) (12.5 g, 13.0 mmol) and XantPhos (15.8 g, 27.2 mmol) were added to the reaction mixture and the mixture was heated at 110° C. for 5 h. The reaction mixture was allowed to cool to room temperature, diluted with dichloromethane (1.0 L) and filtered through CELITE. The filtrate was concentrated under reduced pressure to obtain the Initial product which was purified by stirring with 5% ethyl acetate in hexane (1.5 L) for 30 min and filtered to obtain ethyl (E)-3-(5-(benzylthio)-2-((4-bromo-5-chloro-2-methoxyphenyl)amino)phenyl)acrylate (290 g, 85% yield) as yellow solid. m/z (ESI) 532.2 (M+H)$^+$.

Step 2: 6-(BENZYLTHIO)-1-(4-BROMO-5-CHLORO-2-METHOXYPHENYL)QUINOLIN-2(1H)-ONE To a solution of ethyl (E)-3-(5-(benzylthio)-2-((4-bromo-5-chloro-2-methoxyphenyl)amino)phenyl)acrylate (300.0 g, 5630.0 mmol) in methanol (3.0 L) was added tri(n-butyl) phosphine (50% solution in ethyl acetate, 56.2 mL, 1126 mmol) and the reaction mixture was heated at 70° C. for 5 h. The reaction mixture was allowed to cool to room temperature, concentrated under reduced pressure to obtain the Initial product which was purified by stirring with 5% ethyl acetate in hexane (1.0 mL) and filtered to obtain 6-(benzylthio)-1-(4-bromo-5-chloro-2-methoxyphenyl)quinolin-2(1H)-one (210.0 g, 76.6%) as an off white solid, m/z (ESI) 486.0 (M+H)$^+$.

Step 3: PERFLUOROPHENYL 1-(4-BROMO-5-FLUORO-2-METHOXYPHENYL)-2-OXO-1,2-DIHYDROQUINOLINE-6-SULFONATE To a solution of 6-(benzylthio)-1-(4-bromo-5-chloro-2-methoxyphenyl)quinolin-2(1H)-one (400.0 g, 824.9 mmol) in acetonitrile (2.5 L) and THF (2.5 L) were added acetic acid (1.0 L) and water (700 mL). The resulting mixture was cooled to 0° C. and 1,3-dichloro-5,5-dimethylimidazolidine-2,4-dione (292 g, 1484.8 mmol) was added portionwise over 30 min keeping the internal temperature below 5° C. The resulting suspension was stirred at 0° C. under nitrogen for 45 min. Then a solution of pentafluorophenol (197.4 g, 1072.3 mmol) in acetonitrile (500 mL) was added over 5 min followed by triethylamine (477 mL, 3299 mmol) over 30 min keeping the internal temperature below 5° C. The mixture was continued to be stirred at 0° C. for 50 min. Water (4.0 L) was added and extracted with ethyl acetate (3×2.0 L). The organic layer was washed with brine (2.0 L), dried over sodium sulfate, fdtered and concentrated under reduced pressure to obtain the crude which was purified by stirring with isopropyl alcohol and hexane (1:1, 2.0 L) and filtered to obtain perfluorophenyl 1-(4-bromo-5-fluoro-2-methoxyphenyl)-2-oxo-1,2-dihydro quinoline-6-sulfonate (360 g, 72%) as a white solid. m/z (ESI) 610.6 (M+H)$^+$.

Step 4: (P)-PERFLUOROPHENYL 1-(4-BROMO-5-FLUORO-2-METHOXYPHENYL)-2-OXO-1,2-DIHYDRO QUINOLINE-6-SULFONATE & (M)-PERFLUOROPHENYL 1-(4-BROMO-5-FLUORO-2-METHOXYPHENYL)-2-OXO-1,2-DIHYDRO QUINOLINE-6-SULFONATE Perfluorophenyl 1-(4-bromo-5-fluoro-2-methoxyphenyl)-2-oxo-1,2-dihydro quinoline-6-sulfonate (156 g, 255 mmol) was purified via chiral SFC chromatography ((S,S) Whelk-O, 45% isopropanol) to afford (P)-perfluorophenyl 1-(4-bromo-5-chloro-2-methoxyphenyl)-2-oxo-1,2-dihydroquinoline-6-sulfonate (72.66 g, 93% yield) and (M)-perfluorophenyl 1-(4-bromo-5-chloro-2-methoxyphenyl)-2-oxo-1,2-dihydroquinoline-6-sulfonate (76.13 g, 98% yield) as white solids, m/z (ESI) 610.6 (M+H)$^+$.

Step 5: (P)-1-(4-BROMO-5-CHLORO-2-METHOXYPHENYL)-N-(4-METHOXYBENZYL)-2-OXO-N-(PYRIMIDIN-2-YL)-1,2-DIHYDROQUINOLINE-6-SULFONAMIDE N-(4-Methoxybenzyl)pyrimidin-2-amine (9.72 g, 45.1 mmol) and (P)-perfluorophenyl 1-(4-bromo-5-chloro-2-methoxyphenyl)-2-oxo-1,2-dihydroquinoline-6-sulfonate (25.06 g, 41.0 mmol) were added to a 500-mL flask. The flask was flushed with N$_2$ stream then tetrahydrofuran (136 mL) was added and the reaction was cooled to 2° C. under N$_2$. Sodium tert-pentoxide (30% solution in THF, 197 mL, 492 mmol) was added over 30 min via addition funnel maintaining internal temperature around 5° C., and the pale yellow solution turned orange upon the addition. The reaction was stirred for 30 min in the ice bath. The reaction was then quenched with sat. aq. NH$_4$Cl and diluted with EtOAc. The layers were separated and the water layer was extracted twice with EtOAc. The combined organics were dried with Na$_2$SO$_4$, filtered, and evaporated. IPA was added and a white precipitate crashed out. The solvent was evaporated to approximately 100 mL then additional IPA was added and the reaction was stirred for 18 h. The slurry was filtered and the solid was washed with IPA. The solid was taken up in 150 mL of MTBE and heated at 40° C. for 2 hours. The slurry was cooled to ambient temperature and filtered to obtain a white solid. The impure material was dissolved in 500 mL of 10% MeOH/DCM and stirred with 500 mL of sat. aq. NaHCO$_3$ for 30 minutes. The layers were separated and the water layer was extracted twice with 10% MeOH/DCM. The combined organics layers were dried and evaporated. The filtrates from IPA and MTBE titrations were combined and loaded onto 25 g silica cartridge and purified by column chromatography (RediSep Rf Gold 120 g column, gradient elution 10% to 50% 3:1 EtOAc:EtOH in heptane with 10% dichloromethane additive). The pure product of the column and the product from the NaHCO$_3$ extraction were combined to afford (P)-1-(4-bromo-5-chloro-2-methoxyphenyl)-N-(4-methoxybenzyl)-2-oxo-N-(pyrimidin-2-yl)-1,2-dihydroquinoline-6-sulfonamide (16.94 g, 26.4 mmol, 64% yield) as a pale yellow foam. $^1$H NMR (500 MHz, DMSO-d$_6$) δ ppm 8.58 (d, J=4.9 Hz, 2H), 8.39 (d, J=2.1 Hz, 1H), 8.13 (d, J=9.6 Hz, 1H), 7.96 (dd, J=9.1, 2.3 Hz, 1H), 7.76 (s, 1H), 7.73 (s, 1H), 7.29 (d, J=8.8 Hz, 2H), 7.13 (t, J=4.9 Hz, 1H), 6.87 (d, J=8.8 Hz, 2H), 6.78 (d, J=9.6 Hz, 1H), 6.74 (d, J=9.1 Hz, 1H), 5.36 (s, 2H), 3.72 (s, 3H), 3.71 (s, 3H). m/z (ESI, positive ion) 642.8 (M+H)$^+$.

Intermediate J: N-(4-METHOXYBENZYL)PYRIDAZIN-3-AMINE

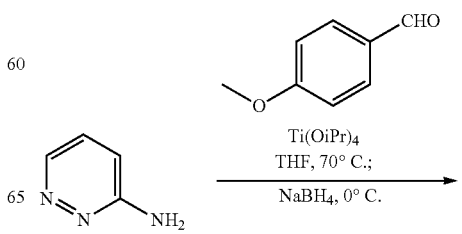

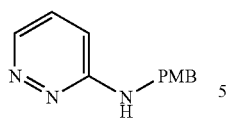

To a 25-mL round-bottomed flask was added 4-methoxybenzaldehyde (1.00 g, 7.34 mmol) and pyridazin-3-amine (0.838 g, 8.81 mmol) in tetrahydrofuran (10 mL). Then, titanium(IV) isopropoxide (6.46 mL, 22.03 mmol) was added, and the reaction mixture was stirred at 70° C. for 16 h. Then the reaction mixture was cooled to 0° C., and sodium borohydride (0.556 g, 14.69 mmol) was added portionwise. The reaction mixture was then stirred for 2 h at 0° C. The reaction mixture was diluted with water (20 mL) and filtered. The filtrate was then extracted with EtOAc (3×50 mL). The organic extract was washed with sat. aq. NaCl (30 mL) and dried over $Na_2SO_4$. The solution was filtered and concentrated in vacuo to give the Initial product as a orange oil. The Initial product was absorbed onto a plug of silica gel and purified by chromatography through a Redi-Sep prepacked silica gel column (40 g), eluting with 0% to 15% MeOH in $CH_2Cl_2$ to provide N-(4-methoxybenzyl) pyridazin-3-amine (0.680 g, 3.16 mmol, 43.0% yield) as yellow solid. m/z (ESI, positive ion) 216.2 (M+H)$^+$.

Intermediate K: (P)-1-(4-BROMO-5-FLUORO-2-METHOXYPHENYL)-N-(4-METHOXYBENZYL)-2-OXO-N-(PYRIDAZIN-3-YL)-1,2-DIHYDROQUINOLINE-6-SULFONAMIDE

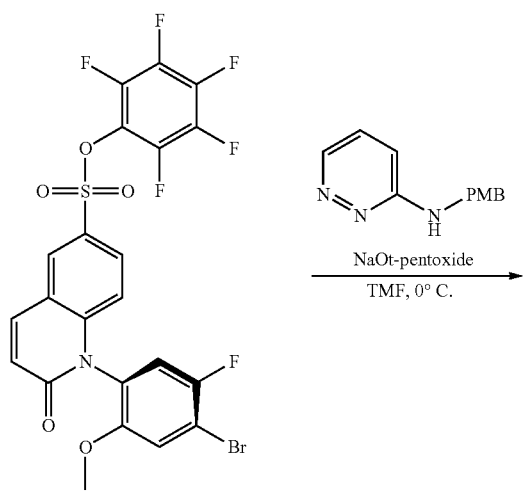

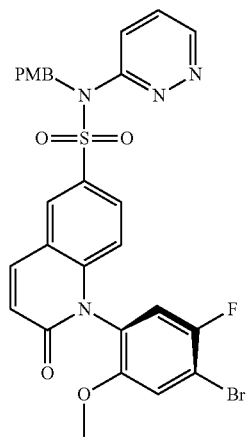

A 100-mL recovery flask containing perfluorophenyl (P)-1-(4-bromo-5-fluoro-2-methoxyphenyl)-2-oxo-1,2-dihydroquinoline-6-sulfonate (5.00 g, 8.41 mmol) and N-(4-methoxybenzyl)pyridazin-3-amine (1.902 g, 8.83 mmol) was flushed with nitrogen and subsequently charged with THF (34 mL). The solution was cooled to 0° C., and sodium tert-pentoxide (8.4 mL, 11.78 mmol, 1.4 M in THF) was added slowly. The pale yellow solution was stirred at 0° C. for 15 min, and then volatiles were removed in vacuo. Water was added to cause formation of a white precipitate. This precipitate was isolated, dissolved in dichloromethane, and treated with heptane to cause formation of (P)-1-(4-bromo-5-fluoro-2-methoxyphenyl)-N-(4-methoxybenzyl)-2-oxo-N-(pyridazin-3-yl)-1,2-dihydroquinoline-6-sulfonamide (4.20 g, 6.71 mmol, 80% yield) as a white precipitate. m/z (ESI, positive ion) 625.0 (M+H)$^+$.

Intermediate L: PERFLUOROPHENYL (P)-1-(4-BROMO-2-METHOXY-5-METHYLPHENYL)-2-OXO-1,2-DIHYDROQUINOLINE-6-SULFONATE

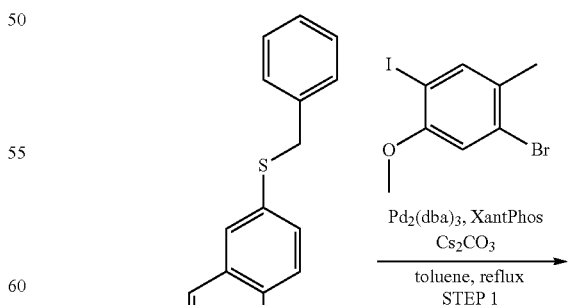

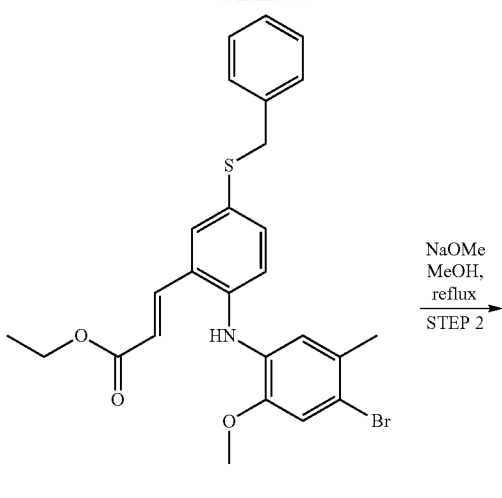

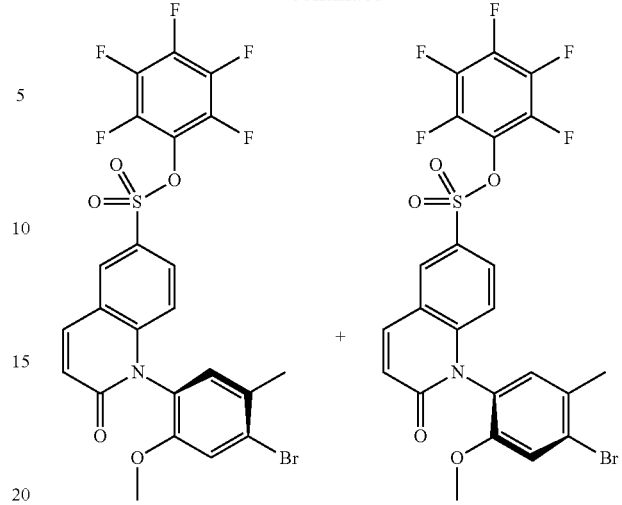

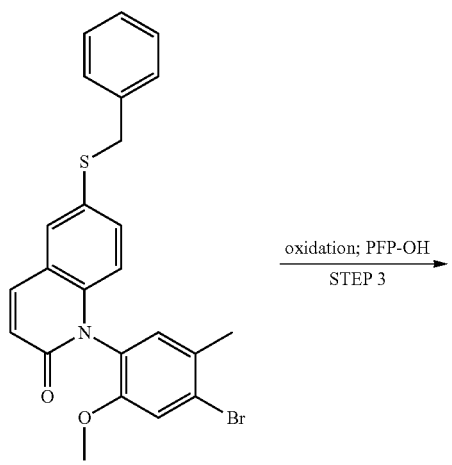

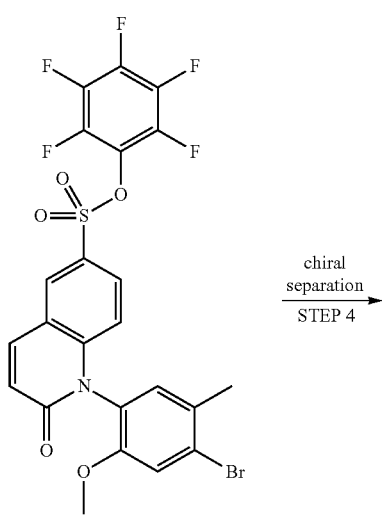

Step 1: (E)-ETHYL 3-(5-(BENZYLTHIO)-2-((4-BROMO-2-METHOXY-5-METHYLPHENYL)AMINO)PHENYL)ACRYLATE A round-bottom flask was charged with (E)-ethyl 3-(2-amino-5-(benzylthio)phenyl)acrylate (4.729 g, 15.09 mmol), 1-bromo-4-iodo-5-methoxy-2-methylbenzene (5.18 g, 15.84 mmol), XantPhos (0.437 g, 0.754 mmol), tris(dibenzylideneacetone)dipalladium(0) (0.345 g, 0.377 mmol), cesium carbonate (9.83 g, 30.2 mmol), and toluene (30 mL) were added. A reflux condenser was attached, and the mixture was heated to reflux. After 4 h, additional portions of tris(dibenzylideneacetone)dipalladium(0) (172 mg) and XantPhos (213 mg) were added. After 2 h, additional portions of cesium carbonate (ca. 2 g) and 1-bromo-4-iodo-5-methoxy-2-methylbenzene (600 mg) were added. Following an additional 30 min of reflux, the mixture was cooled and filtered through CELITE. The filter pad was washed with EtOAc (3×). The filtrate was concentrated. The residue was concentrated from MeOH, and taken up in MeOH. The resulting suspension was heated to boiling, then sonicated and cooled to RT. The mixture was filtered, and the collected solid was washed with MeOH (3×) and dried under a stream of $N_2$ for 48 h to give (E)-ethyl 3-(5-(benzylthio)-2-((4-bromo-2-methoxy-5-methylphenyl)amino)phenyl)acrylate (5.21 g, 10.17 mmol, 67.4% yield) as a bright-yellow solid. $^1$H NMR (400 MHz, DMSO-$d_6$) δ ppm 7.75 (d, J=15.9 Hz, 1H), 7.66 (d, J=2.1 Hz, 1H), 7.42 (s, 1H), 7.37-7.20 (m, 6H), 7.14 (s, 1H), 6.85 (d, J=8.5 Hz, 1H), 6.62 (s, 1H), 6.51 (d, J=15.9 Hz, 1H), 4.23 (s, 2H), 4.15 (q, J=7.0 Hz, 2H), 3.78 (s, 3H), 2.14 (s, 2H), 1.23 (t, J=7.1 Hz, 3H). m/z (ESI) 512.2 (M+H)$^+$.

Step 2: 6-(BENZYLTHIO)-1-(4-BROMO-2-METHOXY-5-METHYLPHENYL)QUINOLIN-2(1H)-ONE A round-bottom flask was charged with (E)-ethyl 3-(5-(benzylthio)-2-((4-bromo-2-methoxy-5-methylphenyl)amino)phenyl)acrylate (5.12 g, 9.99 mmol) and MeOH (50.0 mL) to give a yellow suspension. Sodium methoxide (25 wt % in MeOH, 0.432 mL, 1.998 mmol) was added. A reflux condenser was attached, and the flask was lowered into a 70° C. heating bath. After 1 h, additional portions of MeOH (25 mL) and sodium methoxide solution (ca. 0.85 mL) were added in sequence. After 7 h, the mixture was cooled and concentrated under vacuum. The residue was purified by chromatography on silica gel (80-g Redi-Sep column, 25-g silica gel loading column, loaded as a solution in MeOH-DCM, then eluted with 25-75% EtOAc/heptane containing 10% DCM). The fractions containing product were combined and concentrated to give 6-(benzylthio)-1-(4-bromo-2-methoxy-5-methylphenyl)quinolin-2(1H)-one (4.233 g, 9.08 mmol, 91% yield) as a tan solid. m/z (ESI) 466.1 (M+H)$^+$.

Step 3: PERFLUOROPHENYL 1-(4-BROMO-2-METHOXY-5-METHYLPHENYL)-2-OXO-1,2-DIHYDROQUINOLINE-6-SULFONATE A round-bottom flask was charged with 6-(benzylthio)-1-(4-bromo-2-methoxy-5-methylphenyl)quinolin-2(1H)-one (4.23 g, 9.07 mmol), DCM (71.1 mL), acetic acid (2.67 mL), and water (1.778 mL) to give clear, light-brown solution. The flask was cooled in an ice-water bath for 10 min, then 1,3-dichloro-5,5-dimethylimidazolidine-2,4-dione (3.66 g, 18.59 mmol) was added in one portion. After 40 min, an additional portion of oxidant (850 mg) was added. The mixture was stirred for another 20 min, then 2,3,4,5,6-pentafluorophenol (2.504 g, 13.60 mmol) and triethylamine (5.06 mL, 36.3 mmol) were added in sequence. After 20 min, the mixture was diluted with water. The layers were separated, and the aq. layer was extracted with DCM. The combined organic extracts were dried over sodium sulfate, filtered, and concentrated. The residue was purified by chromatography on silica gel (80-g Redi-Sep Gold column, 25-g silica gel loading column, 10-60% EtOAc/Heptane with 10% DCM) to afford perfluorophenyl 1-(4-bromo-2-methoxy-5-methylphenyl)-2-oxo-1,2-dihydroquinoline-6-sulfonate (3.37 g, 5.71 mmol, 63% yield). m/z (ESI) 590.0 (M+H)$^+$.

Step 4: PERFLUOROPHENYL (P)-1-(4-BROMO-2-METHOXY-5-METHYLPHENYL)-2-OXO-1,2-DIHYDROQUINOLINE-6-SULFONATE Perfluorophenyl 1-(4-bromo-2-methoxy-5-methylphenyl)-2-oxo-1,2-dihydroquinoline-6-sulfonate (22.896 g, 38.79 mmol) was purified using a (S,S) Whelk-O, 5×25 cm column. The mobile phase was run under isocratic conditions; supercritical $CO_2$ with 50% dichloromethane; flow rate: 350 mL/min. The first eluting peak was assigned perfluorophenyl (P)-1-(4-bromo-2-methoxy-5-methylphenyl)-2-oxo-1,2-dihydroquinoline-6-sulfonate (10.425 g). The second eluting peak was assigned perfluorophenyl (M)-1-(4-bromo-2-methoxy-5-methylphenyl)-2-oxo-1,2-dihydroquinoline-6-sulfonate (10.76 g). Data for peak 1: m/z (ESI) 590.0 (M+H)$^+$. Data for peak 2: m/z (ESI) 590.0 (M+H)$^+$.

Intermediate M: N-(2,4-DIMETHOXYBENZYL)ISOXAZOL-3-AMINE

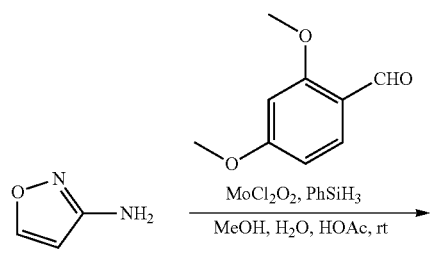

To a solution of isoxazol-3-amine (100 g, 1190 mmol) in mixture of methanol (6500 mL), acetic acid (67.0 mL), and water (100 mL) was added 2,4-dimethoxybenzaldehyde (223 g, 1340 mmol) at ambient temperature under nitrogen atmosphere. The reaction mixture was stirred for 15 min at ambient temperature and molybdenum dichloride dioxide (11.82 g, 59.5 mmol) followed by phenylsilane (218 ml, 1784 mmol) were added. The reaction mixture was stirred at ambient temperature for 16 h. The reaction was then concentrated under reduced pressure. The residue was diluted with dichloromethane (5000 mL), washed with sat. aq. $NaHCO_3$ (2×2000 mL), dried over $Na_2SO_4$, filtered, and concentrated under reduced pressure to afford an orange solid. The solid was purified by chromatography (60-120 mesh silica, gradient elution 0-30% EtOAc:hexane) to afford N-(2,4-dimethoxybenzyl)isoxazol-3-amine (170 g, 726 mmol, 61% yield).

Intermediate N: (P)-1-(4-BROMO-5-FLUORO-2-METHOXYPHENYL)-N-(2,4-DIMETHOXYBENZYL)-N-(ISOXAZOL-3-YL)-2-OXO-1,2-DIHYDROQUINOLINE-6-SULFONAMIDE A 250-mL round-bottom flask was sequentially charged with perfluorophenyl (P)-1-(4-bromo-5-fluoro-2-methoxyphenyl)-2-oxo-1,2-dihydroquinoline-6-sulfonate (2.00 g, 3.37 mmol), tetrahydrofuran (16.8 mL), and N-(2,4-dimethoxybenzyl)isoxazol-3-amine (0.828 g, 3.53 mmol), and the resulting solution was cooled to 0° C. Lithium bis(trimethylsilyl)amide (3.70 mL, 3.70 mmol, 1.0 M in THF) was then added dropwise to the stirred reaction mixture. After 15 min, aqueous HCl solution (1.0 M, 100 mL) and EtOAc (100 mL) were added to the reaction mixture, which was subsequently allowed to warm to ambient temperature. The layers were separated, and the aqueous layer was extracted with EtOAc (2×100 mL). The combined organic layers were then washed with brine (100 mL), dried over anhydrous sodium sulfate, filtered, and concentrated under reduced pressure. The residue was then purified by flash column chromatography (100 g Biotage column, gradient elution, 0-100% EtOAc:heptane with 10% $CH_2Cl_2$ as co-eluent) to afford (P)-1-(4-bromo-5-fluoro-2-methoxyphenyl)-N-(2,4-dimethoxybenzyl)-N-(isoxazol-3-yl)-2-oxo-1,2-dihydroquinoline-6-sulfonamide (1.50 g, 2.33 mmol, 69% yield) as a white solid. m/z (ESI, positive ion) 644.0 $(M+H)^+$.

Intermediate O: RACEMIC PERFLUOROPHENYL 1-(4-BROMO-5-FLUORO-2-METHOXYPHENYL)-2-OXO-1,2-DIHYDRO QUINOLINE-6-SULFONATE

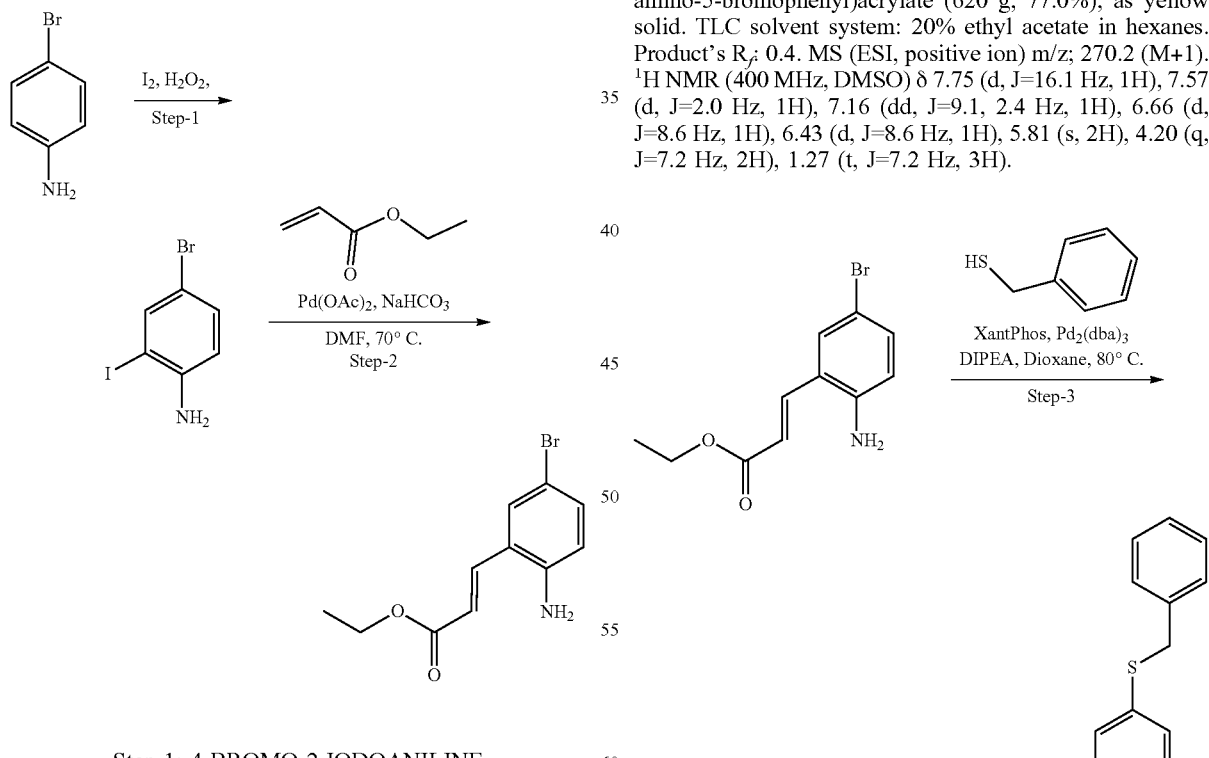

Step-1: 4-BROMO-2-IODOANILINE

To a solution of 4-bromo-aniline (500 g, 2.90 mol, 2.0 equiv, Saibain Chem) in cyclohexane (2.5 L) was added iodine (368 g, 1.45 mol, 1.0 equiv, Qualigens) and the mixture was heated at 50° C. After 30 min, the reaction mixture became homogenous. 30% aqueous hydrogen peroxide solution (250 mL, Spectrochem) was added to the reaction mixture. The reaction was heated for 4 h at 50° C. The reaction was cooled to room temperature, diluted with ethyl acetate (5.0 L) and washed with aqueous sodium-sulphite (2.5 Kg in 4.0 L) solution. The organic layer was washed with water (3.0 L) and brine (3.0 L) dried over magnesium sulfate, filtered and concentrated under reduced pressure to obtain the Initial product which was purified by column chromatography (silica gel; mesh size 60-120, elution 0-20% ethyl acetate and hexanes) to get 4-bromo-2-iodoaniline (650 g, 75.0%), as off white solid. TLC solvent system: 100% hexanes. Product's $R_f$: 0.6. MS (ESI, positive ion) m/z: 297.0 (M+1). $^1$H NMR (400 MHz, CDCl$_3$) δ 7.72 (d, J=2.5 Hz, 1H), 7.23 (dd, J=8.4, 2.1 Hz, 1H), 6.62 (d, J=8.3 Hz, 1H), 4.09 (s, 2H).

Step-2: ETHYL (E)-3-(2-AMINO-5-BROMOPHENYL)ACRYLATE

To a solution of 4-bromo-2-iodoaniline (750 g, 2.51 mol, 1.0 equiv) in DMF (5.0 L) was added ethyl acrylate (277 g, 2.76 mol, 1.1 equiv, Avra) and sodium bicarbonate (680 g, 6.29 mol, 2.5 equiv). The reaction mixture was degassed with nitrogen for 20 min followed by the addition of palladium acetate (28.8 g, 128.27 mmol, 0.05 equiv, Hindustan Platinum). The reaction mixture was heated at 70° C. for 3 h. The reaction was filtered through CELITE® and the CELITE® bed was washed with ethyl acetate (2×500 mL). The filtrate was concentrated under reduced pressure to obtain the crude residue which was purified by column chromatography (silica gel; mesh size 60-120, elution 0-20% ethyl acetate in hexanes) to obtain (E)-ethyl 3-(2-amino-5-bromophenyl)acrylate (620 g, 77.0%), as yellow solid. TLC solvent system: 20% ethyl acetate in hexanes. Product's $R_f$: 0.4. MS (ESI, positive ion) m/z: 270.2 (M+1). $^1$H NMR (400 MHz, DMSO) δ 7.75 (d, J=16.1 Hz, 1H), 7.57 (d, J=2.0 Hz, 1H), 7.16 (dd, J=9.1, 2.4 Hz, 1H), 6.66 (d, J=8.6 Hz, 1H), 6.43 (d, J=8.6 Hz, 1H), 5.81 (s, 2H), 4.20 (q, J=7.2 Hz, 2H), 1.27 (t, J=7.2 Hz, 3H).

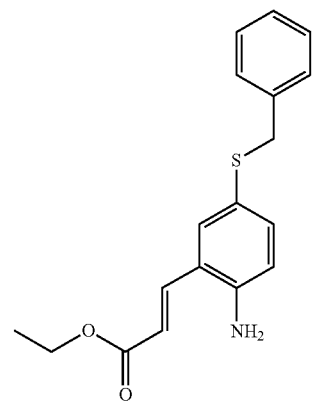

Step-3: ETHYL (E)-3-(2-AMINO-5-(BENZYL-THIO)PHENYL)ACRYLATE

To a solution of (E)-ethyl 3-(2-amino-5-bromophenyl) acrylate (620 g, 2.29 mol, 1.0 equiv) in 1,4-dioxane (4.0 L) was added DIPEA (1.26 L, 8.88 mol, 3.9 equiv, GLR) and degassed with nitrogen for 20 mins. XantPhos (92.9 g, 106 mmol, 0.05 equiv, GLR), and tris(dibenzylideneacetone) dipalladium (84 g, 91.0 mmol, 0.04 equiv, Hindustan Platinum) was added to the reaction mixture. The mixture was purged with nitrogen and heated to 80° C. for 30 mins. The reaction was cooled to RT and benzyl mercaptan (455.5 g, 3.67 mol, 1.6 equiv, Alfa Aesar) was added and the reaction was heated at 80° C. for an additional 4 h. The reaction was cooled to room temperature and diluted with ethyl acetate (4.0 L). The mixture was filtered through CELITE® and the CELITE® bed was washed with ethyl acetate (2×1.0 L). The filtrate was concentrated under reduced pressure to obtain the Initial product which was purified by chromatography (silica gel; mesh size 60-120, elution 0-40% ethyl acetate and petroleum ether) to obtain (E)-ethyl 3-(2-amino-5-(benzylthio)phenyl)acrylate (520 g, 72.0%), as yellow solid. TLC solvent system: 30% ethyl acetate in hexanes. Product's $R_f$: 0.4. MS (ESI, positive ion) m/z; 314.1 (M+1). $^1$H NMR (400 MHz, DMSO) δ 7.79 (d, J=16.1 Hz, 1H), 7.37 (d, J=2.0 Hz, 1H), 7.25-7.17 (m, 5H) 7.10 (dd, J=8.4, 2.1 Hz, 1H), 6.61 (d, J=8.3 Hz, 1H), 6.32 (d, J=15.2 Hz, 1H), 5.75 (s, 2H), 4.20 (q, J=7.2 Hz, 2H), 4.01 (s, 2H), 1.27 (t, J=7.2 Hz, 3H).

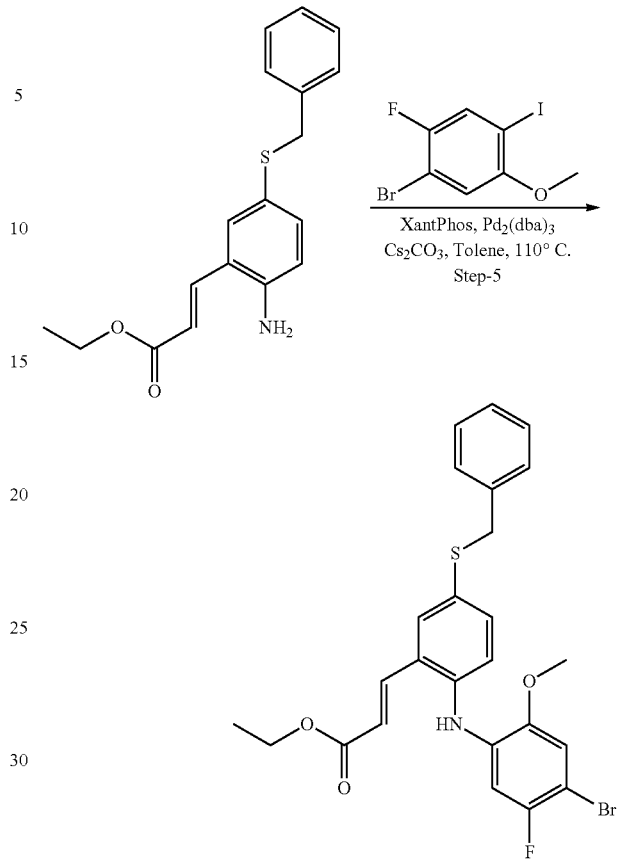

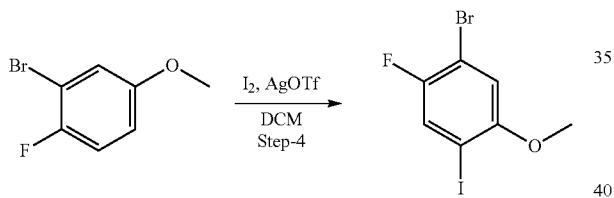

Step-4: 1-BROMO-2-FLUORO-4-IODO-5-METHOXYBENZENE

To a solution of 2-bromo-1-fluoro-4-methoxybenzene (500.0 g, 2.44 mol, 1.0 equiv) in DCM (5.0 L) was added silver trifluoromethane sulfonate (686.0 g, 2.68 mol, 1.1 equiv, Angene) and the reaction mixture was stirred for 20 mins. Iodine (678.0 g, 2.68 mol, 1.1 equiv) was added to the reaction and the mixture was stirred at room temperature for 16 h. The mixture was diluted with DCM (3.0 L) and filtered through CELITE®. The CELITE bed was washed with DCM (2×1.0 L) and the filtrate was washed with 20% aqueous sodium thiosulfate (3.0 L) and saturated aqueous sodium bicarbonate solution (3.0 L). The organic layer was dried over sodium sulfate, filtered and concentrated under reduced pressure to obtain the Initial product which was purified by chromatography (silica gel; mesh size 60-120, elution 0-5% ethyl acetate and petroleum ether) to get 1-bromo-2-fluoro-4-iodo-5-methoxybenzene (720 g, 87%), as off-white solid. TLC solvent system: 100% hexanes. Product's $R_f$: 0.6. MS (ESI, positive ion) m/z: 331.0 (M+1). $^1$H NMR (400 MHz, CDCl$_3$) δ 7.55 (d, J=7.2 Hz, 1H), 6.95 (d, J=5.6 Hz, 1H), 3.89 (s, 3H).

Step-5: ETHYL (E)-3-(5-(BENZYLTHIO)-2-((4-BROMO-5-FLUORO-2-METHOXYPHENYL)AMINO)PHENYL) ACRYLATE To a solution of (E)-ethyl 3-(2-amino-5-(benzylthio)phenyl)acrylate (300 g, 958.1 mmol, 1.0 equiv) and 1-bromo-2-fluoro-4-iodo-5-methoxybenzene (348.0 g, 1051.6 mmol, 1.1 equiv) in toluene (2.5 L) was added Cs$_2$CO$_3$ (468 g, 1436.3 mmol, 1.5 equiv, Spectrochem) and the mixture was degassed with nitrogen for 20 mins. Pd$_2$(dba)$_3$ (35 g, 38.2 mmol, 0.04 equiv, Hindustan Platinum) and XantPhos (44.6 g, 76.4 mmol, 0.08 equiv, GLR) were added to the reaction mixture and the mixture was heated at 110° C. for 5 h. The reaction mixture was allowed to cool to room temperature, diluted with dichloromethane (2.0 L) and filtered through CELITE® The filtrate was concentrated under reduced pressure to obtain the Initial product which was purified by stirring with 5% ethyl acetate in hexanes (3.0 L) for 30 min and filtered to obtain (E)-ethyl 3-(5-(benzylthio)-2-((4-bromo-5-fluoro-2-methoxyphenyl)amino)phenyl)acrylate (350 g, 71%) as yellow solid. TLC solvent system: 30% ethyl acetate in hexanes. Product's $R_f$: 0.5. MS (ESI, positive ion) m/z; 516.2 (M+1). $^1$H NMR (400 MHz, DMSO) δ 7.73-7.61 (m, 3H), 7.34-7.15 (m, 6H), 7.02 (d, J=11.4 Hz, 1H), 6.60 (d, J=21.2 Hz, 1H), 6.33 (d, J=14.1 Hz, 1H), 4.26 (s, 2H), 4.16-4.09 (m, 2H), 3.81 (s, 3H), 1.22 (t, J=7.2 Hz, 3H). Note: NH proton not observed.

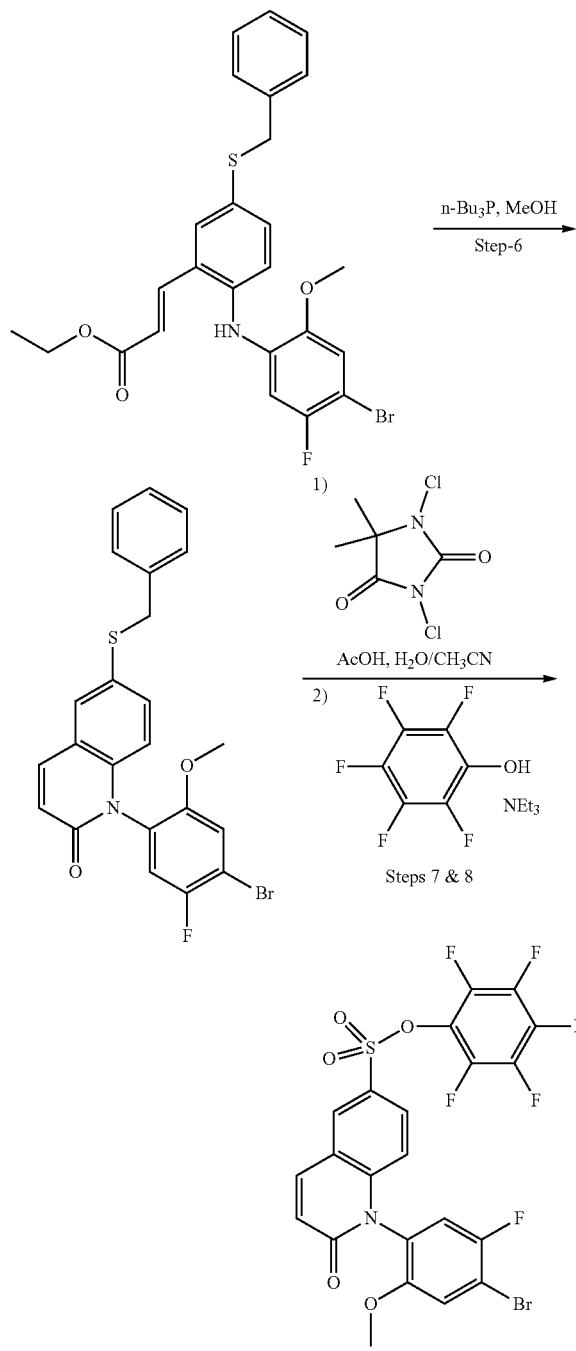

Step-6: 6-(BENZYLTHIO)-1-(4-BROMO-5-FLUORO-2-METHOXYPHENYL)QUINOLIN-2(1H)-ONE

To a solution of (E)-ethyl 3-(5-(benzylthio)-2-((4-bromo-5-fluoro-2-methoxyphenyl)amino)phenyl)acrylate (250.0 g, 484.0 mmol, 1.0 equiv) in methanol (2.5 L) was added tri(n-butyl)phosphine (50% solution in ethyl acetate, 48.9 mL, 96.8 mmol, 0.2 equiv, Spectrochem) and the reaction mixture was heated at 70° C. for 5 h. The reaction mixture was allowed to cool to rt, concentrated under reduced pressure to obtain the Initial product which was purified by stirring with 5% ethyl acetate in hexanes (1.0 mL) and filtered to obtain 6-(benzylthio)-1-(4-bromo-5-fluoro-2-methoxyphenyl)quinolin-2(1H)-one (201.0 g, 88%) as off white solid. TLC solvent system: 30% ethyl acetate in hexanes. Product's $R_f$: 0.3. MS (ESI, positive ion) m/z; 470.0 (M+1). $^1$H NMR (400 MHz, DMSO) δ 7.92 (d, J=9.1 Hz, 1H), 7.79 (d, J=1.7 Hz, 1H), 7.65 (d, J=6.1 Hz, 1H), 7.57 (d, J=8.8 Hz, 1H), 7.40-7.22 (m, 6H), 6.68 (d, J=9.6 Hz, 1H), 6.56 (d, J=8.8 Hz, 1H), 4.24 (s, 2H), 3.69 (s, 3H).

Steps 7 & 8: PERFLUOROPHENYL 1-(4-BROMO-5-FLUORO-2-METHOXYPHENYL)-2-OXO-1,2-DIHYDRO QUINOLINE-6-SULFONATE To a solution of 6-(benzylthio)-1-(4-bromo-5-fluoro-2-methoxyphenyl)quinolin-2(1H)-one (250.0 g, 531.5 mmol, 1.0 equiv) in acetonitrile (2.5 L) were added acetic acid (200 mL) and water (130 mL). The resulting mixture was cooled to 0° C. and 1,3-dichloro-5,5-dimethylimidazolidine-2,4-dione (188.5 g, 956.7 mmol, 1.8 equiv, Aldrich) was added portion-wise over 20 min keeping the internal temperature below 5° C. The resulting suspension was stirred at 0-5° C. under nitrogen for 45 min. Then a solution of pentafluorophenol (127.2 g, 690.95 mmol, 1.3 equiv, Apollo) in acetonitrile (200 mL) was added over 5 min followed by NEt$_3$ (307.7 mL, 2.12 mol, 4.0 equiv) over 20 min keeping the internal temperature below 5° C. The mixture was continued to be stirred at 0-5° C. for 30 min. Water (4.0 L) was added and extracted with ethyl acetate (2×2.0 L). The organic layer was washed with brine (1.0 L), dried over sodium sulfate, filtered and concentrated under reduced pressure to obtain the crude which was purified by stirring with isopropyl alcohol:hexanes (1:1, 1.0 L) and filtered to obtain racemic perfluorophenyl 1-(4-bromo-5-fluoro-2-methoxyphenyl)-2-oxo-1,2-dihydroquinoline-6-sulfonate (190 g, 60%) as white solid. TLC solvent system: 30% ethyl acetate in petroleum ether, Product's $R_f$: 0.4. MS (ESI, positive ion) m/z; 594.2 (M+1). $^1$H-NMR (400 MHz, DMSO) δ 8.60 (d, J=2.0 Hz, 1H), 8.26 (d, J=9.8 Hz, 1H), 7.95 (dd, J=2.2, 9.1 Hz, 1H), 7.70 (t, J=8.6 Hz, 2H), 6.95-6.88 (m, 2H), 3.72 (s, 3H).

Intermediate P: (P)-1-(4-BROMO-5-FLUORO-2-METHOXYPHENYL)-N-(ISOXAZOL-3-YL)-N-(4-METHOXYBENZYL)-2-OXO-1,2-DIHYDRO-QUINOLINE-6-SULFONAMIDE Step 1: (P)-PERFLUOROPHENYL 1-(4-BROMO-5-FLUORO-2-METHOXYPHENYL)-2-OXO-1,2-DIHYDROQUINOLINE-6-SULFONATE Racemic perfluorophenyl 1-(4-bromo-5-fluoro-2-methoxyphenyl)-2-oxo-1,2-dihydroquinoline-6-sulfonate (See Steps 7&8 of Intermediate O above, 76.90 g) was separated via Chiralcel OJ column (40% MeOH/60% CO$_2$) to give (P)-perfluorophenyl 1-(4-bromo-5-fluoro-2-methoxyphenyl)-2-oxo-1,2-dihydroquinoline-6-sulfonate and (M)-perfluorophenyl 1-(4-bromo-5-fluoro-2-methoxyphenyl)-2-oxo-1,2-dihydroquinoline-6-sulfonate as pale yellow flocculent solids. Data for peak 1: m/z (ESI) 594.0 (M+H)$^+$. Data for peak 2: m/z (ESI) 594.0 (M+H)$^+$.

Step 2: (P)-1-(4-BROMO-5-FLUORO-2-METHOXYPHENYL)-N-(ISOXAZOL-3-YL)-N-(4-METHOXYBENZYL)-2-OXO-1,2-DIHYDRO-QUINOLINE-6-SULFONAMIDE

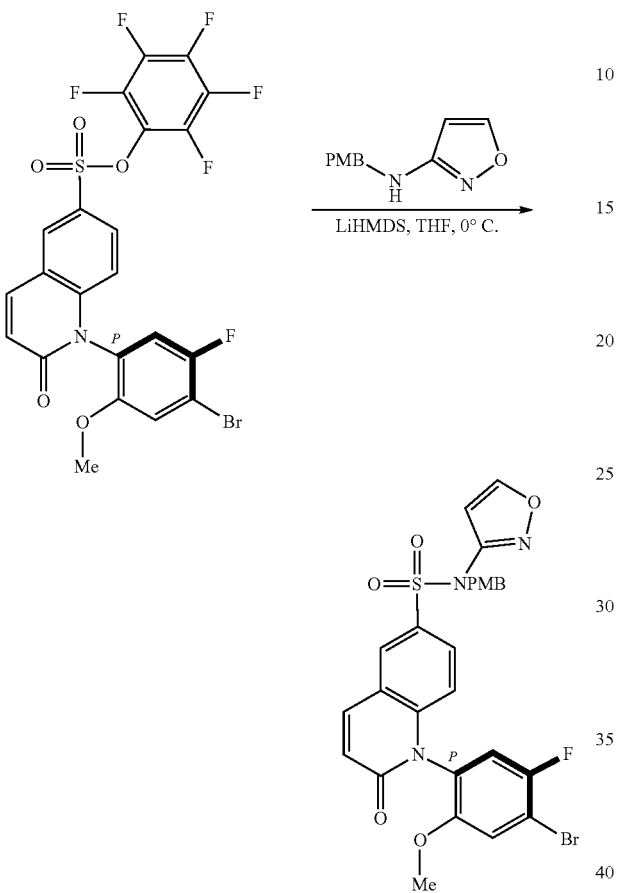

A 250-mL round-bottomed flask was charged with (P)-perfluorophenyl 1-(4-bromo-5-fluoro-2-methoxyphenyl)-2-oxo-1,2-dihydroquinoline-6-sulfonate (See Step 1 of Intermediate B1 above, 11.34 g, 19.08 mmol), and N-(4-methoxybenzyl)isoxazol-3-amine (4.09 g, 20.04 mmol), then purged with nitrogen. Tetrahydrofuran (191 mL) was introduced, and the resultant brown solution cooled to 0° C. A solution of lithium bis(trimethylsilyl)amide in THF (1.0 M, 21.0 mL, 21.0 mmol) was added dropwise via syringe to the stirred reaction mixture over 10 min. After 15 min, 1.0 N HCl (100 mL) was introduced and the resultant reaction mixture was allowed to warm to RT. The mixture was diluted with and EtOAc (100 mL) and the layers were separated, and the aqueous layer was further extracted with EtOAc (2×100 mL). The combined organic layers were then washed with brine (100 mL), dried over anhydrous sodium sulfate, filtered, and concentrated under reduced pressure. The residue was then purified by flash column chromatography (100-g Biotage column, eluent: gradient, 0 to 100% EtOAc in heptane with 10% $CH_2Cl_2$ as an additive) to afford (P)-1-(4-bromo-5-fluoro-2-methoxyphenyl)-N-(isoxazol-3-yl)-N-(4-methoxybenzyl)-2-oxo-1,2-dihydroquinoline-6-sulfonamide (9.54 g, 15.53 mmol, 81% yield) as a white amorphous solid. $^1$H NMR (400 MHz, DMSO-$d_6$) δ=8.82 (d, J=2.0 Hz, 1H), 8.38 (d, J=2.3 Hz, 1H), 8.17 (d, J=9.4 Hz, 1H), 7.76 (t, J=5.1 Hz, 1H), 7.68 (d, J=6.1 Hz, 1H), 7.63 (d, J=8.5 Hz, 1H), 7.26 (d, J=7.9 Hz, 2H), 6.91-6.78 (m, 4H), 6.74 (d, J=2.0 Hz, 1H), 4.92 (s, 2H), 3.73-3.69 (m, 6H), 3.32 (s, 1H). m/z (ESI) 615.1 (M+H)$^+$.

EXAMPLES

Example 1: (P)-1-(4-(2,2-DIMETHYLCYCLO-PROPYL)-5-FLUORO-2-METHOXYPHENYL)-N-(ISOXAZOL-3-YL)-2-OXO-1,2-DIHYDROQUI-NOLINE-6-SULFONAMIDE

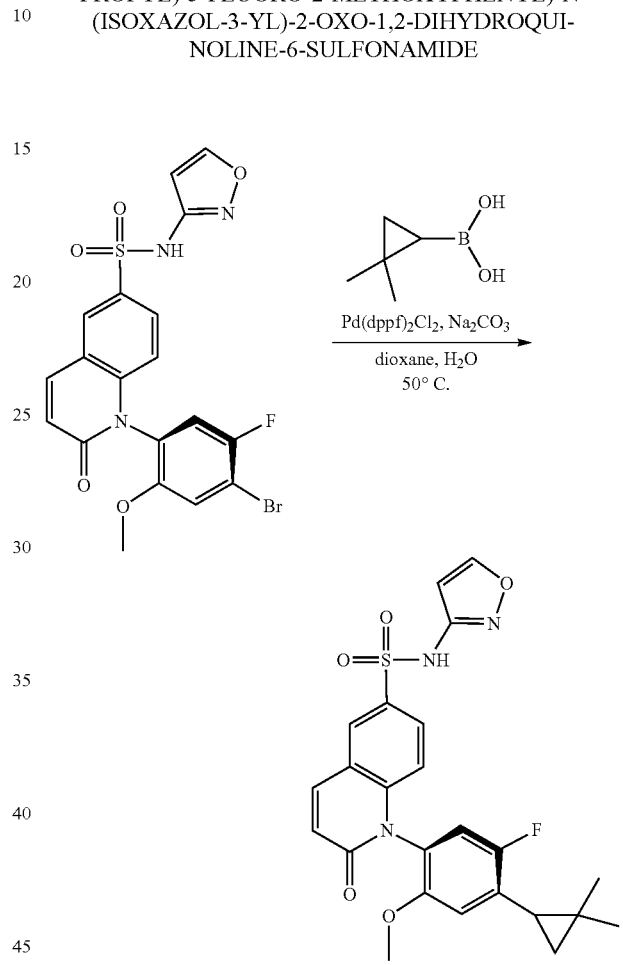

A 5-mL vial was charged with (P)-1-(4-bromo-5-fluoro-2-methoxyphenyl)-N-(isoxazol-3-yl)-2-oxo-1,2-dihydroquinoline-6-sulfonamide (150 mg, 0.303 mmol), 1,1'-bis(diphenylphosphino)ferrocene palladium(II)dichloride dichloromethane adduct (49.6 mg, 0.061 mmol), and (2,2-dimethylcyclopropyl)boronic acid (69.2 mg, 0.607 mmol). The reaction vessel was then sequentially charged with 1,4-dioxane (3 mL) and an aqueous solution of sodium carbonate (1 mL, 1.9 M) via syringe. The vial was sealed with a PTFE-lined cap, and the resultant red mixture was sparged with nitrogen for 10 min. The reaction mixture was the heated to 50° C. After 16 h, the mixture was allowed to cool to ambient temperature, and 1 M HCl was added carefully followed by EtOAc. The layers separated, and the aqueous layer was extracted with EtOAc. The combined organic layers were concentrated to dryness. The brown residue was purified by reverse phase HPLC using a XBridge Prep Shield RP18 19×100 mm column. The mobile phase was run under a gradient elution; 35-85% water/acetonitrile with 0.1% trifluoroacetic acid; flow rate: 40 mL/min. This afforded (P)-1-(4-(2,2-dimethylcyclopropyl)-5-fluoro-2-methoxyphenyl)-N-(isoxazol-3-yl)-2-oxo-1,2-dihydroquinoline-6-sulfonamide (0.029 g, 0.060 mmol, 20% yield) as a brown solid. $^1$H NMR (400 MHz, DMSO-d$_6$) δ ppm 11.65 (s, 1H), 8.74 (d, J=1.9 Hz, 1H), 8.36 (s, 1H), 8.15-8.27 (m, 1H), 7.81-7.88 (m, 1H), 7.29 (dd, J=8.6, 1.1 Hz, 1H), 6.94-7.04 (m, 1H), 6.76-6.80 (m, 1H), 6.67-6.73 (m, 1H), 6.45 (s, 1H), 3.65 (s, 3H), 1.90-1.98 (m, 1H), 1.28 (s, 3H), 1.05-1.18 (m, 1H), 0.87-0.95 (m, 4H). m/z (ESI, negative ion) 482.0 (M–H)$^+$.

Example 2: (P)-1-(4-(2,2-DIMETHYLCYCLOPROPYL)-2-METHOXYPHENYL)-N-(ISOXAZOL-3-YL)-2-OXO-1,2-DIHYDROQUINOLINE-6-SULFONAMIDE

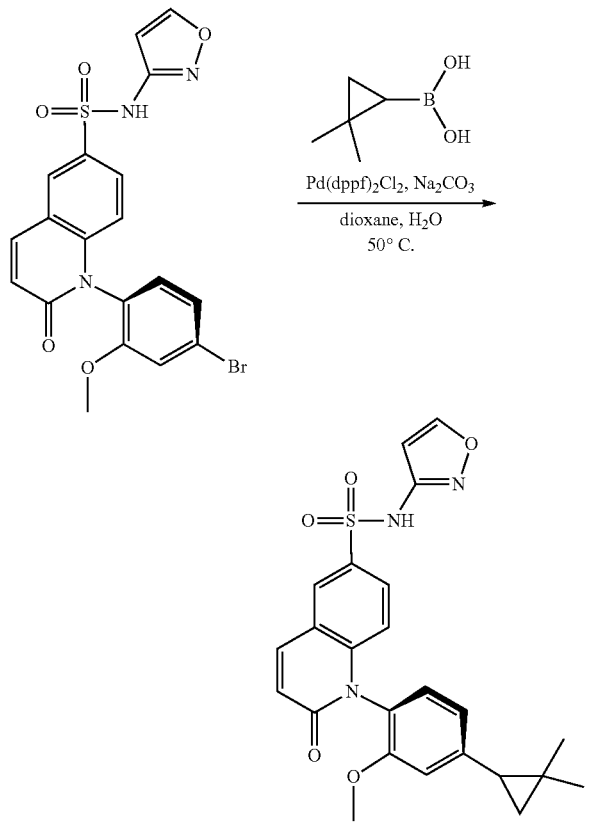

A 5-mL vial was charged with (P)-1-(4-bromo-2-methoxyphenyl)-N-(isoxazol-3-yl)-2-oxo-1,2-dihydroquinoline-6-sulfonamide (150 mg, 0.303 mmol), 1,1'-bis(diphenylphosphino)ferrocene palladium(ii)dichloride dichloromethane adduct (51.4 mg, 0.063 mmol), and (2,2-dimethylcyclopropyl)boronic acid (71.8 mg, 0.630 mmol). The reaction vessel was then sequentially charged with 1,4-dioxane (3 mL) and an aqueous solution of sodium carbonate (1 mL, 1.9 M) via syringe. The vial was sealed with a PTFE-lined cap, and the resultant red mixture was sparged with nitrogen for 10 min. The reaction mixture was the heated to 50° C. After 16 h, the mixture was allowed to cool to ambient temperature, and 1 M HCl was added carefully followed by EtOAc. The layers separated, and the aqueous layer was extracted with EtOAc. The combined organic layers were concentrated to dryness. The brown residue was purified by reverse phase HPLC using a XBridge Prep Shield RP18 19×100 mm column. The mobile phase was run under a gradient elution; 35-85% water/acetonitrile with 0.1% trifluoroacetic acid; flow rate: 40 mL/min. This afforded (P)-1-(4-(2,2-dimethylcyclopropyl)-2-methoxyphenyl)-N-(isoxazol-3-yl)-2-oxo-1,2-dihydroquinoline-6-sulfonamide (0.024 g, 0.052 mmol, 16% yield) as a brown solid. $^1$H NMR (400 MHz, DMSO-d$_6$) δ ppm 11.62 (s, 1H), 8.72 (d, J=1.9 Hz, 1H), 8.34 (d, J=2.3 Hz, 1H), 8.18 (d, J=9.7 Hz, 1H), 7.82 (dd, J=8.9, 2.1 Hz, 1H), 7.14 (d, J=7.9 Hz, 1H), 7.04 (dd, J=14.0, 1.6 Hz, 1H), 6.90 (ddd, J=10.9, 8.1, 1.3 Hz, 1H), 6.77 (d, J=9.7 Hz, 1H), 6.67 (d, J=8.9 Hz, 1H), 6.44 (d, J=1.9 Hz, 1H), 3.65 (s, 3H), 1.99 (dd, J=8.2, 6.1 Hz, 1H), 1.25 (s, 3H), 0.96-1.03 (m, 1H), 0.91 (s, 3H), 0.85 (dd, J=8.5, 4.8 Hz, 1H). m/z (ESI, negative ion) 464.0 (M–H)$^+$.

Examples 3, 4, and 5: TRANS-1-(5-FLUORO-2-METHOXY-4-(2-(TRIFLUOROMETHYL)CYCLOPROPYL)PHENYL)-N-(ISOXAZOL-3-YL)-2-OXO-1,2-DIHYDROQUINOLINE-6-SULFONAMIDE, (P)-1-(5-FLUORO-2-METHOXY-4-((1S,2S)-2-(TRIFLUOROMETHYL)CYCLOPROPYL)PHENYL)-N-(ISOXAZOL-3-YL)-2-OXO-1,2-DIHYDROQUINOLINE-6-SULFONAMIDE, and (P)-1-(5-FLUORO-2-METHOXY-4-((1R,2R)-2-(TRIFLUOROMETHYL)CYCLOPROPYL)PHENYL)-N-(ISOXAZOL-3-YL)-2-OXO-1,2-DIHYDROQUINOLINE-6-SULFONAMIDE, Respectively

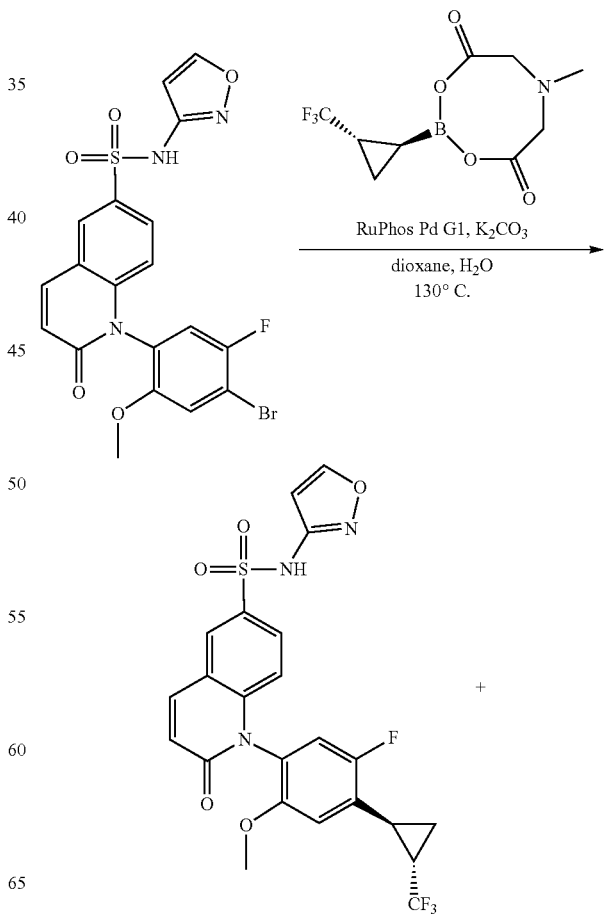

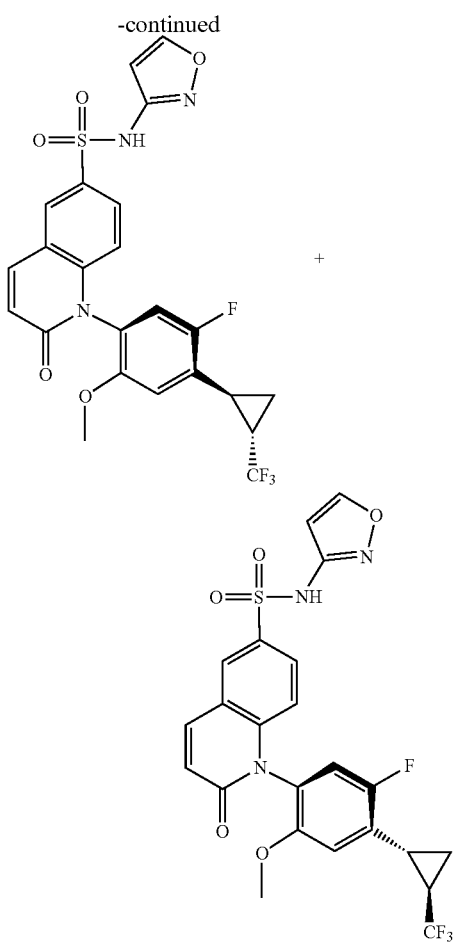

A vial was charged with 1-(4-bromo-5-fluoro-2-methoxyphenyl)-N-(isoxazol-3-yl)-2-oxo-1,2-dihydroquinoline-6-sulfonamide (Intermediate A) (0.200 g, 0.405 mmol), trans-6-methyl-2-[2-(trifluoromethyl)cyclopropyl]-1,3,6,2-dioxazaborocane-4,8-dione (0.322 g, 1.214 mmol), chloro-(2-dicyclohexylphosphino-2',6'-diisopropoxy-1,1'-biphenyl)[2-(2-aminoethyl)phenyl]palladium(II)-methyl-t-butyl ether adduct (0.066 g, 0.081 mmol), and potassium carbonate (0.224 g, 1.618 mmol). 1,4-Dioxane (1.5 mL) and water (0.5 mL) were added, the vial was flushed with argon, and the reaction was heated at 130° C. for six hours. The reaction was then diluted with ethyl acetate and washed twice with 1 N HCl solution. The aqueous layer was extracted with ethyl acetate, and the combined organic extracts were washed with brine, dried with sodium sulfate, filtered, and concentrated. The material was purified via column chromatography (RediSep Gold 40 g column, gradient elution 0-75% [3:1 EtOAc/EtOH]:heptane) to afford trans-1-(5-fluoro-2-methoxy-4-(2-(trifluoromethyl)cyclopropyl)phenyl)-N-(isoxazol-3-yl)-2-oxo-1,2-dihydroquinoline-6-sulfonamide (0.072 g, 0.138 mmol, 34% yield) as an off-white solid. $^1$H NMR (500 MHz, DMSO-$d_6$) δ ppm 11.52-11.84 (m, 1H), 8.72 (d, J=1.6 Hz, 1H), 8.35 (d, J=2.1 Hz, 1H), 8.20 (d, J=9.6 Hz, 1H), 7.83 (dt, J=9.0, 2.6 Hz, 1H), 7.36 (d, J=9.9 Hz, 1H), 7.00 (t, J=6.0 Hz, 1H), 6.73-6.85 (m, 2H), 6.44 (d, J=1.3 Hz, 1H), 3.66 (s, 3H), 2.53-2.67 (m, 2H), 1.43-1.62 (m, 2H). m/z (ESI, positive ion) 523.8 (M+H)$^+$.

Diastereomers and atropisomers were separated from trans-1-(5-fluoro-2-methoxy-4-(2-(trifluoromethyl)cyclopropyl)phenyl)-N-(isoxazol-3-yl)-2-oxo-1,2-dihydroquinoline-6-sulfonamide (63 mg) using two successive chiral SFC chromatography steps. For the first separation, a (S,S) Whelk-O, 2×15 cm column was used. The mobile phase was run under isocratic conditions; supercritical $CO_2$ with 30% methanol; flow rate: 80 mL/min. The first eluting peak from this separation was then separated further using a Chiralcel OJ 2×25 cm column. The mobile phase was run under isocratic conditions; supercritical $CO_2$ with 20% ethanol; flow rate: 65 mL/min. The first eluting peak was assigned (P)-1-(5-fluoro-2-methoxy-4-((1S,2S)-2-(trifluoromethyl)cyclopropyl)phenyl)-N-(isoxazol-3-yl)-2-oxo-1,2-dihydroquinoline-6-sulfonamide (16 mg), and the second eluting peak was assigned (P)-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide (12 mg). Both materials were isolated as white solids. Data for peak 1: $^1$H NMR (500 MHz, DMSO-$d_6$) δ ppm 11.48-11.87 (m, 1H), 8.71 (d, J=1.3 Hz, 1H), 8.34 (d, J=1.8 Hz, 1H), 8.20 (d, J=9.6 Hz, 1H), 7.83 (dd, J=8.8, 1.8 Hz, 1H), 7.36 (d, J=10.1 Hz, 1H), 6.99 (d, J=6.7 Hz, 1H), 6.69-6.85 (m, 2H), 6.43 (d, J=1.6 Hz, 1H), 3.66 (s, 3H), 2.52-2.59 (m, 2H), 1.53-1.63 (m, 2H). m/z (ESI, positive ion) 524.0 (M+H)$^+$. Data for peak 2: $^1$H NMR (500 MHz, DMSO-$d_6$) δ ppm 11.49-11.76 (m, 1H), 8.72 (d, J=1.3 Hz, 1H), 8.35 (d, J=1.8 Hz, 1H), 8.20 (d, J=9.9 Hz, 1H), 7.82 (dd, J=9.1, 2.1 Hz, 1H), 7.36 (d, J=9.9 Hz, 1H), 7.00 (d, J=6.7 Hz, 1H), 6.78 (dd, J=9.1, 7.0 Hz, 2H), 6.44 (d, J=1.3 Hz, 1H), 3.66 (s, 3H), 2.53-2.63 (m, 2H), 1.48-1.63 (m, 2H). m/z (ESI, positive ion) 524.0 (M+H)$^+$.

Examples 6 & 7: (P)-1-(5-FLUORO-2-METHOXY-4-((1R,2R)-2-METHYLCYCLOPROPYL)PHENYL)-N-(ISOXAZOL-3-YL)-2-OXO-1,2-DIHYDROQUINOLINE-6-SULFONAMIDE and (P)-1-(5-FLUORO-2-METHOXY-4-((1S,2S)-2-METHYLCYCLOPROPYL)PHENYL)-N-(ISOXAZOL-3-YL)-2-OXO-1,2-DIHYDROQUINOLINE-6-SULFONAMIDE, Respectively

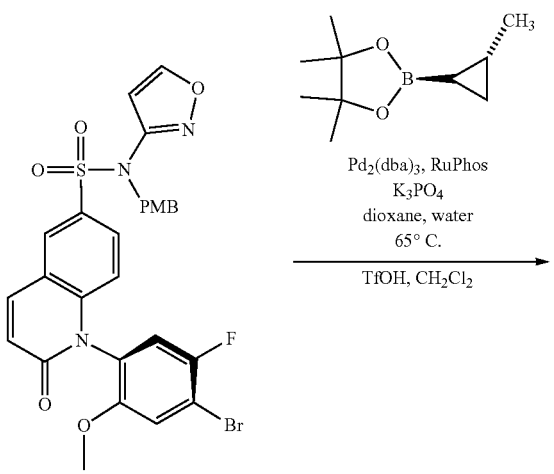

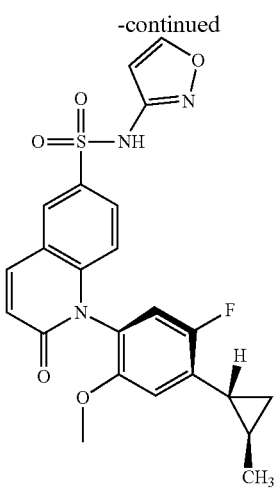

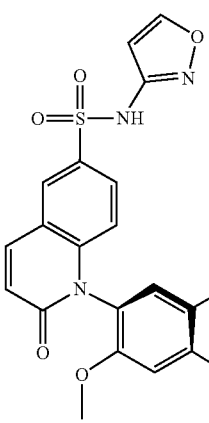

A 40-mL vial was charged with tris(dibenzylideneacetone)dipalladium(0) (22 mg, 0.024 mmol), 2-dicyclohexylphosphino-2',6'-diisopropoxybiphenyl (23 mg, 0.049 mmol), (P)-1-(4-bromo-5-fluoro-2-methoxyphenyl)-N-(isoxazol-3-yl)-N-(4-methoxybenzyl)-2-oxo-1,2-dihydroquinoline-6-sulfonamide (300 mg, 0.488 mmol), potassium phosphate (518 mg, 2.441 mmol), trans-2-methyl-cyclopropyl boronic acid pinacol ester (116 mg, 0.635 mmol), 1,4-dioxane (1.0 mL), and water (0.3 mL). The vial was sparged with nitrogen for 30 seconds and then heated to 65° C. After stirring for 6 h, the reaction was filtered through a phase separator, washing with dichloromethane. The filtrate was concentrated in vacuo, and the residue was retaken in dichloromethane (1 mL) and treated with trifluoromethanesulfonic acid (0.13 mL, 1.5 mmol). After stirring for 2 h, volatiles were removed in vacuo, and the residue was purified using a Chiralcel OJ-H, 2×25 cm column. The mobile phase was run under isocratic conditions; supercritical CO₂ with 25% methanol; flow rate: 80 mL/min. The first eluting peak was assigned (P)-1-(5-fluoro-2-methoxy-4-((1R,2R)-2-methylcyclopropyl)phenyl)-N-(isoxazol-3-yl)-2-oxo-1,2-dihydroquinoline-6-sulfonamide (20 mg). The second eluting peak was assigned (P)-1-(5-fluoro-2-methoxy-4-((1S,2S)-2-methylcyclopropyl)phenyl)-N-(isoxazol-3-yl)-2-oxo-1,2-dihydroquinoline-6-sulfonamide (16 mg). Data for peak 1: ¹H NMR (500 MHz, METHANOL-d₄) δ ppm 8.43 (br s, 1H), 8.29 (br s, 1H), 8.07 (d, J=9.6 Hz, 1H), 7.87 (br d, J=8.6 Hz, 1H), 7.01 (d, J=9.6 Hz, 1H), 6.81 (br dd, J=14.5, 9.1 Hz, 2H), 6.74 (d, J=6.5 Hz, 1H), 6.47 (br s, 1H), 3.64 (s, 3H), 1.81-1.93 (m, 1H), 1.21-1.29 (m, 4H), 1.08-1.18 (m, 1H), 0.82-0.91 (m, 1H). m/z (ESI, positive ion) 470.0 (M+H)⁺. Data for peak 2: ¹H NMR (500 MHz, METHANOL-d₄) δ ppm 8.43 (br s, 1H), 8.29 (s, 1H), 8.07 (d, J=9.6 Hz, 1H), 7.87 (br d, J=8.6 Hz, 1H), 7.01 (d, J=9.9 Hz, 1H), 6.83 (br d, J=8.6 Hz, 1H), 6.80 (d, J=9.6 Hz, 1H), 6.73 (d, J=6.5 Hz, 1H), 6.47 (br s, 1H), 3.64 (s, 3H), 1.83-1.91 (m, 1H), 1.22-1.29 (m, 4H), 1.07-1.13 (m, 1H), 0.84-0.91 (m, 1H). m/z (ESI, positive ion) 470.0 (M+H)⁺.

Examples 8 & 9: (P)-1-(5-FLUORO-2-METHOXY-4-((1R,2R)-2-PHENYLCYCLOPROPYL)PHENYL)-N-(ISOXAZOL-3-YL)-2-OXO-1,2-DIHYDROQUINOLINE-6-SULFONAMIDE and (P)-1-(5-FLUORO-2-METHOXY-4-((1S,2S)-2-PHENYLCYCLOPROPYL)PHENYL)-N-(ISOXAZOL-3-YL)-2-OXO-1,2-DIHYDROQUINOLINE-6-SULFONAMIDE, Respectively

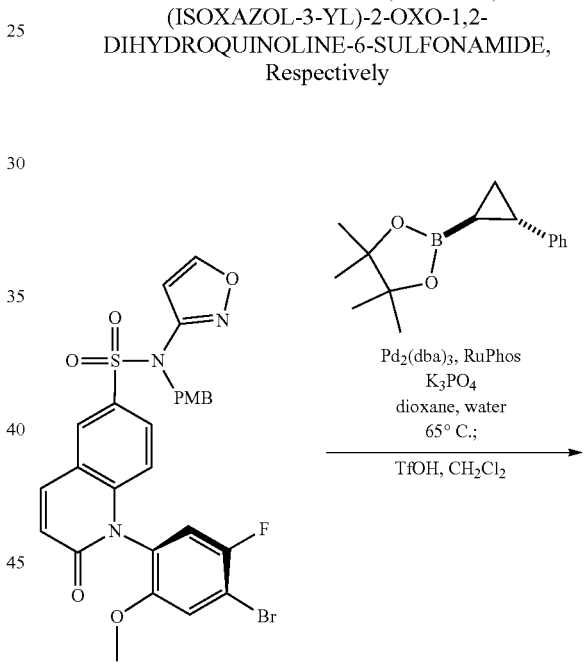

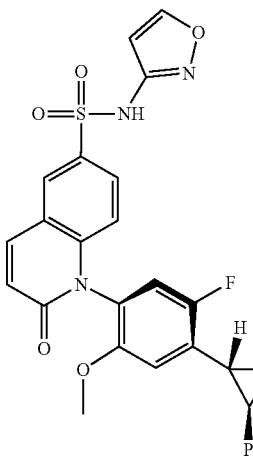

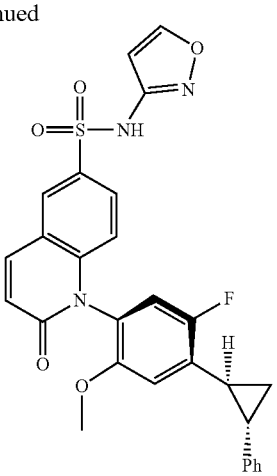

The title compounds were prepared according to the method of Examples 6 & 7, except that trans-2-phenylcyclopropylboronic acid pinacol ester (155 mg, 0.635 mmol) was used instead of trans-2-methyl-cyclopropyl boronic acid pinacol ester. The purification was accomplished using a Chiralcel OJ-H, 2×25 cm column. The mobile phase was run under isocratic conditions; supercritical $CO_2$ with 45% methanol; flow rate: 70 mL/min. The first eluting peak was assigned (P)-1-(5-fluoro-2-methoxy-4-((1R,2R)-2-phenylcyclopropyl)phenyl)-N-(isoxazol-3-yl)-2-oxo-1,2-dihydroquinoline-6-sulfonamide (6 mg). The second eluting peak was assigned (P)-1-(5-fluoro-2-methoxy-4-((1S,2S)-2-phenylcyclopropyl)phenyl)-N-(isoxazol-3-yl)-2-oxo-1,2-dihydroquinoline-6-sulfonamide (4 mg). Data for peak 1: $^1$H NMR (500 MHz, CHLOROFORM-d) δ ppm 8.27 (s, 1H), 8.11 (d, J=2.1 Hz, 1H), 7.78 (d, J=9.6 Hz, 1H), 7.74 (dd, J=9.0, 2.2 Hz, 1H), 7.31-7.38 (m, 3H), 7.20-7.25 (m, 3H), 6.93 (d, J=9.3 Hz, 1H), 6.86 (d, J=9.6 Hz, 1H), 6.79 (d, J=9.1 Hz, 1H), 6.74 (d, J=6.2 Hz, 1H), 6.62 (s, 1H), 3.71 (s, 3H), 2.42 (td, J=7.4, 4.9 Hz, 1H), 2.35 (td, J=7.5, 4.8 Hz, 1H), 1.56-1.63 (m, 2H). m/z (ESI, positive ion) 532.0 (M+H)⁺. Data for peak 2: $^1$H NMR (500 MHz, CHLOROFORM-d) δ ppm 8.27 (br s, 1H), 8.11 (d, J=1.8 Hz, 1H), 7.78 (d, J=9.6 Hz, 1H), 7.75 (dd, J=9.1, 2.1 Hz, 1H), 7.43 (br s, 1H), 7.31-7.38 (m, 2H), 7.23-7.26 (m, 3H), 6.92 (d, J=9.3 Hz, 1H), 6.86 (d, J=9.6 Hz, 1H), 6.79 (d, J=9.1 Hz, 1H), 6.74 (d, J=6.5 Hz, 1H), 6.62 (br s, 1H), 3.71 (s, 3H), 2.40-2.48 (m, 1H), 2.32-2.39 (m, 1H), 1.55-1.60 (m, 2H). m/z (ESI, positive ion) 532.0 (M+H)⁺.

Examples 10 & 11: (P)-(R)-1-(4-(2,2-DIFLUORO-CYCLOPROPYL)-5-FLUORO-2-METHOXYPHE-NYL)-N-(ISOXAZOL-3-YL)-2-OXO-1,2-DIHYD-ROQUINOLINE-6-SULFONAMIDE and (P)-(S)-1-(4-(2,2-DIFLUOROCYCLOPROPYL)-5-FLUORO-2-METHOXYPHENYL)-N-(ISOXAZOL-3-YL)-2-OXO-1,2-DIHYDROQUINOLINE-6-SULFONAMIDE, Respectively

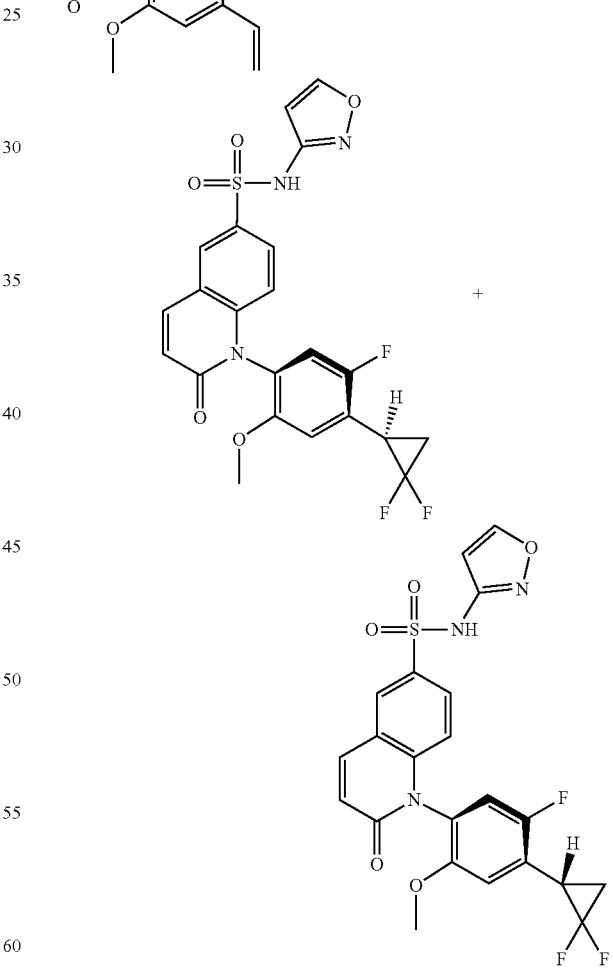

To a vial containing (P)-1-(5-fluoro-2-methoxy-4-vinylphenyl)-N-(isoxazol-3-yl)-N-(4-methoxybenzyl)-2-oxo-1,2-dihydroquinoline-6-sulfonamide (500 mg, 0.890 mmol), (trifluoromethyl)trimethylsilane (0.33 mL, 2.2 mmol) in tetrahydrofuran (3.0 mL), sodium iodide (66.7 mg, 0.445 mmol) was added portionwise. After 10 min, the reaction was warmed to 60° C. After 3 h, the reaction was cooled to rt, and volatiles were removed in vacuo. The residue was dissolved in trifluoroacetic acid (1 mL) and stirred at 40° C. for 4 h. Volatiles were then removed in vacuo, and the residue was purified using a Chiralcel OJ-H, 2×15 cm column. The mobile phase was run under isocratic conditions; supercritical $CO_2$ with 25% methanol; flow rate: 80 mL/min. The first eluting peak was assigned (P)—(R)-1-(4-(2,2-difluorocyclopropyl)-5-fluoro-2-methoxyphenyl)-N-(isoxazol-3-yl)-2-oxo-1,2-dihydroquinoline-6-sulfonamide. The second eluting peak was assigned (P)—(S)-1-(4-(2,2-difluorocyclopropyl)-5-fluoro-2-methoxyphenyl)-N-(isoxazol-3-yl)-2-oxo-1,2-dihydroquinoline-6-sulfonamide. Data for peak 1: $^1$H NMR (500 MHz, METHANOL-$d_4$) δ ppm 8.16-8.34 (m, 2H), 8.07 (d, J=9.6 Hz, 1H), 7.81-7.95 (m, 1H), 7.15 (d, J=9.3 Hz, 1H), 7.09 (d, J=6.2 Hz, 1H), 6.69-6.89 (m, 2H), 6.24 (br s, 1H), 3.70 (s, 3H), 2.98-3.03 (m, 1H), 1.90-2.13 (m, 2H). m/z (ESI, positive ion) 491.8 (M+H)$^+$. Data for peak 2: $^1$H NMR (500 MHz, METHANOL-$d_4$) δ ppm 8.43 (br s, 1H), 8.30 (s, 1H), 8.09 (d, J=9.6 Hz, 1H), 7.89 (br d, J=8.8 Hz, 1H), 7.17 (d, J=9.3 Hz, 1H), 7.09 (d, J=6.5 Hz, 1H), 6.76-6.84 (m, 2H), 6.47 (br s, 1H), 3.70 (s, 3H), 2.98-3.09 (m, 1H), 1.91-2.10 (m, 2H). m/z (ESI, positive ion) 491.8 (M+H)$^+$.

Examples 12 & 13: (P)-1-(5-CHLORO-2-METHOXY-4-((1S,2S)-2-(TRIFLUOROMETHYL)CYCLOPROPYL)PHENYL)-2-OXO-N-(PYRIMIDIN-2-YL)-1,2-DIHYDROQUINOLINE-6-SULFONAMIDE and (P)-1-(5-CHLORO-2-METHOXY-4-((1R,2R)-2-(TRIFLUOROMETHYL)CYCLOPROPYL)PHENYL)-2-OXO-N-(PYRIMIDIN-2-YL)-1,2-DIHYDROQUINOLINE-6-SULFONAMIDE, Respectively

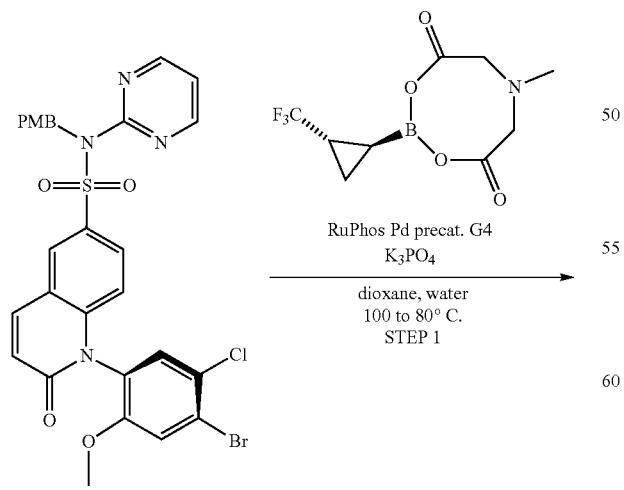

Step 1: TRANS-(P)-1-(5-CHLORO-2-METHOXY-4-(2-(TRIFLUOROMETHYL)CYCLOPROPYL)PHENYL)-N-(4-METHOXYBENZYL)-2-OXO-N-(PYRIMIDIN-2-YL)-1,2-DIHYDROQUINOLINE-6-SULFONAMIDE A 40-mL vial was charged with RuPhos Pd 4$^{th}$ generation precatalyst (372 mg, 0.438 mmol), potassium phosphate (864 mg, 4.38 mmol), (P)-1-(4-bromo-5-chloro-2-methoxyphenyl)-N-(4-methoxybenzyl)-2-oxo-N-(pyrimidin-2-yl)-1,2-dihydroquinoline-6-sulfonamide (937 mg, 1.46 mmol), and trans-6-methyl-2-(2-(trifluoromethyl)cyclopropyl)-1,3,6,2-dioxazaborocane-4,8-dione (696 mg, 2.63 mmol). The vial was capped and backfilled with nitrogen. 1,4-Dioxane (4.5 mL) and water (1.5 mL) were added, and the reaction mixture was sparged with nitrogen for 15 min. The vial was then heated to 100° C. for 4 h and then at 80° C. for 16 h. The reaction was cooled to rt, diluted with EtOAc, and quenched with water. The layers were separated and the aqueous extract was extracted thrice with EtOAc. The organic extracts were combined, washed with brine, dried over $Na_2SO_4$, and concentrated. The residue was purified via silica gel chromatography (gradient elution 20-80% [3:1 EtOAc:EtOH]:heptane) to afford trans-(P)-1-(5-chloro-2-methoxy-4-(2-(trifluoromethyl)cyclopropyl)phenyl)-N-(4-methoxybenzyl)-2-oxo-N-(pyrimidin-2-yl)-1,2-dihydroquinoline-6-sulfonamide (401 mg, 0.598 mmol, 41% yield). m/z (ESI, positive ion) 671.0 $(M+H)^+$.

Step 2: (P)-1-(5-CHLORO-2-METHOXY-4-((1S,2S)-2-(TRIFLUOROMETHYL)CYCLOPROPYL)PHENYL)-2-OXO-N-(PYRIMIDIN-2-YL)-1,2-DIHYDROQUINOLINE-6-SULFONAMIDE AND (P)-1-(5-CHLORO-2-METHOXY-4-((1R,2R)-2-(TRIFLUOROMETHYL)CYCLOPROPYL)PHENYL)-2-OXO-N-(PYRIMIDIN-2-YL)-1,2-DIHYDROQUINOLINE-6-SULFONAMIDE trans-(P)-1-(5-Chloro-2-methoxy-4-(2-(trifluoromethyl)cyclopropyl)phenyl)-N-(4-methoxybenzyl)-2-oxo-N-(pyrimidin-2-yl)-1,2-dihydroquinoline-6-sulfonamide (401 mg, 0.598 mmol) was taken up in dichloromethane (5 mL), cooled to 0° C., and trifluoromethanesulfonic acid (250 μL, 2.82 mmol) was added. After stirring at 0° C. for 30 min, the reaction was quenched by the dropwise addition of the reaction mixture into vigorously stirred sat. $NaHCO_3$. After gas evolution had ceased, the mixture was extracted four times with dichloromethane. The organic extracts were combined, washed with brine, dried over $Na_2SO_4$, and concentrated. The residue was purified using a (S,S) Whelk-O, 2×15 cm column. The mobile phase was run under isocratic conditions; supercritical $CO_2$ with 40% methanol; flow rate: 80 mL/min. The first peak was further purified using a Chiralcel OJ-H, 3×25 cm column. The mobile phase was run under isocratic conditions; supercritical $CO_2$ with 20% ethanol; flow rate: 120 mL/min. The first eluting peak was assigned (P)-1-(5-chloro-2-methoxy-4-((1S,2S)-2-(trifluoromethyl)cyclopropyl)phenyl)-2-oxo-N-(pyrimidin-2-yl)-1,2-dihydroquinoline-6-sulfonamide (43 mg). The second eluting peak was assigned (P)-1-(5-chloro-2-methoxy-4-((1R,2R)-2-(trifluoromethyl)cyclopropyl)phenyl)-2-oxo-N-(pyrimidin-2-yl)-1,2-dihydroquinoline-6-sulfonamide (37 mg). Data for peak 1: $^1H$ NMR (500 MHz, DMSO-$d_6$) δ ppm 11.59-12.12 (m, 1H), 8.49 (d, J=4.7 Hz, 2H), 8.45 (d, J=1.8 Hz, 1H), 8.23 (d, J=9.6 Hz, 1H), 7.96 (dd, J=9.0, 2.2 Hz, 1H), 7.55 (s, 1H), 7.03 (br s, 1H), 7.00 (s, 1H), 6.76 (d, J=9.6 Hz, 1H), 6.73 (d, J=9.1 Hz, 1H), 3.69 (s, 3H), 2.58-2.67 (m, 1H), 2.52-2.55 (m, 1H), 1.59-1.71 (m, 1H), 1.49 (dt, J=9.5, 5.8 Hz, 1H). m/z (ESI, positive ion) 551.0 $(M+H)^+$. Data for peak 2: $^1H$ NMR (500 MHz, DMSO-$d_6$) δ ppm 11.71-12.06 (m, 1H), 8.41-8.54 (m, 3H), 8.23 (d, J=9.6 Hz, 1H), 7.95 (dd, J=9.0, 2.2 Hz, 1H), 7.54 (s, 1H), 6.93-7.09 (m, 2H), 6.65-6.83 (m, 2H), 3.68 (s, 3H), 2.55-2.68 (m, 2H), 1.45-1.60 (m, 2H). m/z (ESI, positive ion) 551.0 $(M+H)^+$.

Examples 14 & 15: (P)-1-(5-CHLORO-2-METHOXY-4-((1R,2R)-2-(TRIFLUOROMETHYL)CYCLOPROPYL)PHENYL)-2-OXO-N-(PYRIDAZIN-3-YL)-1,2-DIHYDROQUINOLINE-6-SULFONAMIDE and (P)-1-(5-CHLORO-2-METHOXY-4-((1S,2S)-2-(TRIFLUOROMETHYL)CYCLOPROPYL)PHENYL)-2-OXO-N-(PYRIDAZIN-3-YL)-1,2-DIHYDROQUINOLINE-6-SULFONAMIDE, Respectively

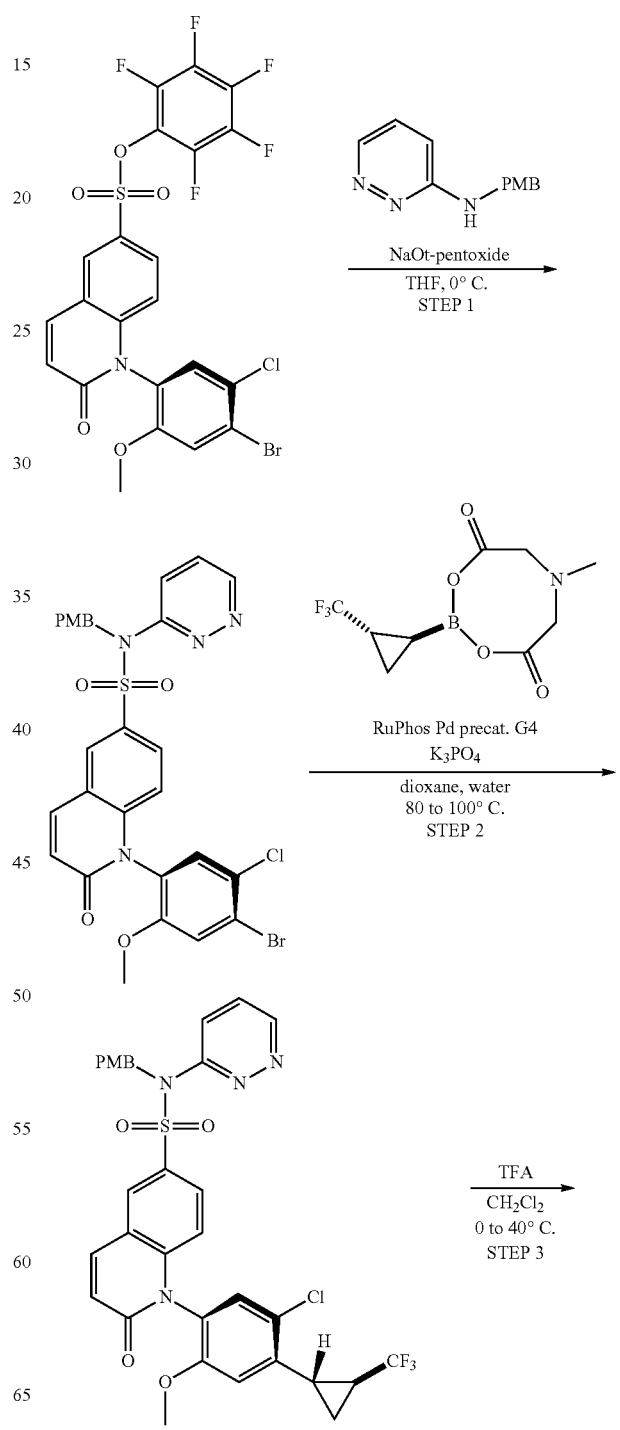

-continued

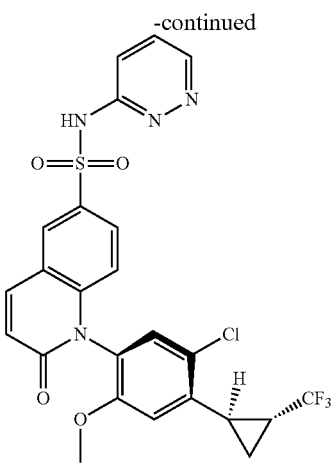

+

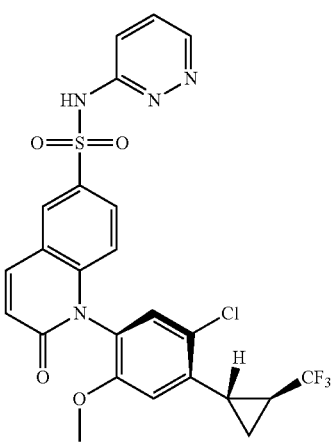

Step 1: (P)-1-(4-BROMO-5-CHLORO-2-METHOXYPHENYL)-N-(4-METHOXYBENZYL)-2-OXO-N-(PYRIDAZIN-3-YL)-1,2-DIHYDROQUINOLINE-6-SULFONAMIDE A 100-mL round-bottom flask was charged with (P)-perfluorophenyl 1-(4-bromo-5-chloro-2-methoxyphenyl)-2-oxo-1,2-dihydroquinoline-6-sulfonate (5.00 g, 8.19 mmol) and N-(4-methoxybenzyl)pyridazin-3-amine (1.939 g, 9.01 mmol). The flask was flushed with nitrogen and then charged with tetrahydrofuran (54.6 mL). After all solids had dissolved, the reaction mixture was cooled to 0° C., and sodium tert-pentoxide (6.7 mL, 9.4 mmol, 1.4 M in THF) was added dropwise over 5-10 minutes. After 1.5 h, the reaction was quenched by addition of sat. aq. ammonium chloride. The heterogeneous mixture was diluted with water and extracted thrice with EtOAc. The combined organic extracts were washed with brine, dried over $Na_2SO_4$ and concentrated. The resulting dark crude oil was purified via silica gel chromatography (gradient elution 20-100% [3:1 EtOAc:EtOH]:heptane) to afford (P)-1-(4-bromo-5-chloro-2-methoxyphenyl)-N-(4-methoxybenzyl)-2-oxo-N-(pyridazin-3-yl)-1,2-dihydroquinoline-6-sulfonamide (2.84 g, 4.42 mmol, 54% yield). m/z (ESI, positive ion) 641.0 $(M+H)^+$.

Step 2: TRANS-(P)-1-(5-CHLORO-2-METHOXY-4-(2-(TRIFLUOROMETHYL)CYCLOPROPYL)PHENYL)-N-(4-METHOXYBENZYL)-2-OXO-N-(PYRIDAZIN-3-YL)-1,2-DIHYDROQUINOLINE-6-SULFONAMIDE A 40-mL vial was charged with RuPhos Pd $4^{th}$ generation precatalyst (0.331 g, 0.389 mmol), potassium phosphate (0.992 g, 4.67 mmol), (P)-1-(4-bromo-5-chloro-2-methoxyphenyl)-N-(4-methoxybenzyl)-2-oxo-N-(pyridazin-3-yl)-1,2-dihydroquinoline-6-sulfonamide (1.00 g, 1.56 mmol), and trans-6-methyl-2-(2-(trifluoromethyl)cyclopropyl)-1,3,6,2-dioxazaborocane-4,8-dione (0.743 g, 2.80 mmol). The vial was capped and backfilled with nitrogen. 1,4-Dioxane (5.8 mL) and water (1.9 mL) were added, and the reaction mixture was sparged with nitrogen for 15 min. The vial was then heated to 80° C. for 16 h. The reaction was cooled to rt, and then additional portions of trans-6-methyl-2-(2-(trifluoromethyl)cyclopropyl)-1,3,6,2-dioxazaborocane-4,8-dione (0.200 g, 0.744 mmol) and RuPhos Pd $4^{th}$ generation precatalyst (0.100 g, 0.118 mmol) were added. After stirring an additional 5 h at 100° C., the reaction was quenched with water and extracted thrice with EtOAc. The organic extracts were combined, washed with brine, dried over $Na_2SO_4$, and concentrated. The residue was purified via silica gel chromatography (gradient elution 55-85% [3:1 EtOAc:EtOH]:heptane) to afford trans-(P)-1-(5-chloro-2-methoxy-4-(2-(trifluoromethyl)cyclopropyl)phenyl)-N-(4-methoxybenzyl)-2-oxo-N-(pyridazin-3-yl)-1,2-dihydroquinoline-6-sulfonamide (450 mg, 0.671 mmol, 43% yield). m/z (ESI, positive ion) 671.0 $(M+H)^+$.

Step 3: (P)-1-(5-CHLORO-2-METHOXY-4-((1R,2R)-2-(TRIFLUOROMETHYL)CYCLOPROPYL)PHENYL)-2-OXO-N-(PYRIDAZIN-3-YL)-1,2-DIHYDROQUINOLINE-6-SULFONAMIDE AND (P)-1-(5-CHLORO-2-METHOXY-4-((1S,2S)-2-(TRIFLUOROMETHYL)CYCLOPROPYL)PHENYL)-2-OXO-N-(PYRIDAZIN-3-YL)-1,2-DIHYDROQUINOLINE-6-SULFONAMIDE trans-(P)-1-(5-Chloro-2-methoxy-4-(2-(trifluoromethyl)cyclopropyl)phenyl)-N-(4-methoxybenzyl)-2-oxo-N-(pyridazin-3-yl)-1,2-dihydroquinoline-6-sulfonamide (450 mg, 0.671 mmol) was taken up in dichloromethane (0.5 mL), cooled to 0° C., and trifluoroacetic acid (1.8 mL) was added. After stirring at rt for 1 h and then at 40° C. for 1 h, the reaction was cooled to rt, diluted with dichloromethane, and quenched by the dropwise addition of the reaction mixture into vigorously stirred sat. $NaHCO_3$. After gas evolution had ceased, the mixture was extracted thrice with dichloromethane. The organic extracts were combined, washed with brine, dried over $Na_2SO_4$, and concentrated. The residue was purified using a (S,S) Whelk-O, 2×25 cm column. The mobile phase was run under isocratic conditions; supercritical $CO_2$ with 50% methanol; flow rate: 80 mL/min. The first peak was further purified using a Chiralcel OJ-H, 3×25 cm column. The mobile phase was run under isocratic conditions; supercritical $CO_2$ with 25% methanol; flow rate: 80 mL/min. The first eluting peak was assigned (P)-1-(5-chloro-2-methoxy-4-((1R,2R)-2-(trifluoromethyl)cyclopropyl)phenyl)-2-oxo-N-(pyridazin-3-yl)-1,2-dihydroquinoline-6-sulfonamide (51 mg). The second eluting peak was assigned (P)-1-(5-chloro-2-methoxy-4-((1S,2S)-2-(trifluoromethyl)cyclopropyl)phenyl)-2-oxo-N-(pyridazin-3-yl)-1,2-dihydroquinoline-6-sulfonamide (50 mg). Data for peak 1: $^1H$ NMR (500 MHz, DMSO-$d_6$) δ ppm 14.17-14.77

(m, 1H), 8.33 (d, J=2.1 Hz, 1H), 8.28-8.32 (m, 1H), 8.18 (d, J=9.6 Hz, 1H), 7.86-7.95 (m, 1H), 7.83 (dd, J=9.0, 2.2 Hz, 1H), 7.67 (dd, J=9.5, 4.0 Hz, 1H), 7.54 (s, 1H), 7.00 (s, 1H), 6.75 (d, J=9.6 Hz, 1H), 6.69 (d, J=9.1 Hz, 1H), 3.69 (s, 3H), 2.58-2.65 (m, 1H), 2.51-2.54 (m, 1H), 1.64 (dt, J=8.8, 6.2 Hz, 1H), 1.49 (dt, J=9.3, 5.7 Hz, 1H). m/z (ESI, positive ion) 551.0 (M+H)$^+$. Data for peak 2: $^1$H NMR (600 MHz, DMSO-d$_6$) δ ppm 13.96-14.63 (m, 1H), 8.29-8.35 (m, 2H), 8.17 (d, J=9.8 Hz, 1H), 7.82 (br dd, J=8.9, 1.3 Hz, 2H), 7.60-7.68 (m, 1H), 7.52 (s, 1H), 7.01 (s, 1H), 6.74 (d, J=9.4 Hz, 1H), 6.70 (d, J=9.1 Hz, 1H), 3.69 (s, 3H), 2.55-2.69 (m, 2H), 1.44-1.59 (m, 2H). m/z (ESI, positive ion) 551.0 (M+H)$^+$.

Examples 16 & 17: (P)-1-(5-FLUORO-2-METHOXY-4-((1R,2R)-2-(TRIFLUOROMETHYL)CYCLOPROPYL)PHENYL)-2-OXO-N-(PYRIDAZIN-3-YL)-1,2-DIHYDROQUINOLINE-6-SULFONAMIDE and (P)-1-(5-FLUORO-2-METHOXY-4-((1S,2S)-2-(TRIFLUOROMETHYL)CYCLOPROPYL)PHENYL)-2-OXO-N-(PYRIDAZIN-3-YL)-1,2-DIHYDROQUINOLINE-6-SULFONAMIDE, Respectively

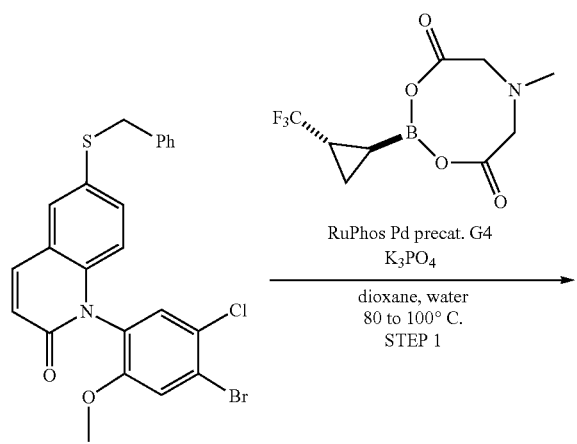

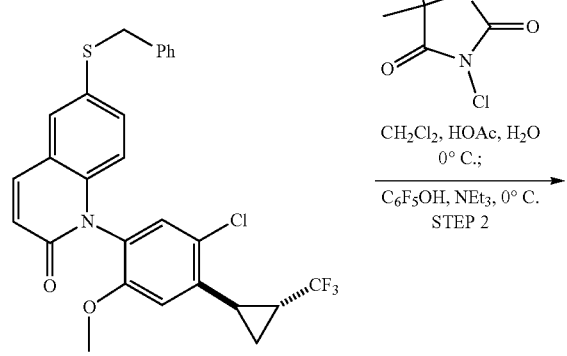

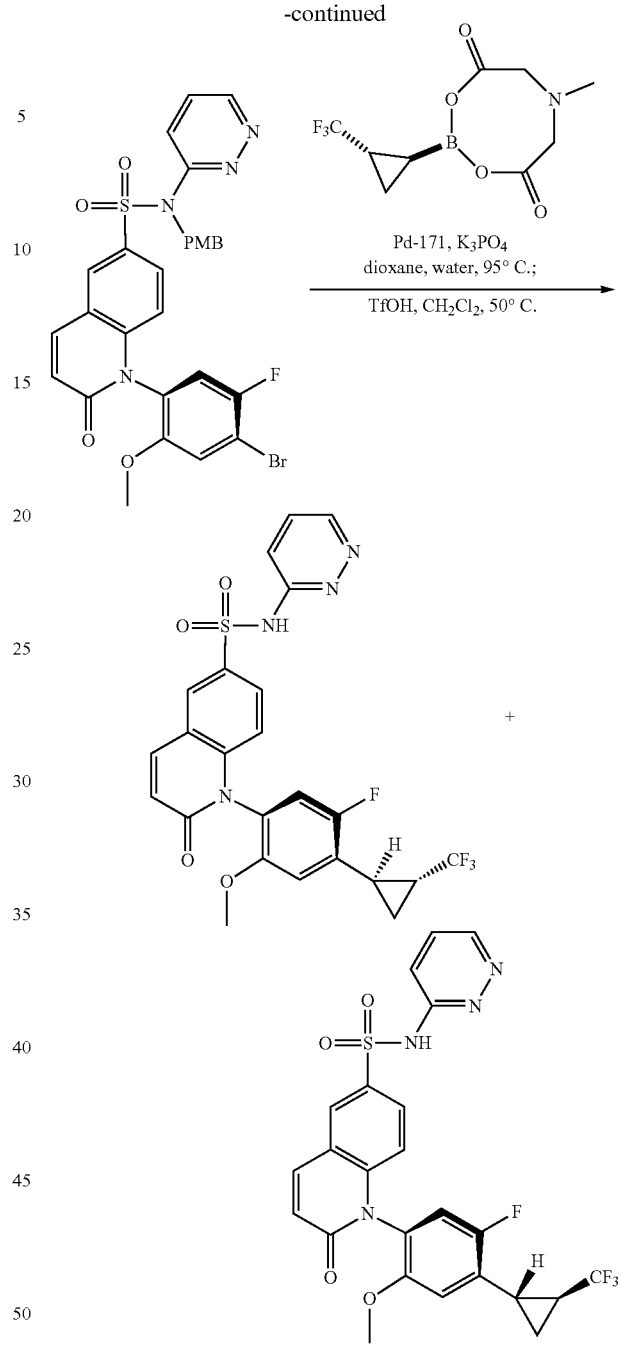

A 40-mL vial was charged with Pd-171 (80 mg, 0.12 mmol), (P)-1-(4-bromo-5-fluoro-2-methoxyphenyl)-N-(4-methoxybenzyl)-2-oxo-N-(pyridazin-3-yl)-1,2-dihydroquinoline-6-sulfonamide (500 mg, 0.799 mmol), potassium phosphate (509 mg, 2.40 mmol), and trans-6-methyl-2-(2-(trifluoromethyl)cyclopropyl)-1,3,6,2-dioxazaborocane-4,8-dione (318 mg, 1.20 mmol), 1,4-dioxane (3.0 mL) and water (1.0 mL). The vial was sparged with nitrogen and then heated to 95° C. After stirring for 6 h, the mixture was filtered through a phase separator, washing with dichloromethane. Volatiles were removed in vacuo. The residue was taken up in dichloromethane (1 mL) and treated with trifluoromethanesulfonic acid (0.2 mL, 2.4 mmol). After heating at 50° C. for 1 h, volatiles were removed, and the product was purified using a (S,S) Whelk-O, 2×25 cm column. The mobile phase was run under isocratic conditions; supercritical CO₂ with 40% methanol; flow rate: 80 mL/min. The first peak was further purified using a Chiralcel OJ-H, 3×25 cm column. The mobile phase was run under isocratic conditions; supercritical CO₂ with 25% methanol; flow rate: 80 mL/min. The first eluting peak was assigned (P)-1-(5-fluoro-2-methoxy-4-((1R,2R)-2-(trifluoromethyl)cyclopropyl)phenyl)-2-oxo-N-(pyridazin-3-yl)-1,2-dihydroquinoline-6-sulfonamide (31 mg). The second eluting peak was assigned (P)-1-(5-fluoro-2-methoxy-4-((1S,2S)-2-(trifluoromethyl)cyclopropyl)phenyl)-2-oxo-N-(pyridazin-3-yl)-1,2-dihydroquinoline-6-sulfonamide (37 mg). Data for peak 1: ¹H NMR (500 MHz, METHANOL-d₄) δ ppm 8.34 (d, J=2.1 Hz, 1H), 8.18-8.29 (m, 1H), 8.11 (d, J=9.6 Hz, 1H), 7.87-7.97 (m, 2H), 7.59 (dd, J=9.6, 4.2 Hz, 1H), 7.12 (d, J=9.6 Hz, 1H), 6.96 (d, J=6.5 Hz, 1H), 6.82 (d, J=8.8 Hz, 1H), 6.80 (d, J=9.6 Hz, 1H), 3.69 (s, 3H), 2.59 (dt, J=8.8, 6.0 Hz, 1H), 2.20-2.28 (m, 1H), 1.45-1.53 (m, 2H). m/z (ESI, positive ion) 535.0 (M+H)⁺. Data for peak 2: ¹H NMR (500 MHz, METHANOL-d₄) δ ppm 8.33 (d, J=2.1 Hz, 1H), 8.20-8.29 (m, 1H), 8.10 (d, J=9.6 Hz, 1H), 7.83-7.96 (m, 2H), 7.58 (dd, J=9.5, 4.3 Hz, 1H), 7.11 (d, J=9.6 Hz, 1H), 6.94 (d, J=6.5 Hz, 1H), 6.82 (d, J=9.1 Hz, 1H), 6.79 (d, J=9.6 Hz, 1H), 3.69 (s, 3H), 2.53-2.64 (m, 1H), 2.21-2.34 (m, 1H), 1.42-1.53 (m, 2H). m/z (ESI, positive ion) 535.0 (M+H)⁺.

Examples 18 & 19: (P)-1-(5-CHLORO-2-METHOXY-4-((1R,2R)-2-(TRIFLUOROMETHYL)CYCLOPROPYL)PHENYL)-N-(ISOXAZOL-3-YL)-2-OXO-1,2-DIHYDROQUINOLINE-6-SULFONAMIDE and (P)-1-(5-CHLORO-2-METHOXY-4-((1S,2S)-2-(TRIFLUOROMETHYL)CYCLOPROPYL)PHENYL)-N-(ISOXAZOL-3-YL)-2-OXO-1,2-DIHYDROQUINOLINE-6-SULFONAMIDE, Respectively

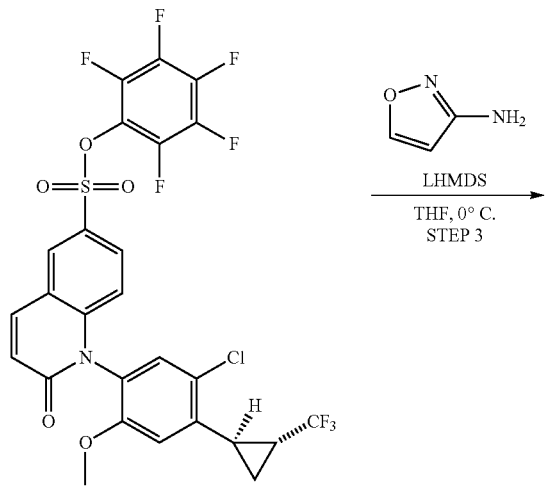

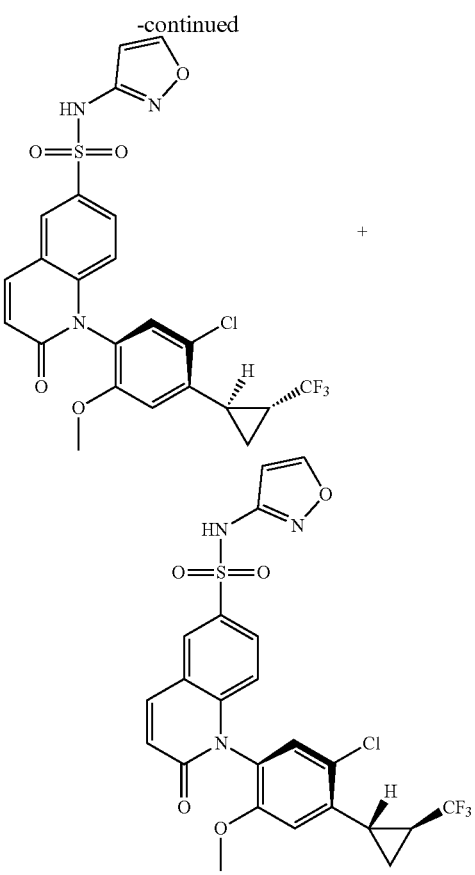

Step 1: 6-(BENZYLTHIO)-1-(5-CHLORO-2-METHOXY-4-(2-(TRIFLUOROMETHYL)CYCLOPROPYL)PHENYL)QUINOLIN-2(1H)-ONE A 40-mL vial was charged with 6-(benzylthio)-1-(4-bromo-5-chloro-2-methoxyphenyl)quinolin-2(1H)-one (1.50 g, 3.08 mmol), trans-6-methyl-2-(2-(trifluoromethyl)cyclopropyl)-1,3,6,2-dioxazaborocane-4,8-dione (1.23 g, 4.62 mmol), potassium phosphate (1.96 g, 9.24 mmol), RuPhos Pd 4$^{th}$ generation precatalyst (0.786 g, 0.924 mmol). The vial was capped and backfilled with nitrogen before 1,4-dioxane (15.4 mL) and water (5.1 mL) were added. The reaction mixture was stirred vigorously and sparged with nitrogen. After heating to 80° C. for 16 h, additional RuPhos Pd 4$^{th}$ generation precatalyst (150 mg, 0.176 mmol) was added, and the reaction was heated to 100° C. for 8 h. After cooling to rt, the reaction was poured onto a mixture of EtOAc and water and extracted thrice with EtOAc. The combined organic extracts were washed with brine, dried over Na₂SO₄ and concentrated. The residue was purified via column chromatography (gradient elution 10-75% EtOAc:heptane) to afford 6-(benzylthio)-1-(5-chloro-2-methoxy-4-(2-(trifluoromethyl)cyclopropyl)phenyl)quinolin-2(1H)-one (1.00 g, 1.94 mmol, 63% yield). ¹H NMR (500 MHz, DMSO-d₆) δ ppm 7.94 (d, J=9.6 Hz, 1H), 7.78 (d, J=2.1 Hz, 1H), 7.48 (d, J=2.3 Hz, 1H), 7.38 (ddd, J=8.8, 5.2, 2.1 Hz, 1H), 7.31-7.35 (m, 2H), 7.26-7.31 (m, 2H), 7.19-7.25 (m, 1H), 6.99 (d, J=6.2 Hz, 1H), 6.66 (d, J=9.6 Hz, 1H), 6.48 (dd, J=8.7, 6.9 Hz, 1H), 4.23 (s, 2H), 3.69 (s, 3H), 2.53-2.66 (m, 2H), 1.53-1.66 (m, 1H), 1.45-1.52 (m, 1H). m/z (ESI, positive ion) 516.0 (M+H)⁺.

Step 2: PERFLUOROPHENYL TRANS-1-(5-CHLORO-2-METHOXY-4-(2-(TRIFLUOROMETHYL)CYCLOPROPYL)PHENYL)-2-OXO-1,2-DIHYDROQUINOLINE-6-SULFONATE A 25-mL round-bottom flask was charged with trans-6-(benzylthio)-1-(5-chloro-2-methoxy-4-(2-(trifluoromethyl)cyclopropyl)phenyl)quinolin-2(1H)-one (1.00 g, 1.94 mmol) followed by acetonitrile (6.1 mL), water (0.15 mL), and acetic acid (0.23 mL). This solution was cooled to 0° C., and 1,3-dichloro-5,5-dimethyl-2,4-imidazolidinedione (0.382 g, 1.94 mmol) was added. After 90 min at 0° C., additional 1,3-dichloro-5,5-dimethyl-2,4-imidazolidinedione (0.191 g, 0.969 mmol) was added. After 15 min, pentafluorophenol (0.428 g, 2.34 mmol) was added followed by dropwise addition of triethylamine (1.1 mL, 7.8 mmol). After 30 min at 0° C., the reaction was warmed to rt, diluted with EtOAc (25 mL) and 1:1 water:brine (50 mL). The mixture was stirred briefly before extracting thrice with EtOAc. The combined organics were washed with brine, dried over $Na_2SO_4$ and concentrated. The residue was purified via column chromatography (gradient elution 0-35% [3:1 EtOAc:EtOH]:heptane) to afford perfluorophenyl trans-1-(5-chloro-2-methoxy-4-(2-(trifluoromethyl)cyclopropyl)phenyl)-2-oxo-1,2-dihydroquinoline-6-sulfonate (760. mg, 1.19 mmol, 61% yield). $^1$H NMR (500 MHz, DMSO-$d_6$) δ ppm 8.54-8.69 (m, 1H), 8.24 (d, J=9.9 Hz, 1H), 7.96 (ddd, J=9.0, 4.3, 2.3 Hz, 1H), 7.63 (d, J=1.6 Hz, 1H), 7.04 (d, J=3.4 Hz, 1H), 6.80-6.91 (m, 2H), 3.71 (s, 3H), 2.53-2.67 (m, 2H), 1.54-1.69 (m, 1H), 1.47-1.54 (m, 1H). m/z (ESI, positive ion) 639.9 (M+H)$^+$.

Step 3: (P)-1-(5-CHLORO-2-METHOXY-4-((1R,2R)-2-(TRIFLUOROMETHYL)CYCLOPROPYL)PHENYL)-N-(ISOXAZOL-3-YL)-2-OXO-1,2-DIHYDROQUINOLINE-6-SULFONAMIDE AND (P)-1-(5-CHLORO-2-METHOXY-4-((1R,2R)-2-(TRIFLUOROMETHYL)CYCLOPROPYL)PHENYL)-N-(ISOXAZOL-3-YL)-2-OXO-1,2-DIHYDROQUINOLINE-6-SULFONAMIDE A 40-mL vial was charged with perfluorophenyl trans-1-(5-chloro-2-methoxy-4-(2-(trifluoromethyl)cyclopropyl)phenyl)-2-oxo-1,2-dihydroquinoline-6-sulfonate (781 mg, 1.22 mmol) and isoxazol-3-amine (123 mg, 1.47 mmol). Tetrahydrofuran (8.1 mL) was added via syringe, and the reaction was cooled to 0° C. Lithium bis(trimethylsilyl)amide (1.5 mL, 1.5 mmol, 1.0 M in THF) was added dropwise via syringe. After stirring at 0° C. for 1 h, additional lithium bis(trimethylsilyl)amide (1.2 mL, 1.2 mmol, 1.0 M in THF) was added, and the reaction was stirred for 1 h at 0° C. The reaction was quenched with sat. aq. ammonium chloride and extracted four times with EtOAc. The organic extracts were combined, washed with brine, dried over $Na_2SO_4$, and concentrated. The residue was purified via column chromatography (gradient elution 10-65% [3:1 EtOAc:EtOH]:heptane) to afford trans-1-(5-chloro-2-methoxy-4-(2-(trifluoromethyl)cyclopropyl)phenyl)-N-(isoxazol-3-yl)-2-oxo-1,2-dihydroquinoline-6-sulfonamide (611 mg, 1.13 mmol, 93% yield). This product was further purified using a (S,S) Whelk-O, 2×25 cm column. The mobile phase was run under isocratic conditions; supercritical $CO_2$ with 50% methanol; flow rate: 80 mL/min. The first peak was further purified using two in-line Chiralcel OJ-H, 3×25 cm and Chiralcel OJ-H, 3×15 cm columns. The mobile phase was run under isocratic conditions; supercritical $CO_2$ with 30% methanol; flow rate: 80 mL/min. The first eluting peak was assigned (P)-1-(5-chloro-2-methoxy-4-((1R,2R)-2-(trifluoromethyl)cyclopropyl)phenyl)-N-(isoxazol-3-yl)-2-oxo-1,2-dihydroquinoline-6-sulfonamide (70 mg). The second eluting peak was assigned (P)-1-(5-chloro-2-methoxy-4-((1S,2S)-2-(trifluoromethyl)cyclopropyl)phenyl)-N-(isoxazol-3-yl)-2-oxo-1,2-dihydroquinoline-6-sulfonamide (70 mg). Data for peak 1: $^1$H NMR (500 MHz, DMSO-$d_6$) δ ppm 11.64 (s, 1H), 8.71 (d, J=1.8 Hz, 1H), 8.34 (d, J=2.3 Hz, 1H), 8.20 (d, J=9.6 Hz, 1H), 7.83 (dd, J=9.0, 2.2 Hz, 1H), 7.56 (s, 1H), 7.00 (s, 1H), 6.77 (dd, J=9.3, 6.2 Hz, 2H), 6.43 (d, J=1.8 Hz, 1H), 3.69 (s, 3H), 2.58-2.66 (m, 1H), 2.51-2.54 (m, 1H), 1.64 (dt, J=8.9, 6.2 Hz, 1H), 1.50 (dt, J=9.5, 5.8 Hz, 1H). m/z (ESI, positive ion) 540.0 (M+H)$^+$. Data for peak 2: $^1$H NMR (500 MHz, DMSO-$d_6$) δ ppm 11.64 (s, 1H), 8.71 (d, J=1.8 Hz, 1H), 8.35 (d, J=2.3 Hz, 1H), 8.20 (d, J=9.6 Hz, 1H), 7.82 (dd, J=9.0, 2.2 Hz, 1H), 7.56 (s, 1H), 7.01 (s, 1H), 6.71-6.88 (m, 2H), 6.43 (d, J=1.8 Hz, 1H), 3.69 (s, 3H), 2.55-2.67 (m, 2H), 1.46-1.60 (m, 2H). m/z (ESI, positive ion) 540.0 (M+H)$^+$.

Examples 20 & 21: (P)-1-(5-FLUORO-2-METHOXY-4-((1R,2R)-2-(TRIFLUOROMETHYL)CYCLOPROPYL)PHENYL)-2-OXO-N-(PYRIMIDIN-2-YL)-1,2-DIHYDROQUINOLINE-6-SULFONAMIDE and (P)-1-(5-FLUORO-2-METHOXY-4-((1S,2S)-2-(TRIFLUOROMETHYL)CYCLOPROPYL)PHENYL)-2-OXO-N-(PYRIMIDIN-2-YL)-1,2-DIHYDROQUINOLINE-6-SULFONAMIDE, Respectively

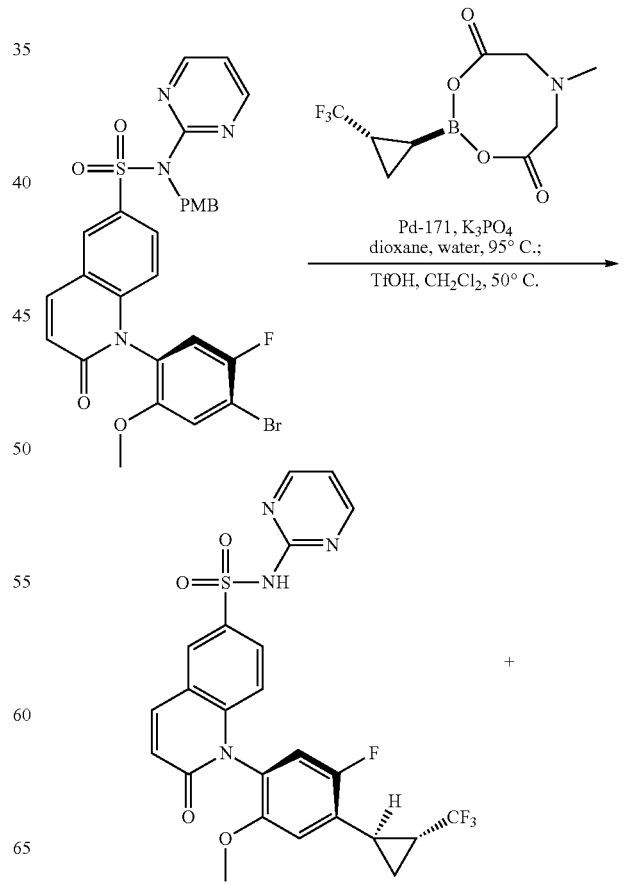

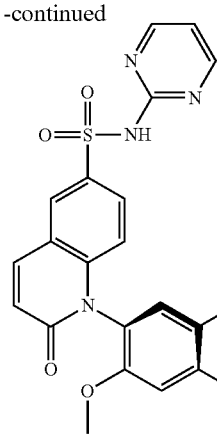

A 40-mL vial was charged with Pd-171 (80 mg, 0.12 mmol), (P)-1-(4-bromo-5-fluoro-2-methoxyphenyl)-N-(4-methoxybenzyl)-2-oxo-N-(pyrimidin-2-yl)-1,2-dihydroquinoline-6-sulfonamide (500 mg, 0.799 mmol), potassium phosphate (509 mg, 2.40 mmol), and trans-6-methyl-2-(2-(trifluoromethyl)cyclopropyl)-1,3,6,2-dioxazaborocane-4,8-dione (318 mg, 1.20 mmol), 1,4-dioxane (3.0 mL) and water (1.0 mL). The vial was sparged with nitrogen and then heated to 95° C. After stirring for 6 h, the mixture was filtered through a phase separator, washing with dichloromethane. Volatiles were removed in vacuo. The residue was taken up in dichloromethane (1 mL) and treated with trifluoromethanesulfonic acid (0.2 mL, 2.4 mmol). After heating at 50° C. for 1 h, volatiles were removed, and the product was purified using a (S,S) Whelk-O, 2×25 cm column. The mobile phase was run under isocratic conditions; supercritical $CO_2$ with 40% methanol; flow rate: 80 mL/min. The first peak was further purified using a Chiralcel OJ-H, 3×25 cm column. The mobile phase was run under isocratic conditions; supercritical $CO_2$ with 25% methanol; flow rate: 80 mL/min. The second and third eluting peaks were isolated, and each was taken up in PhMe (1 mL) and heated to 100° C. for 1 h. Solvent was then removed.

The second peak was further purified using a (S,S) Whelk-01, 2.1×25 cm column. The mobile phase was run under isocratic conditions; supercritical $CO_2$ with 35% methanol; flow rate: 80 mL/min. The first eluting peak was assigned (P)-1-(5-fluoro-2-methoxy-4-((1R,2R)-2-(trifluoromethyl)cyclopropyl)phenyl)-2-oxo-N-(pyrimidin-2-yl)-1,2-dihydroquinoline-6-sulfonamide (14.3 mg). $^1$H NMR (500 MHz, CHLOROFORM-d) δ ppm 10.89-11.97 (m, 1H), 8.65 (d, J=4.9 Hz, 2H), 8.42 (d, J=1.8 Hz, 1H), 8.06 (dd, J=8.8, 2.1 Hz, 1H), 7.85 (d, J=9.9 Hz, 1H), 7.01 (t, J=4.8 Hz, 1H), 6.96 (d, J=9.3 Hz, 1H), 6.84 (d, J=9.6 Hz, 1H), 6.69-6.78 (m, 2H), 3.69 (s, 3H), 2.48-2.58 (m, 1H), 2.03 (dq, J=8.8, 5.8 Hz, 1H), 1.50 (dt, J=9.7, 5.6 Hz, 1H), 1.32-1.41 (m, 1H). m/z (ESI, positive ion) 534.9 (M+H)$^+$.

The third peak from above was further purified using a (S,S) Whelk-01, 2.1×25 cm column. The mobile phase was run under isocratic conditions; supercritical $CO_2$ with 40% methanol; flow rate: 80 mL/min. The first eluting peak was assigned (P)-1-(5-fluoro-2-methoxy-4-((1S,2S)-2-(trifluoromethyl)cyclopropyl)phenyl)-2-oxo-N-(pyrimidin-2-yl)-1,2-dihydroquinoline-6-sulfonamide (13.7 mg). $^1$H NMR (500 MHz, CHLOROFORM-d) δ ppm 10.75-12.14 (m, 1H), 8.65 (d, J=4.7 Hz, 2H), 8.42 (d, J=1.6 Hz, 1H), 8.05 (dd, J=8.8, 1.8 Hz, 1H), 7.85 (d, J=9.6 Hz, 1H), 7.01 (t, J=4.8 Hz, 1H), 6.95 (d, J=9.3 Hz, 1H), 6.85 (d, J=9.6 Hz, 1H), 6.70-6.78 (m, 2H), 3.70 (s, 3H), 2.45-2.63 (m, 1H), 1.97-2.14 (m, 1H), 1.45-1.55 (m, 1H), 1.32-1.42 (m, 1H). m/z (ESI, positive ion) 535.0 (M+H)$^+$.

Example 22: (P)-1-(5-FLUORO-2-METHOXY-4-(1-(TRIFLUOROMETHYL)CYCLOPROPYL)PHENYL)-N-(ISOXAZOL-3-YL)-2-OXO-1,2-DIHYDROQUINOLINE-6-SULFONAMIDE

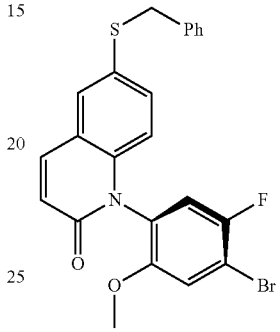

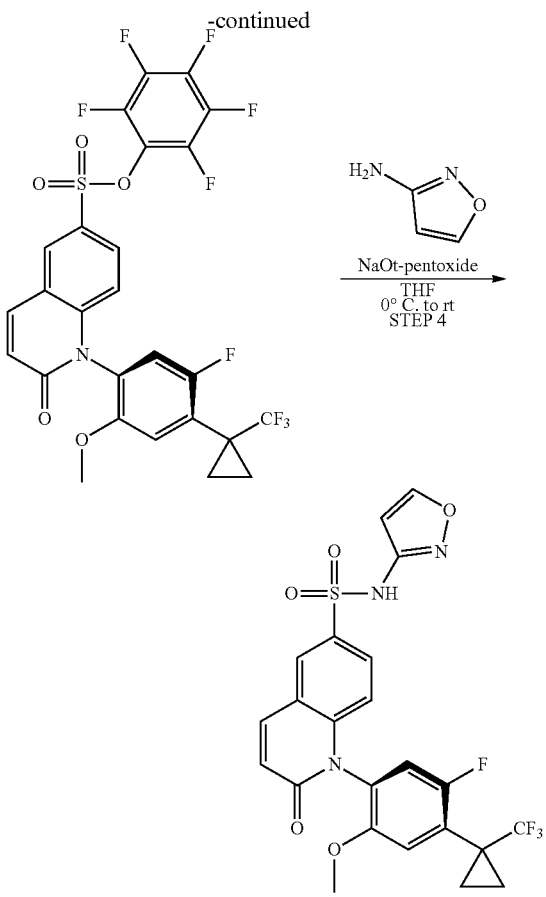

Step 1: (P)-6-(BENZYLTHIO)-1-(5-FLUORO-2-METHOXY-4-(3,3,3-TRIFLUOROPROP-1-EN-2-YL)PHENYL)QUINOLIN-2(1H)-ONE A 100-mL round-bottom flask was charged with (P)-6-(benzylthio)-1-(4-bromo-5-fluoro-2-methoxyphenyl)quinolin-2(1H)-one (2.00 g, 4.25 mmol), potassium phosphate (2.71 g, 12.8 mmol), and bis-(di-tert-butyl(4-dimethylaminophenyl)phosphine)dichloropalladium(II) (0.602 g, 0.850 mmol). The vial was flushed with nitrogen before 1,4-dioxane (18 mL), water (6.1 mL), and 1-(trifluoromethyl) vinylboronic acid hexylene glycol ester (1.1 mL, 5.3 mmol) were added. The vessel was warmed to 50° C. and stirred at this temperature for 16 h. The reaction was cooled to room temperature, diluted with EtOAc and water, and extracted thrice with EtOAc. The combined organic extracts were washed with brine, dried over $Na_2SO_4$, and concentrated. Purification via column chromatography (gradient elution 5-60% EtOAc:heptane) yielded (P)-6-(benzylthio)-1-(5-fluoro-2-methoxy-4-(3,3,3-trifluoroprop-1-en-2-yl)phenyl) quinolin-2(1H)-one (1.80 g, 3.71 mmol, 87% yield). $^1$H NMR (500 MHz, DMSO-$d_6$) δ ppm 7.96 (d, J=9.3 Hz, 1H), 7.80 (d, J=2.3 Hz, 1H), 7.49 (d, J=9.6 Hz, 1H), 7.42 (dd, J=8.8, 2.3 Hz, 1H), 7.32-7.35 (m, 2H), 7.26-7.31 (m, 2H), 7.19-7.26 (m, 2H), 6.68 (d, J=9.6 Hz, 1H), 6.50 (d, J=8.8 Hz, 1H), 6.43 (d, J=1.0 Hz, 1H), 6.18 (s, 1H), 4.24 (s, 2H), 3.69 (s, 3H). m/z (ESI, positive ion) 486.0 (M+H)$^+$.

Step 2: (P)-6-(BENZYLTHIO)-1-(5-FLUORO-2-METHOXY-4-(1-(TRIFLUOROMETHYL)CYCLOPROPYL)PHENYL)QUINOLIN-2(1H)-ONE A 40-mL vial was charged with (P)-6-(benzylthio)-1-(5-fluoro-2-methoxy-4-(3,3,3-trifluoroprop-1-en-2-yl)phenyl) quinolin-2(1H)-one (516 mg, 1.06 mmol), triethylammonium bis(catecholato)iodomethylsilicate (1.30 g, 2.67 mmol), and 2,4,5,6-tetrakis(carbazol-9-yl)-1,3-dicyanobenzene (85 mg, 0.11 mmol). The vial was flushed with nitrogen before DMSO (11 mL) was added. The mixture was sparged with nitrogen, irradiated with blue LEDs in a Penn OC Photoreactor ml at 5% intensity, 1000 rpm stirring, and 4500 rpm fan speed for 6 h, and then at 50% intensity, 1000 rpm stirring, and 4500 rpm fan speed for 2.5 h. The reaction was diluted with EtOAc and washed thrice with 2 N NaOH. The organic extract was washed with water then brine, dried over $Na_2SO_4$, and concentrated. The residue was purified by column chromatography (gradient elution 10-60% EtOAc:heptane) to afford (P)-6-(benzylthio)-1-(5-fluoro-2-methoxy-4-(1-(trifluoromethyl)cyclopropyl)phenyl)quinolin-2(1H)-one (193 mg, 0.386 mmol, 36% yield). $^1$H NMR (500 MHz, DMSO-$d_6$) δ ppm 7.95 (d, J=9.3 Hz, 1H), 7.79 (d, J=2.3 Hz, 1H), 7.42 (dd, J=8.8, 2.1 Hz, 1H), 7.39 (d, J=9.6 Hz, 1H), 7.31-7.36 (m, 3H), 7.26-7.30 (m, 2H), 7.19-7.25 (m, 1H), 6.67 (d, J=9.6 Hz, 1H), 6.45 (d, J=8.8 Hz, 1H), 4.23 (s, 2H), 3.69 (s, 3H), 1.44-1.53 (m, 2H), 1.28-1.36 (m, 2H). m/z (ESI, positive ion) 500.0 (M+H)$^+$.

Step 3: PERFLUOROPHENYL (P)-1-(5-FLUORO-2-METHOXY-4-(1-(TRIFLUOROMETHYL)CYCLOPROPYL)PHENYL)-2-OXO-1,2-DIHYDROQUINOLINE-6-SULFONATE A 40-mL vial was charged with (P)-6-(benzylthio)-1-(5-fluoro-2-methoxy-4-(1-(trifluoromethyl)cyclopropyl)phenyl)quinolin-2(1H)-one (560 mg, 1.12 mmol), acetonitrile (4.25 mL), water (0.11 mL), and acetic acid (0.16 mL). The solution was cooled to 0° C. before 1,3-dichloro-5,5-dimethyl-2,4-imidazolidinedione (331 mg, 1.68 mmol) was added in two portions. After 1 h, pentafluorophenol (248 mg, 1.35 mmol) and then triethylamine (0.625 mL, 4.48 mmol) were added sequentially. After 5 min, the reaction was quenched by the addition of 1 N HCl and extracted 5 times with EtOAc. The combined organic extracts were washed with brine, dried over $Na_2SO_4$, and concentrated. The residue was purified by column chromatography (gradient elution 25-50% EtOAc:heptane) to afford perfluorophenyl (P)-1-(5-fluoro-2-methoxy-4-(1-(trifluoromethyl)cyclopropyl) phenyl)-2-oxo-1,2-dihydroquinoline-6-sulfonate (403 mg, 0.646 mmol, 58% yield). $^1$H NMR (500 MHz, DMSO-$d_6$) δ ppm 8.60 (d, J=2.3 Hz, 1H), 8.26 (d, J=9.6 Hz, 1H), 7.99 (dd, J=9.1, 2.3 Hz, 1H), 7.53 (d, J=9.9 Hz, 1H), 7.40 (d, J=6.5 Hz, 1H), 6.89 (d, J=9.6 Hz, 1H), 6.82 (d, J=9.1 Hz, 1H), 3.71 (s, 3H), 1.45-1.54 (m, 2H), 1.27-1.36 (m, 2H). m/z (ESI, positive ion) 624.0 (M+H)$^+$.

Step 4: (P)-1-(5-FLUORO-2-METHOXY-4-(1-(TRIFLUOROMETHYL)CYCLOPROPYL)PHENYL)-N-(ISOXAZOL-3-YL)-2-OXO-1,2-DIHYDROQUINOLINE-6-SULFONAMIDE A 2-dram vial was charged with isoxazol-3-amine (0.019 mL, 0.28 mmol), perfluorophenyl (P)-1-(5-fluoro-2-methoxy-4-(1-(trifluoromethyl)cyclopropyl)phenyl)-2-oxo-1,2-dihydroquinoline-6-sulfonate (150 mg, 0.241 mmol), and THF (1.6 mL). The vial was cooled to 0° C., and sodium tert-pentoxide (0.34 mL, 0.48 mmol, 1.4 M in THF) was added. The resulting yellow solution was stirred at 0° C. for 1 h. The reaction was then diluted with EtOAc, quenched through the addition of 1 N HCl, and extracted thrice with EtOAc. The combined organic extracts were washed with brine, dried over $Na_2SO_4$, and concentrated in vacuo. The residue was purified via column chromatography (gradient elution 20-70% EtOAc:heptane) to afford (P)-1-(5-fluoro-2-methoxy-4-(1-(trifluoromethyl)cyclopropyl)phenyl)-N-(isoxazol-3-yl)-2-oxo-1,2-dihydroquinoline-6-sulfonamide (54 mg, 0.10 mmol, 43% yield). $^1$H NMR (500 MHz, DMSO-$d_6$) δ ppm 11.65 (s, 1H), 8.72 (d, J=1.6 Hz, 1H), 8.36 (d, J=2.1 Hz, 1H), 8.22 (d, J=9.6 Hz, 1H), 7.85 (dd, J=9.0, 2.2 Hz, 1H), 7.45 (d, J=9.9 Hz, 1H), 7.36 (d, J=6.2 Hz, 1H), 6.80 (d, J=9.6 Hz, 1H), 6.74 (d, J=9.1 Hz, 1H), 6.44 (d, J=1.8 Hz, 1H), 3.69 (s, 3H), 1.44-1.53 (m, 2H), 1.24-1.37 (m, 2H). m/z (ESI, positive ion) 524.0 $(M+H)^+$.

Example 23: (P)-1-(5-FLUORO-2-METHOXY-4-(1-(TRIFLUOROMETHYL)CYCLOPROPYL)PHENYL)-2-OXO-N-(PYRIMIDIN-2-YL)-1,2-DIHYDROQUINOLINE-6-SULFONAMIDE 1 h. The reaction was then diluted with EtOAc, quenched through the addition of 1 N HCl, and extracted thrice with EtOAc. The combined organic extracts were washed with brine, dried over $Na_2SO_4$, and concentrated in vacuo. The residue was purified via column chromatography (gradient elution 20-70% EtOAc:heptane) to afford (P)-1-(5-fluoro-2-methoxy-4-(1-(trifluoromethyl)cyclopropyl)phenyl)-2-oxo-N-(pyrimidin-2-yl)-1,2-dihydroquinoline-6-sulfonamide (60 mg, 0.11 mmol, 47% yield). $^1$H NMR (500 MHz, DMSO-$d_6$) δ ppm 11.62-12.01 (m, 1H), 8.50 (d, J=4.7 Hz, 2H), 8.47 (d, J=1.8 Hz, 1H), 8.25 (d, J=9.6 Hz, 1H), 7.99 (dd, J=9.0, 2.2 Hz, 1H), 7.44 (d, J=9.9 Hz, 1H), 7.36 (d, J=6.5 Hz, 1H), 7.05 (br s, 1H), 6.78 (d, J=9.6 Hz, 1H), 6.71 (d, J=8.8 Hz, 1H), 3.68 (s, 3H), 1.42-1.54 (m, 2H), 1.23-1.35 (m, 2H). m/z (ESI, positive ion) 535.0 $(M+H)^+$.

Example 24: (P)-1-(5-CHLORO-2-METHOXY-4-(1-(TRIFLUOROMETHYL)CYCLOPROPYL)PHENYL)-N-(ISOXAZOL-3-YL)-2-OXO-1,2-DIHYDROQUINOLINE-6-SULFONAMIDE

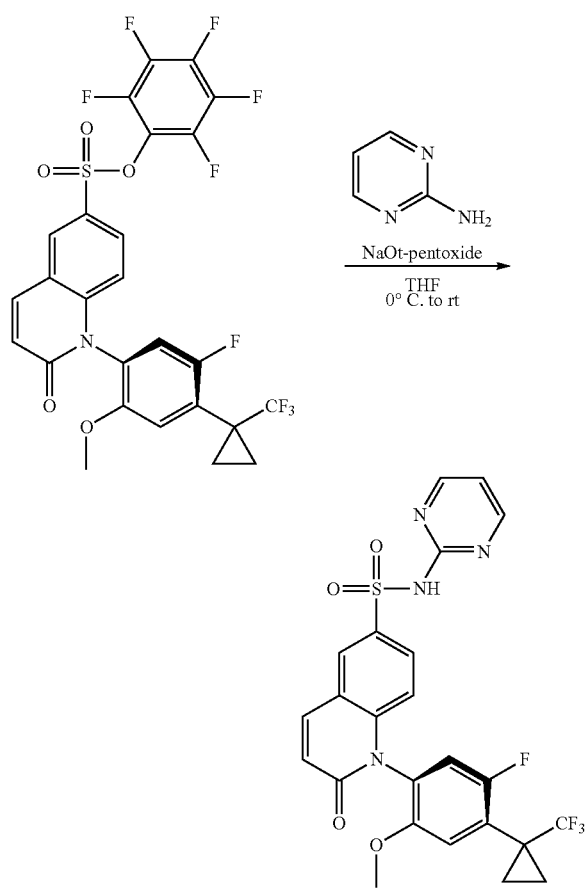

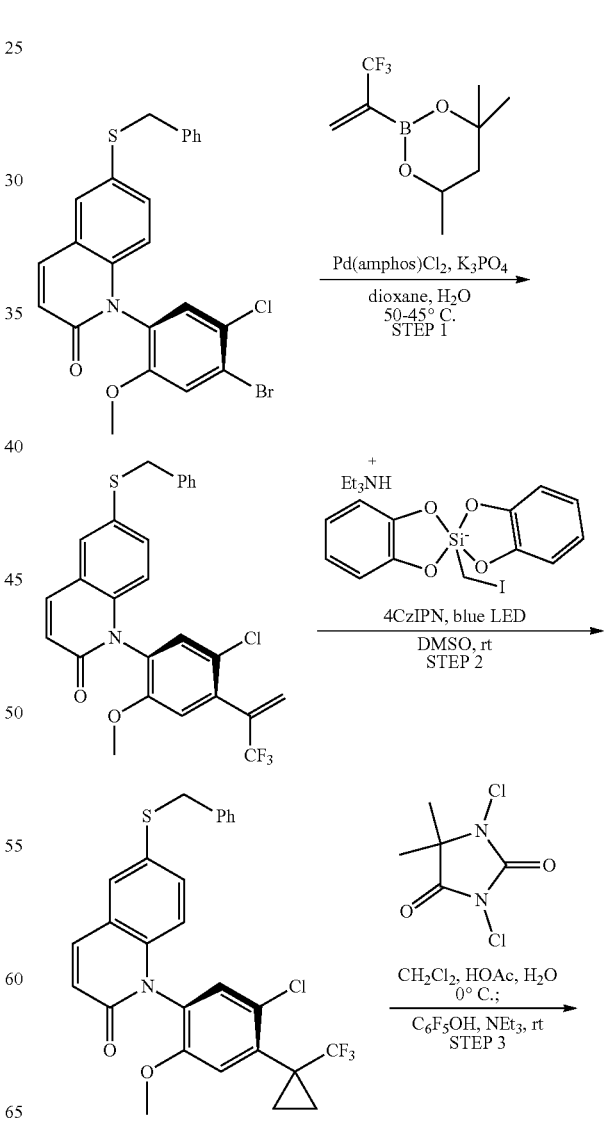

A 2-dram vial was charged with 2-pyrimidinamine (26 mg, 0.28 mmol), perfluorophenyl (P)-1-(5-fluoro-2-methoxy-4-(1-(trifluoromethyl)cyclopropyl)phenyl)-2-oxo-1,2-dihydroquinoline-6-sulfonate (150 mg, 0.241 mmol), and THF (1.6 mL). The vial was cooled to 0° C., and sodium tert-pentoxide (0.34 mL, 0.48 mmol, 1.4 M in THF) was added. The resulting yellow solution was stirred at 0° C. for

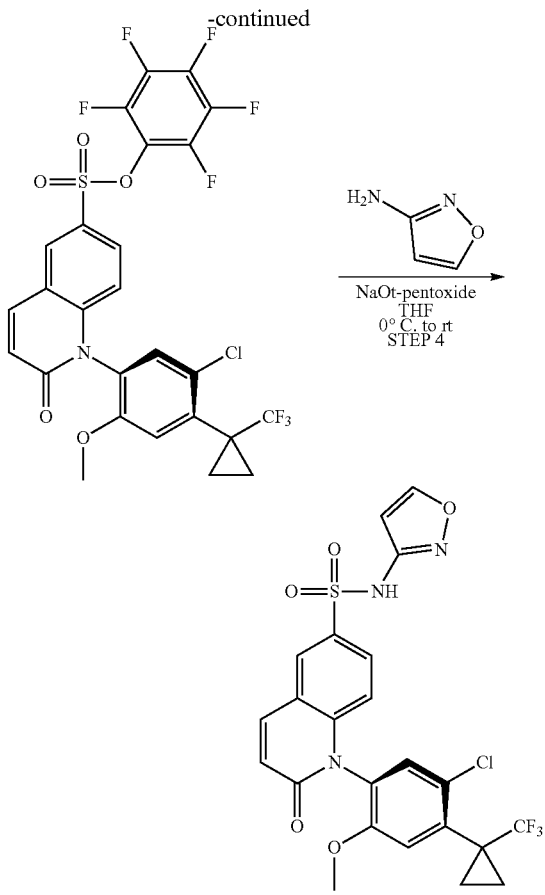

Step 1: (P)-6-(BENZYLTHIO)-1-(5-CHLORO-2-METHOXY-4-(3,3,3-TRIFLUOROPROP-1-EN-2-YL)PHENYL)QUINOLIN-2(1H)-ONE A 250-mL round-bottom flask was charged with (P)-6-(benzylthio)-1-(4-bromo-5-chloro-2-methoxyphenyl)quinolin-2(1H)-one (3.50 g, 7.19 mmol), potassium phosphate (4.58 g, 21.6 mmol), and bis-(di-tert-butyl(4-dimethylaminophenyl)phosphine)dichloropalladium(ii) (1.02 g, 1.44 mmol). The vial was flushed with nitrogen before 1,4-dioxane (27 mL), water (9 mL), and 1-(trifluoromethyl)vinylboronic acid hexylene glycol ester (1.9 mL, 9.4 mmol) were added. The vessel was warmed to 50° C. and stirred at this temperature for 1 h and then stirred at 45° C. for 15.5 h. The reaction was cooled to room temperature, diluted with EtOAc and water, and extracted twice with EtOAc. The combined organic extracts were washed with brine, dried over $Na_2SO_4$, and concentrated. Purification via column chromatography (gradient elution 0-70% EtOAc:heptane) yielded (P)-6-(benzylthio)-1-(5-chloro-2-methoxy-4-(3,3,3-trifluoroprop-1-en-2-yl)phenyl)quinolin-2(1H)-one (3.14 g, 6.26 mmol, 87% yield). $^1$H NMR (500 MHz, DMSO-$d_6$) δ ppm 7.96 (d, J=9.6 Hz, 1H), 7.80 (d, J=2.3 Hz, 1H), 7.66 (s, 1H), 7.44 (dd, J=8.7, 2.2 Hz, 1H), 7.32-7.37 (m, 2H), 7.26-7.31 (m, 3H), 7.18-7.25 (m, 1H), 6.68 (d, J=9.6 Hz, 1H), 6.49 (d, J=8.8 Hz, 1H), 6.45 (s, 1H), 6.04 (s, 1H), 4.24 (s, 2H), 3.70 (s, 3H). m/z (ESI, positive ion) 502.0 (M+H)$^+$.

Step 2: (P)-6-(BENZYLTHIO)-1-(5-CHLORO-2-METHOXY-4-(1-(TRIFLUOROMETHYL)CYCLOPROPYL)PHENYL)QUINOLIN-2(1H)-ONE A 40-mL vial was charged with (P)-6-(benzylthio)-1-(5-chloro-2-methoxy-4-(3,3,3-trifluoroprop-1-en-2-yl)phenyl)quinolin-2(1H)-one (1.10 g, 2.19 mmol), triethylammonium bis(catecholato)iodomethylsilicate (3.20 g, 6.57 mmol), and 2,4,5,6-tetrakis(carbazol-9-yl)-1,3-dicyanobenzene (175 mg, 0.349 mmol). The vial was flushed with nitrogen before DMSO (22 mL) was added. The mixture was sparged with nitrogen for 15 minutes, irradiated with blue LEDs in a Penn OC Photoreactor ml at 50% intensity, 1000 rpm stirring, and 4500 rpm fan speed for 6 h. In parallel, two other identical reactions were set up using 150 mg and 915 mg of (P)-6-(benzylthio)-1-(5-chloro-2-methoxy-4-(3,3,3-trifluoroprop-1-en-2-yl)phenyl)quinolin-2(1H)-one (using similar stoichiometry and concentrations of reagents and solvent). The reactions were combined, diluted with EtOAc, cooled using an ice bath, and washed thrice with 2 N NaOH. The organic extract was washed with twice with water then brine, dried over $Na_2SO_4$, and concentrated. The residue was purified by column chromatography (gradient elution 0-60% EtOAc:heptane) to afford (P)-6-(benzylthio)-1-(5-chloro-2-methoxy-4-(1-(trifluoromethyl)cyclopropyl)phenyl)quinolin-2(1H)-one (712 mg, 1.38 mmol, 35% yield). $^1$H NMR (500 MHz, DMSO-$d_6$) δ ppm 7.95 (d, J=9.3 Hz, 1H), 7.78 (d, J=2.1 Hz, 1H), 7.54 (s, 1H), 7.42 (dd, J=8.8, 2.3 Hz, 1H), 7.40 (s, 1H), 7.31-7.35 (m, 2H), 7.26-7.30 (m, 2H), 7.19-7.25 (m, 1H), 6.67 (d, J=9.3 Hz, 1H), 6.44 (d, J=8.8 Hz, 1H), 4.23 (s, 2H), 3.71 (s, 3H), 1.45-1.69 (m, 2H), 1.32-1.41 (m, 2H). m/z (ESI, positive ion) 516.0 (M+H)$^+$.

Step 3: PERFLUOROPHENYL (P)-1-(5-CHLORO-2-METHOXY-4-(1-(TRIFLUOROMETHYL)CYCLOPROPYL)PHENYL)-2-OXO-1,2-DIHYDROQUINOLINE-6-SULFONATE A vial was charged with (P)-6-(benzylthio)-1-(5-chloro-2-methoxy-4-(1-(trifluoromethyl)cyclopropyl)phenyl)quinolin-2(1H)-one (712 mg, 1.38 mmol), acetonitrile (4.5 mL), water (0.11 mL), and acetic acid (0.17 mL). The solution was cooled to 0° C. before 1,3-dichloro-5,5-dimethyl-2,4-imidazolidinedione (408 mg, 2.07 mmol) was added. After 30 min, pentafluorophenol (305 mg, 1.66 mmol) and then triethylamine (0.77 mL, 5.5 mmol) were added sequentially. After 5 min, the reaction was quenched by the addition of 1 N HCl and extracted 4 times with EtOAc. The combined organic extracts were washed with brine, dried over $Na_2SO_4$, and concentrated. The residue was purified by column chromatography (gradient elution 10-65% EtOAc:heptane) to afford perfluorophenyl (P)-1-(5-chloro-2-methoxy-4-(1-(trifluoromethyl)cyclopropyl)phenyl)-2-oxo-1,2-dihydroquinoline-6-sulfonate (624 mg, 0.975 mmol, 71% yield). $^1$H NMR (500 MHz, DMSO-$d_6$) δ ppm 8.60 (d, J=2.3 Hz, 1H), 8.25 (d, J=9.6 Hz, 1H), 8.00 (dd, J=9.1, 2.3 Hz, 1H), 7.70 (s, 1H), 7.46 (s, 1H), 6.89 (d, J=9.6 Hz, 1H), 6.82 (d, J=9.1 Hz, 1H), 3.74 (s, 3H), 1.57 (br t, J=3.1 Hz, 2H), 1.29-1.46 (m, 2H). m/z (ESI, positive ion) 640.0 (M+H)$^+$.

Step 4: (P)-1-(5-CHLORO-2-METHOXY-4-(1-(TRIFLUOROMETHYL)CYCLOPROPYL)PHENYL)-N-(ISOXAZOL-3-YL)-2-OXO-1,2-DIHYDROQUINOLINE-6-SULFONAMIDE A 2-dram vial was charged with isoxazol-3-amine (0.025 mL, 0.37 mmol), perfluorophenyl (P)-1-(5-chloro-2- methoxy-4-(1-(trifluoromethyl)cyclopropyl)phenyl)-2-oxo-1,2-dihydroquinoline-6-sulfonate (203 mg, 0.317 mmol), and THF (2 mL). The vial was cooled to 0° C., and sodium tert-pentoxide (0.40 mL, 0.56 mmol, 1.4 M in THF) was added. The resulting yellow solution was stirred at 0° C. for 45 min, and then an additional portion of sodium tert-pentoxide (0.10 mL, 0.14 mmol, 1.4 M in THF) was added. After the reaction was stirred for 5 min, it was then quenched through the addition of 1 N HCl and water and extracted thrice with dichloromethane. The combined organic extracts were filtered through a phase separator and concentrated in vacuo. The residue was purified using a Torus Diol, 3×15 cm column. The mobile phase was run under gradient conditions; supercritical $CO_2$ with 10-30% methanol; flow rate: 100 mL/min. This afforded (P)-1-(5-chloro-2-methoxy-4-(1-(trifluoromethyl)cyclopropyl)phenyl)-N-(isoxazol-3-yl)-2-oxo-1,2-dihydroquinoline-6-sulfonamide (77.5 mg, 0.144 mmol, 45% yield). $^1$H NMR (600 MHz, DMSO-$d_6$) δ ppm 11.64 (br s, 1H), 8.72 (d, J=1.8 Hz, 1H), 8.36 (d, J=2.2 Hz, 1H), 8.22 (d, J=9.8 Hz, 1H), 7.86 (dd, J=9.1, 2.2 Hz, 1H), 7.62 (s, 1H), 7.43 (s, 1H), 6.80 (d, J=9.4 Hz, 1H), 6.74 (d, J=9.1 Hz, 1H), 6.44 (d, J=1.8 Hz, 1H), 3.72 (s, 3H), 1.56 (s, 2H), 1.26-1.42 (m, 2H). m/z (ESI, positive ion) 539.8 (M+H)$^+$.

Example 25: (P)-1-(5-CHLORO-2-METHOXY-4-(1-(TRIFLUOROMETHYL)CYCLOPROPYL) PHENYL)-2-OXO-N-(PYRIMIDIN-2-YL)-1,2-DIHYDROQUINOLINE-6-SULFONAMIDE A 2-dram vial was charged with 2-pyrimidinamine (35 mg, 0.37 mmol), perfluorophenyl (P)-1-(5-chloro-2-methoxy-4-(1-(trifluoromethyl)cyclopropyl)phenyl)-2-oxo-1,2-dihydroquinoline-6-sulfonate (203 mg, 0.317 mmol), and THF (2 mL). The vial was cooled to 0° C., and sodium tert-pentoxide (0.40 mL, 0.56 mmol, 1.4 M in THF) was added. The resulting yellow solution was stirred at 0° C. for 20 min, and then quenched through the addition of 1 N HCl and water. The mixture was then extracted thrice with dichloromethane. The combined organic extracts were filtered through a phase separator and concentrated in vacuo. The residue was purified using a Torus Diol, 3×15 cm column. The mobile phase was run under gradient conditions; supercritical $CO_2$ with 10-30% methanol; flow rate: 100 mL/min. This afforded (P)-1-(5-chloro-2-methoxy-4-(1-(trifluoromethyl)cyclopropyl)phenyl)-2-oxo-N-(pyrimidin-2-yl)-1,2-dihydroquinoline-6-sulfonamide (93.0 mg, 0.169 mmol, 53% yield). $^1$H NMR (600 MHz, DMSO-$d_6$) δ ppm 11.60-12.10 (m, 1H), 8.45-8.60 (m, 3H), 8.25 (d, J=9.8 Hz, 1H), 7.99 (dd, J=8.7, 2.2 Hz, 1H), 7.61 (s, 1H), 7.42 (s, 1H), 7.05 (br t, J=4.5 Hz, 1H), 6.78 (d, J=9.8 Hz, 1H), 6.71 (d, J=9.1 Hz, 1H), 3.71 (s, 3H), 1.56 (s, 2H), 1.30-1.45 (m, 2H). m/z (ESI, positive ion) 551.0 (M+H)$^+$.

Examples 26 & 27: (P)-N-(ISOXAZOL-3-YL)-1-(2-METHOXY-5-METHYL-4-((1R,2R)-2-(TRIFLUOROMETHYL)CYCLOPROPYL)PHENYL)-2-OXO-1,2-DIHYDROQUINOLINE-6-SULFONAMIDE and (P)-N-(ISOXAZOL-3-YL)-1-(2-METHOXY-5-METHYL-4-((1S,2S)-2-(TRIFLUOROMETHYL)CYCLOPROPYL) PHENYL)-2-OXO-1,2-DIHYDROQUINOLINE-6-SULFONAMIDE, Respectively

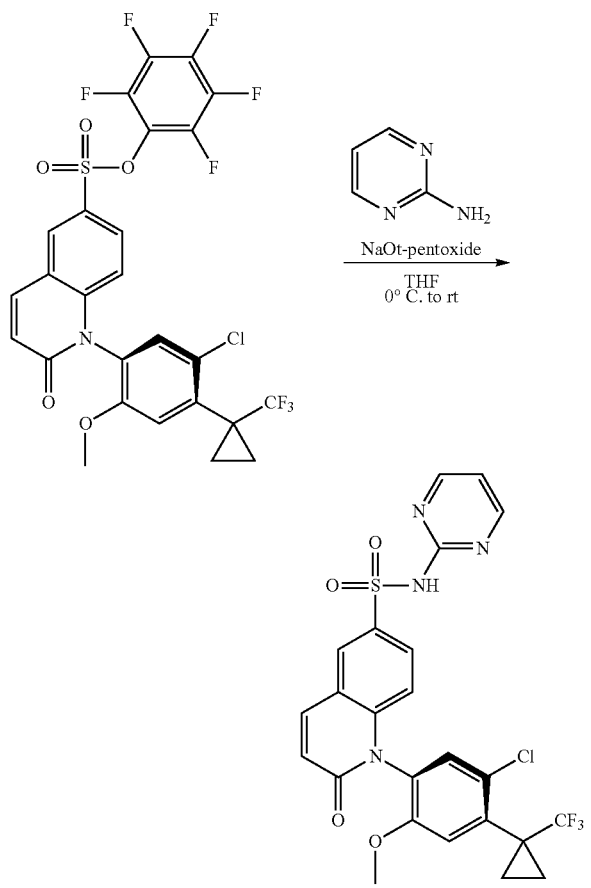

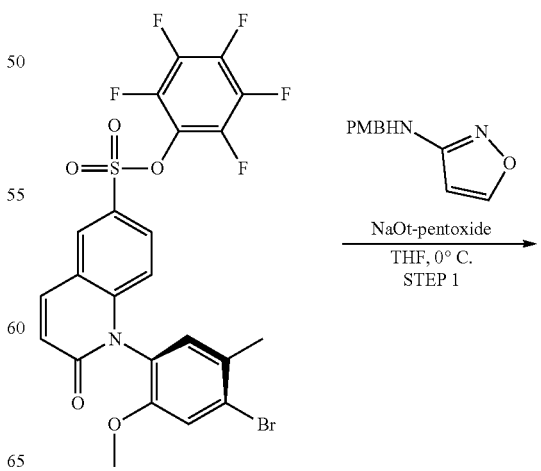

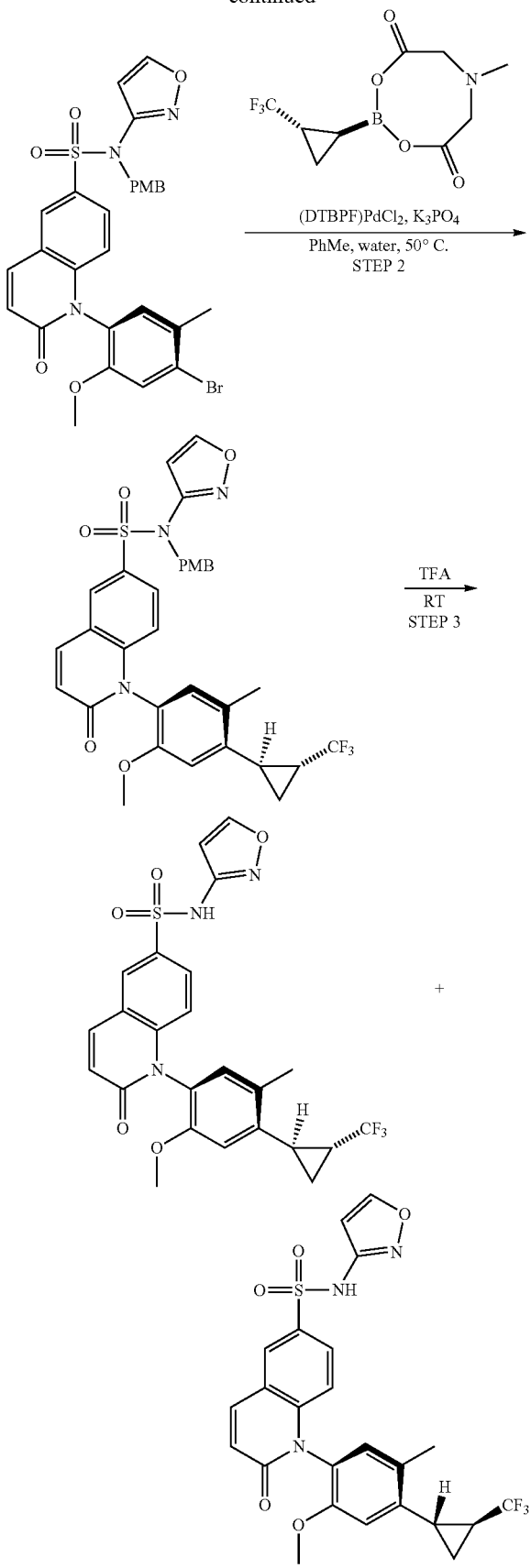

Step 1: (P)-1-(4-BROMO-2-METHOXY-5-METH-YLPHENYL)-N-(ISOXAZOL-3-YL)-N-(4-METHOXYBENZYL)-2-OXO-1,2-DIHYDROQUI-NOLINE-6-SULFONAMIDE A 40-mL vial was charged with N-(4-methoxybenzyl) isoxazol-3-amine (270 mg, 1.32 mmol), perfluorophenyl (P)-1-(4-bromo-2-methoxy-5-methylphenyl)-2-oxo-1,2-dihydroquinoline-6-sulfonate (650 mg, 1.10 mmol), and THF (5.6 mL). The reaction mixture was cooled to 0° C., and sodium tert-pentoxide, (0.60 mL, 1.5 mmol, 30% in THF) was added dropwise. After 30 min, the reaction was quenched via the addition of sat. aq. NH$_4$Cl and extracted 4 times with EtOAc. The combined organic extracts were washed with brine, dried over Na$_2$SO$_4$, filtered, and concentrated. The residue was purified by column chromatography (gradient elution 10-80% [3:1 EtOAc:EtOH]:heptane) to afford (P)-1-(4-bromo-2-methoxy-5-methylphenyl)-N-(isoxazol-3-yl)-N-(4-methoxybenzyl)-2-oxo-1,2-dihydroquinoline-6-sulfonamide (640 mg, 1.05 mmol, 95% yield). $^1$H NMR (500 MHz, DMSO-d$_6$) δ ppm 8.80 (d, J=1.8 Hz, 1H), 8.27-8.40 (m, 1H), 8.15 (d, J=9.6 Hz, 1H), 7.77 (dd, J=9.1, 2.3 Hz, 1H), 7.53 (s, 1H), 7.35 (s, 1H), 7.20-7.30 (m, 2H), 6.84-6.91 (m, 2H), 6.81 (d, J=9.6 Hz, 1H), 6.69-6.75 (m, 2H), 4.91 (s, 2H), 3.71 (s, 3H), 3.69 (s, 3H), 2.32 (s, 3H). m/z (ESI, positive ion) 610.0 (M+H)$^+$.

Step 2: TRANS-(P)-N-(ISOXAZOL-3-YL)-1-(2-METHOXY-5-METHYL-4-(2-(TRIFLUOROM-ETHYL)CYCLOPROPYL)PHENYL)-N-(4-METHOXYBENZYL)-2-OXO-1,2-DIHYDROQUINOLINE-6-SULFONAMIDE A 40-mL vial was charged with (P)-1-(4-bromo-2-methoxy-5-methylphenyl)-N-(isoxazol-3-yl)-N-(4-methoxybenzyl)-2-oxo-1,2-dihydroquinoline-6-sulfonamide (431 mg, 0.706 mmol), [1,1'-bis(di-tert-butylphosphino)ferrocene]dichloropalladium(II) (46 mg, 0.071 mmol), trans-6-methyl-2-(2-(trifluoromethyl)cyclopropyl)-1,3,6,2-dioxazaborocane-4,8-dione (234 mg, 0.883 mmol), potassium phosphate (599 mg, 2.82 mmol) and then flushed with nitrogen. Toluene (3.75 mL) and water (0.94 mL) were added and the reaction mixture was sparged with nitrogen and then heated to 50° C. for 22.5 h. The reaction was then poured onto a 1:1 mixture of brine:water and extracted thrice with EtOAc. The combined organic extracts were washed with brine, dried over Na$_2$SO$_4$, filtered, and concentrated. The residue was purified by column chromatography (gradient elution 0-30% [3:1 EtOAc:EtOH]:heptane) to afford trans-(P)-N-(isoxazol-3-yl)-1-(2-methoxy-5-methyl-4-(2-(trifluoromethyl)cyclopropyl)phenyl)-N-(4-methoxybenzyl)-2-oxo-1,2-dihydroquinoline-6-sulfonamide (404 mg, 0.632 mmol, 89% yield). $^1$H NMR (500 MHz, DMSO-d$_6$) δ ppm 8.79 (dd, J=1.8, 0.8 Hz, 1H), 8.33 (d, J=2.3 Hz, 1H), 8.12 (d, J=9.6 Hz, 1H), 7.76 (td, J=8.7, 2.3 Hz, 1H), 7.24 (d, J=7.8 Hz, 2H), 7.12 (d, J=1.6 Hz, 1H), 6.92 (d, J=3.1 Hz, 1H), 6.85 (d, J=8.3 Hz, 2H), 6.79 (d, J=9.6 Hz, 1H), 6.72 (dd, J=1.8, 1.0 Hz, 1H), 6.65 (dd, J=9.1, 3.9 Hz, 1H), 4.90 (s, 2H), 3.70 (s, 3H), 3.66 (s, 3H), 2.44-2.46 (m, 1H), 2.29-2.38 (m, 4H), 1.40-1.46 (m, 1H), 1.23-1.29 (m, 1H). m/z (ESI, positive ion) 640.0 (M+H)$^+$.

Step 3: (P)-N-(ISOXAZOL-3-YL)-1-(2-METHOXY-5-METHYL-4-((1R,2R)-2-(TRIFLUOROMETHYL)CYCLOPROPYL)PHENYL)-2-OXO-1,2-DIHYDROQUINOLINE-6-SULFONAMIDE AND (P)-N-(ISOXAZOL-3-YL)-1-(2-METHOXY-5-METHYL-4-((1S,2S)-2-(TRIFLUOROMETHYL)CYCLOPROPYL)PHENYL)-2-OXO-1,2-DIHYDROQUINOLINE-6-SULFONAMIDE A 40-mL vial containing trans-(P)-N-(isoxazol-3-yl)-1-(2-methoxy-5-methyl-4-(2-(trifluoromethyl)cyclopropyl)phenyl)-N-(4-methoxybenzyl)-2-oxo-1,2-dihydroquinoline-6-sulfonamide (404 mg, 0.632 mmol) was charged with trifluoroacetic acid (4 mL). The reaction was stirred at rt for 16.75 h. The reaction was then poured onto stirring sat. aq. NaHCO$_3$. After gas evolution had ceased, the mixture was extracted thrice with dichloromethane. The combined organics were washed with brine, dried over Na$_2$SO$_4$, and concentrated. The residue was purified using a Chiralcel OJ-H, 2×25 cm column. The mobile phase was run under isocratic conditions; supercritical CO$_2$ with 30% methanol; flow rate: 60 mL/min. The first eluting peak was assigned (P)-N-(isoxazol-3-yl)-1-(2-methoxy-5-methyl-4-((1R,2R)-2-(trifluoromethyl)cyclopropyl)phenyl)-2-oxo-1,2-dihydroquinoline-6-sulfonamide (127.8 mg). The second eluting peak was assigned (P)-N-(isoxazol-3-yl)-1-(2-methoxy-5-methyl-4-((1S,2S)-2-(trifluoromethyl)cyclopropyl)phenyl)-2-oxo-1,2-dihydroquinoline-6-sulfonamide (123.2 mg). Data for peak 1: $^1$H NMR (600 MHz, DMSO-d$_6$) δ ppm 11.61 (br s, 1H), 8.72 (d, J=1.5 Hz, 1H), 8.34 (d, J=2.2 Hz, 1H), 8.19 (d, J=9.8 Hz, 1H), 7.83 (dd, J=8.7, 2.2 Hz, 1H), 7.11 (s, 1H), 6.91 (s, 1H), 6.77 (d, J=9.4 Hz, 1H), 6.71 (d, J=8.7 Hz, 1H), 6.44 (d, J=1.8 Hz, 1H), 3.65 (s, 3H), 2.42-2.48 (m, 1H), 2.29-2.39 (m, 4H), 1.49-1.58 (m, 1H), 1.40 (dt, J=9.5, 5.4 Hz, 1H). m/z (ESI, positive ion) 520.0 (M+H)$^+$. Data for peak 2: $^1$H NMR (600 MHz, DMSO-d$_6$) δ ppm 11.60 (br s, 1H), 8.71 (d, J=1.5 Hz, 1H), 8.34 (d, J=2.2 Hz, 1H), 8.19 (d, J=9.8 Hz, 1H), 7.82 (dd, J=8.7, 2.2 Hz, 1H), 7.11 (s, 1H), 6.92 (s, 1H), 6.77 (d, J=9.8 Hz, 1H), 6.72 (d, J=9.1 Hz, 1H), 6.44 (d, J=1.8 Hz, 1H), 3.65 (s, 3H), 2.39-2.48 (m, 2H), 2.34 (s, 3H), 1.33-1.50 (m, 2H). m/z (ESI, positive ion) 520.0 (M+H)$^+$.

Examples 28 & 29: (P)-1-(2-METHOXY-5-METHYL-4-((1R,2R)-2-(TRIFLUOROMETHYL)CYCLOPROPYL)PHENYL)-2-OXO-N-(PYRIMIDIN-2-YL)-1,2-DIHYDROQUINOLINE-6-SULFONAMIDE and (P)-1-(2-METHOXY-5-METHYL-4-((1S,2S)-2-(TRIFLUOROMETHYL)CYCLOPROPYL)PHENYL)-2-OXO-N-(PYRIMIDIN-2-YL)-1,2-DIHYDROQUINOLINE-6-SULFONAMIDE, Respectively

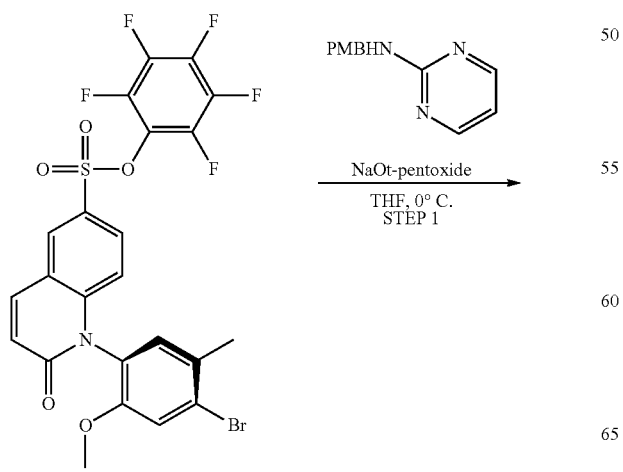

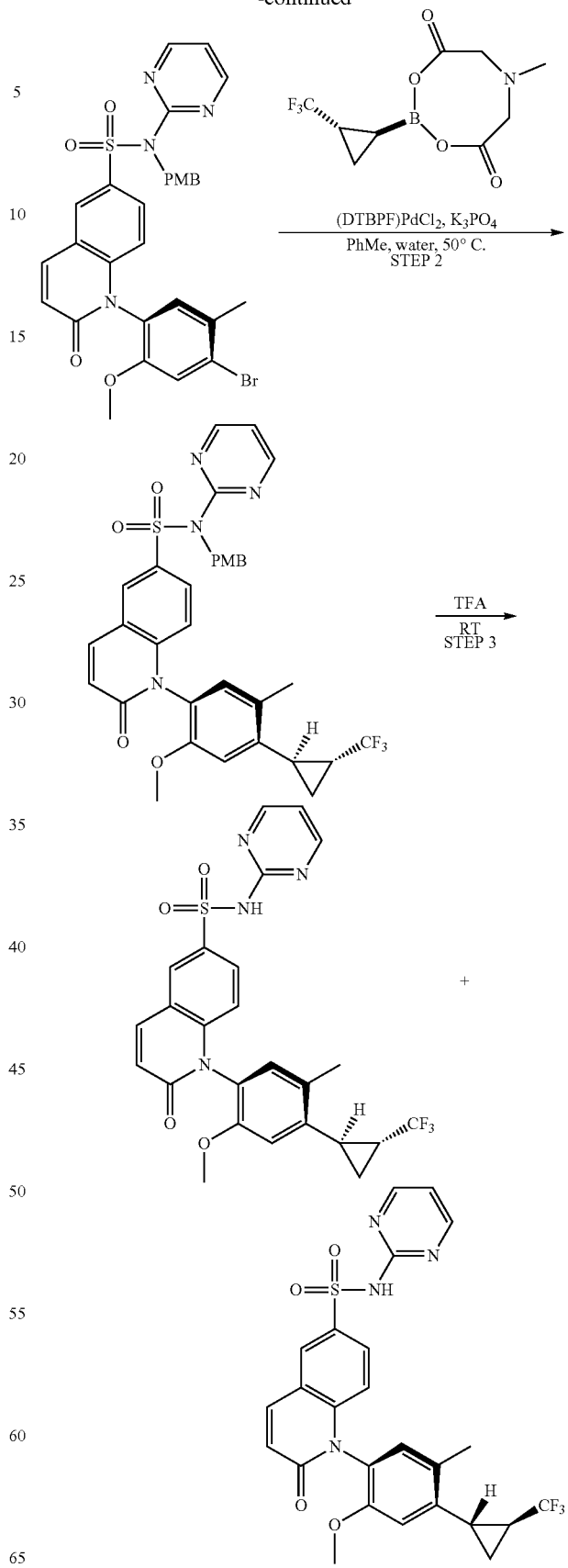

Step 1: (P)-1-(4-BROMO-2-METHOXY-5-METHYLPHENYL)-N-(4-METHOXYBENZYL)-2-OXO-N-(PYRIMIDIN-2-YL)-1,2-DIHYDROQUINOLINE-6-SULFONAMIDE A 40-mL vial was charged with N-(4-methoxybenzyl)pyrimidin-2-amine (284 mg, 1.32 mmol), perfluorophenyl (P)-1-(4-bromo-2-methoxy-5-methylphenyl)-2-oxo-1,2-dihydroquinoline-6-sulfonate (650 mg, 1.10 mmol), and THF (5.6 mL). The reaction mixture was cooled to 0° C., and sodium tert-pentoxide, (0.60 mL, 1.5 mmol, 30% in THF) was added dropwise. After 30 min, the reaction was quenched via the addition of sat. aq. $NH_4Cl$ and extracted 4 times with EtOAc. The combined organic extracts were washed with brine, dried over $Na_2SO_4$, filtered, and concentrated. The residue was purified by column chromatography (gradient elution 50-80% [3:1 EtOAc:EtOH]:heptane with 15% dichloromethane coeluent) to afford (P)-1-(4-bromo-2-methoxy-5-methylphenyl)-N-(4-methoxybenzyl)-2-oxo-N-(pyrimidin-2-yl)-1,2-dihydroquinoline-6-sulfonamide (299 mg, 0.481 mmol, 44% yield). $^1$H NMR (500 MHz, DMSO-$d_6$) δ ppm 8.58 (d, J=4.9 Hz, 2H), 8.38 (d, J=2.3 Hz, 1H), 8.12 (d, J=9.6 Hz, 1H), 7.96 (dd, J=9.0, 2.2 Hz, 1H), 7.53 (s, 1H), 7.33 (s, 1H), 7.28 (d, J=8.8 Hz, 2H), 7.13 (t, J=4.9 Hz, 1H), 6.84-6.90 (m, 2H), 6.77 (d, J=9.6 Hz, 1H), 6.67 (d, J=9.1 Hz, 1 H), 5.35 (s, 2H), 3.72 (s, 3H), 3.67 (s, 3H), 2.32 (s, 3H). m/z (ESI, positive ion) 621.0 $(M+H)^+$.

Step 2: TRANS-(P)-1-(2-METHOXY-5-METHYL-4-(2-(TRIFLUOROMETHYL)CYCLOPROPYL)PHENYL)-N-(4-METHOXYBENZYL)-2-OXO-N-(PYRIMIDIN-2-YL)-1,2-DIHYDROQUINOLINE-6-SULFONAMIDE A 2-dram vial was charged with (P)-1-(4-bromo-2-methoxy-5-methylphenyl)-N-(4-methoxybenzyl)-2-oxo-N-(pyrimidin-2-yl)-1,2-dihydroquinoline-6-sulfonamide (299 mg, 0.481 mmol), [1,1'-bis(di-tert-butylphosphino)ferrocene]dichloropalladium(II) (31 mg, 0.048 mmol), trans-6-methyl-2-(2-(trifluoromethyl)cyclopropyl)-1,3,6,2-dioxazaborocane-4,8-dione (159 mg, 0.601 mmol), potassium phosphate (408 mg, 1.92 mmol) and then flushed with nitrogen. Toluene (2.6 mL) and water (0.65 mL) were added and the reaction mixture was sparged with nitrogen and then heated to 50° C. for 16 h. The reaction was then diluted with EtOAc and water and extracted thrice with EtOAc. The combined organic extracts were washed with brine, dried over $Na_2SO_4$, filtered, and concentrated. The residue was purified by column chromatography (gradient elution 30-80% EtOAc:heptane) to afford trans-(P)-1-(2-methoxy-5-methyl-4-(2-(trifluoromethyl)cyclopropyl)phenyl)-N-(4-methoxybenzyl)-2-oxo-N-(pyrimidin-2-yl)-1,2-dihydroquinoline-6-sulfonamide (307 mg, 0.472 mmol, 98% yield). $^1$H NMR (500 MHz, DMSO-$d_6$) δ ppm 8.57 (d, J=4.7 Hz, 2H), 8.36 (t, J=1.9 Hz, 1H), 8.10 (d, J=9.9 Hz, 1H), 7.89-8.01 (m, 1H), 7.28 (dd, J=8.7, 1.4 Hz, 2H), 7.06-7.17 (m, 2H), 6.92 (d, J=3.9 Hz, 1H), 6.85-6.88 (m, 2H), 6.76 (d, J=9.6 Hz, 1H), 6.61 (dd, J=9.0, 5.6 Hz, 1H), 5.35 (s, 2H), 3.71 (s, 3H), 3.65 (s, 3H), 2.43-2.48 (m, 2H), 2.34 (s, 3H), 1.37-1.46 (m, 1H), 1.26-1.30 (m, 1H). m/z (ESI, positive ion) 651.0 $(M+H)^+$.

Step 3: (P)-1-(2-METHOXY-5-METHYL-4-((1R,2R)-2-(TRIFLUOROMETHYL)CYCLOPROPYL)PHENYL)-2-OXO-N-(PYRIMIDIN-2-YL)-1,2-DIHYDROQUINOLINE-6-SULFONAMIDE AND (P)-1-(2-METHOXY-5-METHYL-4-((1S,2S)-2-(TRIFLUOROMETHYL)CYCLOPROPYL)PHENYL)-2-OXO-N-(PYRIMIDIN-2-YL)-1,2-DIHYDROQUINOLINE-6-SULFONAMIDE A 40-mL vial containing trans-(P)-1-(2-methoxy-5-methyl-4-(2-(trifluoromethyl)cyclopropyl)phenyl)-N-(4-methoxybenzyl)-2-oxo-N-(pyrimidin-2-yl)-1,2-dihydroquinoline-6-sulfonamide (307 mg, 0.472 mmol) was charged with trifluoroacetic acid (2.4 mL). The reaction was stirred at rt for 17.5 h. The reaction was then poured onto stirring sat. aq. $NaHCO_3$. After gas evolution had ceased, the mixture was extracted thrice with dichloromethane. The combined organics were washed with brine, dried over $Na_2SO_4$, and concentrated. The residue was purified using two Chiralpak IG, 2×15 cm columns. The mobile phase was run under isocratic conditions; supercritical $CO_2$ with 35% [4:1 EtOH:dichloromethane]; flow rate: 50 mL/min. The first eluting peak was assigned (P)-1-(2-methoxy-5-methyl-4-((1R,2R)-2-(trifluoromethyl)cyclopropyl)phenyl)-2-oxo-N-(pyrimidin-2-yl)-1,2-dihydroquinoline-6-sulfonamide (76.0 mg). The second eluting peak was assigned (P)-1-(2-methoxy-5-methyl-4-((1S,2S)-2-(trifluoromethyl)cyclopropyl)phenyl)-2-oxo-N-(pyrimidin-2-yl)-1,2-dihydroquinoline-6-sulfonamide (70.1 mg). Data for peak 1: $^1$H NMR (500 MHz, DMSO-$d_6$) δ ppm 11.57-12.09 (m, 1H), 8.50 (d, J=4.9 Hz, 2H), 8.45 (d, J=2.1 Hz, 1H), 8.22 (d, J=9.6 Hz, 1H), 7.96 (dd, J=9.0, 2.2 Hz, 1H), 7.11 (s, 1H), 7.05 (t, J=4.7 Hz, 1H), 6.91 (s, 1H), 6.76 (d, J=9.6 Hz, 1H), 6.68 (d, J=9.1 Hz, 1H), 3.65 (s, 3H), 2.46 (dt, J=9.4, 5.7 Hz, 2H), 2.26-2.37 (m, 4H), 1.48-1.58 (m, 1H), 1.40 (dt, J=9.6, 5.4 Hz, 1H). m/z (ESI, positive ion) 531.0 $(M+H)^+$. Data for peak 2: $^1$H NMR (500 MHz, DMSO-$d_6$) δ ppm 11.67-12.10 (m, 1H), 8.49 (d, J=4.9 Hz, 2H), 8.44 (d, J=2.1 Hz, 1H), 8.22 (d, J=9.6 Hz, 1H), 7.94 (dd, J=9.0, 2.2 Hz, 1H), 7.10 (s, 1H), 7.04 (br t, J=4.7 Hz, 1H), 6.92 (s, 1H), 6.75 (d, J=9.6 Hz, 1H), 6.69 (d, J=8.8 Hz, 1H), 3.64 (s, 3H), 2.40-2.46 (m, 2H), 2.34 (s, 3H), 1.37-1.48 (m, 2H). m/z (ESI, positive ion) 531.0 $(M+H)^+$.

Examples 30 & 31: (P)-1-(4-((1S,2S)-[1,1'-BI(CYCLOPROPAN)]-2-YL)-5-FLUORO-2-METHOXYPHENYL)-N-(ISOXAZOL-3-YL)-2-OXO-1,2-DIHYDROQUINOLINE-6-SULFONAMIDE and (P)-1-(4-((1R,2S)-[1,1'-BI(CYCLOPROPAN)]-2-YL)-5-FLUORO-2-METHOXYPHENYL)-N-(ISOXAZOL-3-YL)-2-OXO-1,2-DIHYDROQUINOLINE-6-SULFONAMIDE, Respectively

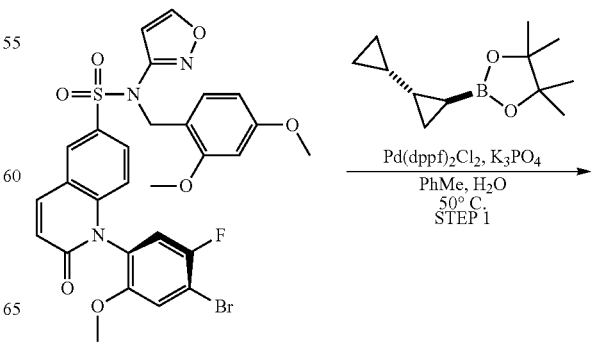

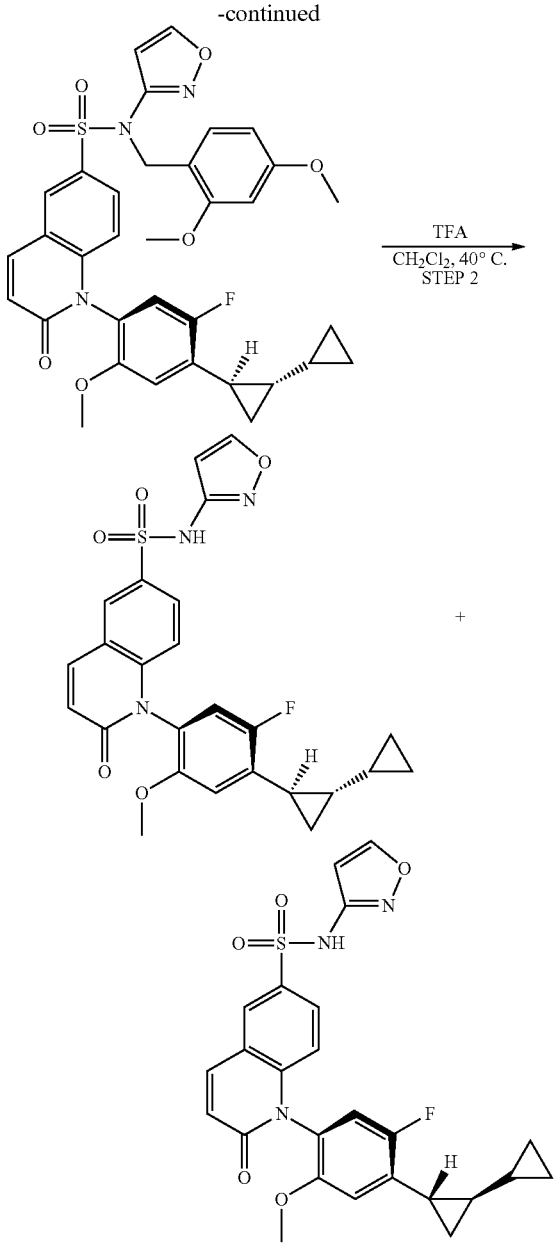

Step 1: TRANS-(P)-1-(4-([1,1'-BI(CYCLOPROPAN)]-2-YL)-5-FLUORO-2-METHOXYPHENYL)-N-(2,4-DIMETHOXYBENZYL)-N-(ISOXAZOL-3-YL)-2-OXO-1,2-DIHYDROQUINOLINE-6-SULFONAMIDE To a vial containing (P)-1-(4-bromo-5-fluoro-2-methoxyphenyl)-N-(2,4-dimethoxybenzyl)-N-(isoxazol-3-yl)-2-oxo-1,2-dihydroquinoline-6-sulfonamide (800 mg, 1.24 mmol), [1,1'-bis(di-tert-butylphosphino)ferrocene]dichloropalladium(II) (81 mg, 0.12 mmol), potassium phosphate (1.05 g, 4.97 mmol), trans-1-cyclopropyl-cyclopropyl-2-boronic acid pinacol ester (310 mg, 1.49 mmol) was added toluene (4.0 mL) and water (1.0 mL). The reaction was flushed with nitrogen and stirred at 50° C. for 16 h. The reaction was then cooled to room temperature, diluted with EtOAc, and washed twice with water. Volatiles were then removed, and the residue was purified by column chromatography (gradient elution, 0-30% [3:1 EtOAc/EtOH]:heptane) to afford 1-(4-([1,1'-bi(cyclopropan)]-2-yl)-5-fluoro-2-methoxyphenyl)-N-(2,4-dimethoxybenzyl)-N-(isoxazol-3-yl)-2-oxo-1,2-dihydroquinoline-6-sulfonamide (589 mg, 0.912 mmol, 74% yield). m/z (ESI, positive ion) 646.0 (M+H)$^+$.

Step 2: (P)-1-(4-(((1S,2S)-[1,1'-BI(CYCLOPROPAN)]-2-YL)-5-FLUORO-2-METHOXYPHENYL)-N-(ISOXAZOL-3-YL)-2-OXO-1,2-DIHYDROQUINOLINE-6-SULFONAMIDE AND (P)-1-(4-(((1R,2S)-[1,1'-BI(CYCLOPROPAN)]-2-YL)-5-FLUORO-2-METHOXYPHENYL)-N-(ISOXAZOL-3-YL)-2-OXO-1,2-DIHYDROQUINOLINE-6-SULFONAMIDE To a vial containing (P)-1-(4-([1,1'-bi(cyclopropan)]-2-yl)-5-fluoro-2-methoxyphenyl)-N-(2,4-dimethoxybenzyl)-N-(isoxazol-3-yl)-2-oxo-1,2-dihydroquinoline-6-sulfonamide (500 mg, 0.774 mmol) in dichloromethane (1 mL), TFA (1 mL) was added. The reaction was allowed to stir at 40° C. for 4 h. Volatiles were removed, and the residue purified by reverse phase HPLC using a XBridge Prep Shield RP18 19×100 mm column. The mobile phase was run under a gradient elution; 25-70% water/acetonitrile with 0.1% formic acid; flow rate: 40 mL/min. The material was further purified using a Chiralcel OJ-H, 2×25 cm column. The mobile phase was run under isocratic conditions; supercritical $CO_2$ with 30% methanol; flow rate: 60 mL/min. The first eluting peak was assigned (P)-1-(4-(((1S,2S)-[1,1'-bi(cyclopropan)]-2-yl)-5-fluoro-2-methoxyphenyl)-N-(isoxazol-3-yl)-2-oxo-1,2-dihydroquinoline-6-sulfonamide (101.5 mg). The second eluting peak was assigned (P)-1-(4-(((1R,2S)-[1,1'-bi(cyclopropan)]-2-yl)-5-fluoro-2-methoxyphenyl)-N-(isoxazol-3-yl)-2-oxo-1,2-dihydroquinoline-6-sulfonamide (136.7 mg). Data for peak 1: $^1$H NMR (500 MHz, CHLOROFORM-d) δ ppm 8.77 (br s, 1H), 8.24 (s, 1H), 8.12 (d, J=1.8 Hz, 1H), 7.68-7.80 (m, 2H), 6.87 (d, J=9.3 Hz, 1H), 6.84 (d, J=9.6 Hz, 1H), 6.76 (d, J=8.8 Hz, 1H), 6.51-6.62 (m, 2H), 3.65 (s, 3H), 1.87-1.98 (m, 1H), 1.20-1.34 (m, 1H), 0.98-1.06 (m, 1H), 0.95 (dt, J=8.7, 5.3 Hz, 1H), 0.89 (dt, J=8.6, 5.5 Hz, 1H), 0.39-0.53 (m, 2H), 0.14-0.28 (m, 2H). m/z (ESI, positive ion) 496.0 (M+H)$^+$. Data for peak 2: $^1$H NMR (500 MHz, CHLOROFORM-d) δ ppm 9.01 (br s, 1H), 8.23 (s, 1H), 8.13 (d, J=1.6 Hz, 1H), 7.75 (dd, J=9.1, 1.8 Hz, 2H), 6.85 (br dd, J=17.3, 9.5 Hz, 2H), 6.77 (d, J=8.8 Hz, 1H), 6.44-6.66 (m, 2H), 3.65 (s, 3H), 1.85-1.99 (m, 1H), 1.22-1.36 (m, 1H), 0.98-1.11 (m, 1H), 0.94 (dt, J=8.6, 5.2 Hz, 1H), 0.88 (dt, J=8.6, 5.5 Hz, 1H), 0.39-0.57 (m, 2H), 0.16-0.32 (m, 2H). m/z (ESI, positive ion) 496.0 (M+H)$^+$.

Examples 32 & 33: (P)-1-(5-FLUORO-2-METHOXY-4-((1S,2S)-2-((TRIFLUOROMETHOXY)METHYL)CYCLOPROPYL)PHENYL)-N-(ISOXAZOL-3-YL)-2-OXO-1,2-DIHYDROQUINOLINE-6-SULFONAMIDE and (P)-1-(5-FLUORO-2-METHOXY-4-((1R,2R)-2-((TRIFLUOROMETHOXY)METHYL)CYCLOPROPYL)PHENYL)-N-(ISOXAZOL-3-YL)-2-OXO-1,2-DIHYDROQUINOLINE-6-SULFONAMIDE, Respectively
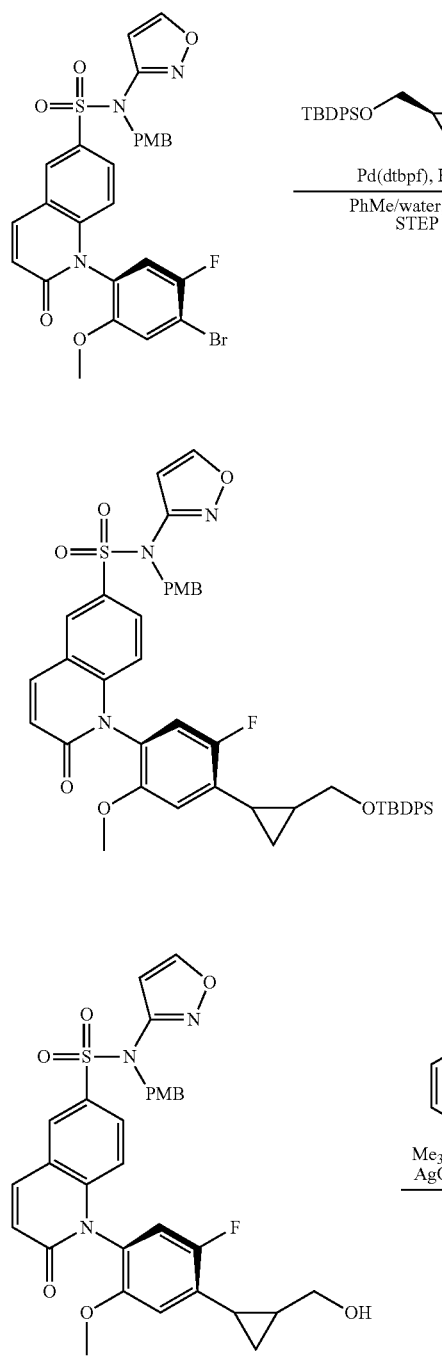
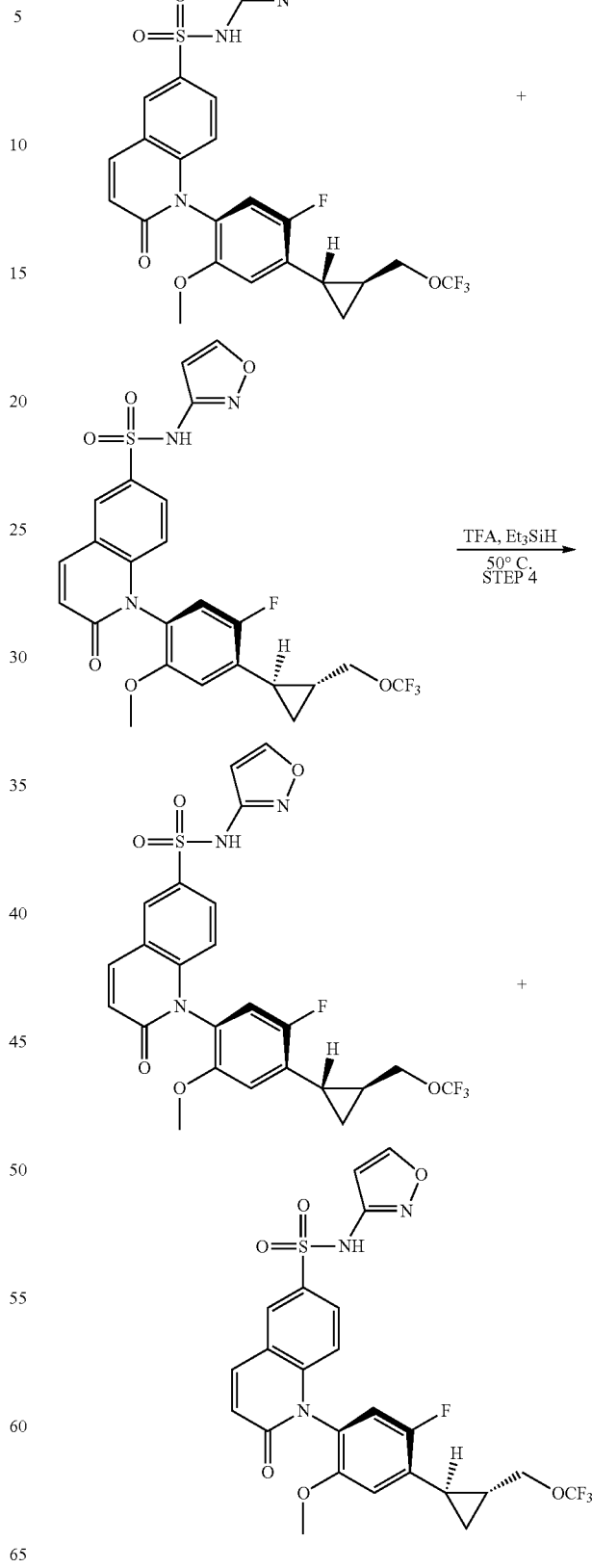

Step 1: (P)-1-(4-(2-(((TERT-BUTYLDIPHENYLSI-LYL)OXY)METHYL)CYCLOPROPYL)-5-FLUORO-2-METHOXYPHENYL)-N-(ISOXA-ZOL-3-YL)-N-(4-METHOXYBENZYL)-2-OXO-1, 2-DIHYDROQUINOLINE-6-SULFONAMIDE A vial was charged with (P)-1-(4-bromo-5-fluoro-2-methoxyphenyl)-N-(isoxazol-3-yl)-N-(4-methoxybenzyl)-2-oxo-1,2-dihydroquinoline-6-sulfonamide (600 mg, 0.976 mmol), [1,1'-bis(di-tert-butylphosphino)ferrocene]dichloropalladium(II) (127 mg, 0.195 mmol), tert-butyldiphenyl(((1R,2R)-2-(4,4,5,5-tetramethyl-1,3,2-dioxaborolan-2-yl)cyclopropyl)methoxy)silane (511 mg, 1.172 mmol) and tripotassium phosphate (829 mg, 3.91 mmol). The vial was purged with nitrogen, and then toluene (3.9 mL) and water (0.98 mL) were added. The reaction was stirred at 50° C. for 16 hours. The reaction mixture was filtered through a plug of Celite and concentrated under reduced pressure. The crude mixture was purified on column to give the desired product as a mixture of trans cyclopropyl isomers (0.96 g).

Step 2: (P)-1-(5-FLUORO-4-(2-(HYDROXYM-ETHYL)CYCLOPROPYL)-2-METHOXYPHE-NYL)-N-(ISOXAZOL-3-YL)-N-(4-METHOXY-BENZYL)-2-OXO-1,2-DIHYDROQUINOLINE-6-SULFONAMIDE To a solution of (P)-1-(4-(2-(((tert-butyldiphenylsilyl)oxy)methyl)cyclopropyl)-5-fluoro-2-methoxyphenyl)-N-(isoxazol-3-yl)-N-(4-methoxybenzyl)-2-oxo-1,2-dihydroquinoline-6-sulfonamide (960.1 mg, 1.138 mmol) in tetrahydrofuran (5.7 mL) was added a solution of tetrabutylammonium fluoride in THF (3.4 mL, 3.41 mmol). The mixture stirred at ambient temperature overnight. After 16 hours, the reaction was diluted partitioned between water and EtOAc. The organic layer was washed with brine, dried over anhydrous magnesium sulfate, filtered and concentrated to give the crude reaction mixture as an oil. The crude was purified by column chromatography, (silica gel: elution 0-50% (3:1 EtOAc/ethanol) in heptane) to give the title compound as an off-white solid (527 mg, 0.87 mmol, 76% yield). m/z (ESI, positive ion) 606.2 (M+H)$^+$.

Step 3: (P)-1-(5-FLUORO-2-METHOXY-4-((1S, 2S)-2-((TRIFLUOROMETHOXY) METHYL)CY-CLOPROPYL)PHENYL)-N-(ISOXAZOL-3-YL)-N-(4-METHOXYBENZYL)-2-OXO-1,2-DIHYDROQUINOLINE-6-SULFONAMIDE AND (P)-1-(5-FLUORO-2-METHOXY-4-((1R,2R)-2-((TRIFLUOROMETHOXY)METHYL)CYCLO-PROPYL) PHENYL)-N-(ISOXAZOL-3-YL)-N-(4-METHOXYBENZYL)-2-OXO-1,2-DIHYDROQUINOLINE-6-SULFONAMIDE, Respectively A vial was charged with potassium fluoride (200 mg, 3.45 mmol), silver trifluoromethanesulfonate (670 mg, 2.6 mmol), Selectfluor® (460 mg, 1.3 mmol), and (P)-1-(5-fluoro-4-(2-(hydroxymethyl)cyclopropyl)-2-methoxyphenyl)-N-(isoxazol-3-yl)-N-(4-methoxybenzyl)-2-oxo-1,2-dihydroquinoline-6-sulfonamide (526 mg, 0.87 mmol) under a stream of nitrogen. The vial was purged with nitrogen, and ethyl acetate (2.18 mL), 2-fluoropyridine (253 mg, 225 µL, 2.61 mmol), and trimethyl(trifluoromethyl)silane (371 mg, 386 µL, 2.61 mmol) were added. The reaction mixture was stirred at room temperature for 48 hours. The reaction mixture was filtered through a plug of Celite, which was washed with ethyl acetate. The filtrate was concentrated, and the product was purified by column chromatography (silica gel: elution 0-40% (3:1 EtOAc/ethanol with 10% DCM) in heptanes). This material was further purified using a Chiralpak AZ-H 2×25 cm, 5 µm column. The mobile phase was run under isocratic conditions; supercritical $CO_2$ with 30% ethanol; flow rate: 60 mL/min. The first eluting peak was assigned: (P)-1-(5-fluoro-2-methoxy-4-((1s,2S)-2-((trifluoromethoxy)methyl)cyclopropyl)phenyl)-N-(isoxazol-3-yl)-N-(4-methoxybenzyl)-2-oxo-1,2-dihydroquinoline-6-sulfonamide (50 mg). The second eluting peak was assigned (P)-1-(5-fluoro-2-methoxy-4-((1R,2R)-2-((trifluoromethoxy)methyl)cyclopropyl)phenyl)-N-(isoxazol-3-yl)-N-(4-methoxybenzyl)-2-oxo-1,2-dihydroquinoline-6-sulfonamide (50.4 mg). m/z (ESI, positive ion) 674.2 (M+H)$^+$.

Step 4: (P)-1-(5-FLUORO-2-METHOXY-4-((1S, 2S)-2-((TRIFLUOROMETHOXY) METHYL)CY-CLOPROPYL)PHENYL)-N-(ISOXAZOL-3-YL)-2-OXO-1,2-DIHYDROQUINOLINE-6-SULFONAMIDE AND (P)-1-(5-FLUORO-2-METHOXY-4-((1R,2R)-2-((TRIFLUOROMETHOXY)METHYL)CYCLOPROPYL)PHENYL)-N-(ISOXAZOL-3-YL)-2-OXO-1,2-DIHYDROQUINOLINE-6-SULFONAMIDE, Respectively Separately, (P)-1-(5-fluoro-2-methoxy-4-((1S,2S)-2-((trifluoromethoxy)methyl)cyclopropyl)phenyl)-N-(isoxazol-3-yl)-N-(4-methoxybenzyl)-2-oxo-1,2-dihydroquinoline-6-sulfonamide (50 mg, 0.074 mmol) and (P)-1-(5-fluoro-2-methoxy-4-((1R,2R)-2-((trifluoromethoxy)methyl)cyclopropyl)phenyl)-N-(isoxazol-3-yl)-N-(4-methoxybenzyl)-2-oxo-1,2-dihydroquinoline-6-sulfonamide (50.4 mg, 0.075 mmol) were dissolved in trifluoroacetic acid (171 mg, 171 µL, 1.5 mmol), and triethylsilane (43 mg, 60 µL, 0.37 mmol) was added to each reaction. The reactions were stirred at 50° C. for 4 hours, and then poured into saturated aqueous sodium bicarbonate and extracted with ethyl acetate. The organic layers were dried over anhydrous magnesium sulfate, filtered, and concentrated. The crude products were purified by column chromatography (silica gel: elution 0-40% (3:1 EtOAc/ethanol) in heptane with 10% DCM) to provide (P)-1-(5-fluoro-2-methoxy-4-((1R,2R)-2-((trifluoromethoxy)methyl)cyclopropyl)phenyl)-N-(isoxazol-3-yl)-2-oxo-1,2-dihydroquinoline-6-sulfonamide (35.5 mg, 0.064 mmol, 86% yield) and (P)-1-(5-fluoro-2-methoxy-4-((1S,2S)-2-((trifluoromethoxy)methyl)cyclopropyl)phenyl)-N-(isoxazol-3-yl)-2-oxo-1,2-dihydroquinoline-6-sulfonamide (38.7 mg, 0.070 mmol, 93% yield). Data for peak 1: $^1$H NMR (500 MHz, chloroform-d) δ 8.27 (d, J=1.69 Hz, 1H), 8.11 (d, J=2.08 Hz, 1H), 7.78 (d, J=9.60 Hz, 1H), 7.74 (dd, J=2.21, 8.95 Hz, 1H), 7.42 (s, 1H), 6.92 (d, J=9.34 Hz, 1H), 6.85 (d, J=9.60 Hz, 1H), 6.76 (d, J=8.95 Hz, 1H), 6.68 (d, J=6.36 Hz, 1H), 6.61 (d, J=1.82 Hz, 1H), 4.03-4.11 (m, 1H), 3.95-4.03 (m, 1H), 3.68 (s, 3H), 2.13-2.19 (m, 1H), 1.64-1.73 (m, 1H), 1.21-1.26 (m, 1H), 1.15 (m, 1H). m/z (ESI, positive ion) 554.1 (M+H)$^+$. Data for peak 2: $^1$H NMR (500 MHz, chloroform-d) δ 8.27 (d, J=1.43 Hz, 1H), 8.11 (d, J=2.08 Hz, 1H), 7.69-7.82 (m, 2H), 7.34 (s, 1H), 6.92 (d, J=9.21 Hz, 1H), 6.85 (d, J=9.60 Hz, 1H), 6.77 (d, J=8.95 Hz, 1H), 6.66 (d, J=6.36 Hz, 1H), 6.62 (d, J=1.82 Hz, 1H), 4.03-4.12 (m, 1H), 3.97-4.03 (m, 1H), 3.68 (s, 3H), 2.13-2.22 (m, 1H), 1.63-1.74 (m, 1H), 1.09-1.26 (m, 2H).

109

Example 34: (P)-1-(5-FLUORO-2-METHOXY-4-((1R,2R)-2-(TRIFLUOROMETHYL)CYCLOPROPYL)PHENYL)-2-OXO-N-(1,2,4-THIADIAZOL-5-YL)-1,2-DIHYDROQUINOLINE-6-SULFONAMIDE

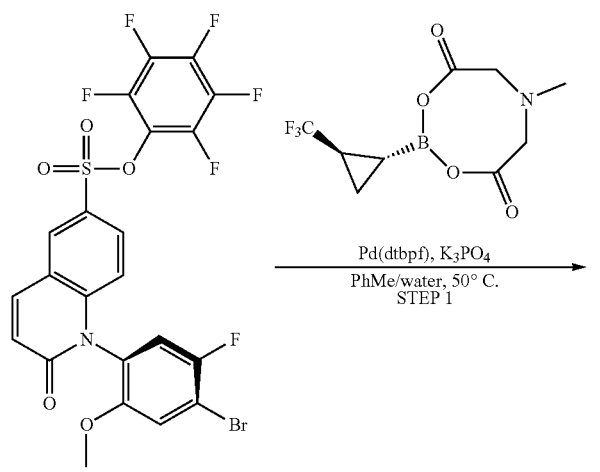

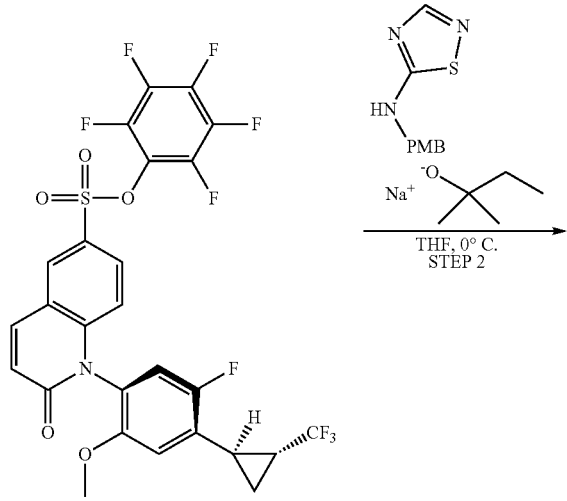

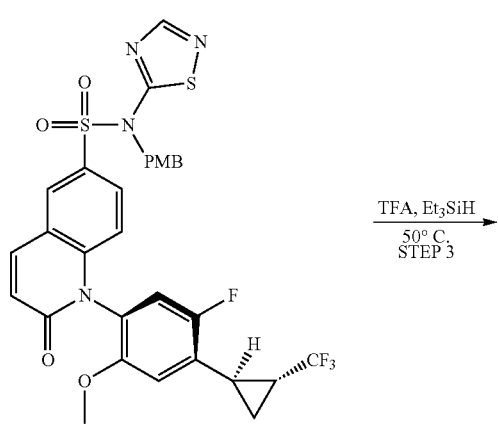

Step 1: PERFLUOROPHENYL (P)-1-(4-BROMO-5-FLUORO-2-METHOXYPHENYL)-2-OXO-1,2-DIHYDROQUINOLINE-6-SULFONATE A vial was charged with perfluorophenyl (P)-1-(4-bromo-5-fluoro-2-methoxyphenyl)-2-oxo-1,2-dihydroquinoline-6-sulfonate (50 mg, 0.084 mmol), [1,1'-bis(di-tert-butylphosphino)ferrocene]dichloropalladium(II) (13 mg, 0.021 mmol), tripotassium phosphate (71 mg, 0.34 mmol), and 6-methyl-2-((1R,2R)-2-(trifluoromethyl)cyclopropyl)-1,3,6,2-dioxazaborocane-4,8-dione (45 mg, 0.17 mmol). The vial was flushed with nitrogen, and then toluene (450 µL) and water (112 µL) were added. The reaction mixture was sparged with nitrogen, capped, and stirred at 50° C. for 14 hours. The reaction mixture was then partitioned between half-saturated aqueous sodium chloride and ethyl acetate. The layers were separated, and the aqueous layer was extracted with ethyl acetate. The combined organic layers were washed with brine, dried over anhydrous sodium sulfate, filtered, and concentrated. The Initial product was adsorbed onto a plug of silica gel and eluted with 60% ethyl acetate/heptane. The filtrate was concentrated to provide perfluorophenyl (P)-1-(5-fluoro-2-methoxy-4-((1R,2R)-2-(trifluoromethyl)cyclopropyl)phenyl)-2-oxo-1,2-dihydroquinoline-6-sulfonate (59 mg, 0.095 mmol, 112% yield). m/z (ESI, positive ion) 624.0 (M+H)+.

Step 2: (P)-1-(5-FLUORO-2-METHOXY-4-((1R,2R)-2-(TRIFLUOROMETHYL) CYCLOPROPYL)PHENYL)-N-(4-METHOXYBENZYL)-2-OXO-N-(1,2,4-THIADIAZOL-5-YL)-1,2-DIHYDROQUINOLINE-6-SULFONAMIDE A vial was charged with N-(4-methoxybenzyl)-1,2,4-thiadiazol-5-amine (121 mg, 0.546 mmol) and perfluorophenyl (P)-1-(5-fluoro-2-methoxy-4-((1R,2R)-2-(trifluoromethyl)cyclopropyl)phenyl)-2-oxo-1,2-dihydroquinoline-6-sulfonate (309.4 mg, 0.496 mmol). The vial was flushed with nitrogen, and then tetrahydrofuran (5.0 mL) was added and the reaction was cooled to 0° C. To the reaction was added sodium tert-pentoxide (1.4 M in THF, 430 µl, 0.60 mmol) slowly via syringe, and the reaction was stirred for 30 minutes at 0° C. After 30 minutes, the reaction mixture was partitioned between saturated aqueous ammonium chloride and DCM. The layers were separated, and the aqueous layer was extracted with DCM. The combined organic layers were concentrated, and the crude product was purified by column chromatography (silica gel: elution 20% to 80% EtOAc in heptane with 10% dichloromethane additive) to provide (P)-1-(5-fluoro-2-methoxy-4-((1R,2R)-2-(trifluoromethyl)cyclopropyl)phenyl)-N-(4-methoxybenzyl)-2-oxo-N-(1,2,4-thiadiazol-5-yl)-1,2-dihydroquinoline-6-sulfonamide (174 mg, 0.263 mmol, 53.0% yield) as a colorless waxy solid. m/z (ESI, positive ion) 660.8 (M+H)⁺.

Step 3: (P)-1-(5-FLUORO-2-METHOXY-4-((1R, 2R)-2-(TRIFLUOROMETHYL) CYCLOPROPYL) PHENYL)-2-OXO-N-(1,2,4-THIADIAZOL-5-YL)-1,2-DIHYDROQUINOLINE-6-SULFONAMIDE To a solution of (P)-1-(5-fluoro-2-methoxy-4-((1R,2R)-2-(trifluoromethyl)cyclopropyl)phenyl)-N-(4-methoxybenzyl)-2-oxo-N-(1,2,4-thiadiazol-5-yl)-1,2-dihydroquinoline-6-sulfonamide (172 mg, 0.260 mmol) in TFA (2.0 mL) was added triethylsilane (151 mg, 0.21 mL, 1.3 mmol), and the reaction was stirred at 50° C. for 2 hours. The reaction mixture was concentrated, and the residue was purified by column chromatography (silica gel: elution 10% to 60% (3:1 EtOAc/ethanol) in heptane with 10% dichloromethane additive) to provide (P)-1-(5-fluoro-2-methoxy-4-((1R,2R)-2-(trifluoromethyl)cyclopropyl)phenyl)-2-oxo-N-(1,2,4-thiadiazol-5-yl)-1,2-dihydroquinoline-6-sulfonamide (64.7 mg, 0.12 mmol, 46% yield) as a white solid. ¹H NMR (500 MHz, DMSO-d6) δ ppm 8.43 (s, 1H), 8.28 (d, J=2.21 Hz, 1H), 8.20 (d, J=9.60 Hz, 1H), 7.80 (dd, J=8.95, 2.21 Hz, 1H), 7.34 (d, J=9.86 Hz, 1H), 7.00 (d, J=6.75 Hz, 1H), 6.76 (d, J=9.60 Hz, 1H), 6.72 (d, J=8.95 Hz, 1H), 3.66 (s, 3H), 2.51-2.58 (m, 2H), 1.56-1.61 (m, 1H), 1.46-1.51 (m, 1H). m/z (ESI, positive ion) 540.8 (M+H)⁺.

Examples 35 & 36: (P)-1-(5-FLUORO-2-METHOXY-4-((1R,2R)-2-(TRIFLUOROMETHYL) CYCLOPROPYL)PHENYL)-N-(OXAZOL-2-YL)-2-OXO-1,2-DIHYDROQUINOLINE-6-SULFONAMIDE and (P)-1-(5-FLUORO-2-METHOXY-4-((1S,2S)-2-(TRIFLUOROMETHYL) CYCLOPROPYL) PHENYL)-N-(OXAZOL-2-YL)-2-OXO-1,2-DIHYDROQUINOLINE-6-SULFONAMIDE, Respectively

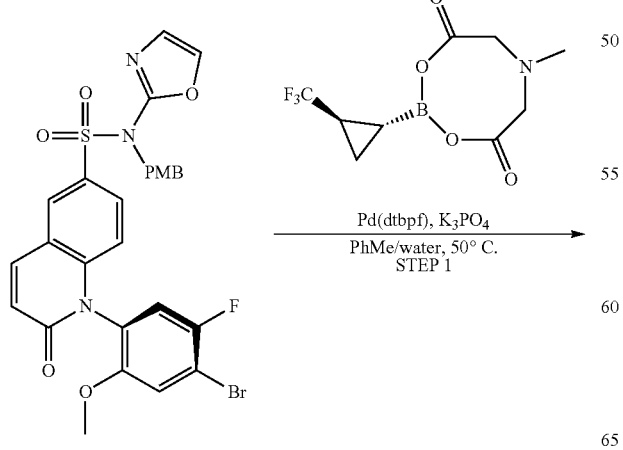

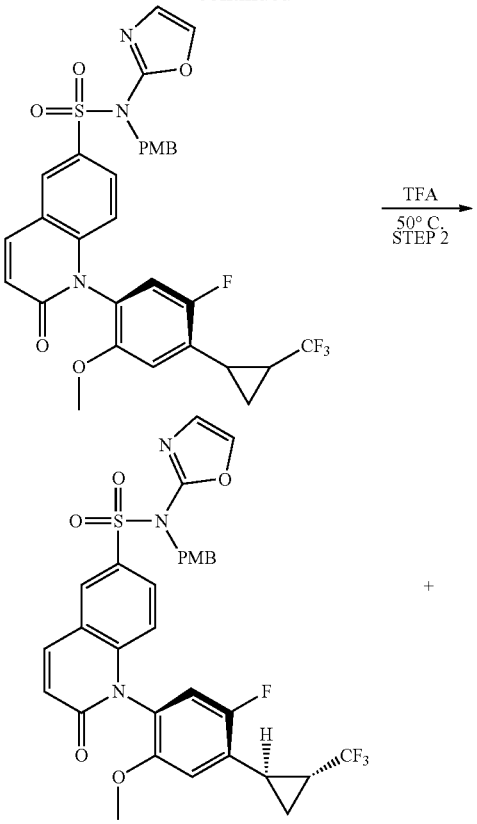

Step 1: (P)-1-(5-FLUORO-2-METHOXY-4-(2-(TRIFLUOROMETHYL)CYCLOPROPYL))-N-(4-METHOXYBENZYL)-N-(OXAZOL-2-YL)-2-OXO-1,2-DIHYDROQUINOLINE-6-SULFONAMIDE A vial was charged with 1-(4-bromo-5-fluoro-2-methoxyphenyl)-N-(4-methoxybenzyl)-N-(oxazol-2-yl)-2-oxo-1,2-dihydroquinoline-6-sulfonamide (1.0 g, 1.7 mmol), 6-methyl-2-((1R,2R)-2-(trifluoromethyl)cyclopropyl)-1,3,6,2-dioxazaborocane-4,8-dione (531 mg, 2.0 mmol), [1,1'-bis(di-tert-butylphosphino)ferrocene]dichloropalladium(II)

(109 mg, 0.17 mmol), and tripotassium phosphate (1.42 g, 6.7 mmol), and then toluene (4.0 mL) and water (1.0 mL) were added. The reaction mixture was flushed with nitrogen, and stirred overnight at 50° C. After 16 hours, the reaction mixture was partitioned between ethyl acetate and brine, and the aqueous layer was extracted with ethyl acetate. The combined organic layers were concentrated, and the crude product was purified by column chromatography (silica gel: elution 0-30% (3:1 EtOAc/ethanol) in heptane) to provide (P)-1-(5-fluoro-2-methoxy-4-(2-(trifluoromethyl) cyclopropyl)phenyl)-N-(4-methoxybenzyl)-N-(oxazol-2-yl)-2-oxo-1,2-dihydroquinoline-6-sulfonamide (780 mg, 1.2 mmol, 72% yield) as a mixture of trans cyclopropyl isomers. m/z (ESI, positive ion) 644.0 (M+H)+.

Step 2: (P)-1-(5-FLUORO-2-METHOXY-4-((1R, 2R)-2-(TRIFLUOROMETHYL) CYCLOPROPYL) PHENYL)-N-(OXAZOL-2-YL)-2-OXO-1,2-DIHYDROQUINOLINE-6-SULFONAMIDE AND (P)-1-(5-FLUORO-2-METHOXY-4-((1S,2S)-2-(TRIFLUOROMETHYL)CYCLOPROPYL) PHENYL)-N—(OXAZOL-2-YL)-2-OXO-1,2-DIHYDROQUINOLINE-6-SULFONAMIDE, Respectively A solution of (P)-1-(5-fluoro-2-methoxy-4-(2-(trifluoromethyl)cyclopropyl)phenyl)-N-(4-methoxybenzyl)-N-(oxazol-2-yl)-2-oxo-1,2-dihydroquinoline-6-sulfonamide (780 mg, 1.2 mmol) in TFA (1.0 mL) was flushed with nitrogen and stirred at 50° C. for 4 hours. The solvent was removed, and crude product was redissolved in DMSO and purified by RP_HPLC (C18, elution 25-70% (ACN/0.1% formic acid) in (water/0.1% formic acid)) as a mixture of trans cyclopropyl isomers. The isomers were separated by chiral chromatography using a OHJ 21×250 cm, 5 µm column. The mobile phase was run under isocratic conditions; supercritical CO2 with 20% ethanol; flow rate: 40 mL/min. The first eluting peak was assigned: (P)-1-(5-fluoro-2-methoxy-4-((1R,2R)-2-(trifluoromethyl)cyclopropyl)phenyl)-N-(oxazol-2-yl)-2-oxo-1,2-dihydroquinoline-6-sulfonamide (144 mg, 0.28 mmol, 23% yield). The second eluting peak was assigned (P)-1-(5-fluoro-2-methoxy-4-((1S,2S)-2-(trifluoromethyl) cyclopropyl)phenyl)-N-(oxazol-2-yl)-2-oxo-1,2-dihydroquinoline-6-sulfonamide (205 mg, 0.39 mmol, 32% yield). Data for peak 1: 1H NMR (500 MHz, chloroform-d) δ ppm 8.24 (br s, 1H), 7.89 (br d, J=8.43 Hz, 1H), 7.77-7.86 (m, 1H), 7.07 (s, 1H), 6.97 (br d, J=9.08 Hz, 1H), 6.91 (br s, 1H), 6.84 (br d, J=7.66 Hz, 1H), 6.70-6.80 (m, 2H), 3.70 (s, 3H), 2.49-2.58 (m, 1H), 1.99-2.10 (m, 1H), 1.44-1.54 (m, 1H), 1.27-1.43 (m, 1H). m/z (ESI, positive ion) 524.2 (M+H)+. Data for peak 2: 1H NMR (500 MHz, chloroform-d) δ ppm 8.24 (br s, 1H), 7.89 (br d, J=7.53 Hz, 1H), 7.84 (br s, 1H), 7.08 (br s, 1H), 6.97 (br d, J=8.17 Hz, 1H), 6.92 (br s, 1H), 6.84 (br s, 1H), 6.75 (br d, J=5.97 Hz, 2H), 3.70 (s, 3H), 2.51-2.59 (m, 1H), 1.98-2.10 (m, 1H), 1.47-1.53 (m, 1H), 1.30-1.45 (m, 1H). m/z (ESI, positive ion) 524.2 (M+H)+.

Example 37: (P)-1-(5-CYANO-2-METHOXY-4-((1S,2S)-2-(TRIFLUOROMETHYL)CYCLOPROPYL)PHENYL)-N-(ISOXAZOL-3-YL)-2-OXO-1,2-DIHYDROQUINOLINE-6-SULFONAMIDE

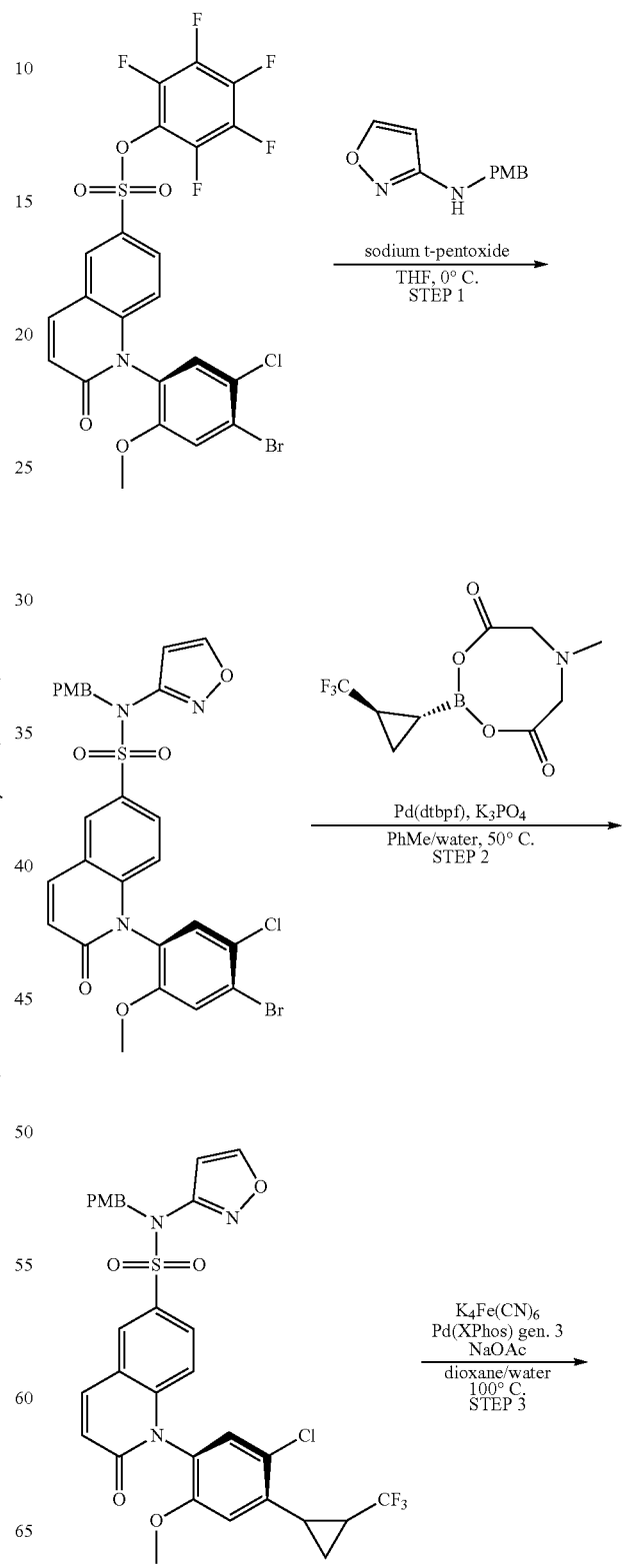

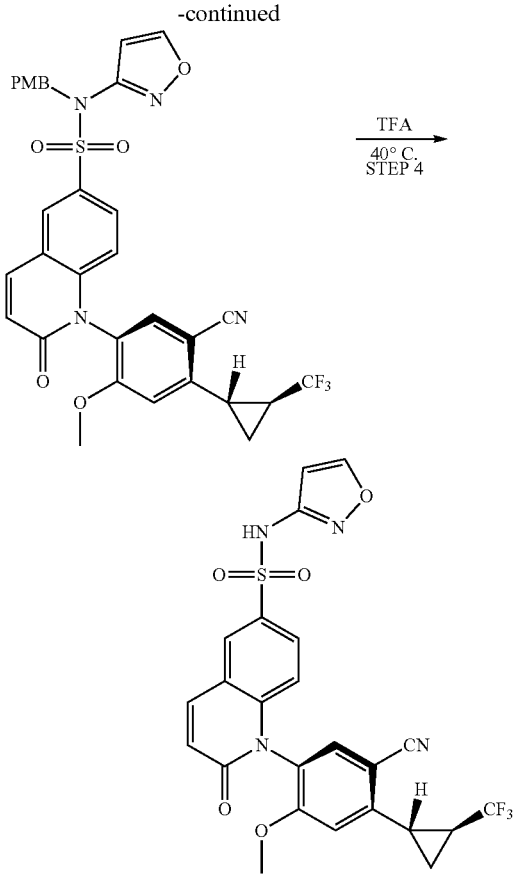

Step 1: (P)-1-(4-BROMO-5-CHLORO-2-METHOXYPHENYL)-N-(ISOXAZOL-3-YL)-N-(4-METHOXYBENZYL)-2-OXO-1,2-DIHYDROQUINOLINE-6-SULFONAMIDE To a 0° C. solution of perfluorophenyl (P)-1-(4-bromo-5-chloro-2-methoxyphenyl)-2-oxo-1,2-dihydroquinoline-6-sulfonate (20 g, 32.7 mmol) and N-(4-methoxybenzyl)isoxazol-3-amine (7.02 g, 34.4 mmol) in tetrahydrofuran (109 mL) was added sodium tert-pentoxide (30% solution in THF, 14.4 mL, 36.0 mmol) dropwise over 15 minutes. The dark red solution was vigorously stirred at 0° C. for 1 hour, but some unreacted starting material was observed. Another 500 mg of N-(4-methoxybenzyl)isoxazol-3-amine was added, followed by 1.7 mL of sodium tert-pentoxide. The mixture was stirred for another 30 minutes. The reaction was quenched with 100 mL 2N aqueous HCl and 150 mL EtOAc. The layers were separated, and the aqueous layer was extracted with EtOAc. The combined organic layers were washed with brine, dried over anhydrous magnesium sulfate, filtered, and concentrated. The mixture was diluted with 2-propanol (500 mL), and a white solid crashed out. The mixture was stirred overnight, and the precipitate was isolated by vacuum filtration, washed with 2-propanol, and dried under a stream of nitrogen to provide (P)-1-(4-bromo-5-chloro-2-methoxyphenyl)-N-(isoxazol-3-yl)-N-(4-methoxybenzyl)-2-oxo-1,2-dihydroquinoline-6-sulfonamide (17.1 g, 27.2 mmol, 83% yield) as an off-white solid. m/z (ESI, positive ion) 524.2 (M+H)$^+$.

Step 2: (P)-1-(5-CHLORO-2-METHOXY-4-(2-(TRIFLUOROMETHYL)CYCLOPROPYL) PHENYL)-N-(ISOXAZOL-3-YL)-N-(4-METHOXYBENZYL)-2-OXO-1,2-DIHYDROQUINOLINE-6-SULFONAMIDE To a solution of (P)-1-(4-bromo-5-chloro-2-methoxyphenyl)-N-(isoxazol-3-yl)-N-(4-methoxybenzyl)-2-oxo-1,2-dihydroquinoline-6-sulfonamide (500 mg, 0.793 mmol) and 6-methyl-2-((1S,2S)-2-(trifluoromethyl)cyclopropyl)-1,3,6,2-dioxazaborocane-4,8-dione (252 mg, 0.951 mmol) in toluene (6.3 mL) was added a solution of potassium phosphate (673 mg, 3.2 mmol) in water (1.6 mL), followed by [1,1'-bis(di-tert-butylphosphino)ferrocene]dichloropalladium(II) (51.7 mg, 0.079 mmol). The reaction mixture was sparged with argon and stirred at 50° C. After 16 hours, the reaction mixture was partitioned between water and ethyl acetate; the organic layer was concentrated. The crude product was purified by column chromatography (silica gel: elution 40-100% ethyl acetate in heptane with 10% DCM) to provide (P)-1-(5-chloro-2-methoxy-4-(2-(trifluoromethyl)cyclopropyl)phenyl)-N-(isoxazol-3-yl)-N-(4-methoxybenzyl)-2-oxo-1,2-dihydroquinoline-6-sulfonamide (400 mg, 0.61 mmol, 76% yield) as a light-yellow oil that solidified overnight. m/z (ESI, positive ion) 659.8 (M+H)$^+$.

Step 3: (P)-1-(5-CYANO-2-METHOXY-4-((1S,2S)-2-(TRIFLUOROMETHYL) CYCLOPROPYL) PHENYL)-N-(ISOXAZOL-3-YL)-N-(4-METHOXYBENZYL)-2-OXO-1,2-DIHYDROQUINOLINE-6-SULFONAMIDE To a suspension of (P)-1-(5-chloro-2-methoxy-4-(2-(trifluoromethyl)cyclopropyl)phenyl)-N-(isoxazol-3-yl)-N-(4-methoxybenzyl)-2-oxo-1,2-dihydroquinoline-6-sulfonamide (400 mg, 0.61 mmol), potassium hexacyanoferrate(II) trihydrate (128 mg, 0.30 mmol), and potassium acetate (7.43 mg, 0.076 mmol) in dioxane (1.5 mL) and water (1.5 mL) in a microwave vial was added (2-Dicyclohexylphosphino-2',4',6'-triisopropyl-1,1'-biphenyl)[2-(2'-amino-1,1'-biphenyl)]palladium(II) methanesulfonate (103 mg, 0.121 mmol). The vial was sparged with argon, capped, and irradiated at 100° C. for 30 minutes. After 30 minutes, the reaction mixture was partitioned between water and ethyl acetate; the organic layer was concentrated. The crude product was purified by column chromatography (silica gel: elution 40-100% ethyl acetate in heptane with 10% DCM) to provide (P)-1-(5-cyano-2-methoxy-4-(2-(trifluoromethyl) cyclopropyl)phenyl)-N-(isoxazol-3-yl)-N-(4-methoxybenzyl)-2-oxo-1,2-dihydroquinoline-6-sulfonamide (245 mg, 0.38 mmol, 62% yield) as a mixture of trans cyclopropyl isomers. The isomers were separated by chiral chromatography using a ASH 21×250 cm, 5 μm column. The mobile phase was run under isocratic conditions; supercritical CO$_2$ with 20% ethanol; flow rate: 40 mL/min. The first eluting peak was assigned: (P)-1-(5-cyano-2-methoxy-4-((1R,2R)-2-(trifluoromethyl) cyclopropyl)phenyl)-N-(isoxazol-3-yl)-N-(4-methoxybenzyl)-2-oxo-1,2-dihydroquinoline-6-sulfonamide (44 mg, 0.068 mmol, 18% yield). The second eluting peak was assigned (P)-1-(5-cyano-2-methoxy-4-((1S,2S)-2-(trifluoromethyl)cyclopropyl)phenyl)-N-(isoxazol-3-yl)-N-(4-methoxybenzyl)-2-oxo-1,2-dihydroquinoline-6-sulfonamide (38 mg, 0.058 mmol, 15% yield). Data for Peak 2: m/z (ESI, positive ion) 650.8 (M+H)$^+$.

Step 4: (P)-1-(5-CYANO-2-METHOXY-4-((1S,2S)-2-(TRIFLUOROMETHYL) CYCLOPROPYL) PHENYL)-N-(ISOXAZOL-3-YL)-2-OXO-1,2-DI-HYDROQUINOLINE-6-SULFONAMIDE A solution of (P)-1-(5-cyano-2-methoxy-4-((1S,2S)-2-(trifluoromethyl)cyclopropyl)phenyl)-N-(isoxazol-3-yl)-N-(4-methoxybenzyl)-2-oxo-1,2-dihydroquinoline-6-sulfonamide (38 mg, 0.058 mmol) in TFA (2 mL) was stirred at 40° C. for 2 hours. After 2 hours, the reaction mixture was concentrated, and the crude product was purified by column chromatography (silica gel: elution 10-60% (3:1 ethyl acetate/ethanol) in heptane with 10% DCM) to provide (P)-1-(5-cyano-2-methoxy-4-((1S,2S)-2-(trifluoromethyl)cyclopropyl)phenyl)-N-(isoxazol-3-yl)-2-oxo-1,2-dihydroquinoline-6-sulfonamide (30 mg, 0.057 mmol, 84% yield) as a white powder. $^1$H NMR (500 MHz, DMSO-$d_6$) δ ppm 11.64 (s, 1H), 8.73 (d, J=1.82 Hz, 1H), 8.37 (d, J=2.21 Hz, 1H), 8.22 (d, J=9.60 Hz, 1H), 7.95 (s, 1H), 7.82 (dd, J=8.95, 2.21 Hz, 1H), 7.06 (s, 1H), 6.80 (t, J=9.67 Hz, 2H), 6.44 (d, J=1.82 Hz, 1H), 3.78 (s, 3H), 2.72-2.79 (m, 1H), 2.63-2.69 (m, 1H), 1.60-1.69 (m, 2H). m/z (ESI, positive ion) 531.0 (M+H)$^+$.

Examples 38 & 39: (P)-N-(ISOXAZOL-3-YL)-1-(2-METHOXY-4-((1R,2R)-2-(TRIFLUOROMETHYL)CYCLOPROPYL)PHENYL)-2-OXO-1,2-DIHYDROQUINOLINE-6-SULFONAMIDE and (P)-N-(ISOXAZOL-3-YL)-1-(2-METHOXY-4-((1S,2S)-2-(TRIFLUOROMETHYL)CYCLOPROPYL) PHENYL)-2-OXO-1,2-DIHYDROQUINOLINE-6-SULFONAMIDE, Respectively

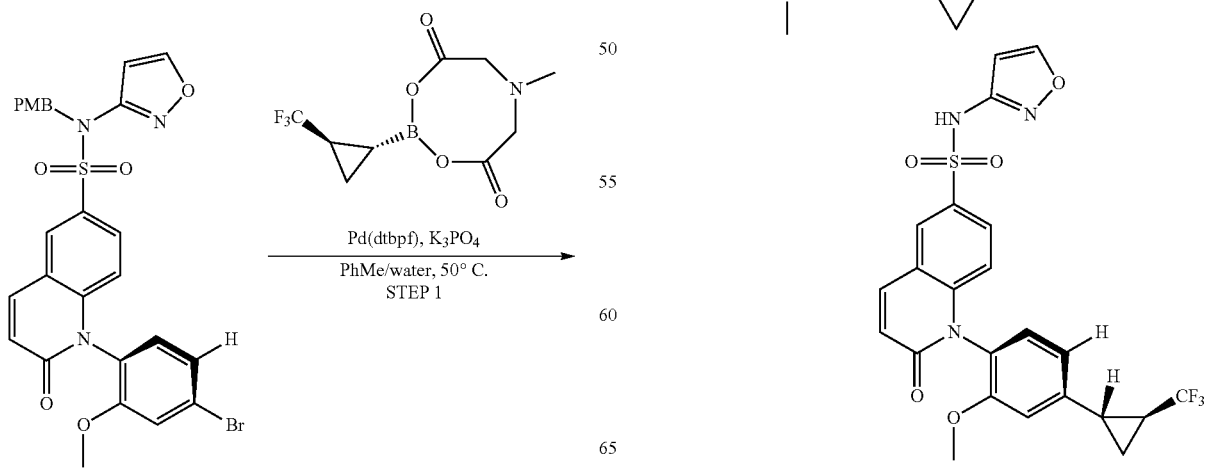

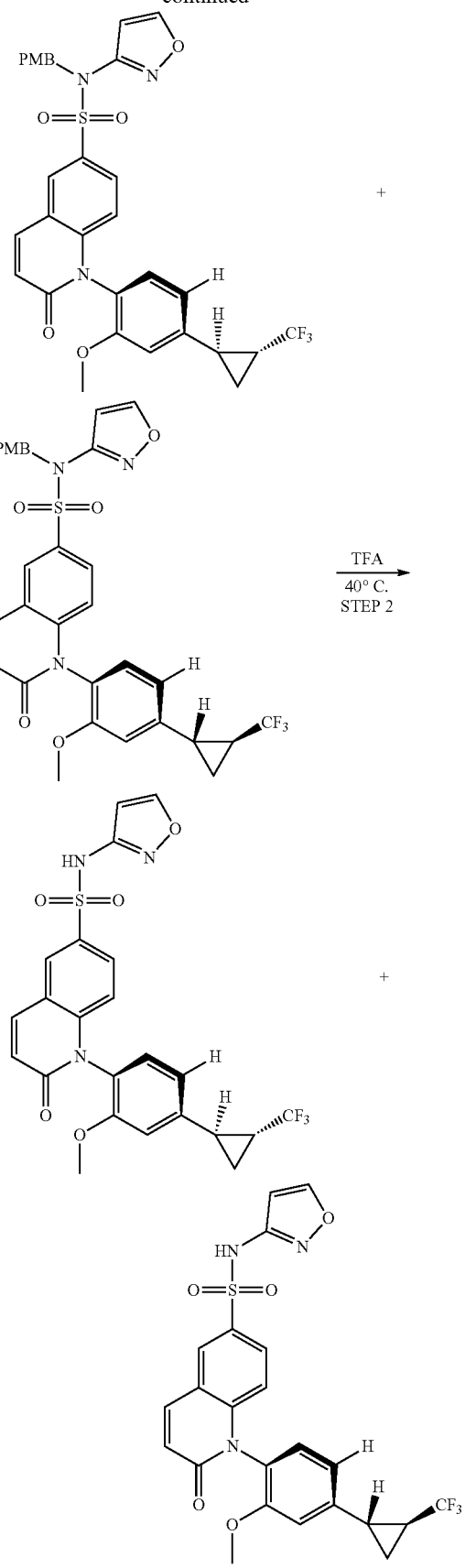

Step 1: (P)-N-(ISOXAZOL-3-YL)-1-(2-METHOXY-4-((1R,2R)-2-(TRIFLUOROMETHYL)CYCLOPROPYL)PHENYL)-N-(4-METHOXYBENZYL)-2-OXO-1,2-DIHYDROQUINOLINE-6-SULFONAMIDE AND (P)-N-(ISOXAZOL-3-YL)-1-(2-METHOXY-4-((1S,2S)-2-(TRIFLUOROMETHYL)CYCLOPROPYL)PHENYL)-N-(4-METHOXYBENZYL)-2-OXO-1,2-DIHYDROQUINOLINE-6-SULFONAMIDE, Respectively To a solution of (P)-1-(4-bromo-2-methoxyphenyl)-N-(isoxazol-3-yl)-N-(4-methoxybenzyl)-2-oxo-1,2-dihydroquinoline-6-sulfonamide (0.90 g, 1.51 mmol) and 6-methyl-2-[(1s,2s)-2-(trifluoromethyl)cyclopropyl]-1,3,6,2-dioxazaborocane-4,8-dione (0.48 g, 1.81 mmol) in toluene (12.00 mL) was added a solution of tripotassium phosphate (1.28 g, 6.0 mmol) in water (3 mL), followed by [1,1'-bis(di-tert-butylphosphino)ferrocene]dichloropalladium(II) (0.098 g, 0.15 mmol). The reaction mixture was sparged with argon and stirred at 50° C. After 16 hours, the reaction mixture was partitioned between water and ethyl acetate; the organic layer was concentrated. The crude product was purified by column chromatography (silica gel: elution 40-100% ethyl acetate in heptane with 10% DCM) to provide (P)-N-(isoxazol-3-yl)-1-(2-methoxy-4-(2-(trifluoromethyl)cyclopropyl)phenyl)-N-(4-methoxybenzyl)-2-oxo-1,2-dihydroquinoline-6-sulfonamide (0.38 g, 0.61 mmol, 40.3% yield) as a mixture of trans cyclopropyl isomers. The mixture of isomers was separated by chiral chromatography using a ASH 21×250 cm, 5 μm column. The mobile phase was run under isocratic conditions; supercritical $CO_2$ with 15% ethanol; flow rate: 50 mL/min. The first eluting peak was assigned: (P)-N-(isoxazol-3-yl)-1-(2-methoxy-4-((1R,2R)-2-(trifluoromethyl)cyclopropyl)phenyl)-N-(4-methoxybenzyl)-2-oxo-1,2-dihydroquinoline-6-sulfonamide (133 mg, 0.213 mmol, 14% yield). The second eluting peak was assigned (P)-N-(isoxazol-3-yl)-1-(2-methoxy-4-((1S,2S)-2-(trifluoromethyl)cyclopropyl)phenyl)-N-(4-methoxybenzyl)-2-oxo-1,2-dihydroquinoline-6-sulfonamide (147 mg, 0.235 mmol, 16% yield).

Step 2: (P)-N-(ISOXAZOL-3-YL)-1-(2-METHOXY-4-((1R,2R)-2-(TRIFLUOROMETHYL)CYCLOPROPYL)PHENYL)-2-OXO-1,2-DIHYDROQUINOLINE-6-SULFONAMIDE AND (P)-N-(ISOXAZOL-3-YL)-1-(2-METHOXY-4-((1S,2S)-2-(TRIFLUOROMETHYL)CYCLOPROPYL)PHENYL)-2-OXO-1,2-DIHYDROQUINOLINE-6-SULFONAMIDE, Respectively Separately, a solution of (P)-N-(isoxazol-3-yl)-1-(2-methoxy-4-((1R,2R)-2-(trifluoromethyl) cyclopropyl)phenyl)-N-(4-methoxybenzyl)-2-oxo-1,2-dihydroquinoline-6-sulfonamide (133 mg, 0.213 mmol) in TFA (2 mL) and a solution of (P)-N-(isoxazol-3-yl)-1-(2-methoxy-4-((1S,2S)-2-(trifluoromethyl) cyclopropyl)phenyl)-N-(4-methoxybenzyl)-2-oxo-1,2-dihydroquinoline-6-sulfonamide (147 mg, 0.235 mmol) in TFA (2 mL) were stirred at 50° C. for 2 hours. After 2 hours, the reactions were concentrated, and the crude products were purified by column chromatography (silica gel: elution 10-60% (3:1 ethyl acetate/ethanol) in heptane with 10% DCM) to provide (P)-N-(isoxazol-3-yl)-1-(2-methoxy-4-((1R,2R)-2-(trifluoromethyl) cyclopropyl)phenyl)-2-oxo-1,2-dihydroquinoline-6-sulfonamide (107 mg, 0.212 mmol, 100% yield) and (P)-N-(isoxazol-3-yl)-1-(2-methoxy-4-((1S,2S)-2-(trifluoromethyl)cyclopropyl) phenyl)-2-oxo-1,2-dihydroquinoline-6-sulfonamide (118 mg, 0.233 mmol, 110% yield) as white powders. Data for (P)-N-(isoxazol-3-yl)-1-(2-methoxy-4-((1R,2R)-2-(trifluoromethyl) cyclopropyl)phenyl)-2-oxo-1,2-dihydroquinoline-6-sulfonamide: $^1$H NMR (500 MHz, DMSO-$d_6$) δ ppm 11.61 (s, 1H), 8.72 (d, J=1.82 Hz, 1H), 8.34 (d, J=2.21 Hz, 1H), 8.19 (d, J=9.60 Hz, 1H), 7.82 (dd, J=9.02, 2.27 Hz, 1H), 7.20 (d, J=8.04 Hz, 1H), 7.12 (d, J=1.82 Hz, 1H), 6.99 (dd, J=8.04, 1.82 Hz, 1H), 6.77 (d, J=9.60 Hz, 1H), 6.73 (d, J=8.95 Hz, 1H), 6.44 (d, J=1.69 Hz, 1H), 3.67 (s, 3H), 2.42-2.57 (m, 2H), 1.37-1.47 (m, 2H). m/z (ESI, positive ion) 505.8 (M+H)$^+$. Data for (P)-N-(isoxazol-3-yl)-1-(2-methoxy-4-((1S,2S)-2-(trifluoromethyl) cyclopropyl)phenyl)-2-oxo-1,2-dihydroquinoline-6-sulfonamide: $^1$H NMR (500 MHz, DMSO-$d_6$) δ ppm 11.61 (s, 1H), 8.72 (d, J=1.82 Hz, 1H), 8.34 (d, J=2.21 Hz, 1H), 8.19 (d, J=9.73 Hz, 1H), 7.82 (dd, J=9.02, 2.27 Hz, 1H), 7.20 (d, J=8.04 Hz, 1H), 7.11 (d, J=1.69 Hz, 1H), 7.00 (dd, J=8.04, 1.82 Hz, 1H), 6.77 (d, J=9.60 Hz, 1H), 6.73 (d, J=8.95 Hz, 1H), 6.44 (d, J=1.82 Hz, 1H), 3.67 (s, 3H) 2.52-2.57 (m, 1H) 2.44-2.48 (m, 1H) 1.38-1.48 (m, 2H). m/z (ESI, positive ion) 505.8 (M+H)$^+$.

Example 40: (P)-1-(5-FLUORO-2-METHOXY-4-((1R,2R)-2-(TRIFLUOROMETHYL)CYCLOPROPYL)PHENYL)-2-OXO-N-(1,3,4-THIADIAZOL-2-YL)-1,2-DIHYDROQUINOLINE-6-SULFONAMIDE

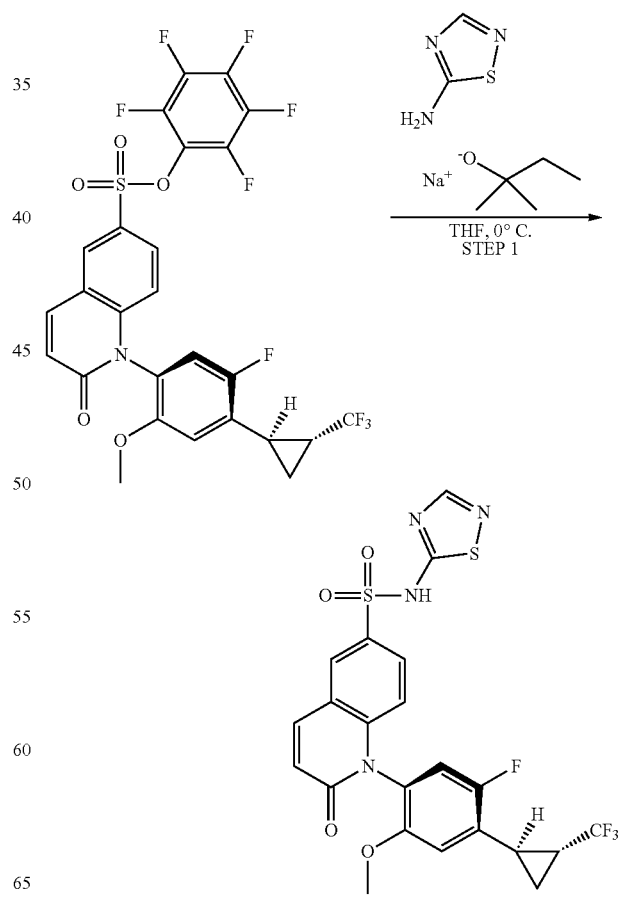

121

Step 1: (P)-1-(5-FLUORO-2-METHOXY-4-((1R, 2R)-2-(TRIFLUOROMETHYL) CYCLOPROPYL) PHENYL)-2-OXO-N-(1,3,4-THIADIAZOL-2-YL)-1,2-DIHYDROQUINOLINE-6-SULFONAMIDE To a suspension of perfluorophenyl (P)-1-(5-fluoro-2-methoxy-4-((1R,2R)-2-(trifluoromethyl)cyclopropyl)phenyl)-2-oxo-1,2-dihydroquinoline-6-sulfonate (500 mg, 0.802 mmol) in tetrahydrofuran (10 mL) and 2-amino-1,3,4-thiadiazole (97 mg, 0.962 mmol) at 0° C. was added sodium tert-pentoxide (0.613 mL, 2.005 mmol). The reaction was stirred at 0° C. for 1 hour, and then quenched with methanol and adsorbed onto silica gel. The crude product was purified by column chromatography (silica gel: elution 0-100% (3:1 ethyl acetate/ethanol) in (9:1 heptane/DCM)) to provide (P)-1-(5-fluoro-2-methoxy-4-((1R,2R)-2-(trifluoromethyl) cyclopropyl)phenyl)-2-oxo-N-(1,3,4-thiadiazol-2-yl)-1,2-dihydroquinoline-6-sulfonamide (322 mg, 0.60 mmol, 74% yield) as a white powder. $^1$H NMR (500 MHz, DMSO-d6) δ ppm 8.70 (s, 1H), 8.24 (d, J=2.2 Hz, 1H), 8.18 (d, J=9.6 Hz, 1H), 7.77 (dd, J=8.9, 2.1 Hz, 1H), 7.33 (d, J=9.9 Hz, 1H), 6.99 (d, J=6.7 Hz, 1H), 6.74 (d, J=9.6 Hz, 1H), 6.70 (d, J=9.0 Hz, 1H), 3.66 (s, 3H), 2.52-2.58 (m, 2H), 1.55-1.61 (m, 1H), 1.44-1.52 (m, 1H). m/z (ESI, positive ion) 541.0 (M+H)$^+$.

Example 41: (P)-1-(5-FLUORO-2-METHOXY-4-((1R,2R)-2-(TRIFLUOROMETHYL)CYCLOPROPYL)PHENYL)-2-OXO-N-(1,3,4-THIADIAZOL-2-YL)-1,2-DIHYDROQUINOLINE-6-SULFONAMIDE

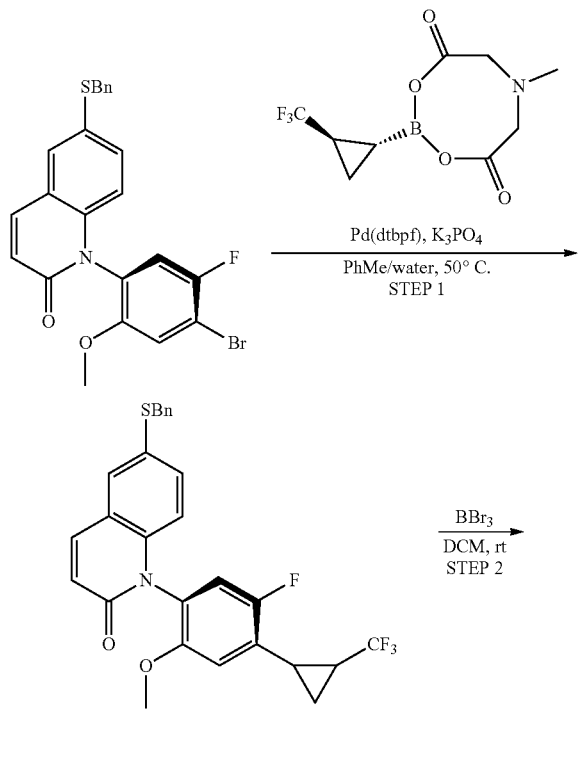

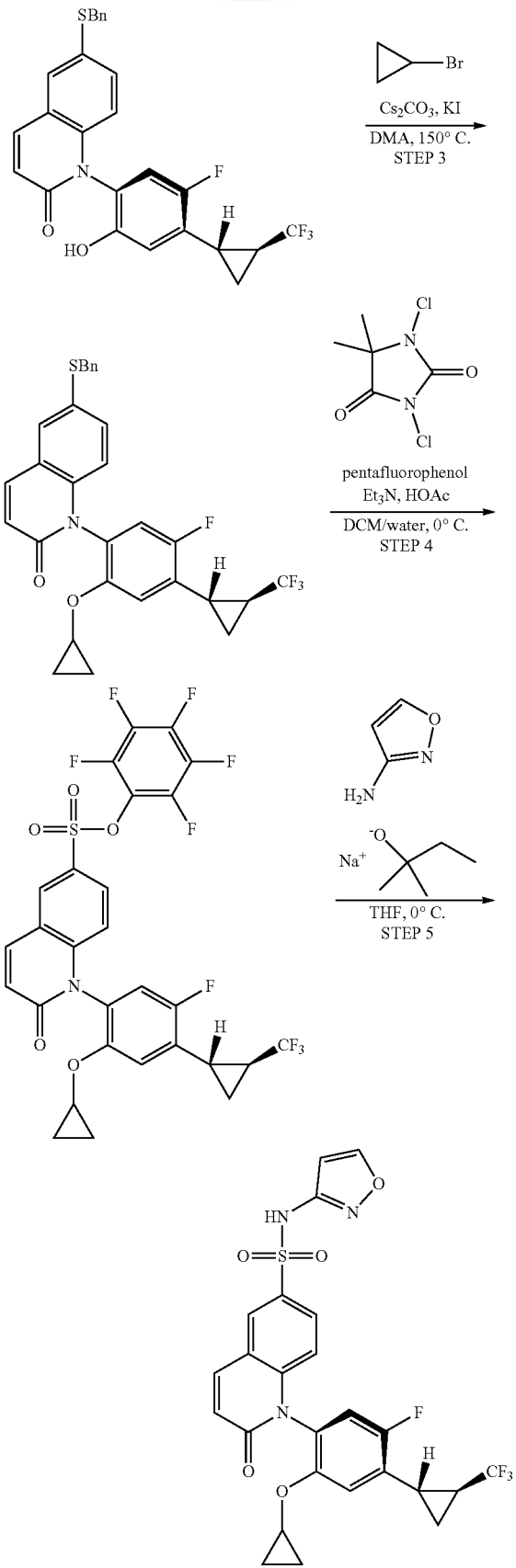

Step 1: (P)-6-(BENZYLTHIO)-1-(5-FLUORO-2-METHOXY-4-(2-(TRIFLUOROMETHYL) CYCLOPROPYL)PHENYL)QUINOLIN-2(1H)-ONE A 1 L three-neck flask, equipped with an overhead stirrer, a reflux condenser and a Claisen adapter with nitrogen outlet, was charged with 6-methyl-2-[(1r,2r)-2-(trifluoromethyl) cyclopropyl]-1,3,6,2-dioxazaborocane-4,8-dione (14.9 g, 56.1 mmol), (P)-6-(benzylthio)-1-(4-bromo-5-fluoro-2-methoxyphenyl)quinolin-2(1H)-one (22.0 g, 46.8 mmol), and potassium phosphate tribasic (39.7 g, 187 mmol). The solids were suspended in toluene (400 mL) and water (100 mL), and the mixture was degassed by bubbling nitrogen for 1 hour. To the reaction was added dichloro[1,1'-bis(di-tert-butylphosphino)ferrocene]palladium(II) (1.52 g, 2.34 mmol), and the reaction mixture was heated to 50° C. with vigorous stirring. After 5.5 hours, the reaction was cooled to ambient temperature and filtered through a pad of Celite. The filter cake was washed with ethyl acetate (200 mL), and the filtrate layers were separated. The aqueous layer was extracted with ethyl acetate (2×100 mL), and the combined organic layers were washed with brine (200 mL), dried over anhydrous sodium sulfate, filtered, and concentrated. The residue was suspended in 25 mL of methanol and 5 mL of water, and the suspension was stirred overnight, and filtered through a sintered glass filter to provide (P)-6-(benzylthio)-1-(5-fluoro-2-methoxy-4-((2-(trifluoromethyl) cyclopropyl)phenyl)quinolin-2(1H)-one (21.81 g, 43.7 mmol, 93% yield) as a mixture of trans cyclopropyl isomers. m/z (ESI, positive ion) 500.2 (M+H)$^+$.

Step 2: (P)-6-(BENZYLTHIO)-1-(5-FLUORO-2-HYDROXY-4-((1S,2S)-2-(TRIFLUOROMETHYL) CYCLOPROPYL)PHENYL)QUINOLIN-2(1H)-ONE To a solution of (P)-6-(benzylthio)-1-(5-fluoro-2-methoxy-4-(2-(trifluoromethyl)cyclopropyl)phenyl)quinolin-2(1H)-one (5.0 g, 10.0 mmol) in dichloromethane (100 mL) was added boron tribromide (1M solution in DCM, 20 mL, 20 mmol), and the reaction was stirred at ambient temperature for 1 hour. The reaction was quenched with saturated aqueous ammonium chloride (100 mL), diluted with DCM (100 mL), and the phases were separated. The organic layer was concentrated to obtain (P)-6-(benzylthio)-1-(5-fluoro-2-hydroxy-4-((1R,2S)-2-(trifluoromethyl) cyclopropyl)phenyl)quinolin-2(1H)-one as mixture of trans cyclopropyl isomers. The cyclopropyl isomers were separated via chiral chromatography using a Whelk-O (S,S) 30×150 cm column. The mobile phase was run under isocratic conditions; supercritical CO$_2$ with 25% methanol; flow rate: 200 mL/min. The first eluting peak was assigned: (P)-6-(benzylthio)-1-(5-fluoro-2-hydroxy-4-((1S,2S)-2-(trifluoromethyl)cyclopropyl)phenyl)quinolin-2(1H)-one (1.60 g, 1.73 mmol, 17% yield). m/z (ESI, positive ion) 486.0 (M+H)$^+$.

Step 3: (P)-6-(BENZYLTHIO)-1-(2-CYCLOPROPOXY-5-FLUORO-4-((1S,2S)-2-(TRIFLUOROMETHYL)CYCLOPROPYL)PHENYL)QUINOLIN-2(1H)-ONE A microwave vial was charged with (P)-6-(benzylthio)-1-(5-fluoro-2-hydroxy-4-((1S,2S)-2-(trifluoromethyl)cyclopropyl)phenyl)quinolin-2(1H)-one (0.84 g, 1.73 mmol), N,N-dimethylacetamide (5.8 mL), cesium carbonate (1.7 g, 5.2 mmol), potassium iodide (0.14 g, 0.87 mmol), and bromocyclopropane (0.209 g, 1.73 mmol). The vial was capped and irradiated for 24 hours at 150° C. The vial was cooled to ambient temperature, and the reaction mixture was diluted with water (100 mL) and extracted with ethyl acetate (2×100 mL). The combined organic layers were dried over anhydrous sodium sulfate, filtered, and concentrated. The crude product was purified by column chromatography (silica gel: elution 0-100% ethyl acetate in heptane with 10% DCM) to provide 6-(benzylthio)-1-(2-cyclopropoxy-5-fluoro-4-((1R,2R)-2-(trifluoromethyl)cyclopropyl)phenyl) quinolin-2(1H)-one (0.65 g, 1.24 mmol, 71% yield) as an off-white solid. m/z (ESI, positive ion) 526.0 (M+H)$^+$.

Step 4: PERFLUOROPHENYL 1-(2-CYCLOPROPOXY-5-FLUORO-4-((1S,2S)-2-(TRIFLUOROMETHYL)CYCLOPROPYL)PHENYL)-2-OXO-1,2-DIHYDROQUINOLINE-6-SULFONATE To a suspension of 6-(benzylthio)-1-(2-cyclopropoxy-5-fluoro-4-((1S,2S)-2-(trifluoromethyl)cyclopropyl)phenyl) quinolin-2(1H)-one (0.65 g, 1.24 mmol) in DCM (11.6 mL), acetic acid (0.44 mL), and water (0.29 mL) at 0° C. was added 1,3-dichloro-5,5-dimethylimidazolidine-2,4-dione (0.61 g, 3.1 mmol) in one portion. The reaction was stirred for 15 minutes at 0° C., and then 2,3,4,5,6-pentafluorophenol (0.455 g, 0.26 mL, 2.47 mmol) was added, followed by dropwise addition of triethylamine (0.313 g, 0.431 mL, 3.09 mmol). The reaction was stirred for two hours. After 2 hours, the reaction was diluted with DCM (10 mL) and the organic layer was separated and concentrated. This crude product was purified by column chromatography (silica gel: elution 0-50% ethyl acetate in heptane) to afford perfluorophenyl 1-(2-cyclopropoxy-5-fluoro-4-((1S,2S)-2-(trifluoromethyl) cyclopropyl)phenyl)-2-oxo-1,2-dihydroquinoline-6-sulfonate (0.562 g, 0.87 mmol, 70% yield) as an off-white solid. m/z (ESI, positive ion) 649-8 (M+H)$^+$.

Step 5: (P)-1-(2-CYCLOPROPOXY-5-FLUORO-4-((1S,2S)-2-(TRIFLUOROMETHYL) CYCLOPROPYL)PHENYL)-N-(ISOXAZOL-3-YL)-2-OXO-1,2-DIHYDROQUINOLINE-6-SULFONAMIDE To a solution of perfluorophenyl 1-(2-cyclopropoxy-5-fluoro-4-((1S,2S)-2-(trifluoromethyl) cyclopropyl)phenyl)-2-oxo-1,2-dihydroquinoline-6-sulfonate (0.562 g, 0.87 mmol) and isoxazol-3-amine (0.080 g, 0.95 mmol) in tetrahydrofuran (4.3 mL) at 0° C. was added sodium tert-pentoxide (0.95 mL, 1.9 mmol) dropwise. The reaction was stirred for 30 minutes, and then partitioned between 1N aqueous HCl and EtOAc. The organic layer was washed with 1N aq. HCl, and the combined aqueous layers were extracted with ethyl acetate. The combined organic layers were washed with brine, dried with sodium sulfate, filtered, and concentrated. The crude product was purified via column chromatography (silica gel: elution 0-10% ethanol in ethyl acetate) to afford 1-(2-cyclopropoxy-5-fluoro-4-((1S,2S)-2-(trifluoromethyl)cyclopropyl)phenyl)-N-(isoxazol-3-yl)-2-oxo-1,2-dihydroquinoline-6-sulfonamide as light yellow solid. The atropisomers were separated by chiral chromatography using a Whelk-O (S,S) 2×15 cm, 5 m column. The mobile phase was run under isocratic conditions; supercritical CO$_2$ with 30% methanol; flow rate: 80 mL/min. The first eluting peak was assigned: (P)-6-(benzylthio)-1-(5-fluoro-2-hydroxy-4-((1S,2S)-2-(trifluoromethyl) cyclopropyl)phenyl)quinolin-2(1H)-one (192 mg, 0.35 mmol, 37% yield). $^1$H NMR (400 MHz, DMSO-d$_6$) δ ppm 11.62 (s, 1H), 8.72 (d, J=1.76 Hz, 1H), 8.34 (d, J=2.18 Hz, 1H), 8.19 (d, J=9.64 Hz, 1H), 7.78-7.87 (m, 1H), 7.36 (d, J=9.95 Hz, 1H), 7.25 (d, J=6.84 Hz, 1H), 6.76 (dd, J=9.28, 5.55 Hz, 2H), 6.42 (d, J=1.55 Hz, 1H), 3.84-3.99 (m, 1H), 2.54-2.61 (m, 2H), 1.42-1.62 (m, 2H), 0.53-0.72 (m, 2H), 0.11-0.41 (m, 2H). m/z (ESI, positive ion) 549.8 (M+H)⁺.
Examples 42 & 43: (P)-1-(5-FLUORO-2-METHOXY-4-(1-(TRIFLUOROMETHYL)CY-CLOPROPYL)PHENYL)-N-(ISOXAZOL-3-YL)-2-OXO-1,2-DIHYDROQUINOLINE-6-SULFONAMIDE and (M)-1-(5-FLUORO-2-METHOXY-4-(1-(TRIFLUOROMETHYL)CYCLOPROPYL)PHENYL)-N-(ISOXAZOL-3-YL)-2-OXO-1,2-DIHYDROQUINOLINE-6-SULFONAMIDE, Respectively
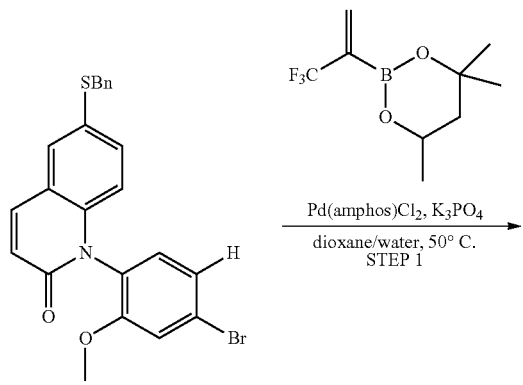
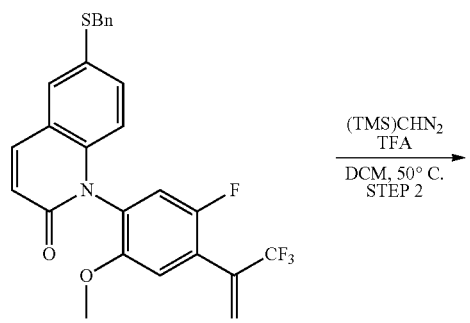
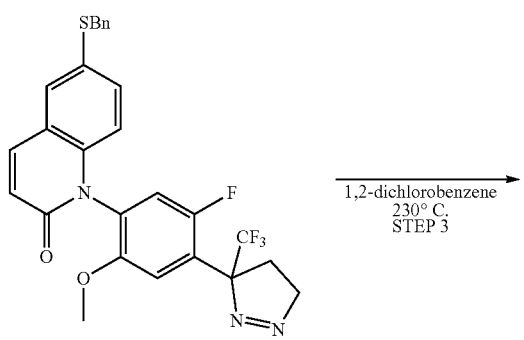
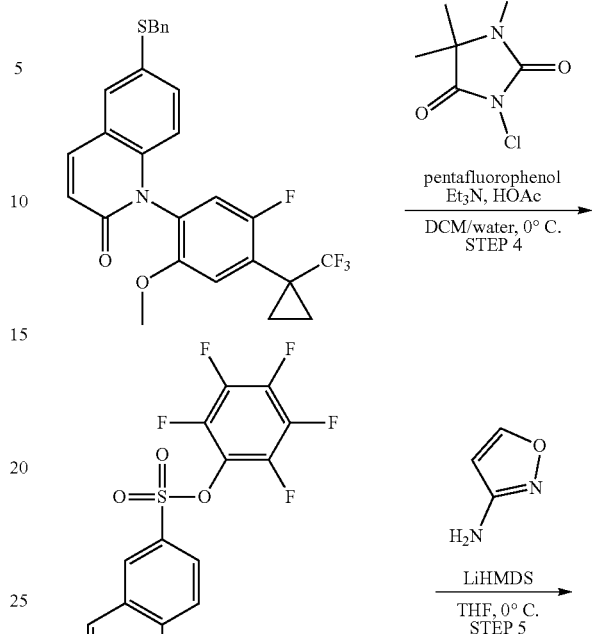
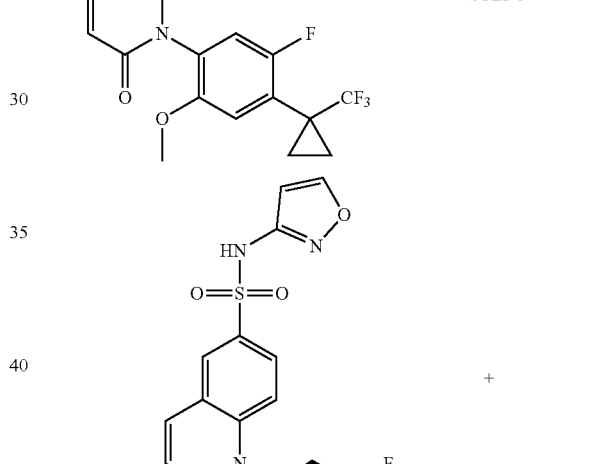
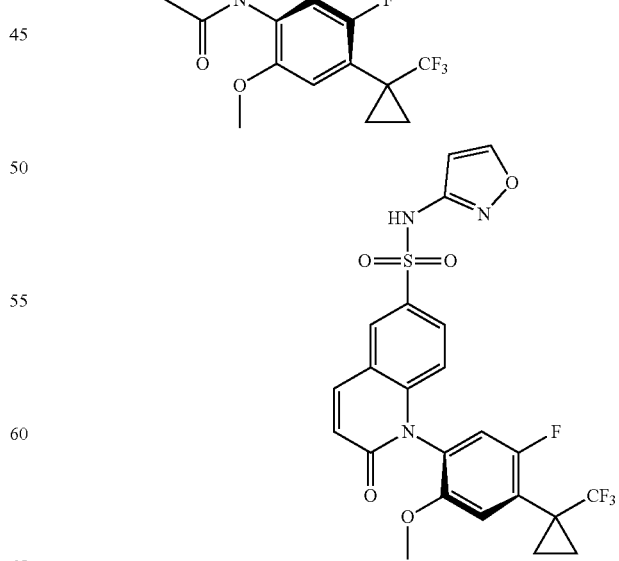

Step 1: 6-(BENZYLTHIO)-1-(5-FLUORO-2-METHOXY-4-(3,3,3-TRIFLUOROPROP-1-EN-2-YL)PHENYL)QUINOLIN-2(1H)-ONE A 20-mL vial was charged with 6-(benzylthio)-1-(4-bromo-5-fluoro-2-methoxyphenyl)quinolin-2(1H)-one (500 mg, 1.063 mmol), 4,4,6-trimethyl-2-(3,3,3-trifluoroprop-1-en-2-yl)-1,3,2-dioxaborinane (472 mg, 2.126 mmol), potassium phosphate tribasic (677 mg, 3.19 mmol), and 1,1-bis[(di-t-butyl-p-methylaminophenyl]palladium(II) chloride (151 mg, 0.213 mmol) and purged with nitrogen. The reaction vessel was then sequentially charged with dioxane (3.8 mL) and water (1.3 mL) via syringe. The vial was sealed and heated to 50° C. After 16 h, the reaction mixture was allowed to cool to ambient temperature and an aqueous solution of 1.0 N HCL (5 mL) was added and the mixture diluted with EtOAc (5 mL). The layers were separated and the aqueous layer was extracted with EtOAc (3×5 mL). The combined organic layers were washed with brine (25 mL), dried over anhydrous sodium sulfate, filtered, and concentrated under reduced pressure to furnish a tan oil, which was purified by flash column chromatography (silica gel: elution 0 to 40% EtOAc in heptane with 5% CH2Cl2 as an additive) to afford 6-(benzylthio)-1-(5-fluoro-2-methoxy-4-(3,3,3-trifluoroprop-1-en-2-yl)phenyl)quinolin-2(1H)-one (516 mg, 1.063 mmol, 100% yield) as a tan solid. m/z (ESI, positive ion) 486.0 (M+H)$^+$.

Step 2: 6-(BENZYLTHIO)-1-(5-FLUORO-2-METHOXY-4-(3-(TRIFLUOROMETHYL)-4,5-DIHYDRO-3H-PYRAZOL-3-YL)PHENYL)QUINOLIN-2(1H)-ONE To a solution of 6-(benzylthio)-1-(5-fluoro-2-methoxy-4-(3,3,3-trifluoroprop-1-en-2-yl)phenyl)quinolin-2(1H)-one (506 mg, 1.04 mmol) in DCM (5.2 mL) was added (trimethylsilyl)diazomethane (2 M in heptane, 1.5 mL, 3.13 mmol). The reaction mixture was stirred at ambient temperature for 30 minutes, at 50° C. for 2 hours, and at ambient temperature overnight. After 16 hours, TFA (798 µl, 10.4 mmol) was carefully added to the stirred reaction mixture via pipette. After 30 min, the reaction was concentrated under reduced pressure and purified by column chromatography (silica gel: elution 0-30% EtOAc:DCM) to afford 6-(benzylthio)-1-(5-fluoro-2-methoxy-4-(3-(trifluoromethyl)-4,5-dihydro-3H-pyrazol-3-yl)phenyl)quinolin-2(1H)-one (430 mg, 0.815 mmol, 78% yield) as a light yellow solid. m/z (ESI, positive ion) 528.0 (M+H)$^+$.

Step 3: 6-(BENZYLTHIO)-1-(5-FLUORO-2-METHOXY-4-(1-(TRIFLUOROMETHYL)CYCLOPROPYL)PHENYL)QUINOLIN-2(1H)-ONE A 140-mL pressure vessel equipped with a pressure relief valve was charged with 6-(benzylthio)-1-(5-fluoro-2-methoxy-4-(3-(trifluoromethyl)-4,5-dihydro-3H-pyrazol-3-yl)phenyl)quinolin-2(1H)-one (1.13 g, 2.14 mmol) and 1,2-dichlorobenzene (10.7 mL). The reaction was stirred at 208° C. for 6 hours, and then at 230° C. for an additional 9 hours. The brown reaction mixture was cooled to ambient temperature purified by column chromatography (silica gel: elution 0-75% EtOAc in heptane) to afford 6-(benzylthio)-1-(5-fluoro-2-methoxy-4-(1-(trifluoromethyl)cyclopropyl)phenyl)quinolin-2(1H)-one (493 mg, 0.99 mmol, 46% yield) as a tan solid. m/z (ESI, positive ion) 500.0 (M+H)$^+$.

Step 4: PERFLUOROPHENYL 1-(5-FLUORO-2-METHOXY-4-(1-(TRIFLUOROMETHYL)CYCLOPROPYL)PHENYL)-2-OXO-1,2-DIHYDROQUINOLINE-6-SULFONATE To a solution of 6-(benzylthio)-1-(5-fluoro-2-methoxy-4-(1-(trifluoromethyl)cyclopropyl)phenyl)quinolin-2(1H)-one (440 mg, 0.881 mmol) in DCM (8.3 mL), acetic acid (311 µL), and water (207 µL) at 0° C. was added 1,3-dichloro-5,5-dimethylimidazolidine-2,4-dione (434 mg, 2.20 mmol). The reaction was stirred for 15 minutes, and then 2,3,4,5,6-pentafluorophenol (185 µL, 1.76 mmol) was added followed by dropwise addition of triethylamine (307 µL, 2.20 mmol). The reaction was stirred for 3 hours, and then concentrated. The crude product was purified by column chromatography (silica gel: elution 0-50% EtOAc:heptane) to afford perfluorophenyl 1-(5-fluoro-2-methoxy-4-(1-(trifluoromethyl)cyclopropyl)phenyl)-2-oxo-1,2-dihydroquinoline-6-sulfonate (500 mg, 0.80 mmol, 91% yield) as an off-white solid. m/z (ESI, positive ion) 623.8 (M+H)$^+$.

Step 5: (P)-1-(5-FLUORO-2-METHOXY-4-(1-(TRIFLUOROMETHYL)CYCLOPROPYL) PHENYL)-N-(ISOXAZOL-3-YL)-2-OXO-1,2-DIHYDROQUINOLINE-6-SULFONAMIDE AND (M)-1-(5-FLUORO-2-METHOXY-4-(1-(TRIFLUOROMETHYL)CYCLOPROPYL) PHENYL)-N-(ISOXAZOL-3-YL)-2-OXO-1,2-DIHYDROQUINOLINE-6-SULFONAMIDE, Respectively To a solution of isoxazol-3-amine (23 µL, 0.31 mmol) in THF (2.4 mL) was added perfluorophenyl 1-(5-fluoro-2-methoxy-4-(1-(trifluoromethyl)cyclopropyl)phenyl)-2-oxo-1,2-dihydroquinoline-6-sulfonate (150 mg, 0.24 mmol). Another portion of THF (2.4 mL) was added and the solution was cooled to 0° C., and then lithium bis(trimethylsilyl)amide (1M in THF) (553 µL, 0.553 mmol) was added dropwise. The reaction was stirred for 30 minutes, and then partitioned between saturated aqueous ammonium chloride and ethyl acetate. The layers were separated and the aqueous layer was extracted with EtOAc (3×5 mL). The combined organic layers were dried over magnesium sulfate, filtered, and concentrated. The residue was diluted with DMSO and filtered through a 0.45 micron filter. The filtrate was purified by reverse phase HPLC (C18: 25-85% (ACN/0.1% formic acid) in (water/0.1% formic acid)). The fractions containing the desired product were combined and lyophilized to afford 1-(5-fluoro-2-methoxy-4-(1-(trifluoromethyl)cyclopropyl)phenyl)-N-(isoxazol-3-yl)-2-oxo-1,2-dihydroquinoline-6-sulfonamide (30 mg, 0.057 mmol). The atropisomers were separated by chiral chromatography, using a ChiralPak AS-H 2×25 cm, 5 mm column. The mobile phase was run under isocratic conditions; supercritical $CO_2$ with 20% methanol; flow rate: 80 mL/min. The first eluting peak was assigned: (P)-1-(5-fluoro-2-methoxy-4-(1-(trifluoromethyl)cyclopropyl)phenyl)-N-(isoxazol-3-yl)-2-oxo-1,2-dihydroquinoline-6-sulfonamide (11.9 mg, 0.023 mmol, 9% yield), and the second peak was assigned: (M)-1-(5-fluoro-2-methoxy-4-(1-(trifluoromethyl) cyclopropyl)phenyl)-N-(isoxazol-3-yl)-2-oxo-1,2-dihydroquinoline-6-sulfonamide (12.3 mg, 0.024 mmol, 10% yield). Data for (P)-atropisomer: $^1$H NMR (400 MHz, ACETONITRILE-$d_3$) δ ppm 8.37-8.42 (m, 1H), 8.27 (d, J=2.28 Hz, 1H), 8.01 (d, J=9.64 Hz, 1H), 7.82 (dd, J=8.97, 2.23 Hz, 1H), 7.36 (d, J=6.32 Hz, 1H), 7.15 (d, J=9.64 Hz, 1H), 6.78 (dd, J=9.33, 4.87 Hz, 2H), 6.47 (d, J=1.87 Hz, 1H), 3.71 (s, 3H), 1.49-1.57 (m, 2H), 1.29 (s, 2H). m/z (ESI, positive ion) 523.8 (M+H)+.
Data for (M)-atropisomer: $^1$H NMR (400 MHz, DMSO-$d_6$) δ ppm 8.36 (br s, 1H), 8.11-8.30 (m, 3H), 7.76 (dd, J=8.81, 2.07 Hz, 1H), 7.39-7.47 (m, 1H), 7.35 (d, J=6.43 Hz, 1H), 6.72 (d, J=9.64 Hz, 1H), 6.60 (d, J=8.71 Hz, 1H), 6.22 (s, 1H), 3.69 (s, 3H), 1.43-1.53 (m, 2H), 1.32 (br s, 2H). m/z (ESI, positive ion) 524.0 (M+H)+.
Example 44: (P)-4-FLUORO-1-(5-FLUORO-2-METHOXY-4-((1R,2R)-2-(TRIFLUOROMETHYL)CYCLOPROPYL)PHENYL)-N-(ISOXAZOL-3-YL)-2-OXO-1,2-DIHYDROQUINOLINE-6-SULFONAMIDE
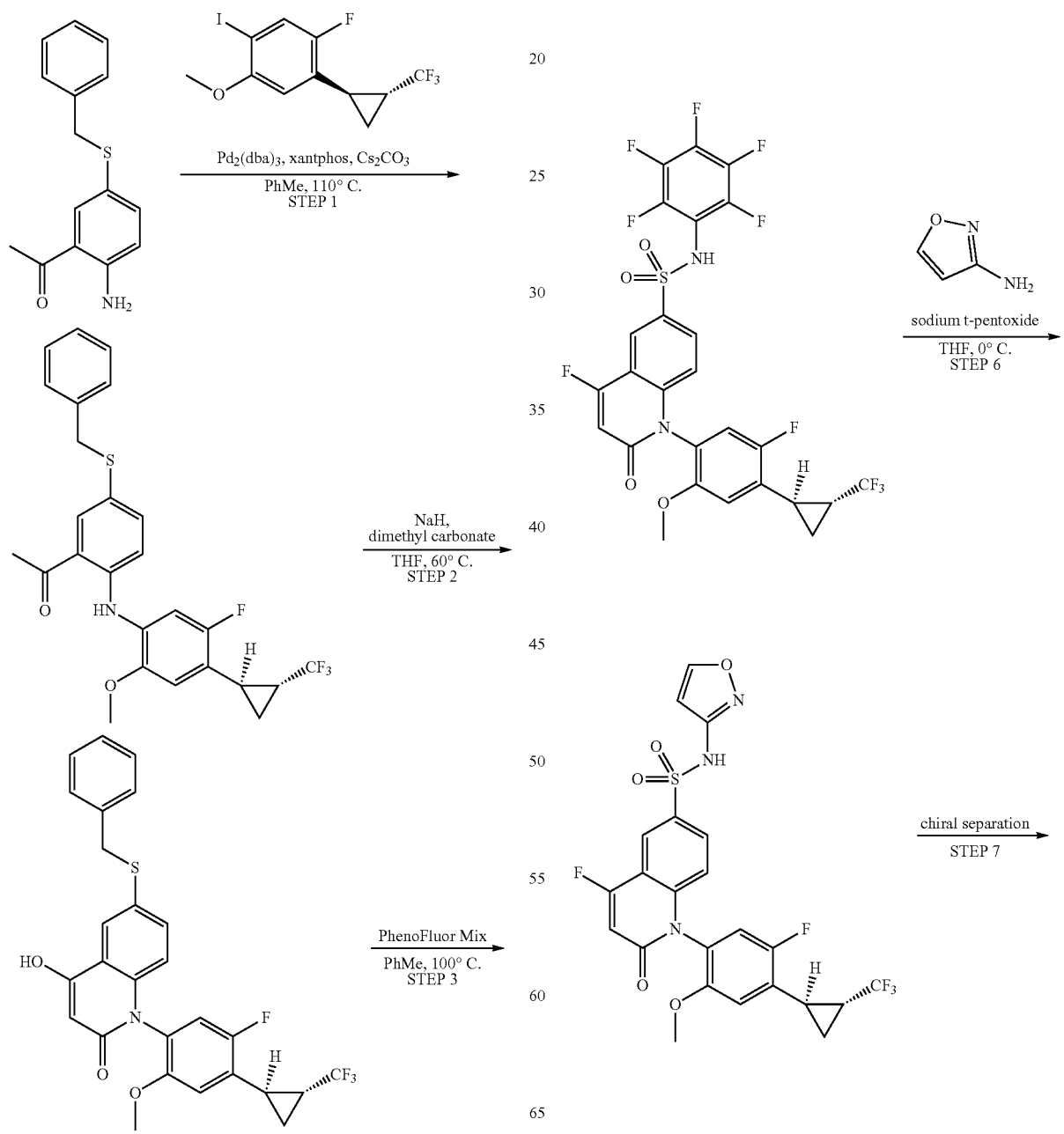

-continued

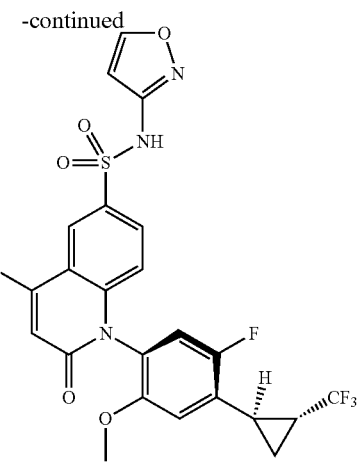

Step 1: 1-(5-(BENZYLTHIO)-2-((5-FLUORO-2-METHOXY-4-((1R,2R)-2-(TRIFLUOROMETHYL)CYCLOPROPYL)PHENYL)AMINO)PHENYL)ETHAN-1-ONE A 100 mL round-bottom flask was charged with caesium carbonate (10.13 g, 31.1 mmol), 1-(2-amino-5-(benzylthio)phenyl)ethan-1-one (2 g, 7.77 mmol), 1-fluoro-5-iodo-4-methoxy-2-((1R,2R)-2-(trifluoromethyl)cyclopropyl)benzene (2.80 g, 7.77 mmol), and toluene (25.9 mL). The mixture was sparged with nitrogen for 20 minutes before tris(dibenzylideneactone)dipalladium (0.356 g, 0.389 mmol) and (5-diphenylphosphanyl-9,9-dimethylxanthen-4-yl)-diphenylphosphane (0.450 g, 0.777 mmol) were added. The reaction was stirred at 110° C. for 18 hours. The reaction was cooled to ambient temperature, diluted with EtOAc, and filtered through CELITE which was washed with EtOAc. The resulting dark solution was evaporated to dryness. The purified by column chromatography (RediSepRf Gold 80 g, gradient elution 10% to 60% EtOAc in heptane) to afford 1-(5-(benzylthio)-2-((5-fluoro-2-methoxy-4-((1R,2R)-2-(trifluoromethyl)cyclopropyl)phenyl)amino)phenyl)ethan-1-one (2.8247 g, 5.77 mmol, 74% yield) as a bright yellow oil. m/z (ESI, positive ion) 490.0 (M+H)$^+$.

Step 2: 6-(BENZYLTHIO)-1-(5-FLUORO-2-METHOXY-4-((1R,2R)-2-(TRIFLUOROMETHYL)CYCLOPROPYL)PHENYL)-4-HYDROXYQUINOLIN-2(1H)-ONE Dimethyl carbonate (2.076 g, 1.940 mL, 23.04 mmol) was added to a slurry of sodium hydride (60% dispersion in mineral oil) (0.922 g, 23.04 mmol) in tetrahydrofuran (57.6 mL). The temperature was raised to 60° C., and the reaction was stirred for 20 min. A solution of 1-(5-(benzylthio)-2-((5-fluoro-2-methoxy-4-((1R,2R)-2-(trifluoromethyl)cyclopropyl)phenyl)amino)phenyl)ethan-1-one (2.82 g, 5.76 mmol) in THF (10 ml) was added and the reaction was stirred at 60° C. for 3 hours. The reaction was cooled to 0° C. and water was added to quench the reaction. The mixture was extracted with ethyl acetate. The organic layer was dried over sodium sulfate and concentrated in vacuo. The crude product was purified by column chromatography (RediSepRf Gold 80 g, gradient elution 10% to 80% 3:1 EtOAc:EtOH in heptane with 10% dichloromethane as additive) to afford 6-(benzylthio)-1-(5-fluoro-2-methoxy-4-((1R,2R)-2-(trifluoromethyl)cyclopropyl)phenyl)-4-hydroxyquinolin-2(1H)-one (1.666 g, 3.23 mmol, 56% yield) as a light orangish solid. m/z (ESI, positive ion) 515.8 (M+H)$^+$.

Step 3: 6-(BENZYLTHIO)-4-FLUORO-1-(5-FLUORO-2-METHOXY-4-((1R,2R)-2-(TRIFLUOROMETHYL)CYCLOPROPYL)PHENYL)QUINOLIN-2(1H)-ONE The PhenoFluor Mix was dried by heating to 140° C. under high vac for 2 hours. After cooling to ambient temperature under vacuum, 6-(benzylthio)-1-(5-fluoro-2-methoxy-4-((1R,2R)-2-(trifluoromethyl)cyclopropyl)phenyl)-4-hydroxyquinolin-2(1H)-one (500 mg, 0.970 mmol) slurried in dry toluene (9.7 mL) was added to the vial. The reaction was stirred at room temperature for half hour and then at 100° C. for 1.5 hours under nitrogen. The reaction was cooled to ambient temperature, diluted with ethyl acetate, and filtered through CELITE that was washed with ethyl acetate. The resulting tan solution was evaporated to dryness. The residue solid was purified by column chromatography (RediSepRf Gold 40 g, gradient elution 10% to 60% EtOAc in heptane with 10% dichloromethane as additive) to afford 6-(benzylthio)-4-fluoro-1-(5-fluoro-2-methoxy-4-((1R,2R)-2-(trifluoromethyl)cyclopropyl)phenyl)quinolin-2(1H)-one (406.8 mg, 0.786 mmol, 81% yield) as a light green solid. m/z (ESI, positive ion) 517.8 (M+H)$^+$.

Step 4 & 5: PERFLUOROPHENYL 4-FLUORO-1-(5-FLUORO-2-METHOXY-4-((1R,2R)-2-(TRIFLUOROMETHYL)CYCLOPROPYL)PHENYL)-2-OXO-1,2-DIHYDROQUINOLINE-6-SULFONATE An acetonitrile (2.45 mL), acetic acid (93 μL) and water (61.4 μL) slurry of 6-(benzylthio)-4-fluoro-1-(5-fluoro-2-methoxy-4-((1R,2R)-2-(trifluoromethyl)cyclopropyl)phenyl)quinolin-2(1H)-one (405 mg, 0.783 mmol) in a 40-mL vial was cooled to 0° C. under nitrogen and 1,3-dichloro-5,5-dimethylhydantoin (308 mg, 1.565 mmol) was added portionwise. The pale green slurry dissolved to give a yellow solution during the addition then a white precipitate crashed out while the reaction was stirred at 0° C. for 30 minutes. Perfluorophenol (223 mg, 1.213 mmol) in acetonitrile (0.5 mL) was added, followed by triethylamine (396 mg, 545 μl, 3.91 mmol). The pale green slurry was stirred at 0° C. for 15 minutes then at ambient temperature for 30 minutes. The reaction was then diluted with dichloromethane, filtered through a phase separator cartridge, and concentrated in vacuo to a yellow solid. The crude product was purified by column chromatography (RediSepRf Gold 24 g, gradient elution 10% to 60% EtOAc in heptane) to afford perfluorophenyl 4-fluoro-1-(5-fluoro-2-methoxy-4-((1R,2R)-2-(trifluoromethyl)cyclopropyl)phenyl)-2-oxo-1,2-dihydroquinoline-6-sulfonate (378.4 mg, 0.590 mmol, 75% yield) as a white solid. m/z (ESI, positive ion) 641.8 (M+H)$^+$.

Step 6: 4-FLUORO-1-(5-FLUORO-2-METHOXY-4-((1R,2R)-2-(TRIFLUOROMETHYL)CYCLOPROPYL)PHENYL)-N-(ISOXAZOL-3-YL)-2-OXO-1,2-DIHYDROQUINOLINE-6-SULFONAMIDE A 40 mL vial was charged with isoxazol-3-amine (73.7 mg, 0.877 mmol) and perfluorophenyl 4-fluoro-1-(5-fluoro-2-methoxy-4-((1R,2R)-2-(trifluoromethyl)cyclopropyl)phenyl)-2-oxo-1,2-dihydroquinoline-6-sulfonate (375 mg, 0.585 mmol). The vial was flushed with nitrogen for 10 minutes before tetrahydrofuran (1.95 mL) was added. The reaction was cooled to −78° C. under nitrogen. Sodium tert-pentoxide, 30% solution in THF (0.491 mL, 1.228 mmol) was added slowly via syringe and the reaction turned yellow upon the addition. The reaction was stirred for 15 minutes at −78° C. Saturated ammonium chloride and dichloromethane were added to the reaction. The layers were separated and the water phase was extracted 2× with dichloromethane. The combined organic layer was dried by filtration through phase separation cartridge and evaporated. The residue was purified by column chromatography (RediSepRf Gold 40 g, gradient elution 10% to 40% 3:1 EtOAc:EtOH in heptane with 10% dichloromethane as additive) to afford 4-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide (296.1 mg, 0.547 mmol, 94% yield) as a white foam. m/z (ESI, positive ion) 541.8 (M+H)$^+$.

Step 7: (P)-4-FLUORO-1-(5-FLUORO-2-METHOXY-4-((1R,2R)-2-(TRIFLUOROMETHYL)CYCLOPROPYL)PHENYL)-N-(ISOXAZOL-3-YL)-2-OXO-1,2-DIHYDROQUINOLINE-6-SULFONAMIDE 4-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide (296 mg, 0.547 mmol) was purified by SFC using a Regis Whelk-O s,s column (2×15 cm, 5 micron), with a mobile phase of 30% methanol using a flowrate of 100 mL/min. This yielded (P)-4-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide (121 mg, 0.223 mmol, 41% yield) was obtained as a white solid. $^1$H NMR (500 MHz, DMSO-d6) δ ppm 11.70 (br s, 1H), 8.73 (d, J=1.69 Hz, 1H), 8.27 (d, J=2.08 Hz, 1H), 7.96 (dd, J=9.08, 2.21 Hz, 1H), 7.37 (d, J=9.86 Hz, 1H), 7.01 (d, J=6.75 Hz, 1H), 6.89 (dd, J=9.02, 1.49 Hz, 1H), 6.80 (d, J=11.68 Hz, 1H), 6.45 (d, J=1.82 Hz, 1H), 3.63 (s, 3H), 2.51-2.59 (m, 2H), 1.55-1.61 (m, 1H), 1.49 (dt, J=9.34, 5.77 Hz, 1H). m/z (ESI, positive ion) 541.8 (M+H)$^+$.

Example 45 & 46: (P)-7-FLUORO-1-(5-FLUORO-2-METHOXY-4-((1R,2R)-2-(TRIFLUOROMETHYL)CYCLOPROPYL)PHENYL)-N-(ISOXAZOL-3-YL)-2-OXO-1,2-DIHYDROQUINOLINE-6-SULFONAMIDE AND (P)-7-FLUORO-1-(5-FLUORO-2-METHOXY-4-((1S,2S)-2-(TRIFLUOROMETHYL)CYCLOPROPYL)PHENYL)-N-(ISOXAZOL-3-YL)-2-OXO-1,2-DIHYDROQUINOLINE-6-SULFONAMIDE

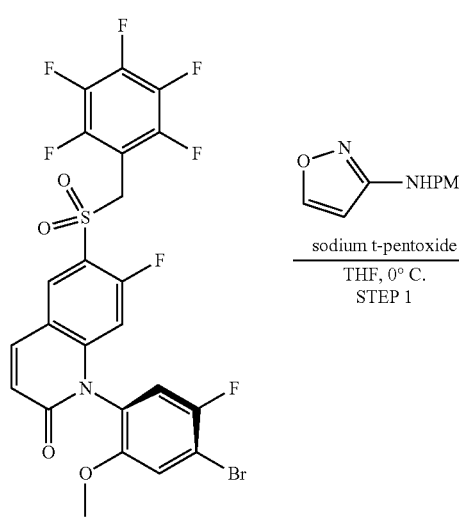

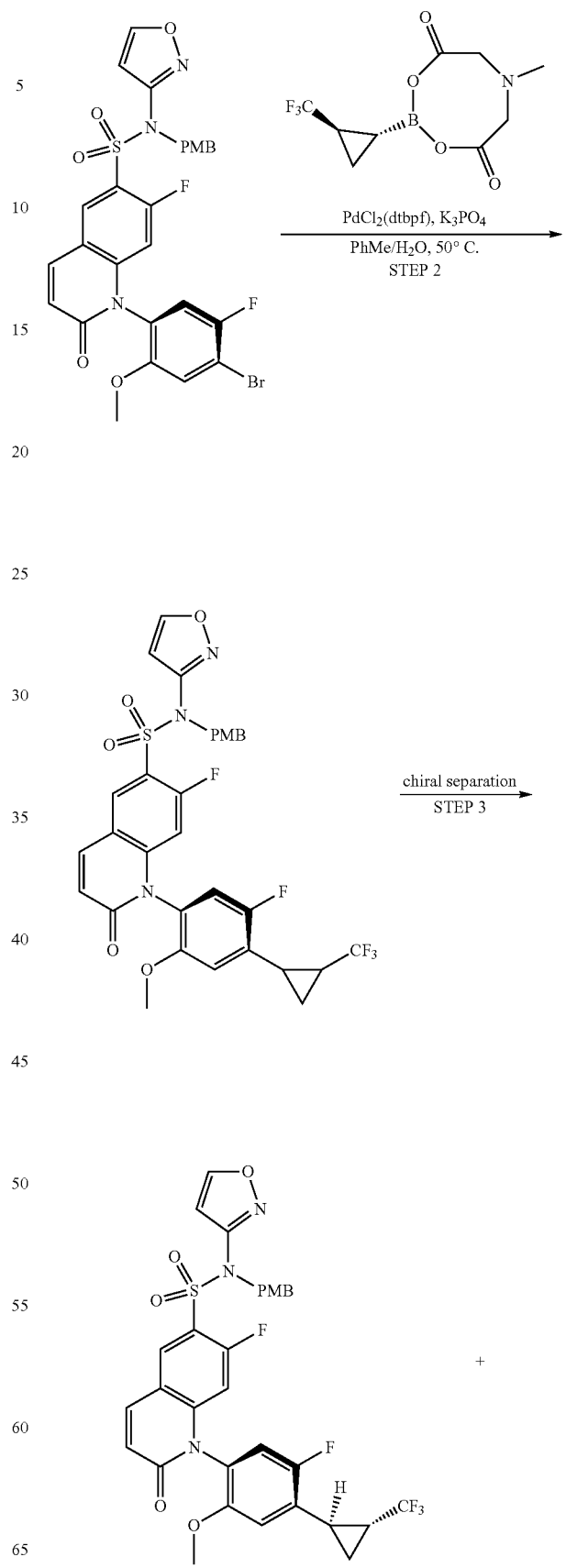

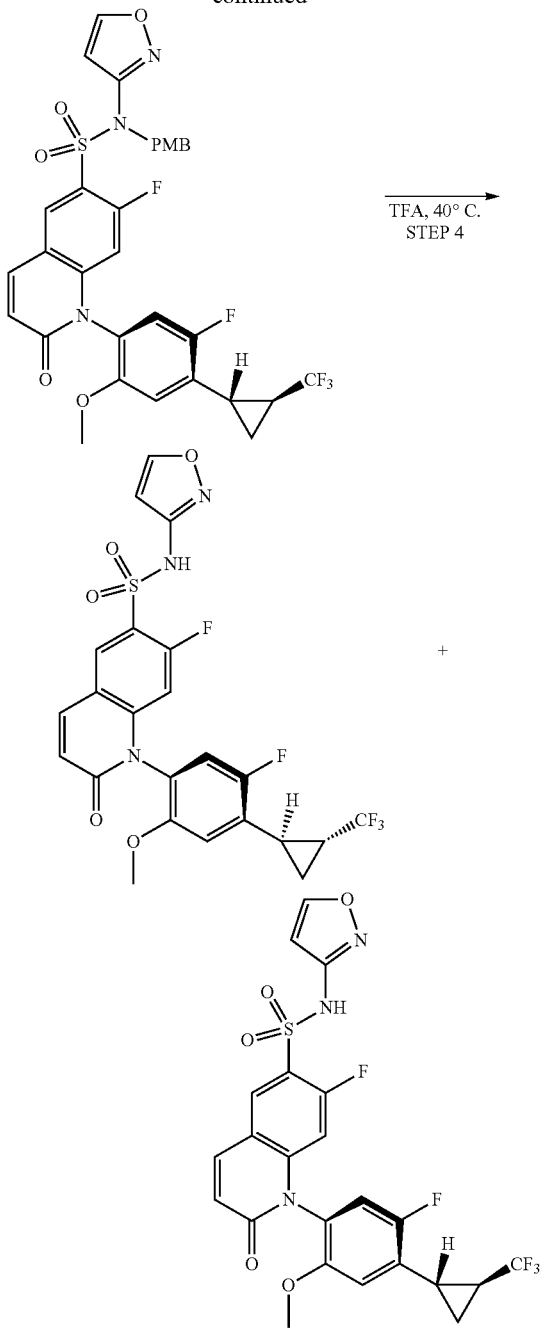

Step 1: (P)-1-(4-BROMO-5-FLUORO-2-METHOXYPHENYL)-7-FLUORO-N-(ISOXAZOL-3-YL)-N-(4-METHOXYBENZYL)-2-OXO-1,2-DIHYDROQUINOLINE-6-SULFONAMIDE A 100 mL round-bottom flask was charged with (P)-perfluorophenyl 1-(4-bromo-5-fluoro-2-methoxyphenyl)-7-fluoro-2-oxo-1,2-dihydroquinoline-6-sulfonate (6.01 g, 9.82 mmol) and N-(4-methoxybenzyl)isoxazol-3-amine (2.48 g, 12.14 mmol). The flask was sparged with nitrogen for 5 minutes prior to the addition of tetrahydrofuran (20 mL). The mixture was cooled to −78° C., following which sodium tert-pentoxide, 30% solution in THF (6 mL, 15.00 mmol) was added dropwise. After 15 minutes, the reaction was quenched with 5 M aqueous ammonium chloride and then warmed to ambient temperature. The mixture was extracted with EtOAc (2×). the organic layer was separated and concentrated under reduce pressure. The residue was purified by column chromatography (Biotage Isolera One, Biotage Sfar silica HC D 20 um 50 g, 0-80% ethyl acetate in heptane with 10% dichloromethane as additive) to provide (P)-1-(4-bromo-5-fluoro-2-methoxyphenyl)-7-fluoro-N-(isoxazol-3-yl)-N-(4-methoxybenzyl)-2-oxo-1,2-dihydroquinoline-6-sulfonamide (5.0 g, 7.91 mmol, 81% yield) as a white solid. m/z (ESI, positive ion) 634.0 (M+H)+.

Step 2: TRANS-(P)-7-FLUORO-1-(5-FLUORO-2-METHOXY-4-(2-(TRIFLUOROMETHYL)CYCLOPROPYL)PHENYL)-N-(ISOXAZOL-3-YL)-N-(4-METHOXYBENZYL)-2-OXO-1,2-DIHYDROQUINOLINE-6-SULFONAMIDE A 100 mL round-bottom flask was charged with (P)-1-(4-bromo-5-fluoro-2-methoxyphenyl)-7-fluoro-N-(isoxazol-3-yl)-N-(4-methoxybenzyl)-2-oxo-1,2-dihydroquinoline-6-sulfonamide (3.914 g, 6.19 mmol), trans-6-methyl-2-(2-(trifluoromethyl)cyclopropyl)-1,3,6,2-dioxazaborocane-4,8-dione (1.972 g, 7.44 mmol), [1,1′-bis(di-tert-butylphosphino)ferrocene]dichloropalladium(ii) (0.484 g, 0.743 mmol), and potassium phosphate tribasic (5.25 g, 24.76 mmol). This flask was capped and purged with nitrogen for 5 minutes before addition of toluene (30.9 mL) and water (7.74 mL). The resulting mixture was sparged with nitrogen for 15 minutes, then stirred at 50° C. After 16 hours, the reaction was cooled to room temperature and extracted with ethyl acetate. The organic layer was separated and solvents were removed under reduced pressure. The residue was purified by flash column chromatography (Biotage Isolera One, Biotage Sfar silica HC D 25 g, eluent 0-70% ethyl acetate in heptane with 10% dichloromethane as additive) to afford (P)-7-fluoro-1-(5-fluoro-2-methoxy-4-(2-(trifluoromethyl)cyclopropyl)phenyl)-N-(isoxazol-3-yl)-N-(4-methoxybenzyl)-2-oxo-1,2-dihydroquinoline-6-sulfonamide (3.748 g, 5.67 mmol, 92% yield) as an off white solid. m/z (ESI, positive ion) 662.2 (M+H)+.

Step 3: (P)-7-FLUORO-1-(5-FLUORO-2-METHOXY-4-((1S,2S)-2-(TRIFLUOROMETHYL)CYCLOPROPYL)PHENYL)-N-(ISOXAZOL-3-YL)-N-(4-METHOXYBENZYL)-2-OXO-1,2-DIHYDROQUINOLINE-6-SULFONAMIDE AND (P)-7-FLUORO-1-(5-FLUORO-2-METHOXY-4-((1R,2R)-2-(TRIFLUOROMETHYL)CYCLOPROPYL)PHENYL)-N-(ISOXAZOL-3-YL)-N-(4-METHOXYBENZYL)-2-OXO-1,2-DIHYDROQUINOLINE-6-SULFONAMIDE (P)-7-fluoro-1-(5-fluoro-2-methoxy-4-(2-(trifluoromethyl)cyclopropyl)phenyl)-N-(isoxazol-3-yl)-N-(4-methoxybenzyl)-2-oxo-1,2-dihydroquinoline-6-sulfonamide (3.748 g, 5.67 mmol) was subjected to SFC via a Chiralpak IE 2×25 cm, 5 μm column; a mobile phase of 35% ethanol using a flowrate of 70 mL/min to generate (P)-7-fluoro-1-(5-fluoro-2-methoxy-4-((1R,2R)-2-(trifluoromethyl)cyclopropyl)phenyl)-N-(isoxazol-3-yl)-N-(4-methoxybenzyl)-2-oxo-1,2-dihydroquinoline-6-sulfonamide (1.68 g, 2.54 mmol, 45% yield) and (P)-7-fluoro-1-(5-fluoro-2-methoxy-4-((1S,2S)-2-(trifluoromethyl)cyclopropyl)phenyl)-N-(isoxazol-3-yl)-N-

(4-methoxybenzyl)-2-oxo-1,2-dihydroquinoline-6-sulfonamide (1.75 g, 2.65 mmol, 47% yield).

Step 4: (P)-7-FLUORO-1-(5-FLUORO-2-METHOXY-4-((1R,2R)-2-(TRIFLUOROMETHYL)CYCLOPROPYL)PHENYL)-N-(ISOXAZOL-3-YL)-2-OXO-1,2-DIHYDROQUINOLINE-6-SULFONAMIDE AND (P)-7-FLUORO-1-(5-FLUORO-2-METHOXY-4-((1S,2S)-2-(TRIFLUOROMETHYL)CYCLOPROPYL)PHENYL)-N-(ISOXAZOL-3-YL)-2-OXO-1,2-DIHYDROQUINOLINE-6-SULFONAMIDE Two 40 mL vials were charged with either (P)-7-fluoro-1-(5-fluoro-2-methoxy-4-((1R,2R)-2-(trifluoromethyl)cyclopropyl)phenyl)-N-(isoxazol-3-yl)-N-(4-methoxybenzyl)-2-oxo-1,2-dihydroquinoline-6-sulfonamide (1.68 g, 2.54 mmol) or (P)-7-fluoro-1-(5-fluoro-2-methoxy-4-((1S,2S)-2-(trifluoromethyl)cyclopropyl)phenyl)-N-(isoxazol-3-yl)-N-(4-methoxybenzyl)-2-oxo-1,2-dihydroquinoline-6-sulfonamide (1.75 g, 2.65 mmol). Then 1,1,1-trifluoroacetic acid (23.84 g, 16 mL, 209 mmol) was added.

The resulting mixtures were stirred for 2.5 hours at 40° C. The reactions were cooled and excess TFA was removed under vacuum. The resulting residues were subjected to reverse phase purification (ISCO, 25-70% acetonitrile in water, 0.1% formic acid additive) to yield (P)-7-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide (0.9991 g, 1.845 mmol, 73% yield) and (P)-7-fluoro-1-(5-fluoro-2-methoxy-4-((1S,2S)-2-(trifluoromethyl)cyclopropyl)phenyl)-N-(isoxazol-3-yl)-2-oxo-1,2-dihydroquinoline-6-sulfonamide (1.1023 g, 2.036 mmol, 80% yield) as white powders after lyophilization. $^1$H NMR (500 MHz, DMSO-d6) δ ppm 11.96 (br s, 1H), 8.72 (d, J=1.8 Hz, 1H), 8.45 (d, J=7.8 Hz, 1H), 8.22 (d, J=9.7 Hz, 1H), 7.35 (d, J=9.9 Hz, 1H), 6.99 (d, J=6.7 Hz, 1H), 6.74 (d, J=9.6 Hz, 1H), 6.53 (d, J=11.9 Hz, 1H), 6.38 (d, J=1.8 Hz, 1H), 3.68 (s, 3H), 2.5-2.6 (m, 2H), 1.5-1.6 (m, 1H), 1.48 (td, J=5.9, 9.3 Hz, 1H), m/z (ESI, positive ion) 542.0 (M+H)$^+$ and $^1$H NMR (500 MHz, DMSO-d6) δ ppm 11.96 (br s, 1H), 8.72 (d, J=1.8 Hz, 1H), 8.45 (d, J=7.8 Hz, 1H), 8.21 (d, J=9.7 Hz, 1H), 7.34 (d, J=9.9 Hz, 1H), 7.00 (d, J=6.7 Hz, 1H), 6.74 (d, J=9.6 Hz, 1H), 6.55 (d, J=11.9 Hz, 1H), 6.38 (d, J=1.8 Hz, 1H), 3.68 (s, 3H), 2.6-2.6 (m, 1H), 2.5-2.6 (m, 1H), 1.4-1.6 (m, 2H), m/z (ESI, positive ion) 542.2 (M+H)$^+$.

Examples 47 & 48: (P)-7-FLUORO-N-(ISOXAZOL-3-YL)-1-(2-METHOXY-4-((1R,2R)-2-(TRIFLUOROMETHYL)CYCLOPROPYL)PHENYL)-2-OXO-1,2-DIHYDROQUINOLINE-6-SULFONAMIDE and (P)-7-FLUORO-N-(ISOXAZOL-3-YL)-1-(2-METHOXY-4-((1S,2S)-2-(TRIFLUOROMETHYL)CYCLOPROPYL)PHENYL)-2-OXO-1,2-DIHYDROQUINOLINE-6-SULFONAMIDE

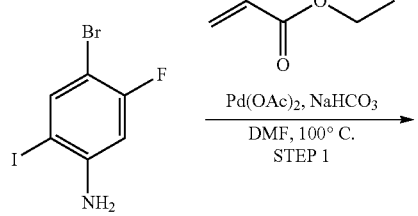

139
-continued
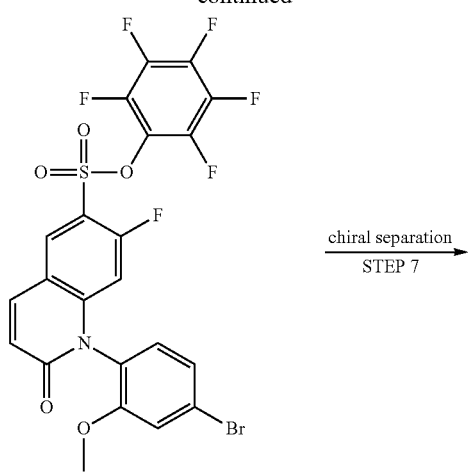
chiral separation
STEP 7 →
140
-continued
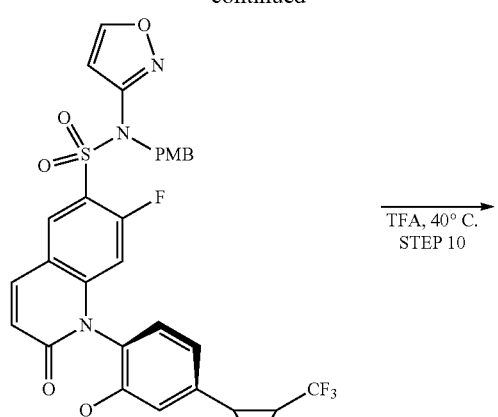
TFA, 40° C.
STEP 10 →
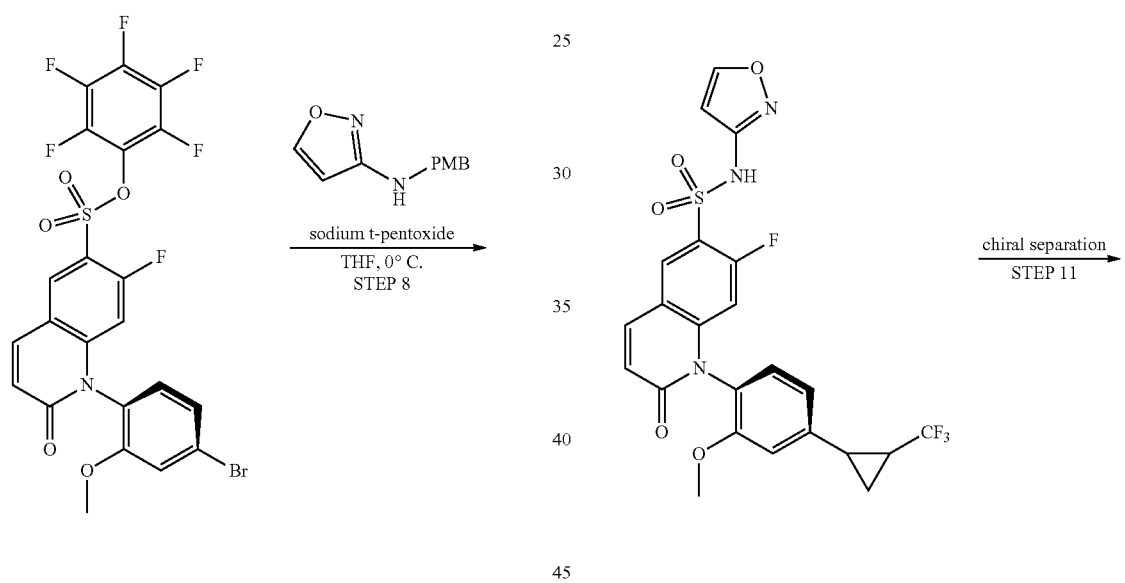
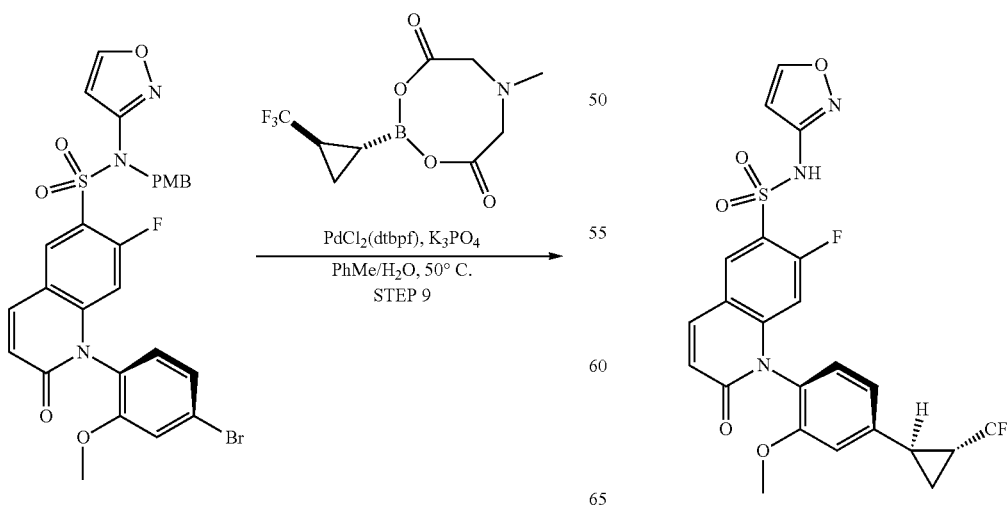
+

141

-continued

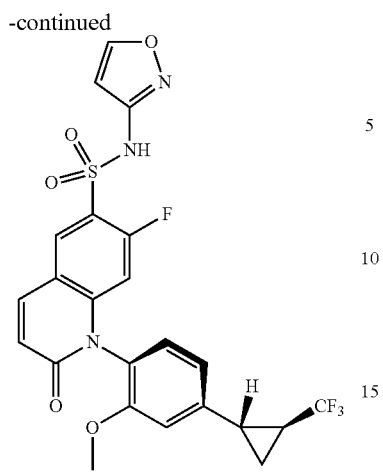

Step 1: ETHYL (E)-3-(2-AMINO-5-BROMO-4-FLUOROPHENYL)ACRYLATE

A 100 mL round-bottom flask was charged with 4-bromo-5-fluoro-2-iodoaniline (15 g, 47.5 mmol), ethyl acrylate (4.99 g, 5.43 mL, 49.9 mmol), sodium bicarbonate (9.97 g, 119 mmol), palladium(ii) acetate (0.533 g, 2.374 mmol) and N, N-dimethylformamide (31.7 mL). The reaction was stirred at 100° C. under nitrogen for 1 hour. The reaction was diluted with ethyl acetate and filtered through CELITE. The filtrate was concentrated and purified by column chromatography (Biotage Snapultra 340 g, 0-60% ethyl acetate in heptane with 10% dichloromethane additive) to yield ethyl (E)-3-(2-amino-5-bromo-4-fluorophenyl)acrylate (11.3 g, 39.2 mmol, 83% yield). m/z (ESI, positive ion) 288.0 (M+H)$^+$.

Step 2: ETHYL (E)-3-(2-AMINO-5-(BENZYLTHIO)-4-FLUOROPHENYL)ACRYLATE

A 250 mL round-bottom flask was charged with ethyl (E)-3-(2-amino-5-bromo-4-fluorophenyl)acrylate (10 g, 34.7 mmol), 1,4-dioxane (87 mL) and n,n-diisopropylethylamine (13.46 g, 18.19 mL, 104 mmol). The mixture was sparged with nitrogen for 20 minutes then bis[tris(dibenzylideneacetone)palladium(0)] (1.589 g, 1.735 mmol), (5-diphenylphosphanyl-9,9-dimethylxanthen-4-yl)-diphenylphosphane (2.008 g, 3.47 mmol), and benzyl mercaptan (5.17 g, 4.88 mL, 41.6 mmol) were added. The reaction was warmed to 80° C. overnight. The reaction was cooled, filtered over CELITE. The CELITE was washed with dichloromethane, and the solvent was removed in vacuo. The crude product was purified by column chromatography (Biotage SNAP ultra 100 g, gradient elution 0-80% ethyl acetate in heptane) to provides ethyl (E)-3-(2-amino-5-(benzylthio)-4-fluorophenyl)acrylate (9.9 g, 29.9 mmol, 86% yield). m/z (ESI, positive ion) 332.0 (M+H)$^+$.

Step 3: ETHYL (E)-3-(5-(BENZYLTHIO)-2-((4-BROMO-2-METHOXYPHENYL)AMINO)-4-FLUOROPHENYL)ACRYLATE A 100 mL round-bottom flask was charged with caesium carbonate (14.35 g, 44.1 mmol), ethyl (E)-3-(2-amino-5-(benzylthio)-4-fluorophenyl)acrylate (3.65 g, 11.01 mmol), 4-bromo-1-iodo-2-methoxybenzene (3.45 g, 11.01 mmol), and toluene (36.7 mL). The mixture was sparged with nitrogen for 20 minutes then tris(dibenzylideneactone)dipalladium (0.555 g, 0.606 mmol) and (5-diphenylphosphanyl-9,9-dimethylxanthen-4-yl)-diphenylphosphane (0.701 g, 1.212 mmol) were added. The reaction was stirred at 110° C. overnight. The reaction mixture was allowed to cool to room temperature, diluted with ethyl acetate and filtered through CELITE. The filtrate was concentrated under reduced pressure to obtain the Initial product which was purified by column chromatography (Biotage Snapultra 50 g, 0-70% ethyl acetate with 10% dichloromethane as additive) to afford ethyl (E)-3-(5-(benzylthio)-2-((4-bromo-2-methoxyphenyl)amino)-4-fluorophenyl)acrylate (1.95 g, 3.78 mmol, 34% yield). m/z (ESI, positive ion) 517.8 (M+H)$^+$.

Step 4: 6-(BENZYLTHIO)-1-(4-BROMO-2-METHOXYPHENYL)-7-FLUOROQUINOLIN-2(1H)-ONE Ethyl (E)-3-(5-(benzylthio)-2-((4-bromo-2-methoxyphenyl)amino)-4-fluorophenyl)acrylate (1.9 g, 3.68 mmol) was dissolved in methanol (9.68 mL). Tributylphosphine (0.223 g, 0.276 mL, 1.104 mmol) was added to the reaction. The reaction was then stirred at 70° C. for 5 hours. Solvent was then removed in vacuo. The crude product was purified by column chromatography (Biotage Snapultra 25 g, 0-80% ethyl acetate in heptane) to afford 6-(benzylthio)-1-(4-bromo-2-methoxyphenyl)-7-fluoroquinolin-2(1H)-one (1.32 g, 2.81 mmol, 76% yield). m/z (ESI, positive ion) 472.0 (M+H)$^+$.

Step 5 & 6: PERFLUOROPHENYL 1-(4-BROMO-2-METHOXYPHENYL)-7-FLUORO-2-OXO-1,2-DIHYDROQUINOLINE-6-SULFONATE A 100 mL round-bottom flask was charged with 6-(benzylthio)-1-(4-bromo-2-methoxyphenyl)-7-fluoroquinolin-2(1H)-one (1.3 g, 2.76 mmol), acetonitrile (14 mL), acetic acid (0.800 mL) and water (0.500 mL). The resulting mixture was cooled to 0° C. and 1,3-dichloro-5,5-dimethyl-2,4-imidazolidinedione (0.871 g, 4.42 mmol) was added portion-wise. The resulting suspension was stirred at 0° C. for 15 minutes. Then a solution of pentafluorophenol (1.017 g, 5.53 mmol) in acetonitrile (14 mL) was added over 10 min, followed by triethylamine, anhydrous (1.398 g, 1.942 mL, 13.82 mmol) over 20 min. The mixture was continued to be stirred for 30 min. Ice water was added and the precipitated solid was filtered and washed with water. The Initial product was purified by stirring with methanol (150 mL), filtered washed with MeOH (50 mL) and dried to obtain perfluorophenyl 1-(4-bromo-2-methoxyphenyl)-7-fluoro-2-oxo-1,2-dihydroquinoline-6-sulfonate (1300 mg, 2.188 mmol, 79% yield) as off white solid. m/z (ESI, positive ion) 593.8 (M+H)$^+$.

Step 7: (P)-PERFLUOROPHENYL 1-(4-BROMO-2-METHOXYPHENYL)-7-FLUORO-2-OXO-1,2-DIHYDROQUINOLINE-6-SULFONATE Perfluorophenyl 1-(4-bromo-2-methoxyphenyl)-7-fluoro-2-oxo-1,2-dihydroquinoline-6-sulfonate was first purified by SFC using a Chiralcel OJ-H column (3×15 cm, 5 micron), with a mobile phase of 15% isopropanol using a flowrate of 160 mL/min. The resulting product was then purified by SFC using a Whelk-O s,s column (2×15 cm, 5 micron), with a mobile phase of 50% 3:1 isopropanol:dichloromethane using a flowrate of 80 mL/min. This yielded (P)-perfluorophenyl 1-(4-bromo-2-methoxyphenyl)-7-fluoro-2-oxo-1,2-dihydroquinoline-6-sulfonate (380 mg, 0.639 mmol, 29% yield).

Step 8: (P)-1-(4-BROMO-2-METHOXYPHENYL)-7-FLUORO-N-(ISOXAZOL-3-YL)-N-(4-METHOXYBENZYL)-2-OXO-1,2-DIHYDROQUINOLINE-6-SULFONAMIDE (P)-Perfluorophenyl 1-(4-bromo-2-methoxyphenyl)-7-fluoro-2-oxo-1,2-dihydroquinoline-6-sulfonate (380 mg, 0.639 mmol) and N-(4-methoxybenzyl)isoxazol-3-amine (157 mg, 0.767 mmol) were dissolved in tetrahydrofuran (3.20 mL). The solution was cooled to −78° C. Sodium tert-pentoxide, 30% solution in THF (384 µl, 0.959 mmol) was added to the solution slowly. The reaction was allowed to warm to room temperature and stirred for 30 minutes. The reaction was quenched with 5 M aqueous ammonium chloride, extracted with EtOAc (2×). The organic layer was separated and concentrated under reduced pressure. The residue was purified by column chromatography (Biotage Snapultra 100 g, 0-80% ethyl acetate in heptane with 10% dichloromethane additive) to provide (P)-1-(4-bromo-2-methoxyphenyl)-7-fluoro-N-(isoxazol-3-yl)-N-(4-methoxybenzyl)-2-oxo-1,2-dihydroquinoline-6-sulfonamide (316 mg, 0.514 mmol, 80% yield) as a white solid. m/z (ESI, positive ion) 613.8 (M+H)$^+$.

Step 9: TRANS-(P)-7-FLUORO-N-(ISOXAZOL-3-YL)-1-(2-METHOXY-4-(2-(TRIFLUOROMETHYL)CYCLOPROPYL)PHENYL)-N-(4-METHOXYBENZYL)-2-OXO-1,2-DIHYDROQUINOLINE-6-SULFONAMIDE A 40 mL vial was charged with (P)-1-(4-bromo-2-methoxyphenyl)-7-fluoro-N-(isoxazol-3-yl)-N-(4-methoxybenzyl)-2-oxo-1,2-dihydroquinoline-6-sulfonamide (316 mg, 0.514 mmol), trans-6-methyl-2-(2-(trifluoromethyl)cyclopropyl)-1,3,6,2-dioxazaborocane-4,8-dione (164 mg, 0.617 mmol), [1,1'-bis(di-tert-butylphosphino)ferrocene]dichloropalladium(ii) (67.0 mg, 0.103 mmol), and potassium phosphate tribasic (437 mg, 2.057 mmol). This vial was capped and purged with nitrogen for 5 minutes before addition of toluene (2.57 mL) and water (0.643 mL). The resulting mixture was sparged with nitrogen for 10 minutes and then stirred at 50° C. for 4 hours. The crude mixture was extracted with ethyl acetate. The organic layer was separated and concentrated. The crude product was purified by column chromatography (Biotage snapultra 10 g, 0-60% ethyl acetate in heptane with 10% dichloromethane as additive) to yield trans-(P)-7-fluoro-N-(isoxazol-3-yl)-1-(2-methoxy-4-(2-(trifluoromethyl)cyclopropyl)phenyl)-N-(4-methoxybenzyl)-2-oxo-1,2-dihydroquinoline-6-sulfonamide (340 mg, 0.528 mmol, 103% yield). m/z (ESI, positive ion) 644.0 (M+H)$^+$.

Step 10: TRANS-(P)-7-FLUORO-N-(ISOXAZOL-3-YL)-1-(2-METHOXY-4-(2-(TRIFLUOROMETHYL)CYCLOPROPYL)PHENYL)-2-OXO-1,2-DIHYDROQUINOLINE-6-SULFONAMIDE (P)-7-Fluoro-N-(isoxazol-3-yl)-1-(2-methoxy-4-(2-(trifluoromethyl)cyclopropyl)phenyl)-N-(4-methoxybenzyl)-2-oxo-1,2-dihydroquinoline-6-sulfonamide (340 mg, 0.528 mmol) was dissolved in trifluoroacetic acid (26.4 mL). The reaction was stirred at 40° C. for 4 hours. Solvent was removed by a stream of nitrogen. The Initial product was purified by column chromatography (Biotage Snapultra 10 g, 0-60% ethyl acetate in heptane with 10% dichloromethane as additive) to yield trans-(P)-7-fluoro-N-(isoxazol-3-yl)-1-(2-methoxy-4-(2-(trifluoromethyl)cyclopropyl)phenyl)-2-oxo-1,2-dihydroquinoline-6-sulfonamide.

Step 11: (P)-7-FLUORO-N-(ISOXAZOL-3-YL)-1-(2-METHOXY-4-((1R,2R)-2-(TRIFLUOROMETHYL)CYCLOPROPYL)PHENYL)-2-OXO-1,2-DIHYDROQUINOLINE-6-SULFONAMIDE AND (P)-7-FLUORO-N-(ISOXAZOL-3-YL)-1-(2-METHOXY-4-((1S,2S)-2-(TRIFLUOROMETHYL)CYCLOPROPYL)PHENYL)-2-OXO-1,2-DIHYDROQUINOLINE-6-SULFONAMIDE trans-(P)-7-Fluoro-N-(isoxazol-3-yl)-1-(2-methoxy-4-(2-(trifluoromethyl)cyclopropyl)phenyl)-2-oxo-1,2-dihydroquinoline-6-sulfonamide was purified by SFC via two Chiralpak AS-H, 5 µm columns (3×25 cm+3×25 cm); a mobile phase of 25% ethanol using a flowrate of 80 mL/min to generate (P)-7-fluoro-N-(isoxazol-3-yl)-1-(2-methoxy-4-((1R,2R)-2-(trifluoromethyl)cyclopropyl)phenyl)-2-oxo-1,2-dihydroquinoline-6-sulfonamide (44 mg, 0.085 mmol, 16% yield) and (P)-7-fluoro-N-(isoxazol-3-yl)-1-(2-methoxy-4-((1S,2S)-2-(trifluoromethyl)cyclopropyl)phenyl)-2-oxo-1,2-dihydroquinoline-6-sulfonamide (36 mg, 0.068 mmol, 13% yield). $^1$H NMR (500 MHz, DMSO-d6) δ ppm 11.95 (br s, 1H), 8.60 (s, 1H), 8.38 (d, J=7.7 Hz, 1H), 8.18 (d, J=9.6 Hz, 1H), 7.21 (d, J=8.0 Hz, 1H), 7.10 (d, J=1.7 Hz, 1H), 6.99 (dd, J=8.1, 1.8 Hz, 1H), 6.70 (d, J=9.6 Hz, 1H), 6.29-6.36 (m, 2H), 3.69 (s, 3H), 2.93 (br s, 1H), 2.52-2.56 (m, 1H), 1.38-1.47 (m, 2H); m/z (ESI, positive ion) 524.0 (M+H)$^+$ and $^1$H NMR (500 MHz, DMSO-d6) δ ppm 11.96 (br s, 1H), 8.60 (s, 1H), 8.38 (d, J=7.5 Hz, 1H), 8.18 (d, J=9.6 Hz, 1H), 7.21 (d, J=7.9 Hz, 1H), 7.12 (d, J=1.7 Hz, 1H), 6.98 (dd, J=8.1, 1.8 Hz, 1H), 6.70 (d, J=9.6 Hz, 1H), 6.29-6.36 (m, 2H), 3.69 (s, 3H), 2.93 (br s, 1H), 2.52-2.56 (m, 1H), 1.34-1.46 (m, 2H); m/z (ESI, positive ion) 524.0 (M+H)$^+$.

BIOLOGICAL EXAMPLES

The following assays were used in testing the exemplary compounds of the invention. Data for those examples tested in accordance with the procedures described below are presented in Table 1 below.

Ionworks Barracuda (IWB) Automated Patch Clamp Assay (Same Protocol for Both Hu Man and Mouse)

Human NaV1.7 currents were recorded in population patch-clamp mode with the IWB automated electrophysiology system (Molecular Devices, LLC, Sunnyvale, Calif.). Spiking HEK cells (without Kir2.1 transfection) were cultured and prepared for recordings as previously described for IonWorks Quattro testing[1]. The external solution consisted of the following (in mM): NaCl 140, KCl 5, CaCl$_2$ 2, MgCl$_2$ 1, HEPES 10, and glucose 11, pH 7.4, with N-methyl-D-glucamine at 320 mOsmol. The internal solution consisted of the following (in mM): KCl 70, KF 70, MgCl$_2$ 0.25, HEDTA 5, and HEPES 10, pH 7.25, with Nmethyl-D-glucamine, 300 mOsmol. From a holding potential of −110 mV, currents were elicited by a train of 26 depolarizations of 150 ms duration to −20 mV at a frequency of 5 Hz. Cells were then clamped to −20 mV for a period of 4 minutes in the presence of a single concentration of test compound. Following this compound incubation period, cells were clamped to −110 mV for three seconds to recover unbound channels and put through the same 26 pulse voltage protocol as above. Peak inward current during the 26th pulse to −20 mV in the presence of compound was divided by the peak inward current evoked by the 26th pulse to −20 mV in the absence of compound to determine percent inhibition. Concentration-response curves of percent inhibition as a function of concentration were generated to calculate $IC_{50}$ values as described in Kornecook, T. J.; Yin, R.; Altmann, S.; et al. Pharmacologic Characterization of AMG8379, a Potent and Selective Small Molecule Sulfonamide Antagonist of the Voltage-Gated Sodium Channel NaV1. 7. *J. Pharmacol. Exp. Ther.* 2017, 362, 146-160.

Microsomal Intrinsic Clearance Assay

The purpose of this assay is to determine the intrinsic clearance of test compound in microsomes from preclinical species and human by monitoring the disappearance of test article over time in hepatic microsomes. 20 mg/mL stock, stored at −80° C. microsome was used. List of chemical used: (1) Test article, 10 mM stock (DMSO) or powder from sample bank; (2) Verapamil, 10 mM stock; (3) NADPH, powder (Sigma); (4) Potassium phosphate buffer, 100 mM, pH 7.4; and (5) Tolbutamide (or equivalent). Final incubation concentrations were 0.25 mg/mL microsomal protein and 0.5 µM test article, and incubations are performed in triplicate. The typical time points for the assay were 1, 5, 10, 20, 30, and 40. The assay was carried out in 96-well format, and serially sampled from 400 µL incubation. At the appropriate timepoints, the incubations were quenched with acetonitrile containing internal standard (tolbutamide). Tolbutamide was the default internal standard because it has a signal by positive or negative ion mass spectrometry. The positive control for microsomal intrinsic clearance assay was verapamil. Samples were subjected to LC-MS/MS analysis, and relative amount of compound was calculated by peak area of compound normalized to peak area of internal standard (A/IS). Calculations of intrinsic clearance were performed with Galileo.

Procedure:

Microsomes were removed from −80° C. freezer and thawed at room temperature or in 37° C. water bath. Once thawed, they were stored on ice. Microsomes were added (0.53 mg) to 0.1 M phosphate buffer and 250 µL aliquot was taken per reaction. 10 mM stock of test article was prepared in DMSO. A 1/100 portion was diluted into acetonitrile: water 50:50 to make 100 µM stock. About 2.5 µL of the 100 µM test article stock was added to each reaction to a final concentration of 1.05 µM substrate. (NB: At this stage, concentrations were about 2× higher than the final incubation conditions, to account for about 1:1 dilution with NADPH).

1.9 mM NADPH solution was prepared in 0.1 mM phosphate buffer. 4×250 µL replicate wells of substrate and the microsomes containing 1.05 µM substrate and 0.53 mg/mL protein were the prepared. 3 replicate wells containing 210 µL 1.90 mM NADPH+1 well of buffer (−NADPH) were also prepared. The microsomes, 0.1 M phosphate buffer, and the test article were preincubated for 5 minutes at 37° C. To initiate the reaction, 190 µL of the substrate was added to the wells containing NADPH, to yield a final concentration of 0.25 mg/mL microsomes, 0.5 µM test article, and 1 mM NADPH. 35 µL aliquots were removed at 1, 5, 10, 20, 30, and 40 minutes. The reaction was then quenched at a 1:1 ratio with acetonitrile containing internal standard, placed in a Vortex mixer and centrifuged. The solution was then transferred for bioanalysis by LC-MS/MS.

Open-Field Locomotor Activity in Mice.

On the day of testing, C57Bl/6 male mice were orally administered either NaV1.7 compound or a vehicle control formulation at a dose volume of 10 ml/kg. The vehicle used was 2% HPMC/1% Tween 80 pH 10 with NaOH; DI water at pH 10 w/NaOH; or 2% HPMC/1% Tween 80 pH 2.2.

Two to three hours following test article treatment, depending on the cmax of the each NaV1.7 test compound of the invention, animals were placed into open-field chamber and the animal behavior was monitored over a 30-minute period. For the Thousand Oaks Site Experiments, 16"×16" open-field chamber, KINDER SCIENTIFIC®, San Diego, Calif., was used. For the Cambridge Mass. Site Experiments, 16"×16" open-field chamber, SAN DIEGO INSTRUMENTS®, San Diego, Calif., was used. Locomotor activity (horizontal movement and rearing activity) parameters were measured in an automated manner via infrared photo-beam breaks.

Human CYP 3A4 Induction Assay

Cryopreserved human hepatocytes were seeded in 96-well collagen coated plates at 70,000 cells per well in hepatocyte plating media (HPM, final concentrations: 1× Dulbecco's Modified Eagle's Medium, 0.1 µM dexamethasone, 10% fetal bovine serum, 1× ITS, 1×PSG) followed by incubation at 37° C. under 5% CO2 and 90% relative humidity for 2 days to allow hepatocytes to form a confluent layer. On Day 3, hepatocytes were treated with either test compound or rifampin (20 µM, positive control for CYP3A induction) prepared in hepatocyte incubation media ((HIM, final concentrations: 1× William's Medium E, 0.1 µM dexamethasone, 1×ITS, 1×PSG). Treatment was performed for 72 hours with either 2 concentrations (2 µM or 10 µM) or a range of concentrations (0.001 µM to 100 µM) of the test compound to obtain full dose-response curve. Fresh media containing the relevant concentrations of the test compound was replaced every day until the samples were processed. After 72 hours of incubation, samples were processed for mRNA analysis using bDNA technology using manufacturer's instructions (Affymetrix, Fremont, Calif.). Cell viability was tested at the end of the experiment using MTT assay kit (Roche Diagnostics, Basel, Switzerland). Data was analyzed and presented as percent of control (POC) and $E_{max}$ and $EC_{50}$ obtained when appropriate according to guidance from Center for Drug Evaluation and Research (CDER), 2006, Guidance for Industry, Drug Interaction Studies—Study Design, Data Analysis, and Implications for Dosing and Labeling.

Cryopreserved human hepatocytes were seeded in 96-well collagen coated plates at 70,000 cells per well in hepatocyte plating media (HPM, final concentrations: 1× Dulbecco's Modified Eagle's Medium, 0.1 µM dexamethasone, 10% fetal bovine serum, 1×ITS, 1×PSG) followed by incubation at 37° C. under 5% CO2 and 90% relative humidity for 2 days to allow hepatocytes to form a confluent layer. On Day 3, hepatocytes were treated with either test compound or rifampin (20 µM, positive control for CYP3A induction) prepared in hepatocyte incubation media ((HIM, final concentrations: 1× William's Medium E, 0.1 µM dexamethasone, 1×ITS, 1×PSG). Treatment was performed for 72 hours with either 2 concentrations (2 µM or 10 µM) or a range of concentrations (0.001 µM to 100 µM) of the test compound to obtain full dose-response curve. Fresh media containing the relevant concentrations of the test compound was replaced every day until the samples were processed. After 72 hours of incubation, samples were processed for mRNA analysis using bDNA technology using manufacturer's instructions (Affymetrix, Fremont, Calif.). Cell viability was tested at the end of the experiment using MTT assay kit (Roche Diagnostics, Basel, Switzerland). Data was analyzed and presented as percent of control (POC) and $E_{max}$ and EC$_{50}$ obtained when appropriate, as described in Halladay, J. et al, 2012, An "all-inclusive" 96-well cytochrome P450 induction method: Measuring enzyme activity, mRNA levels, protein levels, and cytotoxicity from one well using cryopreserved human hepatocytes, *Pharmacological and Toxicological Methods*, 66:270-275.

The compounds of the present invention may also be tested in the following in vivo assays.

Rat Formalin Model of Persistent Pain

On the test day, animals (Naïve, male Sprague Dawley rats) weighing between 260-300 g at the start of testing can be obtained from Harlan (Indianapolis, Ind.). All animals may be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing and at least 30 minutes prior to test onset, animals can be acclimated to the individual testing chambers. At test time, each animal can be gently wrapped in a towel with the left hind paw exposed. A dilute solution of formalin (2.5%) in phosphate buffered saline can be injected subcutaneously into the dorsal surface of the left hind paw in a volume to 50 µL with a 30 g needle. Immediately following injection, a small metal band can be affixed to the plantar side of the left hind paw with a drop of LOCTITE (adhesive). Animals may be then placed into the testing chambers and the number of flinches can be recorded between 10 to 40 minutes after formalin injection. A flinch is defined as a quick and spontaneous movement of the injected hind paw not associated with ambulation. Flinches can be quantified with the aid of the Automated Nociception Analyzer built by the University of California, San Diego Department of Anesthesiology. Individual data can be expressed as a % maximal potential effect (% MPE) calculated with the following formula: (−(Individual score−Vehicle average score)/Vehicle average score))*100=% MPE Statistical analysis can be performed by analysis of variance (ANOVA), with post-hoc analysis using Bonferroni compared to the vehicle group for a significant main effect. Data can be represented as mean % MPE+/−standard error for each group.

Rat Open Field Assay

On the test day, animals (Naïve, male Sprague Dawley rats) weighing between 260-300 g at the start of testing may be obtained from Harlan (Indianapolis, Ind.). All animals can be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. In a room separate from the testing room, animals can be pretreated with the appropriate test compound either by oral gavage or intraperitoneal injection at the desired pretreatment time (typically two hours before test onset) and then can be returned to their home cages until the pretreatment has elapsed. At test time, animal can be transferred to the open field testing room in their home cages. Each animal may be placed in a separate testing chamber and the motion tracking system is started. The house lights in the testing room should be turned off and the animals can be allowed to explore the novel open field for 30 minutes. An automated motion tracker, made by San Diego Instruments, San Diego, Calif., can be used to capture animal exploration with the aid of infrared photo beams to detect animal movement. These behaviors include basic movement and vertical rearing, which can be used as the primary endpoints for this assay. At the end of the test, house lights can be turned on and the animals should be removed from the testing apparatus. Data can be expressed as a percent change from the vehicle control using the following equation.

(1−(Test mean/Vehicle mean))*100=% Change.

Statistical analysis can be performed by analysis of variance (ANOVA), with post-hoc analysis using Dunnett to follow up significant main effects.

Mouse Formalin Model of Persistent Pain

Mice (Naïve, male C57Bl/6) weighing between 22-30 g at the start of testing were obtained from Harlan (Indianapolis, Ind.). All animals were housed under a 12/12 h light/dark cycle with lights on at 0630. Rodents were singly housed on solid bottom cages with corn cob bedding and had access to food and water ad libitum. Animals were allowed to habituate to the vivarium for at least five days before testing was begun and were brought into the testing room at least 30 minutes prior to dosing. Animals were pretreated with the appropriate test compound either by oral gavage or intraperitoneal injection at the desired pretreatment time (typically two hours before test onset) and then returned to their home cages. After dosing and at least 5 minutes prior to test onset, animals were acclimated to the individual testing chambers. At test time, each animal was gently wrapped in a cloth glove with the left hind paw exposed. A dilute solution of formalin (2%) in phosphate buffered saline was injected subcutaneously into the dorsal surface of the left hind paw in a volume to 20 µL with a 30 g needle. Animals were then placed into the observation chambers and the behaviors were recorded for 60 minutes following the formalin injection. A pain-like behavior was defined as licking and/or non-weight bearing of the injected hind paw not associated with ambulation.

Statistical analysis was performed by analysis of variance (ANOVA), with post-hoc analysis using the Dunnett post-hoc test compared to the vehicle group for any significant main effect. Data were represented as mean+/−standard error for each group.

Table 1 provides data for compounds exemplified in the present application and priority document thereof, as representative compounds of the present invention, as follows: compound name (as named using ChemDraw Ultra version 15.1; specific stereochemical designations such as P, M, cis, and trans were added); and biological data including in-vitro human Nav 1.7 IWQ data (IC$_{50}$ in uM) and Human CYP3A4 mRNA Induction at 10 uM percent of control (POC) (%), where available. Ex. # refers to Example No. ND means no data was available.

The potency of the compounds of the present invention were evaluated on human Na$_V$1.7 channels using the above described IonWorks Barracuda automated electrophysiology platform that evaluates the ability of compounds to block sodium conductance through Na$_V$1.7 channels. A voltage-protocol that prosecutes both state-dependent as well as use-dependent inhibition was used as these modes of action are thought to be more relevant for the native state of Na$_V$1.7 channels in pain sensing neurons in vivo.

The cytochrome P450 (CYP) is a well-known superfamily of enzymes that are responsible for the oxidative and reductive metabolic transformation of medications used in clinical practice. In addition, the CYP enzymes are commonly associated with causing many clinically relevant drug-drug interactions. Of the CYP enzymes, CYP3A4 is not only the most prevalent CYP enzyme in the liver and intestine, but is responsible for metabolism and elimination of approximately 50% of marketed drugs. In addition, CYP3A4 activity can be induced (or increased) or inhibited (decreased) in response to administration of certain drugs, thereby affecting concentrations of their own or certain concomitant drugs present in the body. Typically, the induction of CYP3A4 is an undesired property of the drug molecule as it can result in the reduction of parent drug concentrations that may put patients at increased risk for lack of efficacy or increased metabolite formation that can lead to safety risk. The CYP3A4 induction property was evaluated in an in vitro induction assay where human hepatocytes were exposed to the test compounds at physiologically relevant concentrations. Changes in the levels of CYP3A4 were evaluated at the end of the experiment and compared against the increased levels upon treatment with rifampin, a well-established CYP3A4 inducer.

Representative compounds of the present invention show either favorable activities against hNav1.7 IWQ or favorable human CYP3A4 induction data as compared to Compound X, which is named 1-(4-cyclopropyl-5-fluoro-2-methoxyphenyl)-N-(isoxazol-3-yl)-2-oxo-1,2-dihydroquinoline-6-sulfonamide, having the structure below:

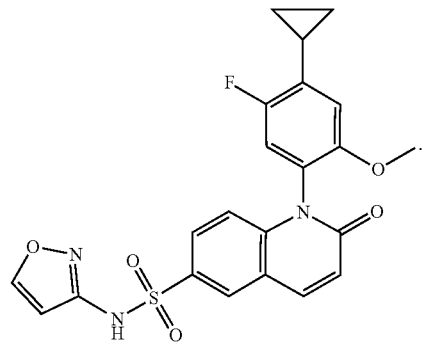 [SMILES: COc1cc(C2CC2)c(F)cc1-n1c(=O)ccc2cc(S(=O)(=O)Nc3ccon3)ccc21]

Compound X was exemplified in International Patent Publication No. WO2014201206A1, Example No. 1145. Preferred compounds of the present invention have both favorable activities against human Nav1.7 IWQ and favorable human CYP3A4 induction data as compared to Compound X.

TABLE 1

BIOLOGICAL DATA

| Ex. # | Compound Name | hNaV1.7 IWB-U IC50 | CYP3A4 mRNA Induct Hu 10 uM POC |
|---|---|---|---|
| A | 1-(4-cyclopropyl-5-fluoro-2-methoxyphenyl)-N-(isoxazol-3-yl)-2-oxo-1,2-dihydroquinoline-6-sulfonamide | 0.048 | 84.31 |
| 1 | (P)-1-(4-(2,2-dimethylcyclopropyl)-5-fluoro-2-methoxyphenyl)-N-(isoxazol-3-yl)-2-oxo-1,2-dihydroquinoline-6-sulfonamide | ND | ND |
| 2 | (P)-1-(4-(2,2-dimethylcyclopropyl)-2-methoxyphenyl)-N-(isoxazol-3-yl)-2-oxo-1,2-dihydroquinoline-6-sulfonamide | ND | ND |
| 3 | trans-1-(5-fluoro-2-methoxy-4-(2-(trifluoromethyl)cyclopropyl)phenyl)-N-(isoxazol-3-yl)-2-oxo-1,2-dihydroquinoline-6-sulfonamide | 0.023 | ND |
| 4 | (P)-1-(5-fluoro-2-methoxy-4-((1S,2S)-2-(trifluoromethyl)cyclopropyl)phenyl)-N-(isoxazol-3-yl)-2-oxo-1,2-dihydroquinoline-6-sulfonamide | 0.011 | 15.9 |
| 5 | (P)-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide | 0.009 | 41.96 |
| 6 | (P)-1-(5-fluoro-2-methoxy-4-((1R,2R)-2-methylcyclopropyl)phenyl)-N-(isoxazol-3-yl)-2-oxo-1,2-dihydroquinoline-6-sulfonamide | 0.020 | 25.49 |
| 7 | (P)-1-(5-fluoro-2-methoxy-4-((1S,2S)-2-methylcyclopropyl)phenyl)-N-(isoxazol-3-yl)-2-oxo-1,2-dihydroquinoline-6-sulfonamide | 0.016 | 41.2 |
| 8 | (P)-1-(5-fluoro-2-methoxy-4-((1R,2R)-2-phenylcyclopropyl)phenyl)-N-(isoxazol-3-yl)-2-oxo-1,2-dihydroquinoline-6-sulfonamide | 0.008 | 27.54 |
| 9 | (P)-1-(5-fluoro-2-methoxy-4-((1S,2S)-2-phenylcyclopropyl)phenyl)-N-(isoxazol-3-yl)-2-oxo-1,2-dihydroquinoline-6-sulfonamide | 0.004 | 37.165 |
| 10 | (P)-(R)-1-(4-(2,2-difluorocyclopropyl)-5-fluoro-2-methoxyphenyl)-N-(isoxazol-3-yl)-2-oxo-1,2-dihydroquinoline-6-sulfonamide | 0.066 | ND |
| 11 | (P)-(S)-1-(4-(2,2-difluorocyclopropyl)-5-fluoro-2-methoxyphenyl)-N-(isoxazol-3-yl)-2-oxo-1,2-dihydroquinoline-6-sulfonamide | 0.059 | ND |
| 12 | (P)-1-(5-chloro-2-methoxy-4-((1S,2S)-2-(trifluoromethyl)cyclopropyl)phenyl)-2-oxo-N-(pyrimidin-2-yl)-1,2-dihydroquinoline-6-sulfonamide | 0.017 | 29.85 |
| 13 | (P)-1-(5-chloro-2-methoxy-4-((1R,2R)-2-(trifluoromethyl)cyclopropyl)phenyl)-2-oxo-N-(pyrimidin-2-yl)-1,2-dihydroquinoline-6-sulfonamide | 0.012 | 92.47 |

TABLE 1-continued

BIOLOGICAL DATA

| Ex. # | Compound Name | hNaV1.7 IWB-U IC50 | CYP3A4 mRNA Induct Hu 10 uM POC |
|---|---|---|---|
| 14 | (P)-1-(5-chloro-2-methoxy-4-((1R,2R)-2-(trifluoromethyl)cyclopropyl)phenyl)-2-oxo-N-(pyridazin-3-yl)-1,2-dihydroquinoline-6-sulfonamide | 0.019 | 46.59 |
| 15 | (P)-1-(5-chloro-2-methoxy-4-((1S,2S)-2-(trifluoromethyl)cyclopropyl)phenyl)-2-oxo-N-(pyridazin-3-yl)-1,2-dihydroquinoline-6-sulfonamide | 0.014 | 69.11 |
| 16 | (P)-1-(5-fluoro-2-methoxy-4-((1R,2R)-2-(trifluoromethyl)cyclopropyl)phenyl)-2-oxo-N-(pyridazin-3-yl)-1,2-dihydroquinoline-6-sulfonamide | 0.019 | 27.11 |
| 17 | (P)-1-(5-fluoro-2-methoxy-4-((1S,2S)-2-(trifluoromethyl)cyclopropyl)phenyl)-2-oxo-N-(pyridazin-3-yl)-1,2-dihydroquinoline-6-sulfonamide | 0.016 | 37.04 |
| 18 | (P)-1-(5-chloro-2-methoxy-4-((1R,2R)-2-(trifluoromethyl)cyclopropyl)phenyl)-N-(isoxazol-3-yl)-2-oxo-1,2-dihydroquinoline-6-sulfonamide | 0.007 | 9.92 |
| 19 | (P)-1-(5-chloro-2-methoxy-4-((1S,2S)-2-(trifluoromethyl)cyclopropyl)phenyl)-N-(isoxazol-3-yl)-2-oxo-1,2-dihydroquinoline-6-sulfonamide | 0.006 | 85.5 |
| 20 | (P)-1-(5-fluoro-2-methoxy-4-((1R,2R)-2-(trifluoromethyl)cyclopropyl)phenyl)-2-oxo-N-(pyrimidin-2-yl)-1,2-dihydroquinoline-6-sulfonamide | 0.024 | 67.47 |
| 21 | (P)-1-(5-fluoro-2-methoxy-4-((1S,2S)-2-(trifluoromethyl)cyclopropyl)phenyl)-2-oxo-N-(pyrimidin-2-yl)-1,2-dihydroquinoline-6-sulfonamide | 0.035 | 34.81 |
| 22 | (P)-1-(5-fluoro-2-methoxy-4-(1-(trifluoromethyl)cyclopropyl)phenyl)-N-(isoxazol-3-yl)-2-oxo-1,2-dihydroquinoline-6-sulfonamide | 0.014 | ND |
| 23 | (P)-1-(5-fluoro-2-methoxy-4-(1-(trifluoromethyl)cyclopropyl)phenyl)-2-oxo-N-(pyrimidin-2-yl)-1,2-dihydroquinoline-6-sulfonamide | 0.016 | 85.95 |
| 24 | (P)-1-(5-chloro-2-methoxy-4-(1-(trifluoromethyl)cyclopropyl)phenyl)-N-(isoxazol-3-yl)-2-oxo-1,2-dihydroquinoline-6-sulfonamide | 0.006 | 100.7 |
| 25 | (P)-1-(5-chloro-2-methoxy-4-(1-(trifluoromethyl)cyclopropyl)phenyl)-2-oxo-N-(pyrimidin-2-yl)-1,2-dihydroquinoline-6-sulfonamide | 0.022 | 88.68 |
| 26 | (P)-N-(isoxazol-3-yl)-1-(2-methoxy-5-methyl-4-((1R,2R)-2-(trifluoromethyl)cyclopropyl)phenyl)-2-oxo-1,2-dihydroquinoline-6-sulfonamide | 0.019 | 35.39 |
| 27 | (P)-N-(isoxazol-3-yl)-1-(2-methoxy-5-methyl-4-((1S,2S)-2-(trifluoromethyl)cyclopropyl)phenyl)-2-oxo-1,2-dihydroquinoline-6-sulfonamide | 0.013 | 64.14 |
| 28 | (P)-1-(2-methoxy-5-methyl-4-((1R,2R)-2-(trifluoromethyl)cyclopropyl)phenyl)-2-oxo-N-(pyrimidin-2-yl)-1,2-dihydroquinoline-6-sulfonamide | 0.042 | 23.36 |
| 29 | (P)-1-(2-methoxy-5-methyl-4-((1S,2S)-2-(trifluoromethyl)cyclopropyl)phenyl)-2-oxo-N-(pyrimidin-2-yl)-1,2-dihydroquinoline-6-sulfonamide | 0.032 | 74.53 |
| 30 | (P)-1-(4-((1S,2S)-[1,1'-bi(cyclopropan)]-2-yl)-5-fluoro-2-methoxyphenyl)-N-(isoxazol-3-yl)-2-oxo-1,2-dihydroquinoline-6-sulfonamide | 0.026 | 60.34 |
| 31 | (P)-1-(4-((1R,2S)-[1,1'-bi(cyclopropan)]-2-yl)-5-fluoro-2-methoxyphenyl)-N-(isoxazol-3-yl)-2-oxo-1,2-dihydroquinoline-6-sulfonamide | 0.009 | 100.7 |
| 32 | (P)-1-(5-fluoro-2-methoxy-4-((1R,2R)-2-((trifluoromethoxy)methyl)cyclopropyl)phenyl)-N-(isoxazol-3-yl)-2-oxo-1,2-dihydroquinoline-6-sulfonamide | 0.009 | 64.54 |

TABLE 1-continued

BIOLOGICAL DATA

| Ex. # | Compound Name | hNaV1.7 IWB-U IC50 | CYP3A4 mRNA Induct Hu 10 uM POC |
|---|---|---|---|
| 33 | (P)-1-(5-fluoro-2-methoxy-4-((1S,2S)-2-((trifluoromethoxy)methyl)cyclopropyl)phenyl)-N-(isoxazol-3-yl)-2-oxo-1,2-dihydroquinoline-6-sulfonamide | 0.004 | 139.9 |
| 34 | (P)-1-(5-fluoro-2-methoxy-4-((1R,2R)-2-(trifluoromethyl)cyclopropyl) phenyl)-2-oxo-N-(1,2,4-thiadiazol-5-yl)-1,2-dihydroquinoline-6-sulfonamide | 0.005 | 12.69 |
| 35 | (P)-1-(5-fluoro-2-methoxy-4-((1R,2R)-2-(trifluoromethyl)cyclopropyl)phenyl)-N-(oxazol-2-yl)-2-oxo-1,2-dihydroquinoline-6-sulfonamide | 0.011 | 53.28 |
| 36 | (P)-1-(5-fluoro-2-methoxy-4-((1S,2S)-2-(trifluoromethyl) cyclopropyl)phenyl)-N-(oxazol-2-yl)-2-oxo-1,2-dihydroquinoline-6-sulfonamide | 0.006 | 102.8 |
| 37 | (P)-1-(5-cyano-2-methoxy-4-((1S,2S)-2-(trifluoromethyl)cyclopropyl)phenyl)-N-(isoxazol-3-yl)-2-oxo-1,2-dihydroquinoline-6-sulfonamide | 0.007 | 16.39 |
| 38 | (P)-N-(isoxazol-3-yl)-1-(2-methoxy-4-((1R,2R)-2-(trifluoromethyl) cyclopropyl)phenyl)-2-oxo-1,2-dihydroquinoline-6-sulfonamide | 0.010 | 29.06 |
| 39 | (P)-N-(isoxazol-3-yl)-1-(2-methoxy-4-((1S,2S)-2-(trifluoromethyl) cyclopropyl)phenyl)-2-oxo-1,2-dihydroquinoline-6-sulfonamide | 0.008 | 38.35 |
| 40 | (P)-1-(5-fluoro-2-methoxy-4-((1R,2R)-2-(trifluoromethyl) cyclopropyl)phenyl)-2-oxo-N-(1,3,4-thiadiazol-2-yl)-1,2-dihydroquinoline-6-sulfonamide | 0.008 | 10.79 |
| 41 | (P)-6-(benzylthio)-1-(5-fluoro-2-hydroxy-4-((1S,2S)-2-(trifluoromethyl)cyclopropyl)phenyl)quinolin-2(1H)-one | 0.008 | 13.21 |
| 42 | (P)-1-(5-fluoro-2-methoxy-4-(1-(trifluoromethyl) cyclopropyl)phenyl)-N-(isoxazol-3-yl)-2-oxo-1,2-dihydroquinoline-6-sulfonamide | 0.020 | ND |
| 43 | (M)-1-(5-fluoro-2-methoxy-4-(1-(trifluoromethyl) cyclopropyl)phenyl)-N-(isoxazol-3-yl)-2-oxo-1,2-dihydroquinoline-6-sulfonamide | 1.630 | ND |
| 44 | (P)-4-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide | 0.005 | 26.89 |
| 45 | (P)-7-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide | 0.008 | 24.57 |
| 46 | (P)-7-fluoro-1-(5-fluoro-2-methoxy-4-((1S,2S)-2-(trifluoromethyl)cyclopropyl)phenyl)-N-(isoxazol-3-yl)-2-oxo-1,2-dihydroquinoline-6-sulfonamide | 0.011 | 53.03 |
| 47 | (P)-7-fluoro-N-(isoxazol-3-yl)-1-(2-methoxy-4-((1R,2R)-2-(trifluoromethyl)cyclopropyl)phenyl)-2-oxo-1,2-dihydroquinoline-6-sulfonamide | 0.012 | 14.245 |
| 48 | (P)-7-fluoro-N-(isoxazol-3-yl)-1-(2-methoxy-4-((1S,2S)-2-(trifluoromethyl)cyclopropyl)phenyl)-2-oxo-1,2-dihydroquinoline-6-sulfonamide | 0.011 | 54.02 |

The foregoing invention has been described in some detail by way of illustration and example, for purposes of clarity and understanding. Those skilled in the art understand that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited herein are hereby incorporated by reference in their entirety for all purposes to the same extent as if each individual patent, patent application or publication were so individually denoted.

What is claimed is:

1. A compound of Formula (I):

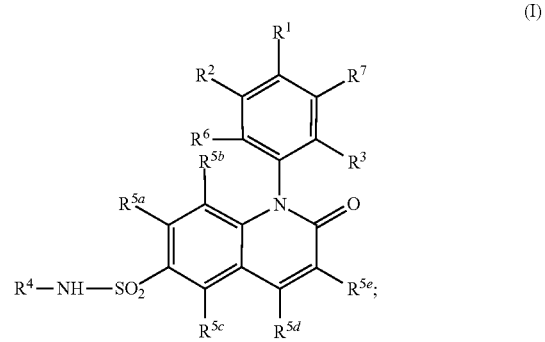

(I)

an enantiomer, diastereoisomer, atropisomer thereof, a mixture thereof, or a pharmaceutically acceptable salt thereof, wherein:

$R^1$ is a cyclopropyl ring; or a 4-, 5-, 6-, 7-, or 8-membered bicyclic ring containing 0, 1, 2 or 3 N atoms and 0, 1, or 2 atoms selected from O and S; and wherein said cyclopropyl ring or bicyclic ring is substituted by 0, 1, 2 or 3 $R^{1a}$ groups selected from hydroxy, halo, $C_{1-8}$alk, $C_{1-8}$haloalk, —O—$C_{1-4}$alk, —O—$C_{1-8}$haloalk, —C(=O)$C_{1-4}$alk, —O—C(=O)$C_{1-4}$alk, —NH$_2$, —NH$C_{1-4}$alk, —N($C_{1-4}$alk)$C_{1-4}$alk, 3-, 4-, or 5-membered cycloalkyl, or 6-membered aryl;

$R^2$ is H, halo, CN, $C_{1-6}$alk, or $C_{1-6}$haloalk;

$R^3$ is $C_{1-6}$alk, $C_{1-6}$haloalk, —O—$C_{1-6}$alk, —O-cyclopropyl, or —O-cyclobutyl;

$R^4$ is a 5- to 6-membered heteroaryl;

Each of $R^6$ and $R^7$ is hydrogen; and

Each of $R^{5a}$; $R^{5b}$; $R^{5c}$; $R^{5d}$; and $R^{5e}$ is independently hydrogen or halo, wherein the compound is not

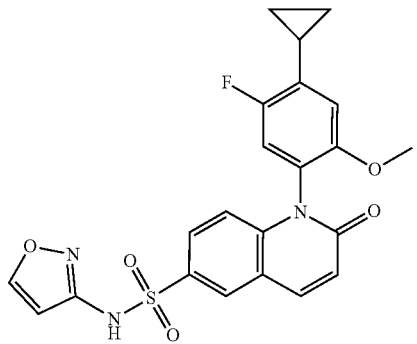 [SMILES: COc1cc(C2CC2)c(F)cc1-n1c(=O)ccc2cc(S(=O)(=O)Nc3ccon3)ccc21]

or a salt or tautomer thereof.

2. The compound according to claim 1, an enantiomer, diastereoisomer, atropisomer thereof, a mixture thereof, or a pharmaceutically acceptable salt thereof, wherein $R^{1a}$ is selected from halo, $C_{1-8}$alk, —O—$C_{1-4}$alk, $C_{1-8}$haloalk, cyclopropyl, or phenyl; wherein said $C_{1-8}$haloalk is $C_{1-8}$fluoroalkyl.

3. The compound according to claim 1, an enantiomer, diastereoisomer, atropisomer thereof, a mixture thereof, or a pharmaceutically acceptable salt thereof, wherein $R^1$ is a cyclopropyl ring; or a 4-, 5-, or 6-membered bicyclic ring; wherein said bicyclic ring contains 0 N, O, and S atoms; and wherein said cyclopropyl ring or bicyclic ring is substituted by 1, 2 or 3 $R^{1a}$ groups selected from F, —CF$_3$, —O—CF$_3$, —C(CH$_3$)$_3$, cyclopropyl, or phenyl.

4. The compound according to claim 1, an enantiomer, diastereoisomer, atropisomer thereof, a mixture thereof, or a pharmaceutically acceptable salt thereof, wherein $R^1$ is a cyclopropyl ring or bicyclo[1.1.0]butan-1-yl ring; wherein each ring is substituted by 1 or 2 F or —CF$_3$ substituents.

5. The compound according to claim 1, an enantiomer, diastereoisomer, atropisomer thereof, a mixture thereof, or a pharmaceutically acceptable salt thereof, wherein $R^1$ is a cyclopropyl ring substituted by 1 or 2 F or —CF$_3$; wherein said cyclopropyl ring is a trans isomer.

6. The compound according to claim 1, an enantiomer, diastereoisomer, atropisomer thereof, a mixture thereof, or a pharmaceutically acceptable salt thereof, wherein $R^1$ is a bicyclo[1.1.0]butan-1-yl ring substituted by 1 or 2 F or —CF$_3$.

7. The compound according to claim 1, an enantiomer, diastereoisomer, atropisomer thereof, a mixture thereof, or a pharmaceutically acceptable salt thereof, wherein $R^2$ is H, fluoro, chloro, CN, methyl, CF$_3$, CHF$_2$, or CH$_2$F.

8. The compound according to claim 1, an enantiomer, diastereoisomer, atropisomer thereof, a mixture thereof, or a pharmaceutically acceptable salt thereof, wherein $R^2$ is H, fluoro, chloro, CN, or methyl.

9. The compound according to claim 1, an enantiomer, diastereoisomer, atropisomer thereof, a mixture thereof, or a pharmaceutically acceptable salt thereof, wherein $R^2$ is H or fluoro.

10. The compound according to claim 1, an enantiomer, diastereoisomer, atropisomer thereof, a mixture thereof, or a pharmaceutically acceptable salt thereof, wherein $R^3$ is methoxy.

11. The compound according to claim 1, an enantiomer, diastereoisomer, atropisomer thereof, a mixture thereof, or a pharmaceutically acceptable salt thereof, wherein $R^4$ is a 5-membered heteroaryl.

12. The compound according to claim 1, an enantiomer, diastereoisomer, atropisomer thereof, a mixture thereof, or a pharmaceutically acceptable salt thereof, wherein $R^4$ is a 6-membered heteroaryl.

13. The compound according to claim 1, an enantiomer, diastereoisomer, atropisomer thereof, a mixture thereof, or a pharmaceutically acceptable salt thereof, wherein $R^4$ is isoxazolyl, pyridazinyl, thiazolyl, thiadiazolyl, oxazolyl, or pyrimidinyl.

14. The compound according to claim 1, an enantiomer, diastereoisomer, atropisomer thereof, a mixture thereof, or a pharmaceutically acceptable salt thereof, wherein a) each of $R^{5a}$; $R^{5b}$; $R^{5c}$; $R^{5d}$; and $R^{5e}$ is hydrogen; b) $R^{5a}$ is F; and each of $R^{5b}$; $R^{5c}$; $R^{5d}$; and $R^{5e}$ is hydrogen; or c) $R^{5d}$ is F; and each of $R^{5a}$; $R^{5b}$; $R^{5c}$; and $R^{5e}$ is hydrogen.

15. The compound according to claim 1, an enantiomer, diastereoisomer, atropisomer thereof, a mixture thereof, or a pharmaceutically acceptable salt thereof, wherein said compound of Formula (I) is of Formula (Ia):

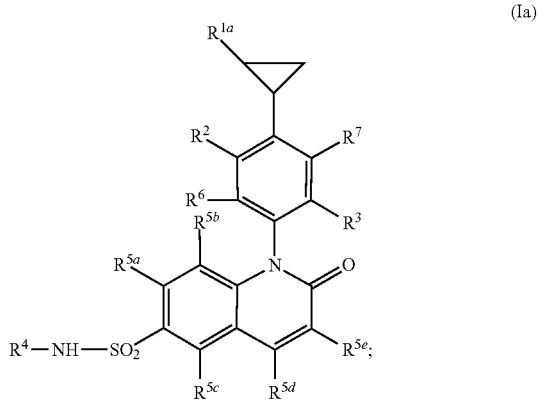

(Ia)

wherein each $R^{1a}$ is independently fluoro, methyl, —O—CF$_3$, CF$_3$, cyclopropyl, or phenyl.

16. The compound according to claim 15, an enantiomer, diastereoisomer, atropisomer thereof, a mixture thereof, or a pharmaceutically acceptable salt thereof, wherein $R^{1a}$ is CF$_3$ or methyl; the cyclopropyl ring is a trans isomer; $R^2$ is H or F; $R^4$ is isoxazolyl, pyridazinyl, thiazolyl, or thiadiazolyl; and $R^{5a}$ is H or F.

17. The compound according to claim 15, an enantiomer, diastereoisomer, atropisomer thereof, a mixture thereof, or a pharmaceutically acceptable salt thereof, wherein $R^{1a}$ is $CF_3$ or methyl; the cyclopropyl ring is a cis isomer; $R^2$ is H or F; $R^4$ is isoxazolyl, pyridazinyl, thiazolyl, or thiadiazolyl; and $R^{5a}$ is H or F.

18. The compound according to claim 15, an enantiomer, diastereoisomer, atropisomer thereof, a mixture thereof, or a pharmaceutically acceptable salt thereof, wherein $R^{1a}$ is $CF_3$; the cyclopropyl ring is a trans isomer; $R^2$ is H; $R^4$ is isoxazolyl, pyridazinyl, thiazolyl, or thiadiazolyl; and $R^{5a}$ is F.

19. The compound according to claim 15, an enantiomer, diastereoisomer, atropisomer thereof, a mixture thereof, or a pharmaceutically acceptable salt thereof, wherein $R^{1a}$ is $CF_3$; the cyclopropyl ring is a trans isomer; $R^2$ is F; $R^4$ is isoxazolyl, pyridazinyl, thiazolyl, or thiadiazolyl; and $R^{5a}$ is H.

20. The compound according to claim 18, an enantiomer, diastereoisomer, atropisomer thereof, a mixture thereof, or a pharmaceutically acceptable salt thereof, wherein $R^4$ is isoxazolyl.

21. The compound according to claim 19, an enantiomer, diastereoisomer, atropisomer thereof, a mixture thereof, or a pharmaceutically acceptable salt thereof, wherein $R^4$ is isoxazolyl.

22. The compound according to claim 1, an enantiomer, diastereoisomer, atropisomer thereof, a mixture thereof, or a pharmaceutically acceptable salt thereof, wherein said compound is an atropisomer and is the P atropisomer.

23. The compound according to claim 1, an enantiomer, diastereoisomer, atropisomer thereof, a mixture thereof, or a pharmaceutically acceptable salt thereof, wherein the compound is selected from:
 a) (P)-1-(5-fluoro-2-methoxy-4-((1S,2S)-2-(trifluoromethyl)cyclopropyl)phenyl)-N-(isoxazol-3-yl)-2-oxo-1,2-dihydroquinoline-6-sulfonamide;
 b) (P)-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide;
 c) (P)-1-(5-fluoro-2-methoxy-4-((1S,2S)-2-methylcyclopropyl)phenyl)-N-(isoxazol-3-yl)-2-oxo-1,2-dihydroquinoline-6-sulfonamide;
 d) (P)-1-(5-fluoro-2-methoxy-4-((1R,2R)-2-phenylcyclopropyl)phenyl)-N-(isoxazol-3-yl)-2-oxo-1,2-dihydroquinoline-6-sulfonamide;
 e) (P)-1-(5-fluoro-2-methoxy-4-((1S,2S)-2-phenylcyclopropyl)phenyl)-N-(isoxazol-3-yl)-2-oxo-1,2-dihydroquinoline-6-sulfonamide;
 f) (P)-1-(5-fluoro-2-methoxy-4-((1S,2S)-2-(trifluoromethyl)cyclopropyl)phenyl)-2-oxo-N-(pyridazin-3-yl)-1,2-dihydroquinoline-6-sulfonamide;
 g) (P)-1-(5-chloro-2-methoxy-4-((1R,2R)-2-(trifluoromethyl)cyclopropyl)phenyl)-N-(isoxazol-3-yl)-2-oxo-1,2-dihydroquinoline-6-sulfonamide;
 h) (P)-1-(5-fluoro-2-methoxy-4-((1R,2R)-2-(trifluoromethyl)cyclopropyl)
 i) phenyl)-2-oxo-N-(1,2,4-thiadiazol-5-yl)-1,2-dihydroquinoline-6-sulfonamide;
 j) (P)-1-(5-cyano-2-methoxy-4-((1S,2S)-2-(trifluoromethyl)cyclopropyl)phenyl)-N-(isoxazol-3-yl)-2-oxo-1,2-dihydroquinoline-6-sulfonamide;
 k) (P)-N-(isoxazol-3-yl)-1-(2-methoxy-4-((1R,2R)-2-(trifluoromethyl) cyclopropyl)phenyl)-2-oxo-1,2-dihydroquinoline-6-sulfonamide;
 l) (P)-N-(isoxazol-3-yl)-1-(2-methoxy-4-((1S,2S)-2-(trifluoromethyl) cyclopropyl)phenyl)-2-oxo-1,2-dihydroquinoline-6-sulfonamide;
 m) (P)-1-(5-fluoro-2-methoxy-4-((1R,2R)-2-(trifluoromethyl) cyclopropyl)phenyl)-2-oxo-N-(1,3,4-thiadiazol-2-yl)-1,2-dihydroquinoline-6-sulfonamide;
 n) (P)-6-(benzylthio)-1-(5-fluoro-2-hydroxy-4-((1S,2S)-2-(trifluoromethyl)cyclopropyl)phenyl)quinolin-2 (1H)-one;
 o) (P)-4-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide;
 p) (P)-7-fluoro-1-(5-fluoro-2-methoxy-4-((1R,2R)-2-(trifluoromethyl)cyclopropyl)phenyl)-N-(isoxazol-3-yl)-2-oxo-1,2-dihydroquinoline-6-sulfonamide; or
 q) (P)-7-fluoro-N-(isoxazol-3-yl)-1-(2-methoxy-4-((1R,2R)-2-(trifluoromethyl)cyclopropyl)phenyl)-2-oxo-1,2-dihydroquinoline-6-sulfonamide.

24. A pharmaceutical composition comprising a compound according to claim 1, an enantiomer, diastereoisomer, atropisomer thereof, a mixture thereof, or a pharmaceutically acceptable salt thereof, and a pharmaceutically acceptable excipient.

25. A method of treating pain, cough, or itch, the method comprising administering to a patient in need thereof a therapeutically effective amount of a compound according to claim 1, an enantiomer, diastereoisomer, atropisomer thereof, a mixture thereof, or a pharmaceutically acceptable salt thereof.

26. The method according to claim 25; wherein the pain is selected from chronic pain, acute pain, neuropathic pain, pain associated with rheumatoid arthritis, pain associated with osteoarthritis, pain associated with cancer, peripheral diabetic neuropathy, and neuropathic low back pain.

27. The method according to claim 25; wherein the cough is selected from post viral cough, viral cough, or acute viral cough.

* * * * *